(12) United States Patent
Cole et al.

(10) Patent No.: US 7,883,712 B2
(45) Date of Patent: Feb. 8, 2011

(54) **IDENTIFICATION OF VIRULENCE ASSOCIATED REGIONS RD1 AND RD5 LEADING TO IMPROVE VACCINE OF *M. BOVIS* BCG AND *M. MICROTI***

(75) Inventors: Stewart Cole, Clamart (FR); Alexander S. Pym, London (GB); Roland Brosch, Paris (FR); Priscille Brodin, Paris (FR); Laleh Majlessi, Montigny le Bretonneux (FR); Caroline Demangel, Paris (FR); Claude Leclerc, Paris (FR)

(73) Assignee: Institut Pasteur, Paris (FR)

( * ) Notice: Subject to any disclaimer, the term of this patent is extended or adjusted under 35 U.S.C. 154(b) by 1305 days.

(21) Appl. No.: 10/510,021

(22) PCT Filed: Apr. 1, 2003

(86) PCT No.: PCT/IB03/01789

§ 371 (c)(1),
(2), (4) Date: Oct. 1, 2004

(87) PCT Pub. No.: WO03/085098

PCT Pub. Date: Oct. 16, 2003

(65) Prior Publication Data

US 2005/0220811 A1    Oct. 6, 2005

(30) Foreign Application Priority Data

Apr. 5, 2002    (EP)    ................... 02290864

(51) Int. Cl.
*A61K 39/04*    (2006.01)
*C07H 21/02*    (2006.01)
*C07H 21/04*    (2006.01)

(52) U.S. Cl. .................. 424/248.1; 536/23.1; 536/23.7; 424/9.1; 424/9.2; 424/234.1

(58) Field of Classification Search .................. 424/9.1, 424/9.2, 234.1, 248.1; 536/23.1, 23.7
See application file for complete search history.

(56) References Cited

FOREIGN PATENT DOCUMENTS

WO    WO 99/04005    1/1999
WO    WO 99/45119    9/1999

OTHER PUBLICATIONS

Mahairas et al., "Molecular Analysis of Genetic Differences Between *Mycobacterium bovis* BCG and Virulent *M. bovis*", Journal of Bacteriology, vol. 178, No. 5, pp. 1274-1282, (Mar. 1996).
Andersen et al., "Recall of Long-Lived Immunity to *Mycobacterium tuberculosis* Infection in Mice", J. Immunol., vol. 154, No. 7, pp. 3359-3372, (1995), taken from Database NCBI, XP-002209499, (Apr. 27, 1996).
Andersen et al., "Regulatory Polynucleotide Containing *M. tuberculosis* 1hp/orflc Operons.",Database EBI, XP-002209498, (5 pages), (Jun. 7, 1999).
Berthet et al., "A *Mycobacterium tuberculosis* Operon Encoding esat-6 and a Novel Low-Molecular-Mass Culture Filtrate Protein (CFP-10)", Microbiology, vol. 144, pp. 3195-3203, (1998).
Berthet et al., "Mycobacterium Tuberculosis H37Rv esat6 Promoter Region, L45 Antigen Homologous Protein LHP (1hp) Gene, Complete cds, and Early Secreted Antigenic Target 6 kDa (esat6) Gene, Partial cds.", Database EBI, XP-002209500, (2 pages), (Jun. 29, 1998).
Zhang Ye et al., "The Signalling Pathway for BCG-Induced Interleukin-6 Production in Human Bladder Cancer Cells", Biochemical Pharmacology, vol. 63, No. 2, pp. 273-282, (2002).
Mustafa, "Biotechnology in the Development of New Vaccines and Diagnostic Reagents Against Tuberculosis", Current Pharmaceutical Biotechnology, vol. 2, No. 2, pp. 157-173, (2001).
Brosch et al., "A New Evolutionary Scenario for the *Mycobacterium tuberculosis* Complex", PNAS, vol. 99, No. 6, pp. 3684-3689, (2002).
Brosch et al., "The Evolution of Mycobacterial Pathogenicity: Clues From Comparative Genomics", Trends in Microbiology, vol. 9, No. 9, pp. 452-458, (2001).

*Primary Examiner*—Rodney P. Swartz
(74) *Attorney, Agent, or Firm*—Finnegan, Henderson, Farabow, Garrett & Dunner LLP

(57) ABSTRACT

The present invention relates to a strain of *M. bovis* BCG or *M. microti*, wherein said strain has integrated part or all of the RD1 region responsible for enhanced immunogenicity of the tubercle bacilli, especially the ESAT-6 and CFP-10 genes. These strains will be referred as the *M bovis* BCG::RDI or *M. microti*::RD1 strains and are useful as a new improved vaccine for preventing tuberculosis and as a therapeutical product enhancing the stimulation of the immune system for the treatment of bladder cancer. These strains are also useful for the expression and presentation of heterologous antigens and molecule that are of therapeutic or prophylactic interest.

18 Claims, 25 Drawing Sheets

Figures 1A, 1B:
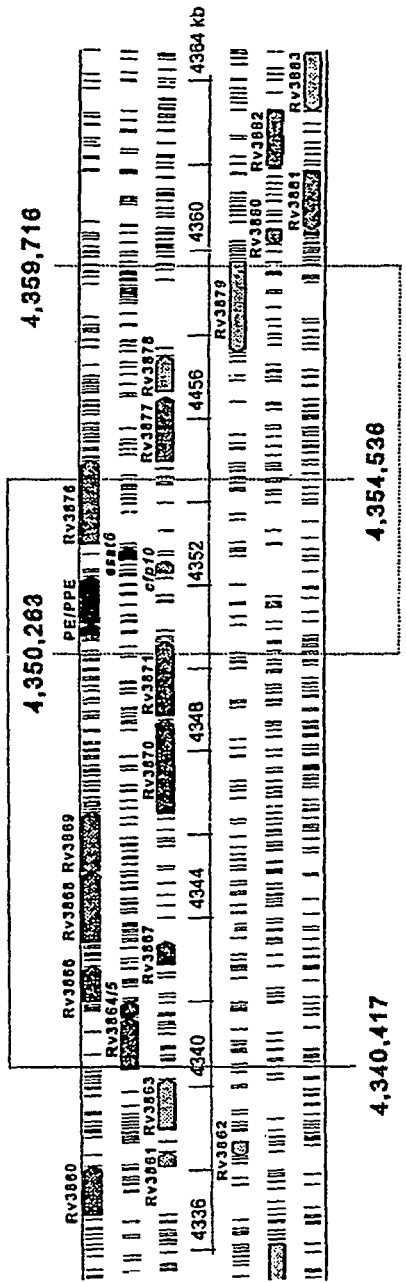

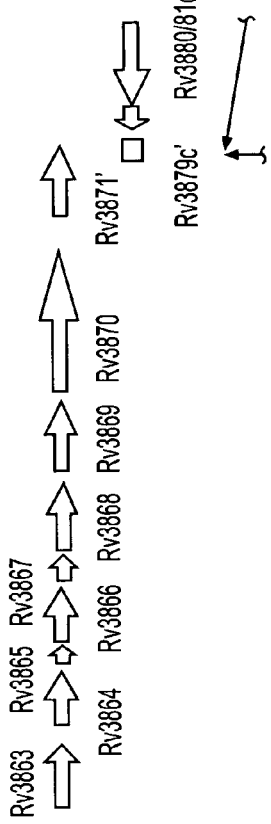
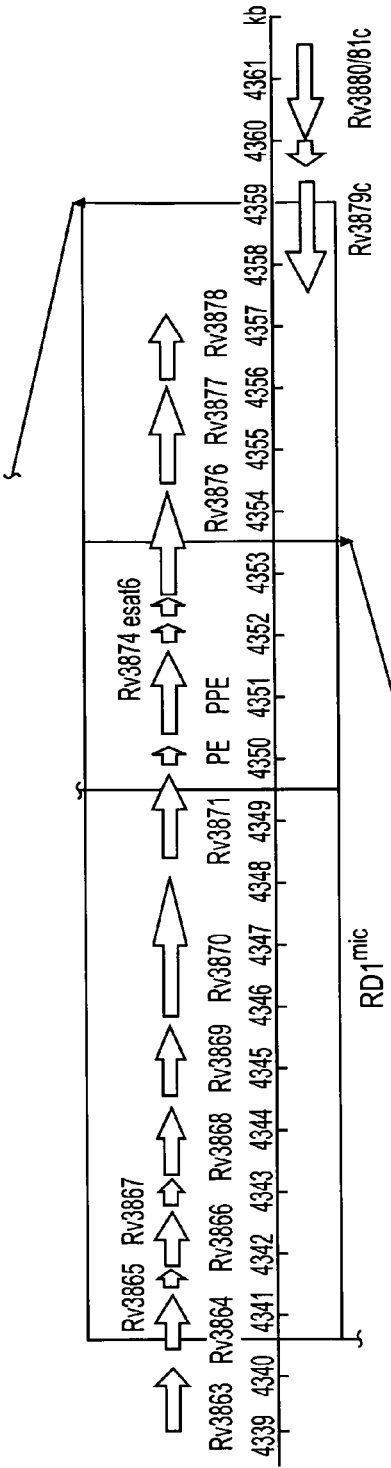
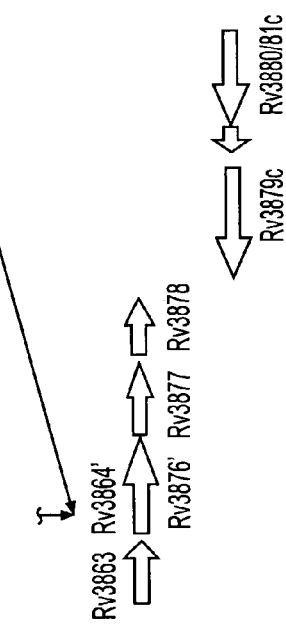
FIG. 6A
FIG. 6B
FIG. 6C

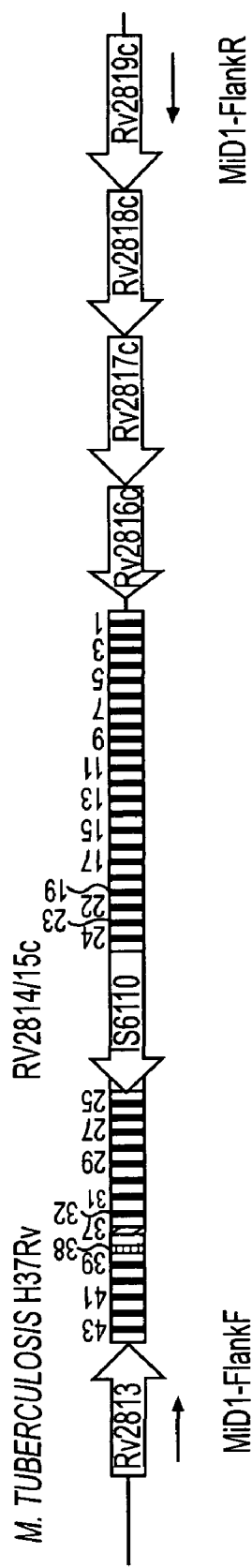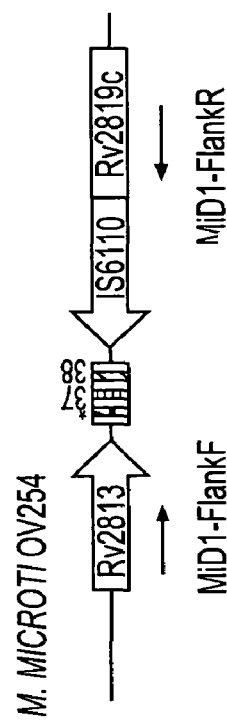
FIG. 7A
FIG. 7B

SEQUENCE LISTING

```
<160> NUMBER OF SEQ ID NOS: 75

<210> SEQ ID NO 1
<211> LENGTH: 31808
<212> TYPE: DNA
<213> ORGANISM: Mycobacterium tuberculosis
<220> FEATURE:
<223> OTHER INFORMATION: Insert of cosmid RD1-2F9 corresponding to
      sequence in the genome of micybacterium tuberculosis H37Rv

<400> SEQUENCE: 1
gatccgacca caccagcccg gcacccgcg gggatactcg ccccgtccgc cgtccggaga        60
tcgctgcccc gcgccaccgc ctggccggca cgctgctgcc gctacgccac cagggccgcc     120
gcgcctgcct tcagctccac tgcgtccatt gccggacccg gcttggccac gccagccgga     180
ggccccgcca ccgagcacct gggccgaccc cgccctggcg ccgatacgca gtcggacgcg     240
acccggcgag cgtggttggc gacgcatggt gcggctggtc acctttggcc ttgtcggcct     300
gggccggtcg ggcatgcagc gccaggaggc ccaattcgaa gcaacgatac gaaccgtcct     360
gcatggcaac cacaaggtcg ccgtgctggg caaggaggt gtgggaaaga cgtcggttgc      420
ggcgtgcgtc ggatcgatcc ttgccgaact gcgccagcag gaccgtatcg tcgggatcga     480
cgccgacacc gccttcggca ggctgagcag ccgaatcgat cctcgagcag ctggttcgtt     540
ctgggagctg accaccgaca cgaatctgcg gtccttcacc gatatcaccg cgcgcctggg     600
ccgaaattcc gcgggactgt acgtcctggc aggccagccg gcatccggtc cgcgccgggt     660
gctcgatccg gccatctacc gcgaagccgc cctaaggttg gatcaccatt tcgcaatctc     720
ggtgatcgac tgcggttcct ccatggaggc ggcggtcacc caggaagtat tgcgcgatgt     780
ggatgctctg atcgtggtgt cctcgccctg ggcggatggt gcctccgctg ccgccaacac     840
catcgaatgg ctgtcggatt atggcctgac aggtttgttg cgacgcagca tcgtggtgct     900
caacgattcg gacggacacg ccgacaagcg caccaagtca ttgctggccc aggaattcat     960
cgaccacggg cagcctgtgg tcgaggtgcc cttcgatccc catttgcggc ccggggggt    1020 catcgatatg agccacgaaa tggccccgac gacgcggctg aaaatcctgc aggtcgccgc    1080
gacggtgacg gcgtacttcg cgtcgcgacc cgccgacgca cacggcagcc cgccccggtg    1140
acctggctgg ctgacccggt cggcaacagc aggatcgccc gagcgcaggc ctgcaaaacg    1200
tcaatctcgg cgcccatcgt cgaatcctgg cgggcgcaac gcggcgcgca atgtggacag    1260
cgcgagaaat cttgtcgatg ttctcgcgct gtccacatcc agggcatctc accgccactg    1320
ttccgcagac ccctcgaacc agcggtccag gcggcggttg cgtcatgccg attgggcaga    1380
```

-continued

```
cacccggtgg tcgcgcaccg ggtaaccgtt gcgctcggcc agggatcgca gctggcccaa      1440
cgcgaatgcc cgcgcccggc ctgattcggg aattacgacc cctgcccaca gcccttccgc      1500
acccgcggac tcgacggcgt cgcgtgcaca cagccaccgg cgcgggcaag cccggcacag      1560
ggtcttggcc tcgtcgtcgg gagtcgtcgt ccaacgatcg ggatcttgcg tgcaaacgcc      1620
gagcgggacc tcatacaggg cggttactgt catgtctacg ttcctccaga aagcgttgca      1680
ggttgtagcc tctgccgcga aagcgtatcg cattaaccat agcgatgcaa cagtttcctc      1740
ctctgcctgc ctagcggtgc tgcggctccg gttcggcgag ctccgagctc tagtgcgcgc      1800
accgccgagt accagggcat agatcctgtt aatcagctgt gtatctggcc tcgccggcgc      1860
gtatccgacc ccttcgggca gatcttccag gaaaagtgtt ctgacatgcg acagttcagg      1920
tgtgaagtga actgtagcgg cagttcggtt tggctaggaa actatttcca tagcgggccg      1980
tcgcgtcgct agatccaaaa tgtagcgaag tcatagcagt agaagggtgc aacggttagg      2040
atggcgggcg agcggaaagt ctgcccaccg tcccggctag tacccgcgaa taagggatca      2100
acgcagatgt ctaaagcagg gtcgactgtc ggaccggcgc cgctggtcgc gtgcagcggc      2160
ggcacatcag acgtgattga gccccgtcgc ggtgtcgcga tcattggcca ctcgtgccga      2220
gtcggcaccc agatcgacga ttctcgaatc tctcagacac atctgcgagc ggtatccgat      2280
gatggacggt ggcggatcgt cggcaacatc ccgagaggta tgttcgtcgg cggacgacgc      2340
ggcagctcgg tgaccgtcag cgataagacc ctaatccgat tcggcgatcc ccctggaggc      2400
aaggcgttga cgttcgaagt cgtcaggccg tcggattccg ctgcacagca cggccgcgta      2460
caaccatcag cggacctgtc ggacgacccg gcgcacaacg ctgcgccggt cgcaccggac      2520
cccggcgtgg ttcgcgcagg ggcggccgcg gctgcgcgcc gtcgtgaact tgacatcagc      2580
caacgcagct tggcggccga cgggatcatc aacgcgggcg cgctcatcgc gttcgagaaa      2640
ggccgtagtt ggccccggga acggaccccgg gcaaaactcg aagaagtgct gcagtggccc      2700
gctggaacca tcgcgcgaat ccgtcggggc gagcccaccg agcccgcaac aaaccccgac      2760
gcgtcccccg gactccggcc tgccgacggc ccggcgtcct tgatcgcgca ggctgtcacc      2820
gccgccgtag acggctgcag tctggctatc gcagcgttgc cggcgaccga ggaccccgag      2880
ttcaccgaac gtgccgcgcc gatccttgct gatttgcgcc agctcgaggc gattgccgtc      2940
caagcaaccc gcatcagccg gattaccccg gaattgatca aggcgttggg cgcggtacgt      3000
cgccaccacg acgaattaat gaggctggga gcaaccgccc ctggtgccac actggcgcag      3060
cgcttatatg ccgcacggcg gcgcgcgaac ctttccaccc tggagactgc ccaagcggcc      3120
ggcgtcgcag aagaaatgat cgtcggcgcc gaagccgagg aagagttgcc agccgaggcc      3180
accgaagcga tcgaagcact gatccgtcag atcaattgag gtcggctccg agcgtcccac      3240
aagtacaggc acgccgtaac gctcaagttc aacggtccgg ggaacgcgcg cgttctccgg      3300
cgtttgacgg tgcgttccat cgtgccgcga acttgaaaac gccagcgtca ccaaaaaatt      3360
cgtgcaccaa cccccctccg agcgctgcta agctcaatgt gcagtgcaaa ggtgcagata      3420
atgatggcgc accggaacgg cgagcgtaag gaaacacata aatggcatcg ggtagcggtc      3480
tttgcaagac gacgagtaac tttatttggg gccagttact cttgcttgga gagggaatcc      3540
ccgacccagg cgacatttc aacaccggtt cgtcgctgtt caaacaaatc agcgacaaaa      3600
tgggactcgc cattccgggc accaactgga tcggccaagc ggcggaagct tacctaaacc      3660
agaacatcgc gcaacaactt cgcgcacagg tgatgggcga tctcgacaaa ttaaccggca      3720
```

```
acatgatctc gaatcaggcc aaatacgtct ccgatacgcg cgacgtcctg cgggccatga    3780
agaagatgat tgacggtgtc tacaaggttt gtaagggcct cgaaaagatt ccgctgctcg    3840
gccacttgtg gtcgtgggag ctcgcaatcc ctatgtccgg catcgcgatg gccgttgtcg    3900
gcggcgcatt gctctatcta acgattatga cgctgatgaa tgcgaccaac ctgaggggaa    3960
ttctcggcag gctgatcgag atgttgacga ccttgccaaa gttccccggc ctgcccgggt    4020
tgcccagcct gcccgacatc atcgacggcc tctggccgcc gaagttgccc gacattccga    4080
tccccggcct gcccgacatc ccgggcctac ccgacttcaa atggccgccc accccggca    4140
gcccgttgtt cccgacctc ccgtcgttcc cagggttccc cgggttcccg gagttccccg    4200
ccatccccgg gttccccgca ctgcccgggt tgcccagcat cccaacttg ttccccggct    4260
tgccgggtct gggcgacctg ctgcccggcg taggcgattt gggcaagtta cccacctgga    4320
ctgagctggc cgctttgcct gacttcttgg gcggcttcgc cggcctgccc agcttgggtt    4380
ttggcaatct gctcagcttt gccagtttgc ccaccgtggg tcaggtgacc gccaccatgg    4440
gtcagctgca acagctcgtg gcggccggcg gtggcccag ccaactggcc agcatgggca    4500
gccaacaagc gcaactgatc tcgtcgcagg cccagcaagg aggccagcag cacgccaccc    4560
tcgtgagcga caagaaggaa gacgaggaag gcgtggccga ggcggagcgt gcacccatcg    4620
acgctggcac cgcggccagc caacgggggc aggaggggac cgtcctttga tcggacaccg    4680
agtcgccagc aggtctgtgc catagcgagt cgaagccata gcgagtagaa agttaaacgt    4740
agaggagggt tcaacccatg accggatttc tcggtgtcgt gccttcgttc ctgaaggtgc    4800
tggcgggcat gcacaacgag atcgtgggtg atatcaaaag ggcgaccgat acggtcgccg    4860
ggattagcgg acgagttcag cttacccatg gttcgttcac gtcgaaattc aatgacacgc    4920
tgcaagagtt tgagaccacc cgtagcagca cgggcacggg tttgcaggga gtcaccagcg    4980
gactggccaa taatctgctc gcagccgccg gcgcctacct caaggccgac gatggcctag    5040
ccggtgttat cgacaagatt ttcggttgat catgacgggt ccgtccgctg caggccgcgc    5100
gggcaccgcc gacaacgtgg tcggcgtcga ggtaaccatc gacggcatgt tggtgatcgc    5160
cgatcggtta cacctggttg atttccctgt cacgcttggg attcggccga atatcccgca    5220
agaggatctg cgagacatcg tctgggaaca ggtgcagcgt gacctcacag cgcaaggggt    5280
gctcgacctc cacggggagc cccaaccgac ggtcgcggag atggtcgaaa ccctgggcag    5340
gccagatcgg accttggagg gtcgctggtg gcggcgcgac attggcggcg tcatggtgcg    5400
cttcgtcgtg tgccgcaggg gcgaccgcca tgtgatcgcg gcgcgcacg gcgacatgct    5460
ggtgctgcag ttggtggcgc cgcaggtcgg cttggcgggc atggtgacag cggtgctggg    5520
gcccgccgaa cccgccaacg tcgaacccct gacgggtgtg gcaaccgagc tagccgaatg    5580
cacaaccgcg tcccaattga cgcaatacgg tatcgcaccg gcctcggccc gcgtctatgc    5640
cgagatcgtg ggtaacccga ccggctgggt ggagatcgtt gccagccaac gccacccgg    5700
cggcaccacg acgcagaccg acgccgccgc tggcgtcctg gactccaagc tcggtaggct    5760
ggtgtcgctt cccgccgtg ttggaggcga cctgtacgga agcttcctgc ccggcactca    5820
gcagaacttg gagcgtgcgc tggacggctt gctagagctg ctccctgcgg gcgcttggct    5880
agatcacacc tcagatcacg cacaagcctc ctcccgaggc tgacccctca catctccgct    5940
acgacttcag aaagggacgc catggtggac ccgccgggca acgacgacga ccacggtgat    6000
ctcgacgccc tcgatttctc cgccgccac accaacgagg cgtcgccgct ggacgcctta    6060
gacgactatg cgccggtgca gaccgatgac gccgaaggcg acctggacgc cctccatgcg    6120
```

```
ctcaccgaac gcgacgagga gccggagctg gagttgttca cggtgaccaa ccctcaaggg    6180
tcggtgtcgg tctcaaccct gatggacggc agaatccagc acgtcgagct gacggacaag    6240
gcgaccagca tgtccgaagc gcagctggcc gacgagatct tcgttattgc cgatctggcc    6300
cgccaaaagg cgcgggcgtc gcagtacacg ttcatggtgg agaacatcgg tgaactgacc    6360
gacgaagacg cagaaggcag cgccctgctg cgggaattcg tggggatgac cctgaatctg    6420
ccgacgccgg aagaggctgc cgcagccgaa gccgaagtgt cgccacccg ctacgatgtc     6480 gactacacct cccggtacaa ggccgatgac tgatcgcttg gccagtctgt tcgaaagcgc    6540
cgtcagcatg ttgccgatgt cggaggcgcg gtcgctagat ctgttcaccg agatcaccaa    6600
ctacgacgaa tccgcttgcg acgcatggat cggccggatc cggtgtgggg acaccgaccg    6660
ggtgacgctg tttcgcgcct ggtattcgcg ccgcaatttc ggacagttgt cgggatcggt    6720
ccagatctcg atgagcacgt taaacgccag gattgccatc gggggggctgt acggcgatat    6780 cacctacccg gtcacctcgc cgctagcgat caccatgggc tttgccgcat gcgaggcagc    6840
gcaaggcaat tacgccgacg ccatggaggc cttagaggcc gccccggtcg cgggttccga    6900
gcacctggtg gcgtggatga aggcggttgt ctacggcgcg gccgaacgct ggaccgacgt    6960
gatcgaccag gtcaagagtg ctgggaaatg gccggacaag ttttggccg cgcggccgg     7020 tgtggcgcac ggggttgccg cggcaaacct ggccttgttc accgaagccg aacgccgact    7080
caccgaggcc aacgactcgc cgccggtga ggcgtgtgcg cgcgccatcg cctggtatct     7140
ggcgatggca cggcgcagcc agggcaacga aagcgccgcg gtggcgctgc tggaatggtt    7200
acagaccact caccccgagc ccaaagtggc tgcggcgctg aaggatccct cctaccggct    7260
gaagacgacc accgccgaac agatcgcatc ccgcgccgat ccctgggatc cgggcagtgt    7320
cgtgaccgac aactccggcc gggagcggct gctcgccgag gcccaagccg aactcgaccg    7380
ccaaattggg ctcacccggg ttaaaaatca gattgaacgc taccgcgcgg cgacgctgat    7440
ggcccgggtc cgcgccgcca agggtatgaa ggtcgcccag cccagcaagc acatgatctt    7500
caccggaccg cccggtaccg gcaagaccac gatcgcgcgg gtggtggcca atatcctggc    7560
cggcttaggc gtcattgccg aacccaaact cgtcgagacg tcgcgcaagg acttcgtcgc    7620
cgagtacgag gggcaatcgg cggtcaagac cgctaagacg atcgatcagg cgctgggcgg    7680
ggtgcttttc atcgacgagg cttatgcgct ggtgcaggaa agagacggcc gcaccgatcc    7740
gttcggtcaa gaggcgctgg acacgctgct ggcgcggatg gagaacgacc gggaccggct    7800
ggtggtgatc atcgccgggt acagctccga catagatcgg ctgctggaaa ccaacgaggg    7860
tctgcggtcg cggttcgcca ctcgcatcga gttcgacacc tattccccg aggaactcct     7920 cgagatcgcc aacgtcattg ccgctgctga tgattcggcg ttgaccgcag aggcggccga    7980
gaactttctt caggccgcca agcagttgga gcagcgcatg ttgcgcggcc ggcgcgccct    8040
ggacgtcgcc ggcaacggtc ggtatgcgcg ccagctggtg gaggccagcg agcaatgccg    8100
ggacatgcgt ctagcccagg tcctcgatat cgacaccctc gacgaagacc ggcttcgcga    8160
gatcaacggc tcagatatgg cggaggctat cgccgcggtg cacgcacacc tcaacatgag    8220
agaatgaact atggggcttc gcctcaccac caaggttcag gttagcggct ggcgttttct    8280
gctgcgccgg ctcgaacacg ccatcgtgcg ccggacacac cggatgtttg acgacccgct    8340
gcagttctac agccgctcga tcgctcttgg catcgtcgtc gcggtcctga ttctggcggg    8400
tgccgcgctg ctggcgtact tcaaaccaca aggcaaactc ggcggcacca gcctgttcac    8460
```

```
cgaccgcgcg accaaccagc tttacgtgct gctgtccgga cagttgcatc cggtctacaa   8520
cctgacttcg gcgcggctgg tgctgggcaa tccggccaac ccggccaccg tgaagtcctc   8580
cgaactgagc aagctgccga tgggccagac cgttggaatc cccggcgccc ctacgccac    8640
gcctgtttcg gcgggcagca cctcgatctg gaccctatgc gacaccgtcg cccgagccga   8700
ctccacttcc ccggtagtgc agaccgcggt catcgcgatg ccgttggaga tcgatgcttc   8760
gatcgatccg ctccagtcac acgaagcggt gctggtgtcc taccagggcg aaacctggat   8820
cgtcacaact aagggacgcc acgccataga tctgaccgac cgcgccctca cctcgtcgat   8880
ggggatcaccg gtgacggcca ggccaacccc gatctcggag gcatgttca acgcgctgcc    8940
tgatatgggg ccctggcagc tgccgccgat accggcggcg ggcgcgccca attcgcttgg   9000
cctacctgat gatctagtga tcggatcggt cttccagatc cacaccgaca agggcccgca   9060
atactatgtg gtgctgcccg acggcatcgc gcaggtcaac gcgacaaccg ctgcggcgct   9120
gcgcgccacc caggcgcacg ggctggtcgc gccaccggca atggtgccca gtctggtcgt   9180
cagaatcgcc gaacgggtat acccctcacc gctacccgat gaaccgctca agatcgtgtc   9240
ccggccgcag gatcccgcgc tgtgctggtc atggcaacgc agcgccggcg accagtcgcc   9300
gcagtcaacg gtgctgtccg gccggcatct gccgatatcg ccctcagcga tgaacatggg   9360
gatcaagcag atccacggga cggcgaccgt ttacctcgac ggcggaaaat tcgtggcact   9420
gcaatccccc gatcctcgat acaccgaatc gatgtactac atcgatccac agggcgtgcg   9480
ttatggggtg cctaacgcgg agacagccaa gtcgctgggc ctgagttcac cccaaaacgc   9540
gccctgggag atcgttcgtc tcctggtcga cggtccggtg ctgtcgaaag atgccgcact   9600
gctcgagcac gacacgctgc ccgctgaccc tagcccccga aaagttcccg ccggagcctc   9660
cggagccccc tgatgacgac caagaagttc actcccacca ttacccgtgg ccccggttg    9720
accccgggcg agatcagcct cacgccgccc gatgacctgg gcatcgacat cccaccgtcg   9780
ggcgtccaaa agatccttcc ctacgtgatg ggtggcgcca tgctcggcat gatcgccatc   9840
atggtggccg gcggcaccag gcagctgtcg ccgtacatgt tgatgatgcc gctgatgatg   9900
atcgtgatga tggtcggcgg tctggccggt agcaccggtg gtggcggcaa gaaggtgccc   9960
gaaatcaacg ccgaccgcaa ggagtacctg cggtatttgg caggactacg cacccgagtg  10020
acgtcctcgg ccacctctca ggtggcgttc ttctcctacc acgcaccgca tcccgaggat  10080
ctgttgtcga tcgtcggcac ccaacggcag tggtcccggc cggccaacgc cgacttctat  10140
gcggccaccc gaatcggtat cggtgaccag ccggcggtgg atcgattatt gaagccggcc  10200
gtcggcgggg agttggccgc cgccagcgca gcacctcagc cgttcctgga gccggtcagt  10260
catatgtggg tggtcaagtt tctacgaacc catggattga tccatgactg cccgaaactg  10320
ctgcaactcc gtaccttccc gactatcgcg atcggcgggg acttggcggg ggcagccggc  10380
ctgatgacgg cgatgatctg tcacctagcc gtgttccacc caccggacct gctgcagatc  10440
cgggtgctca ccgaggaacc cgacgacccc gactggtcct ggctcaaatg gcttccgcac  10500
gtacagcacc agaccgaaac cgatgcgcc gggtccaccc ggctgatctt cacgcgccag   10560
gaaggtctgt cggacctggc cgcgcgcggg ccacacgcac ccgattcgct tcccggcggc  10620
ccctacgtag tcgtcgtcga cctgaccggc ggcaaggctg gattcccgcc cgacggtagg  10680
gccggtgtca cggtgatcac gttgggcaac catcgcggct cggcctaccg catcagggtg  10740
cacgaggatg ggacggctga tgaccggctc cctaaccaat cgtttcgcca ggtgacatcg  10800
gtcaccgatc ggatgtcgcc gcagcaagcc agccgtatcg cgcgaaagtt ggccggatgg  10860
```

```
tccatcacgg gcaccatcct cgacaagacg tcgcgggtcc agaagaaggt ggccaccgac   10920
tggcaccagc tggtcggtgc gcaaagtgtc gaggagataa caccttcccg ctggaggatg   10980
tacaccgaca ccgaccgtga ccggctaaag atcccgtttg gtcatgaact aaagaccggc   11040
aacgtcatgt acctggacat caaagagggc gcggaattcg gcgccggacc gcacggcatg   11100
ctcatcggga ccacggggtc tgggaagtcc gaattcctgc gcaccctgat cctgtcgctg   11160
gtggcaatga ctcatccaga tcaggtgaat ctcctgctca ccgacttcaa aggtggttca   11220
accttcctgg gaatggaaaa gcttccgcac actgccgctg tcgtcaccaa catgccgag   11280 gaagccgagc tcgtcagccg gatgggcgag gtgttgaccg gagaactcga tcggcgccag   11340
tcgatcctcc gacaggccgg gatgaaagtc ggcgcggccg agccctgtc cggcgtggcc   11400 gaatacgaga agtaccgcga acgcggtgcc gacctacccc cgctgccaac gcttttcgtc   11460
gtcgtcgacg agttcgccga gctgttgcag agtcacccgg acttcatcgg gctgttcgac   11520
cggatctgcc gcgtcgggcg gtcgctgagg gtccatctgc tgctggctac ccagtcgctg   11580
cagaccggcg gtgttcgcat cgacaaactg gagccaaacc tgacatatcg aatcgcattg   11640
cgcaccacca gctctcatga atccaaggcg gtaatcggca caccggaggc gcagtacatc   11700
accaacaagg agagcggtgt cgggtttctc cgggtcggca tggaagaccc ggtcaagttc   11760
agcaccttct acatcagtgg gccatacatg ccgccggcgg caggcgtcga aaccaatggt   11820
gaagccggag ggcccggtca acagaccact agacaagccg cgcgcattca caggttcacc   11880
gcggcaccgg ttctcgagga ggcgccgaca ccgtgacccg cgccggcgac gatgcaaagc   11940
gcagcgatga ggaggagcgg cgccaacggc ccgcgccggc gacgatgcaa agcgcagcga   12000
tgaggaggag cggcgcgcat gactgctgaa ccggaagtac ggacgctgcg cgaggttgtg   12060
ctggaccagc tcggcactgc tgaatcgcgt gcgtacaaga tgtggctgcc gccgttgacc   12120
aatccggtcc cgctcaacga gctcatcgcc cgtgatcggc gacaacccct gcgatttgcc   12180
ctggggatca tggatgaacc gcgccgccat ctacaggatg tgtggggcgt agacgtttcc   12240
ggggccggcg gcaacatcgg tattgggggc gcacctcaaa ccgggaagtc gacgctactg   12300
cagacgatgg tgatgtcggc cgccgccaca cactcaccgc gcaacgttca gttctattgc   12360
atcgacctag gtggcggcgg gctgatctat ctcgaaaacc ttccacacgt cggtggggta   12420
gccaatcggt ccgagcccga caaggtcaac cgggtggtcg cagagatgca agccgtcatg   12480
cggcaacggg aaaccacctt caaggaacac cgagtgggct cgatcgggat gtaccggcag   12540
ctgcgtgacg atccaagtca acccgttgcg tccgatccat acggcgacgt ctttctgatc   12600
atcgacggat ggcccggttt tgtcggcgag ttccccgacc ttgagggca ggttcaagat   12660 ctggccgccc aggggctggc gttcggcgtc cacgtcatca tctccacgcc acgctggaca   12720
gagctgaagt cgcgtgttcg cgactacctc ggcaccaaga tcgagttccg gcttggtgac   12780
gtcaatgaaa cccagatcga ccggattacc cgcgagatcc cggcgaatcg tccgggtcgg   12840
gcagtgtcga tggaaaagca ccatctgatg atcggcgtgc ccaggttcga cggcgtgcac   12900
agcgccgata acctggtgga ggcgatcacc gcggggggtga cgcagatcgc ttcccagcac   12960
accgaacagg cacctccggt gcgggtcctg ccggagcgta tccacctgca cgaactcgac   13020
ccgaacccgc cgggaccaga gtccgactac cgcactcgct gggagattcc gatcggcttg   13080
cgcgagacgg acctgacgcc ggctcactgc cacatgcaca cgaacccgca cctactgatc   13140
ttcggtgcgg ccaaatcggg caagacgacc attgcccacg cgatcgcgcg cgccatttgt   13200
```

```
gcccgaaaca gtccccagca ggtgcggttc atgctcgcgg actaccgctc gggcctgctg    13260
gacgcggtgc cggacaccca tctgctgggc gccggcgcga tcaaccgcaa cagcgcgtcg    13320
ctagacgagg ccgttcaagc actggcggtc aacctgaaga agcggttgcc gccgaccgac    13380
ctgacgacgg cgcagctacg ctcgcgttcg tggtggagcg gatttgacgt cgtgcttctg    13440
gtcgacgatt ggcacatgat cgtgggtgcc gccgggggga tgccgccgat ggcaccgctg    13500
gccccgttat tgccggcggc ggcagatatc gggttgcaca tcattgtcac ctgtcagatg    13560
agccaggctt acaaggcaac catggacaag ttcgtcggcg ccgcattcgg gtcgggcgct    13620
ccgacaatgt tcctttcggg cgagaagcag gaattcccat ccagtgagtt caaggtcaag    13680
cggcgccccc ctggccaggc atttctcgtc tcgccagacg gcaaagaggt catccaggcc    13740
ccctacatcg agcctccaga agaagtgttc gcagcacccc caagcgccgg ttaagattat    13800
ttcattgccg gtgtagcagg acccgagctc agcccggtaa tcgagttcgg gcaatgctga    13860
ccatcgggtt tgtttccggc tataaccgaa cggtttgtgt acgggataca aatacaggga    13920
gggaagaagt aggcaaatgg aaaaaatgtc acatgatccg atcgctgccg acattggcac    13980
gcaagtgagc gacaacgctc tgcacggcgt gacggccggc tcgacggcgc tgacgtcggt    14040
gaccgggctg gttccgcgg gggccgatga ggtctccgcc caagcggcga cggcgttcac    14100
atcggagggc atccaattgc tggcttccaa tgcatcggcc caagaccagc tccaccgtgc    14160
gggcgaagcg gtccaggacg tcgcccgcac ctattcgcaa atcgacgacg cgccgccgg    14220
cgtcttcgcc gaataggccc ccaacacatc ggagggagtg atcaccatgc tgtggcacgc    14280
aatgccaccg gagctaaata ccgcacggct gatggccggc gcgggtccgg ctccaatgct    14340
tgcggcggcc gcgggatggc agacgctttc ggcggctctg gacgctcagg ccgtcgagtt    14400
gaccgcgcgc ctgaactctc tgggagaagc ctggactgga ggtggcagcg acaaggcgct    14460
tgcggctgca acgccgatgg tggtctggct acaaaccgcg tcaacacagg ccaagacccg    14520
tgcgatgcag gcgacggcgc aagccgcggc atacacccag gccatggcca cgacgccgtc    14580
gctgccggag atcgccgcca accacatcac ccaggccgtc cttacggcca ccaacttctt    14640
cggtatcaac acgatcccga tcgcgttgac cgagatggat tatttcatcc gtatgtggaa    14700
ccaggcagcc ctggcaatgg aggtctacca ggccgagacc gcggttaaca cgcttttcga    14760
gaagctcgag ccgatggcgt cgatccttga tcccggcgcg agccagagca cgacgaaccc    14820
gatcttcgga atgccctccc ctggcagctc aacaccggtt ggccagttgc cgccggcggc    14880
tacccagacc ctcggccaac tgggtgagat gagcggcccg atgcagcagc tgacccagcc    14940
gctgcagcag gtgacgtcgt tgttcagcca ggtgggcggc accggcggcg gcaacccagc    15000
cgacgaggaa gccgcgcaga tgggcctgct cggcaccagt ccgctgtcga accatccgct    15060
ggctggtgga tcaggcccca gcgcgggcgc gggcctgctg cgcgcggagt cgctacctgg    15120
cgcaggtggg tcgttgaccc gcacgccgct gatgtctcag ctgatcgaaa agccggttgc    15180
cccctcggtg atgccggcgg ctgctgccgg atcgtcggcg acgggtggcg ccgctccggt    15240
gggtgcggga gcgatgggcc agggtgcgca atccggcggc tccaccaggc cgggtctggt    15300
cgcgccggca ccgctcgcgc aggagcgtga agaagacgac gaggacgact gggacgaaga    15360
ggacgactgg tgagctcccg taatgacaac agacttcccg gccacccggg ccggaagact    15420
tgccaacatt ttggcgagga aggtaaagag agaaagtagt ccagcatggc agagatgaag    15480
accgatgccg ctaccctcgc gcaggaggca ggtaatttcg agcggatctc cggcgacctg    15540
aaaacccaga tcgaccaggt ggagtcgacg gcaggttcgt tgcagggcca gtggcgcggc    15600
```

```
gcggcgggga cggccgccca ggccgcggtg gtgcgcttcc aagaagcagc caataagcag    15660
aagcaggaac tcgacgagat ctcgacgaat attcgtcagg ccggcgtcca atactcgagg    15720
gccgacgagg agcagcagca ggcgctgtcc tcgcaaatgg gcttctgacc cgctaatacg    15780
aaaagaaacg gagcaaaaac atgacagagc agcagtggaa tttcgcgggt atcgaggccg    15840
cggcaagcgc aatccaggga aatgtcacgt ccattcattc cctccttgac gaggggaagc    15900
agtccctgac caagctcgca gcggcctggg gcggtagcgg ttcggaggcg taccagggtg    15960
tccagcaaaa atgggacgcc acggctaccg agctgaacaa cgcgctgcag aacctggcgc    16020
ggacgatcag cgaagccggt caggcaatgg cttcgaccga aggcaacgtc actgggatgt    16080
tcgcataggg caacgccgag ttcgcgtaga atagcgaaac acgggatcgg gcagttcga    16140 ccttccgtcg gtctcgccct ttctcgtgtt tatacgtttg agcgcactct gagaggttgt    16200
catggcggcc gactacgaca agctcttccg gccgcacgaa ggtatggaag ctccggacga    16260 tatgcagcg cagccgttct tcgaccccag tgcttcgttt ccgccggcgc ccgcatcggc    16320
aaacctaccg aagcccaacg gccagactcc gcccccgacg tccgacgacc tgtcggagcg    16380
gttcgtgtcg gccccgccgc cgccacccc accccacct ccgcctccgc caactccgat    16440
gccgatcgcc gcaggagagc cgccctcgcc ggaaccggcc gcatctaaac cacccacacc    16500
ccccatgccc atcgccggac ccgaaccggc cccacccaaa ccaccacac ccccatgcc    16560 catcgccgga cccgaaccgg ccccacccaa accaccacca cctccgatgc ccatcgccgg    16620
acctgcaccc accccaaccg aatcccagtt ggcgcccccc agaccaccga caccacaaac    16680
gccaaccgga gcgccgcagc aaccggaatc accggcgccc cacgtaccct cgcacgggcc    16740
acatcaaccc cggcgcaccg caccagcacc gccctgggca aagatgccaa tcggcgaacc    16800
cccgcccgct ccgtccagac cgtctgcgtc cccggccgaa ccaccgaccc ggcctgcccc    16860
ccaacactcc cgacgtgcgc gccggggtca ccgctatcgc acagacaccg aacgaaacgt    16920
cgggaaggta gcaactggtc catccatcca ggcgcggctg cgggcagagg aagcatccgg    16980
cgcgcagctc gcccccggaa cggagccctc gccagcgccg ttgggccaac cgagatcgta    17040
tctggctccg cccacccgcc ccgcgccgac agaacctccc cccagcccct cgccgcagcg    17100
caactccggt cggcgtgccg agcgacgcgt ccaccccgat ttagccgccc aacatgccgc    17160
ggcgcaacct gattcaatta cggccgcaac cactggcggt cgtcgccgca agcgtgcagc    17220
gccggatctc gacgcgacac agaaatcctt aaggccggcg gccaagggc cgaaggtgaa    17280 gaaggtgaag ccccagaaac cgaaggccac gaagccgccc aaagtggtgt cgcagcgcgg    17340
ctggcgacat tgggtgcatg cgttgacgcg aatcaacctg ggcctgtcac ccgacgagaa    17400
gtacgagctg gacctgcacg ctcgagtccg ccgcaatccc cgcgggtcgt atcagatcgc    17460
cgtcgtcggt ctcaaaggtg gggctggcaa aaccacgctg acagcagcgt ggggtcgac    17520 gttggctcag gtgcgggccg accggatcct ggctctagac gcggatccag cgccggaaa    17580 cctcgccgat cgggtagggc gacaatcggg cgcgaccatc gctgatgtgc ttgcagaaaa    17640
agagctgtcg cactacaacg acatccgcgc acacactagc gtcaatgcgg tcaatctgga    17700
agtgctgccg gcaccggaat acagctcggc gcagcgcgcg ctcagcgacg ccgactggca    17760
tttcatcgcc gatcctgcgt cgaggtttta caacctcgtc ttggctgatt gtggggccgg    17820
cttcttcgac ccgctgaccc gcggcgtgct gtccacggtg tccggtgtcg tggtcgtggc    17880
aagtgtctca atcgacggcg cacaacaggc gtcggtcgcg ttggactggt tgcgcaacaa    17940
```

```
cggttaccaa gatttggcga gccgcgcatg cgtggtcatc aatcacatca tgccgggaga   18000
acccaatgtc gcagttaaag acctggtgcg gcatttcgaa cagcaagttc aacccggccg   18060
ggtcgtggtc atgccgtggg acaggcacat tgcggccgga accgagattt cactcgactt   18120
gctcgaccct atctacaagc gcaaggtcct cgaattggcc gcagcgctat ccgacgattt   18180
cgagagggct ggacgtcgtt gagcgcacct gctgttgctg ctggtcctac cgccgcgggg   18240
gcaaccgctg cgcggcctgc caccacccgg gtgacgatcc tgaccggcag acggatgacc   18300
gatttggtac tgccagcggc ggtgccgatg gaaacttata ttgacgacac cgtcgcggtg   18360
cttttccgagg tgttggaaga cacgccggct gatgtactcg gcggcttcga ctttaccgcg   18420
caaggcgtgt gggcgttcgc tcgtcccgga tcgccgccgc tgaagctcga ccagtcactc   18480
gatgacgccg gggtggtcga cgggtcactg ctgactctgg tgtcagtcag tcgcaccgag   18540
cgctaccgac cgttggtcga ggatgtcatc gacgcgatcg ccgtgcttga cgagtcacct   18600
gagttcgacc gcacggcatt gaatcgcttt gtggggggcgg cgatcccgct tttgaccgcg   18660
cccgtcatcg ggatggcgat gcgggcgtgg tgggaaactg ggcgtagctt gtggtggccg   18720
ttggcgattg gcatcctggg gatcgctgtg ctggtaggca gcttcgtcgc gaacaggttc   18780
taccagagcg gccacctggc cgagtgccta ctggtcacga cgtatctgct gatcgcaacc   18840
gccgcagcgc tggccgtgcc gttgccgcgc ggggtcaact cgttggggc gccacaagtt   18900
gccggcgccg ctacggccgt gctgttttttg accttgatga cgcggggcgg ccctcggaag   18960
cgtcatgagt tggcgtcgtt tgccgtgatc accgctatcg cggtcatcgc ggccgccgct   19020
gccttcggct atggatacca ggactgggtc cccgcggggg ggatcgcatt cgggctgttc   19080
attgtgacga atgcggccaa gctgaccgtc gcggtcgcgc ggatcgcgct gccgccgatt   19140
ccggtacccg gcgaaaccgt ggacaacgag gagttgctcg atcccgtcgc gaccccggag   19200
gctaccagcg aagaaacccc gacctggcag gccatcatcg cgtcggtgcc cgcgtccgcg   19260
gtccggctca ccgagcgcag caaactggcc aagcaacttc tgatcggata cgtcacgtcg   19320
ggcaccctga ttctggctgc cggtgccatc gcggtcgtgg tgcgcgggca cttctttgta   19380
cacagcctgg tggtcgcggg tttgatcacg accgtctgcg gatttcgctc gcggctttac   19440
gccgagcgct ggtgtgcgtg ggcgttgctg gcggcgacgg tcgcgattcc gacgggtctg   19500
acggccaaac tcatcatctg gtacccgcac tatgcctggc tgttgttgag cgtctacctc   19560
acggtagccc tggttgcgct cgtggtggtc gggtcgatgg ctcacgtccg gcgcgtttca   19620
ccggtcgtaa aacgaactct ggaattgatc gacggcgcca tgatcgctgc catcattccc   19680
atgctgctgt ggatcaccgg ggtgtacgac acggtccgca atatccggtt ctgagccgga   19740
tcggctgatt ggcggttcct gacagaacat cgaggacacg gcgcaggttt gcataccttc   19800
ggcgcccgac aaaattgctg cgattgagcgt gtggcgcgtc cggtaaaatt tgctcgatgg   19860
ggaacacgta taggagatcc ggcaatggct gaaccgttgg ccgtcgatcc caccggcttg   19920
agcgcagcgg ccgcgaaatt ggccggcctc gttttccgc agcctccggc gccgatcgcg   19980
gtcagcggaa cggattcggt ggtagcagca atcaacgaga ccatgccaag catcgaatcg   20040
ctggtcagtg acgggctgcc cggcgtgaaa gccgccctga ctcgaacagc atccaacatg   20100
aacgcggcg cggacgtcta tgcgaagacc gatcagtcac tgggaaccag tttgagccag   20160
tatgcattcg gctcgtcggg cgaaggcctg gctggcgtcg cctcggtcgg tggtcagcca   20220
agtcaggcta cccagctgct gagcacaccc gtgtcacagg tcacgaccca gctcggcgag   20280
acggccgctg agctggcacc ccgtgttgtt gcgacggtgc cgcaactcgt tcagctggct   20340
```

```
ccgcacgccg ttcagatgtc gcaaaacgca tcccccatcg ctcagacgat cagtcaaacc   20400
gcccaacagg ccgcccagag cgcgcagggc ggcagcggcc caatgcccgc acagcttgcc   20460
agcgctgaaa aaccggccac cgagcaagcg gagccggtcc acgaagtgac aaacgacgat   20520
cagggcgacc agggcgacgt gcagccggcc gaggtcgttg ccgcggcacg tgacgaaggc   20580
gccggcgcat caccgggcca gcagcccggc ggggcgttc ccgcgcaagc catggatacc   20640
ggagccggtg cccgcccagc ggcgagtccg ctggcggccc ccgtcgatcc gtcgactccg   20700
gcaccctcaa caaccacaac gttgtagacc gggcctgcca gcggctccgt ctcgcacgca   20760
gcgcctgttg ctgtcctggc ctcgtcagca tgcggcggcc agggcccggt cgagcaaccc   20820
ggtgacgtat tgccagtaca gccagtccgc gacggccaca cgctggacgg ccgcgtcagt   20880
cgcagtgtgc gcttggtgca gggcaatctc ctgtgagtgg gcagcgtagg cccggaacgc   20940
ccgcagatga gcggcctcgc ggccggtagc ggtgctggtc atgggcttca tcagctcgaa   21000
ccacagcatg tgccgctcat cgcccggtgg attgacatcc accggcgccg gcggcaacaa   21060
gtcgagcaaa cgctgatcgg tagtgtcggc cagctgagcc gccgccgagg ggtcgacgac   21120
ctccagccgc gaccggcccg tcattttgcc gctctccgga atgtcatctg gctccagcac   21180
aatcttggcc acaccgggat ccgaactggc caactgctcc gcggtaccga tcaccgcccg   21240
cagcgtcatg tcgtggaaag ccgcccaggc ttgcacggcc aaaaccgggt aggtggcaca   21300
gcgtgcaatt tcgtcaaccg ggattgcgtg atccgcgctg gccaagtaca ccttattcgg   21360
caattccatc ccgtcgggta tgtaggccag cccatagctg ttggcacga cgatggaacc   21420 gtcggtggtc accgcggtga tccagaagaa cccgtagtcg cccgcgttgt tgtcggacgc   21480
gttgagcgcc gccgcgatgc gtcgcgccaa ccgcagcgca tcaccgcggc cacgctggcg   21540
ggcgctggca gctgcagtgg cggcgtcgcg tgccgcccga ccgccgacca ccgggatcat   21600
cgacaccggc gtaccgtcat ctgcagactc gctgcgatcg ggtttgtcga tgtgatcggt   21660
cgacggcggg cggcaggag gtgccgtccg cgccgaggcc gcccgcgtgc tcggtgccgc   21720
cgccttgtcc gaggtagcca ccggcgcccg cccagtggca gcatgcgacc ccgcgcccga   21780
ggccgcggcc gtacccacgc tcgaacgcgc gcccgctccc acggcggtac cgctcggcgc   21840
ggcggccgcc gcccgtgcgc ccgggacacc ggacgccgca gccggcgtca cgacgcggcg   21900
ggattcgtcc gcatgggcag gccccgactg cgtcccccg cccgcatgct ggcccggcac   21960
accaggttgc tccgccaacg ccgcgggttt gacgtgcggc gccggctcgc ccctggggt   22020 gcccggtgtt gctggaccag acggaccggg agtggccggt gtaaccggct ggggcccagg   22080
cgatggcgcc ggtgccggag ccggctgcgg gtgtggagcg ggagctgggg taacgggcgt   22140
ggccggggtt gccggtgtgg ccggggcgac cgggggggtg accggcgtga tcggggttgg   22200
ctcgcctggt gtgcccggtt tgaccggggt caccggggtg accggcttgc ccggggtcac   22260
cggcgtgacg ggagtgccgg gcgttggtgt gatcggagtt accggcgctc ccgggatggg   22320
tgtgattggg gttcccgggg tgatcggggt tcccggggtg atcggggttc ccggtgtgcc   22380
cggtgtgccc ggggatggca cgaccagggt aggcacgtct gggggtggcg gcgacttctg   22440
ctgaagcaaa tcctcgagtg cgttcttcgg aggtttccaa ttcttggatt ccagcacccg   22500
ctcagcggtc tcggcgacca gactgacatt ggccccatgc gtcgccgtga ccaatgaatt   22560
gatggcggta tggcgctcat cagcatccag gctagggtca ttctccagga tatcgatctc   22620
ccgttgagcg ccatccacat tattgccgat atcggattta gcttgctcaa tcaacccggc   22680
```

```
aatatgcctg tgccaggtaa tcaccgtggc gagataatcc tgcagcgtca tcaattgatt   22740
gatgtttgca cccagggcgc cgttggcagc attggcggcg ccgccggacc ataggccgcc   22800
ttcgaagacg tggcctttct gctggcggca ggtgtccaat acatcggtga ccctttgcaa   22860
aacctggcta tattcctggg cccggtcata gaaagtgtct tcatcggctt ccacccagcc   22920
gcccggatcc agcatctgtc tggcatagct gcccgtcggc ctggtaatac tcatccccta   22980
ctgccctccc caaaccgcca gatcgcctcg cggatcaccg tccggttggc ctccggcatt   23040
tcacgccggc tcggccgctg gatccacccc gcgccggtat tcgcagtaac ccgttgaatc   23100
cgcgcgcatg atgcaccgct tgggcgatca gccgggtggt cacctcgctt gcgctggccg   23160
cgctgtcgca cggggcgctc ggtggtaacg gacgtcataa ttaaccagcg taaccgaacc   23220
taagaccagc tagctgcggc aatattggcg accaggacta tggcgccctc cgaacccggc   23280
cgatccatgt caaaacattg acaatgcgta ctcacgccgt gtcgggcgcg ctgaatgacc   23340
gcattgcggc gctcattcgg tgcgtagtcg ctaccaccgc aacaatgggc ttaggccatt   23400
ccttcgttca tcgcgcggga catggccgat aacgcagcgg tcagctgctc gcccgccgcg   23460
tcgttatacg cggacgccgc ggcctgcgca ttgtgcagcg cctcgttgac ccgctgagcg   23520
accgcctcgg cacccagctt cttcagcaaa ccatcttcga tgcgcaggcc ggtgagccac   23580
tggtgcccat tgatcgtcac ttcgacggtc tcggcttcgt cggtggcgcg gaaggatccg   23640
ttgttcatct gattgagcgt cccgtctagg gccgactgaa accgcgccgc cagcgtcaac   23700
gcccgggcga catgcgggtc caattcgtcc atgctcactt cgactcctta ctgtcctggc   23760
gccgacggtt accaatgacg gcctcggtcc atgcccgatc ctcggtgtag agcgcctcgt   23820
cttcctgctg agaacccttg gacttggcgc ccccttgtcc ctgatgcgcg cacccatcg    23880 gcattcccat gccaccgccg cccagcgcgg cgccgccgcc ggcccttccc tggcctaagc   23940
cggcaatgtc accagcgcca gcgggccgca ccgattcggc gccccgatc gcggatccca    24000 acggcgccga cggcaccccg ccgcctccac cgccaccgag cgatgccgct ttgaccgcca   24060
cgtcgcccga cagcgctgcg gcttcccgcc cagccgacgt cagctgcgcc gccgtgtcag   24120
ccgggaggcc accacccggc gatccggtag gcggaaccat cggtgcggct ggcatcccgg   24180
taccgggagt cacaccggag ccgtcagacg gcggcatcag gaagccaggg atcaatccct   24240
gctcttgcgg aggcggggc gggtcgatct tgatggcggg gggaggcttc ggcgggttta    24300
ccggttccag ggctgccttg ttgttgtatt cggtcagcac cttctccgac ctctgctgat   24360
actccgcgta caccgggaga atttggtcgc gggccgaagg gttttccgcg taaagccgtt   24420
cgagcccgac tatgtcttca taagtcggat gttcccgcct agcccacacg tgcagctgcg   24480
cgacatattg agcctgcttg gccatcgcag cgctcaattt ggccatgtgg agtatccatt   24540
gccgttgttg atcgagcgaa gcctcgcaag cggtagccgc atcgccttcc cagttgtcaa   24600
acccccggaa ccgcttgacg tcgccttgca gcgtcaggtt gaaagtgttc cacccatccg   24660
caaagtgcgc gagcgatgcg ccttggtcgc ccgtttcgag cttccttgcc gcttctttga   24720
gatccatgaa gttgggttca ccggccgtgg ccaccctcgg cgtatcggtt agttcggccg   24780
aactgtcccc tccgacggcc ccggccgatt ctgcctgcac agttccttcg ccgtcgttgt   24840
ccagcgcggt cgcagcctcc tcatcaacct cgccatacgc cttggccgcg ttgcgcagcg   24900
aggtcgccag acgctgccgc tctttggcac cggccgccag gtattccgc atgttgtcgg    24960 cggacaatac cagctgttgg gcggcgtttt tagccgccgt gagttcgcac ggtgtgatgg   25020
ggacatcagt cggtgggtcc gccatcgggg cctccacctc gttggccctg ttcaaaatct   25080
```

```
cttgctgatc caccgtcacg gtctgcgact gcgtcatatc ggatcatcct ccttagtgct   25140
atagccatta tcgtcgctaa actgaaaggt tcctgcacta atttgatgcc gcccgttcat   25200
gccggcatcg cgaacggatc gccctacttc ggcagcgcca tctggtagcg gctttcctcg   25260 ggtgggaaa cccggcgaat cggcagctgc cgatgccgcg gggtaccgat cacattgtgc    25320
cgcagaatca cccggtcaat accgggatgc gggccgagat aggtcgtcgc attcggccac   25380 gccacctttta cctcctgccc gatgtgtgcg ccgatcaacc gggcaaattc ctcgaactgt   25440
ggcccgactg tgaccatcgc acctgccgcc ccgcacgca ccacgaactg ggtgaatgtc    25500
tgagcgtcac ccaggttgag ggcgatgtcg acatcgtcga agggcatgta gaccgggcat   25560
cggttcaccg tctcgccgac cagtacccca gctgacccga tcggcagctg gcagtggcgg   25620
ttggccacca gatgctggcc ttgcagcgcg ggccgctgcc cgccaaatag gcgggcgaag   25680
cccctgggtg tcttgggctt gtccgccgtg gtcagcaaca ccgtggactg cggggccatc   25740
cccggcgcga cccggactct ggtgatggtg tggtccgcgc gcgccgacca ccatacatcc   25800
ggacctccgg gcgccgcgta ggcggcagtg taggcatcgc gccccttgat catcgaccat   25860
ttctcccgca caaagccgat gtcggtggcg tggtcgtagt catcgaagct gcggccacac   25920
accgcgtcga caccatggct agccagtcga tcggcaatgc gcgtcgcgga cgccaccaaa   25980
taccgggcca gtcctgcgac gccttcatcg cggcgctgcg ccgatttgcg ggtgcgttcc   26040
gggtcggcgc gcagcacgat ccaggtccgg cggttcgccg gcgccgggtc tgtcccgatc   26100
acctgctgat acagactcac cacgtccggc gctgcggtat tgccgacgcg gtagccggct   26160
gagacgatat cggcctccaa gtcgggacag tgcaccgaca ggagctcctc caccagtccg   26220
gtgtccagca tgtcgtcggt gtgggcttgc ccgtcgacga tgaccgtcgg cgtgaatggt   26280
cggggaatga gctcgattac ggcgaccaga aactcgcctt gcagcgcac cgcaacgtga    26340 tctcctggct tcacggtggc cccgaccaca ggttctgacg aggaatccgg gggccgtcgg   26400
cgccgccgca accacgcgta caccgccgcc acccagccgg tgatccggcg gccgtagaaa   26460
gtgaccgtgg ccacgatgac gcccaacgag gccagcgcaa tccccgccca ccagtagcgc   26520
gtctccaaga atgcgatgat gcatggcggg gccaacgcgg aggcaagcaa ggcgtgcccg   26580
gtgctgaacc gcagccctaa aggatttctc atcggcggct cagcgcccgt ctagccagcg   26640
cgcccaggcc cagggccaac gtaaggccga cggccaccaa cgccacagcc gtaatcgggc   26700
gacgatcggg acccggctcc accaccgggg gtggaagtcg tctgacgttg tatgcgcccg   26760
aagcagggcc gggcggaatg tcccacgtca gcgcggccac cgcatcgatg acgccggcgc   26820
cgaccaggtc gtcgaccccg cccccggggt gtctcgcggt ggcggtgatc cggtggatga   26880
tctgcgccgg cgtcaggtcg gggaaccgct gccgaagcag ggccgccaga cccgacacat   26940
atgccgcggc aaacgaggtg ccggcgatgg gtaccggccc ctcccggcct tgcagcgcat   27000
tcaccggttc accggtgtcg ccgagcgcga cgatgttttc tgcgggcgcg ccacgtcca    27060 cccacggtcc gtgcatcgag aacgagctgg gcatccggt ctggccgata ccgccgacgc    27120
ttaacaccag cggtgcgtac cacgccgggg tgacaacggt ctgcacattg ttccagccgc   27180
gtgggtcgcc gggtgtggac gggtccggcg ccggattctg tacgcaatcg ccaccggtgt   27240
tgccggccgc gaccaccacc accacgcctt tgacgttgac cgcatagtcg atggatgcac   27300
ccagtgaggt ttcatcgatc ggcctgctca ccttgtagca ggcggcttca ctgatgttga   27360
tcacacccac gccgaggttg gcggcgtgca ccacggcgcg ggcaagactg cggatggaac   27420
```

```
cggcggccgg ggtggcgttg gggtcattcg ggttggcttg tgagccgacc ggttcgaagg   27480
cctcagacgt ctgacgtagc gagagcagtc gagcgtcggg cgcgacgccg acgaacccgt   27540
cggtgggcgc gggccggccc gcgatgatgg atgctgtgag agtcccatgg gcatcacagt   27600
cagacaggcc gttaccggcc tggtcgacga aatcgccgcc aggttccgcc gggacccgtg   27660
gcgaagcgtc gacaccggtg tcgatcaccg ccaccgtcac cccggccccg gtcgcgaact   27720
tgtgggcatc ggccacgccc agatacgtgt tgctccacgg cggatcgtgg aacccggacc   27780
ccggcagcgt ggtgggcgac gcgcacaaaa cgcgctgttc ggtaggctga tccgggcccg   27840
tcacgtcggg cggcaacgcg cccggatcga tcggcggtgg cgtgatggcc gatgcgggcg   27900
acgcggtgag caacgccagc gccaccgtga tcagaaagat acggtgcact cccagaacac   27960
tccattcgtt gagattcatt gcgattcatt gagctgcgtt gctaccttgg gccacttgac   28020
ggacctgtgt gcattttaga cgtaacggct gggcaaacaa cgctgtcacg cctgggctgg   28080
tccgccgcgc cgaccagggc gcgtaggcgc tgtacctgga ccacgccggg actcaacggt   28140
tttgctaccg cactagccga tatgcggctg ctaccaaacg atcgcggcca tgtctcggtt   28200
gtctgagcac acgctgcgta tcgcggcatc gatgtcggtg gcggtgatga tctgcagatc   28260
ctgaaccgat accggttggc ccgcacgttt ttgcgcaacc acccgggtgt cccggaaccc   28320
ttcggcgcgt tcgatcacgt tgcgggcgaa ccgaccgttt tgcatagcgt cgataccgtg   28380
ctgcccacta ggggtggtgt agttacggat ggtggtgacc gcgtcgagga atacctcccg   28440
tgcggcgtca tcgagctggc tggcgcgcgg tgtagcgtag cggtgtccaa tctcgacgat   28500
ctccaccggc gaataagact cgaaccgcag cttcggttg aaccgccag ccaaacccgg   28560 gttcacggtg aggaattcat ccacctgatc ctcatagccg gccccgatga acagaagtc   28620 gaatcggtgt gtttccaatt gaaccaggag ttgattgacc gcctccatgc cgatcatgtc   28680
cggtgttccg tcttgatgac gttcgatcag cgagtagaac tcgtccatga aaatgattcg   28740
cccgagtgac ttttcgatca gctcgttcgt cttgggtcct gactccccga tgtagtgccc   28800
acagaagtcc gatcggcgaa cttctcgaat ttcggggtga cgcacgatcc ccatgccggc   28860
gtagatcttg ccgagcgctt cagcggtggt tgtcttacct gtgcctggtg gccccaccag   28920
caacatgtgg ttggtctgcc cctccaccgg taggccgtgc tctaggcgca tcatgcgcac   28980
ctcgagttgg tcttccagcg ccgataccgc ttgcttgacc gccgccaggc ccacctgttt   29040
ggccagcagt tcccggccct cggctagcag ctcgccgcgc cgctgcgctg cattgtcgtc   29100
atcgagctgg tcgcggcttt tcgccgtcga agcatcccaa cggtcggagc ggctggcgat   29160
ggttcgttca tcggtaacaa tcaagcgcag gttcgggtcc gccagggctt ctttggcggc   29220
gtcggtgagc accccgttga tggtggcctt cgacagccag atctgggcct tgtcctcctc   29280
atgcagttgc cggtacacca tcccccgcac atacgccaag tcggcgacca gcagcggaat   29340
atcggccggt ccgatcgccg cggtgagcac gtcggcgccg aaccgctccg atgacctgct   29400
gtgtccgatc acgtccaccc ggtccagcca gtccagggcc actcgcccct gcccgagatg   29460
ggcggcggcg tgggctgcca gcgcacaaat cgacgcggtc accgccggca tgacgatcgc   29520
ctgtggcggc agatcctcgg cggccgtcga caacacgtcg ggccatcgct gcgtgacgta   29580
catcaggaac gcccgagcca gctgatgcca ctggtagttg cgccacgaat ccaatagctc   29640
gcggtttgct aacagggcat cggccttcgc atactccccc gcgatcgtca acgccgacga   29700
cagcgccagc cccacctgag atgcgtcggt caccgtgatc ccgatggatg gtcccagctg   29760
gacctcagcg gccaacgtcc ggccgatccg cgtggtctcg cggtgcagcc actcgctatg   29820
```

```
ggcgttgagc tgcttaagcg aggccagatc gcggtcaccg caggcgatac gacccagcca    29880
cgcgtcggcc atcgacggat cggcctcggt ggcagccaca aactcaggca acgccgccac    29940
gcatccctgg ccattcttga tcgtcatcgc ccgatcgaaa tgccggcgcg cagtgagtaa    30000
atcacccatc gtgtccacca ttctcgacat cgccgccgct gtcaccgcgg ttgcaacgtg    30060
tgtctgtcac tctgtgcctc aaattccgtt ggcaacgttc taccggccta tcgacatcgt    30120
gaccggctca aggctgacat agcggttctc cgcacggaac atttccatct caaccagcca    30180
gttttgtcct gccgcaccga ctttcaccgt tgcccgatcg atttgttcga tggtcacctc    30240
gaagccatgc cgatcgctct cggacagcga ggtaccgggt cgggcaatgg tgatgacact    30300
ggctggccgt ggcgtgggcg aaatcgcgac atcgacaccg ctgccttcag atttgccgtc    30360
atcgccgttc ttgcgccgcc gcacgtactc cacgacgccg acagtggtgc gcggcgcggg    30420
ccgtggtgtg ccgacgatgc tcaactgcgg catgcgtacg ctggcccaac gctcttggtc    30480
gcgagtgtgc acacacaccc gctcaccggc accgacgacg cgaatcacga tcctcttggc    30540
gatcgtgtcg tccgcggcca cgaagacgcg cgacagctca ccggcgtcgg taacgggaat    30600
catcagccgg tccccgttgc tcagcttgcc aatcaacacc cccgacggtc cgatctcggt    30660
gactagctgc gccggcaacg ggcagcgccg ctgtccgcgt aggtgtggac gtggcccgca    30720
catgttggcc gcagccgcgg cggcttgctc accattgagc cgacgcaaga tcacactggg    30780
cggggtaggc gccggcgtcg gtgtgcgcac ggtgatggtc gcggtgcacg tcgcgtccgg    30840
atacaccgtt acgttctgga tgacctcatc ggcacgcagc gtccaggctt gcgagagaac    30900
ccgcgacgaa atcgcctcag ccgggtacgc atacgtcgtc atccaccegg cttcaccgcg    30960 gatagctttc cagcgctgcg cactcccggc taccgcgtcc gaccccagcc ggcgatcaag    31020
ctcagccaag tctgttgcgg tggccagttt ggcgcgcaag ccctgacagc gcaggagct    31080 ggcaacgcgt gggcgaccg aaatggcagc ggccccaacg ctggtacgcc agcgtaaagc    31140
ttgggtgttg ccgatcaccg gaagccgcat gatcagccac gtttcgcgcc gcccggcata    31200
cggcggcgta ccgatctccg cgtcatacac ccgcgggtaa tcgccgacgg tgccggttcg    31260
cgagccgaag gtgacgacgc tgattgaatc gagttccagg tccagcgggt ggcgcagcaa    31320
cggcgcgagc tcaacgacgt caatcacgtt gtcgctttct acggtcaccg accggtgac    31380 cgtagtcgcc cggtgcgctc ggccgagaag ttgcaccgcc accaccgcga caccgtcttg    31440
cacgcggacg ccaccccgg atcggttgtt ggccaaggta attgggtcat tccatttgac    31500
gggacgccga ccccgcagcc ccagtaccgc ccacgaccac gccggctgac cccaccactg    31560
tacgaacacc aaggcgacgc cgaccacgac agccatgacc gcacctagct ggccgccag    31620 cgcccagccc gccgacgcga gcacgaacac tgtccacacc ccggcgaccc gcctcgcact    31680
gcgcgggctg aacccggtca gcttggacgt caacgcgccc tccgtagccg agccccgatt    31740
gccattgcca gcacaccggt ggccactgcg ccgacgaacc cgatagcgat attgcgcgcc    31800
cggtgatc                                                             31808
```

<210> SEQ ID NO 2
<211> LENGTH: 13773
<212> TYPE: DNA
<213> ORGANISM: mycobacterium tuberculosis
<220> FEATURE:
<223> OTHER INFORMATION: Complete DNA sequence of RD1 Rv3867-3877

<400> SEQUENCE: 2

```
atggtggacc cgccgggcaa cgacgacgac cacggtgatc tcgacgccct cgatttctcc      60
gccgcccaca ccaacgaggc gtcgccgctg gacgccttag acgactatgc gccggtgcag     120
accgatgacg ccgaaggcga cctggacgcc ctccatgcgc tcaccgaacg cgacgaggag     180
ccggagctgg agttgttcac ggtgaccaac cctcaagggt cggtgtcggt ctcaaccctg     240
atggacggca gaatccagca cgtcgagctg acggacaagg cgaccagcat gtccgaagcg     300
cagctggccg acgagatctt cgttattgcc gatctggccc gccaaaaggc gcgggcgtcg     360
cagtacacgt tcatggtgga gaacatcggt gaactgaccg acgaagacgc agaaggcagc     420
gccctgctgc gggaattcgt ggggatgacc ctgaatctgc cgacgccgga gaggctgcc      480
gcagccgaag ccgaagtgtt cgccacccgc tacgatgtcg actacacctc ccggtacaag     540
gccgatgact gatcgcttgg ccagtctgtt cgaaagcgcc gtcagcatgt tgccgatgtc     600
ggaggcgcgg tcgctagatc tgttcaccga gatcaccaac tacgacgaat ccgcttgcga     660
cgcatggatc ggccggatcc ggtgtgggga caccgaccgg gtgacgctgt ttcgcgcctg     720
gtattcgcgc cgcaatttcg gacagttgtc gggatcggtc cagatctcga tgagcacgtt     780
aaacgccagg attgccatcg gggggctgta cggcgatatc acctacccgg tcacctcgcc     840
gctagcgatc accatgggct tgccgcatg cgaggcagcg caaggcaatt acgccgacgc     900
catggaggcc ttagaggccg ccccggtcgc gggttccgag cacctggtgg cgtggatgaa     960
ggcggttgtc tacggcgcgg ccgaacgctg gaccgacgtg atcgaccagg tcaagagtgc    1020
tgggaaatgg ccggacaagt ttttggccgg cgcggccggt gtggcgcacg gggttgccgc    1080
ggcaaacctg gccttgttca ccgaagccga acgccgactc accgaggcca acgactcgcc    1140
cgccggtgag gcgtgtgcgc gcgccatcgc ctggtatctg gcgatggcac ggcgcagcca    1200
gggcaacgaa agcgccgcgg tggcgctgct ggaatggtta cagaccactc accccgagcc    1260
caaagtggct gcgcgctga aggatccctc ctaccggctg aagacgacca ccgccgaaca    1320
gatcgcatcc cgcgccgatc cctgggatcc gggcagtgtc gtgaccgaca actccggccg    1380
ggagcggctg ctcgccgagg cccaagccga actcgaccgc caaattgggc tcacccgggt    1440
taaaaatcag attgaacgct accgcgcggc gacgctgatg gcccgggtcc cgccgccaa    1500
gggtatgaag gtcgcccagc ccagcaagca catgatcttc accggaccgc ccggtaccgg    1560
caagaccacg atcgcgcggg tggtggccaa tatcctggcc ggcttaggcg tcattgccga    1620
acccaaactc gtcgagacgt cgcgcaagga cttcgtcgcc gagtacgagg gcaatcggc    1680
ggtcaagacc gctaagacga tcgatcaggc gctgggcggg gtgcttttca tcgacgaggc    1740
ttatgcgctg gtgcaggaaa gagacggccg caccgatccg ttcggtcaag aggcgctgga    1800
cacgctgctg gcgcggatgg agaacgaccg ggaccggctg gtggtgatca tcgccgggta    1860
cagctccgac atagatcggc tgctggaaac caacgagggt ctgcggtcgc ggttcgccac    1920
tcgcatcgag ttcgacacct attccccga ggaactcctc gagatcgcca acgtcattgc    1980
cgctgctgat gattcggcgt tgaccgcaga ggcggccgag aactttcttc aggccgccaa    2040
gcagttggag cagcgcatgt tgcgcggccg gcgcgccctg gacgtcgccg caacggtcg    2100
gtatgcgcgc cagctggtgg aggccagcga gcaatgccgg acatgcgtc tagcccaggt    2160
cctcgatatc gacacccttg acgaagaccg gcttcgcgag atcaacgct cagatatggc    2220
ggaggctatc gccgcggtgc acgcacacct caacatgaga gaatgaacta tggggcttcg    2280
cctcaccacc aaggttcagg ttagcggctg gcgttttctg ctgcgccggc tcgaacacgc    2340
catcgtgcgc cgggacaccc ggatgtttga cgacccgctg cagttctaca gccgctcgat    2400
```

```
cgctcttggc atcgtcgtcg cggtcctgat tctggcgggt gccgcgctgc tggcgtactt    2460
caaaccacaa ggcaaactcg gcggcaccag cctgttcacc gaccgcgcga ccaaccagct    2520
ttacgtgctg ctgtccggac agttgcatcc ggtctacaac ctgacttcgg cgcggctggt    2580
gctgggcaat ccggccaacc cggccaccgt gaagtcctcc gaactgagca agctgccgat    2640
gggccagacc gttggaatcc ccggcgcccc ctacgccacg cctgtttcgg cgggcagcac    2700
ctcgatctgg accctatgcg acaccgtcgc ccgagccgac tccacttccc cggtagtgca    2760
gaccgcggtc atcgcgatgc cgttggagat cgatgcttcg atcgatccgc tccagtcaca    2820
cgaagcggtg ctggtgtcct accagggcga aacctggatc gtcacaacta agggacgcca    2880
cgccatagat ctgaccgacc gcgccctcac ctcgtcgatg gggataccgg tgacggccag    2940
gccaaccccg atctcggagg gcatgttcaa cgcgctgcct gatatggggc cctggcagct    3000
gccgccgata ccggcggcgg gcgcgcccaa ttcgcttggc ctacctgatg atctagtgat    3060
cggatcggtc ttccagatcc acaccgacaa gggcccgcaa tactatgtgg tgctgcccga    3120
cggcatcgcg caggtcaacg cgacaaccgc tgcggcgctg cgcgccaccc aggcgcacgg    3180
gctggtcgcg ccaccggcaa tggtgcccag tctggtcgtc agaatcgccg aacgggtata    3240
cccctcaccg ctaccgatgg aaccgctcaa gatcgtgtcc cggccgcagg atcccgcgct    3300
gtgctggtca tggcaacgca gcgccggcga ccagtcgccg cagtcaacgg tgctgtccgg    3360
ccggcatctg ccgatatcgc cctcagcgat gaacatgggg atcaagcaga tccacgggac    3420
ggcgaccgtt tacctcgacg gcggaaaaat cgtggcactg caatcccccg atcctcgata    3480
caccgaatcg atgtactaca tcgatccaca gggcgtgcgt tatggggtgc ctaacgcgga    3540
gacagccaag tcgctgggcc tgagttcacc ccaaaacgcg ccctgggaga tcgttcgtct    3600
cctggtcgac ggtccggtgc tgtcgaaaga tgccgcactg ctcgagcacg acacgctgcc    3660
cgctgaccct agccccgaa aagttcccgc cggagcctcc ggagcccct gatgacgacc    3720
aagaagttca ctcccaccat tacccgtggc ccccggttga ccccgggcga gatcagcctc    3780
acgccgcccg atgacctggg catcgacatc ccaccgtcgg gcgtccaaaa gatccttccc    3840
tacgtgatgg gtggcgccat gctcggcatg atcgccatca tggtggccgg cggcaccagg    3900
cagctgtcgc cgtacatgtt gatgatgccg ctgatgatga tcgtgatgat ggtcggcggt    3960
ctggccggta gcaccggtgg tggcggcaag aaggtgcccg aaatcaacgc cgaccgcaag    4020
gagtacctgc ggtatttggc aggactacgc acccgagtga cgtcctcggc cacctctcag    4080
gtggcgttct tctcctacca cgcaccgcat cccgaggatc tgttgtcgat cgtcggcacc    4140
caacggcagt ggtcccggcc ggccaacgcc gacttctatg cggccacccg aatcggtatc    4200
ggtgaccagc cggcggtgga tcgattattg aagccggccg tcggcgggga gttggccgcc    4260
gccagcgcag cacctcagcc gttcctggag ccggtcagtc atatgtgggt ggtcaagttt    4320
ctacgaaccc atggattgat ccatgactgc ccgaaactgc tgcaactccg tacctttccg    4380
actatcgcga tcgcggggga cttgcgggg cagccggcc tgatgacggc gatgatctgt    4440
cacctagccg tgttccaccc accggacctg ctgcagatcc gggtgctcac cgaggaaccc    4500
gacgaccccg actggtcctg gctcaaatgg cttccgcacg tacagcacca gaccgaaacc    4560
gatgcggccg ggtccacccg gctgatcttc acgcgccagg aaggtctgtc ggacctggcc    4620
gcgcgcgggc cacacgcacc cgattcgctt cccggcggcc cctacgtagt cgtcgtcgac    4680
ctgaccggcg gcaaggctgg attcccgccc gacggtaggg ccggtgtcac ggtgatcacg    4740
```

```
ttgggcaacc atcgcggctc ggcctaccgc atcagggtgc acgaggatgg gacggctgat    4800
gaccggctcc ctaaccaatc gtttcgccag gtgacatcgg tcaccgatcg gatgtcgccg    4860
cagcaagcca gccgtatcgc gcgaaagttg gccggatggt ccatcacggg caccatcctc    4920
gacaagacgt cgcgggtcca gaagaaggtg gccaccgact ggcaccagct ggtcggtgcg    4980
caaagtgtcg aggagataac accttcccgc tggaggatgt acaccgacac cgaccgtgac    5040
cggctaaaga tcccgtttgg tcatgaacta aagaccggca acgtcatgta cctggacatc    5100
aaagagggcg cggaattcgg cgccggaccg cacggcatgc tcatcgggac cacggggtct    5160
gggaagtccg aattcctgcg caccctgatc ctgtcgctgg tggcaatgac tcatccagat    5220
caggtgaatc tcctgctcac cgacttcaaa ggtggttcaa ccttcctggg aatggaaaag    5280
cttccgcaca ctgccgctgt cgtcaccaac atggccgagg aagccgagct cgtcagccgg    5340
atgggcgagg tgttgaccgg agaactcgat cggcgccagt cgatcctccg acaggccggg    5400
atgaaagtcg gcgcggccgg agccctgtcc ggcgtggccg aatacgagaa gtaccgcgaa    5460
cgcggtgccg acctaccccc gctgccaacg cttttcgtcg tcgtcgacga gttcgccgag    5520
ctgttgcaga gtcacccgga cttcatcggg ctgttcgacc ggatctgccg cgtcgggcgg    5580
tcgctgaggg tccatctgct gctggctacc cagtcgctgc agaccggcgg tgttcgcatc    5640
gacaaactgg agccaaacct gacatatcga atcgcattgc gcaccaccag ctctcatgaa    5700
tccaaggcgg taatcggcac accggaggcg cagtacatca ccaacaagga gagcggtgtc    5760
gggtttctcc gggtcggcat ggaagacccg gtcaagttca gcaccttcta catcagtggg    5820
ccatacatgc cgccggcggc aggcgtcgaa accaatggtg aagccggagg gcccggtcaa    5880
cagaccacta gacaagccgc gcgcattcac aggttcaccg cggcaccggt tctcgaggag    5940
gcgccgacac cgtgacccgc gccggcgacg atgcaaagcg cagcgatgag gaggagcggc    6000
gccaacggcc cgcgccggcg acgatgcaaa gcgcagcgat gaggaggagc ggcgcgcatg    6060
actgctgaac cggaagtacg gacgctgcgc gaggttgtgc tggaccagct cggcactgct    6120
gaatcgcgtg cgtacaagat gtggctgccg ccgttgacca atccggtccc gctcaacgag    6180
ctcatcgccc gtgatcggcg acaacccctg cgatttgccc tggggatcat ggatgaaccg    6240
cgccgccatc tacaggatgt gtggggcgta gacgtttccg gggccggcgg caacatcggt    6300
attgggggcg cacctcaaac cgggaagtcg acgctactgc agacgatggt gatgtcggcc    6360
gccgccacac actcaccgcg caacgttcag ttctattgca tcgacctagg tggcggcggg    6420
ctgatctatc tcgaaaacct tccacacgtc ggtgggtag ccaatcggtc cgagcccgac    6480
aaggtcaacc gggtggtcgc agagatgcaa gccgtcatgc ggcaacggga accaccttc    6540 aaggaacacc gagtgggctc gatcgggatg taccggcagc tgcgtgacga tccaagtcaa    6600
cccgttgcgt ccgatccata cggcgacgtc tttctgatca tcgacggatg gcccggtttt    6660
gtcggcgagt tccccgacct tgaggggcag gttcaagatc tggccgccca ggggctggcg    6720
ttcggcgtcc acgtcatcat ctccacgcca cgctggacag agctgaagtc gcgtgttcgc    6780
gactacctcg gcaccaagat cgagttccgg cttggtgacg tcaatgaaac ccagatcgac    6840
cggattaccc gcgagatccc ggcgaatcgt ccgggtcggg cagtgtcgat ggaaaagcac    6900
catctgatga tcggcgtgcc caggttcgac ggcgtgcaca cgccgataa cctggtggag    6960 gcgatcaccg cggggggtgac gcagatcgct tcccagcaca ccgaacaggc acctccggtg    7020
cgggtcctgc cggagcgtat ccacctgcac gaactcgacc cgaacccgcc gggaccagag    7080
tccgactacc gcactcgctg ggagattccg atcggcttgc gcgagacgga cctgacgccg    7140
```

```
gctcactgcc acatgcacac gaacccgcac ctactgatct tcggtgcggc caaatcgggc    7200
aagacgacca ttgcccacgc gatcgcgcgc gccatttgtg cccgaaacag tccccagcag    7260
gtgcggttca tgctcgcgga ctaccgctcg ggcctgctgg acgcggtgcc ggacacccat    7320
ctgctgggcg ccggcgcgat caaccgcaac agcgcgtcgc tagacgaggc cgttcaagca    7380
ctggcggtca acctgaagaa gcggttgccg ccgaccgacc tgacgacggc gcagctacgc    7440
tcgcgttcgt ggtggagcgg atttgacgtc gtgcttctgg tcgacgattg cacatgatc    7500
gtgggtgccg ccgggggggat gccgccgatg gcaccgctgg ccccgttatt gccggcggcg    7560
gcagatatcg ggttgcacat cattgtcacc tgtcagatga gccaggctta caaggcaacc    7620
atggacaagt tcgtcggcgc cgcattcggg tcgggcgctc cgacaatgtt cctttcgggc    7680
gagaagcagg aattcccatc cagtgagttc aaggtcaagc ggcgcccccc tggccaggca    7740
tttctcgtct cgccagacgg caaagaggtc atccaggccc cctacatcga gcctccagaa    7800
gaagtgttcg cagcaccccc aagcgccggt taagattatt tcattgccgg tgtagcagga    7860
cccgagctca gcccggtaat cgagttcggg caatgctgac catcgggttt gtttccggct    7920
ataaccgaac ggtttgtgta cgggatacaa atacagggag ggaagaagta ggcaaatgga    7980
aaaaatgtca catgatccga tcgctgccga cattggcacg caagtgagcg acaacgctct    8040
gcacggcgtg acggccggct cgacggcgct gacgtcggtg accgggctgg ttcccgcggg    8100
ggccgatgag gtctccgccc aagcggcgac ggcgttcaca tcggagggca tccaattgct    8160
ggcttccaat gcatcggccc aagaccagct ccaccgtgcg ggcgaagcgg tccaggacgt    8220
cgcccgcacc tattcgcaaa tcgacgacgg cgccgccggc gtcttcgccg aataggcccc    8280
caaacacatcg gagggagtga tcaccatgct gtggcacgca atgccaccgg agctaaatac    8340
cgcacggctg atggccggcg cgggtccggc tccaatgctt gcggcggccg cgggatggca    8400
gacgctttcg gcggctctgg acgctcaggc cgtcgagttg accgcgcgcc tgaactctct    8460
gggagaagcc tggactggag gtggcagcga caaggcgctt gcggctgcaa cgccgatggt    8520
ggtctggcta caaaccgcgt caacacaggc caagacccgt gcgatgcagg cgacggcgca    8580
agccgcggca tacacccagg ccatggccac gacgccgtcg ctgccggaga tcgccgccaa    8640
ccacatcacc caggccgtcc ttacggccac caacttcttc ggtatcaaca cgatcccgat    8700
cgcgttgacc gagatggatt atttcatccg tatgtggaac caggcagccc tggcaatgga    8760
ggtctaccag gccgagaccg cggttaacac gcttttcgag aagctcgagc cgatggcgtc    8820
gatccttgat cccggcgcga gccagagcac gacgaacccg atcttcggaa tgccctcccc    8880
tggcagctca acaccggttg gccagttgcc gccggcggct acccagaccc tcggccaact    8940
gggtgagatg agcggcccga tgcagcagct gacccagccg ctgcagcagg tgacgtcgtt    9000
gttcagccag gtgggcggca ccggcggcgg caacccagcc gacgaggaag ccgcgcagat    9060
gggcctgctc ggcaccagtc gctgtcgaa ccatccgctg gctggtggat caggccccag    9120
cgcgggcgcg ggcctgctgc gcgcggagtc gctacctggc gcaggtgggt cgttgacccg    9180
cacgccgctg atgtctcagc tgatcgaaaa gccggttgcc ccctcggtga tgccggcggc    9240
tgctgccgga tcgtcggcga cgggtggcgc cgctccggtg ggtgcgggag cgatgggcca    9300
gggtgcgcaa tccggcggct ccaccaggcc gggtctggtc gcgccggcac cgctcgcgca    9360
ggagcgtgaa gaagacgacg aggacgactg ggacgaagag gacgactggt gagctcccgt    9420
aatgacaaca gacttcccgg ccacccgggc cggaagactt gccaacattt tggcgaggaa    9480
```

```
ggtaaagaga gaaagtagtc cagcatggca gagatgaaga ccgatgccgc taccctcgcg   9540
caggaggcag gtaatttcga gcggatctcc ggcgacctga aaacccagat cgaccaggtg   9600
gagtcgacgg caggttcgtt gcagggccag tggcgcggcg cggcggggac ggccgcccag   9660
gccgcggtgg tgcgcttcca agaagcagcc aataagcaga agcaggaact cgacgagatc   9720
tcgacgaata ttcgtcaggc cggcgtccaa tactcgaggg ccgacgagga gcagcagcag   9780
gcgctgtcct cgcaaatggg cttctgaccc gctaatacga aaagaaacgg agcaaaaaca   9840
tgacagagca gcagtggaat ttcgcgggta tcgaggccgc ggcaagcgca atccagggaa   9900
atgtcacgtc cattcattcc ctccttgacg aggggaagca gtccctgacc aagctcgcag   9960
cggcctgggg cggtagcggt tcggaggcgt accagggtgt ccagcaaaaa tgggacgcca  10020
cggctaccga gctgaacaac gcgctgcaga acctggcgcg gacgatcagc gaagccggtc  10080
aggcaatggc ttcgaccgaa ggcaacgtca ctgggatgtt cgcatagggc aacgccgagt  10140
tcgcgtagaa tagcgaaaca cgggatcggg cgagttcgac cttccgtcgg tctcgccctt  10200
tctcgtgttt atacgtttga gcgcactctg agaggttgtc atggcggccg actacgacaa  10260
gctcttccgg ccgcacgaag gtatggaagc tccggacgat atggcagcgc agccgttctt  10320
cgaccccagt gcttcgtttc cgccggcgcc cgcatcggca aacctaccga agcccaacgg  10380
ccagactccg ccccgacgt ccgacgacct gtcggagcgg ttcgtgtcgg ccccgccgcc  10440
gccaccccca ccccaccctc cgcctccgcc aactccgatg ccgatcgccg caggagagcc  10500
gccctcgccg gaaccggccg catctaaacc cccacaccc cccatgccca tcgccggacc  10560
cgaaccggcc ccacccaaac cacccacacc cccatgccc atcgccggac ccgaaccggc  10620
cccacccaaa ccacccacac ctccgatgcc catcgccgga cctgcaccca ccccaaccga  10680
atcccagttg gcgcccccca gaccaccgac accacaaacg ccaaccggag cgccgcagca  10740
accggaatca ccggcgcccc acgtaccctc gcacgggcca catcaaccc ggcgcaccgc  10800 accagcaccg ccctgggcaa agatgccaat cggcgaaccc ccgcccgctc cgtccagacc  10860
gtctgcgtcc ccggccgaac caccgacccg gcctgccccc caacactccc gacgtgcgcg  10920
ccggggtcac cgctatcgca cagacaccga acgaaacgtc gggaaggtag caactggtcc  10980
atccatccag gcgcggctgc gggcagagga agcatccggc gcgcagctcg ccccgggaac  11040
ggagccctcg ccagcgccgt tgggccaacc gagatcgtat ctggctccgc ccacccgccc  11100
cgcgccgaca gaacctcccc ccagcccctc gccgcagcgc aactccggtc ggcgtgccga  11160
gcgacgcgtc caccccgatt tagccgccca acatgccgcg gcgcaacctg attcaattac  11220
ggccgcaacc actggcggtc gtcgccgcaa gcgtgcagcg ccggatctcg acgcgacaca  11280
gaaatcctta aggccggcgg ccaagggcc gaaggtgaag aaggtgaagc cccagaaacc  11340
gaaggccacg aagccgccca aagtggtgtc gcagcgcggc tggcgacatt gggtgcatgc  11400
gttgacgcga atcaacctgg gcctgtcacc cgacgagaag tacgagctgg acctgcacgc  11460
tcgagtccgc cgcaatcccc gcgggtcgta tcagatcgcc gtcgtcggtc tcaaaggtgg  11520
ggctggcaaa accacgctga cagcagcgtt gggtcgacg ttggctcagg tgcgggccga  11580
ccggatcctg gctctagacg cggatccagg cgccggaaac ctcgccgatc gggtagggcg  11640
acaatcgggc gcgaccatcg ctgatgtgct tgcagaaaaa gagctgtcgc actacaacga  11700
catccgcgca cacactagcg tcaatgcggt caatctggaa gtgctgccgg caccggaata  11760
cagctcggcg cagcgcgcgc tcagcgacgc cgactggcat ttcatcgccg atcctgcgtc  11820
gaggttttac aacctcgtct tggctgattg tggggccggc ttcttcgacc cgctgacccg  11880
```

```
cggcgtgctg tccacggtgt ccggtgtcgt ggtcgtggca agtgtctcaa tcgacggcgc   11940
acaacaggcg tcggtcgcgt tggactggtt gcgcaacaac ggttaccaag atttggcgag   12000
ccgcgcatgc gtggtcatca atcacatcat gccgggagaa cccaatgtcg cagttaaaga   12060
cctggtgcgg catttcgaac agcaagttca acccggccgg gtcgtggtca tgccgtggga   12120
caggcacatt gcggccggaa ccgagatttc actcgacttg ctcgacccta tctacaagcg   12180
caaggtcctc gaattggccg cagcgctatc cgacgatttc gagagggctg gacgtcgttg   12240
agcgcacctg ctgttgctgc tggtcctacc gccgcgggg caaccgctgc gcggcctgcc   12300
accacccggg tgacgatcct gaccggcaga cggatgaccg atttggtact gccagcggcg   12360
gtgccgatgg aaacttatat tgcgacacc gtcgcggtgc tttccgaggt gttggaagac   12420
acgccggctg atgtactcgg cggcttcgac tttaccgcgc aaggcgtgtg ggcgttcgct   12480
cgtcccggat cgccgccgct gaagctcgac cagtcactcg atgacgccgg ggtggtcgac   12540
gggtcactgc tgactctggt gtcagtcagt cgcaccgagc gctaccgacc gttggtcgag   12600
gatgtcatcg acgcgatcgc cgtgcttgac gagtcacctg agttcgaccg cacggcattg   12660
aatcgctttg tggggcggc gatcccgctt ttgaccgcgc ccgtcatcgg gatggcgatg   12720
cgggcgtggt gggaaactgg gcgtagcttg tggtggccgt tggcgattgg catcctgggg   12780
atcgctgtgc tggtaggcag cttcgtcgcg aacaggttct accagagcgg ccacctggcc   12840
gagtgcctac tggtcacgac gtatctgctg atcgcaaccg ccgcagcgct ggccgtgccg   12900
ttgccgcgcg gggtcaactc gttggggcg ccacaagttg ccggcgccgc tacggccgtg   12960
ctgtttttga ccttgatgac gcggggcggc cctcggaagc gtcatgagtt ggcgtcgttt   13020
gccgtgatca ccgctatcgc ggtcatcgcg ccgccgctg ccttcggcta tggataccag   13080
gactgggtcc ccgcgggggg gatcgcattc gggctgttca ttgtgacgaa tgcggccaag   13140
ctgaccgtcg cggtcgcgcg gatcgcgctg ccgccgattc cggtacccgg cgaaaccgtg   13200
gacaacgagg agttgctcga tcccgtcgcg accccggagg ctaccagcga agaaaccccg   13260
acctggcagg ccatcatcgc gtcggtgccc gcgtccgcgg tccggctcac cgagcgcagc   13320
aaactggcca agcaacttct gatcggatac gtcacgtcgg gcaccctgat tctggctgcc   13380
ggtgccatcg cggtcgtggt gcgcgggcac ttctttgtac acagcctggt ggtcgcgggt   13440
ttgatcacga ccgtctgcgg atttcgctcg cggctttacg ccgagcgctg gtgtgcgtgg   13500
gcgttgctgg cggcgacggt cgcgattccg acgggtctga cggccaaact catcatctgg   13560
tacccgcact atgcctggct gttgttgagc gtctacctca cggtagccct ggttgcgctc   13620
gtggtggtcg ggtcgatggc tcacgtccgg cgcgtttcac cggtcgtaaa acgaactctg   13680
gaattgatcg acggcgccat gatcgctgcc atcattccca tgctgctgtg gatcaccggg   13740
gtgtacgaca cggtccgcaa tatccggttc tga   13773
```

<210> SEQ ID NO 3
<211> LENGTH: 3909
<212> TYPE: DNA
<213> ORGANISM: Mycobacterium tuberculosis
<220> FEATURE:
<223> OTHER INFORMATION: RD1-AP34 (a 3909 bp fragment of the M.
      tuberculosis H37Rv genome)

<400> SEQUENCE: 3

```
gaattcccat ccagtgagtt caaggtcaag cggcgccccc ctggccaggc atttctcgtc     60
tcgccagacg gcaaagaggt catccaggcc ccctacatcg agcctccaga agaagtgttc    120
```

-continued

```
gcagcacccc caagcgccgg ttaagattat tcattgccg gtgtagcagg acccgagctc      180
agcccggtaa tcgagttcgg gcaatgctga ccatcgggtt tgtttccggc tataaccgaa     240
cggtttgtgt acgggataca aatacaggga gggaagaagt aggcaaatgg aaaaaatgtc     300
acatgatccg atcgctgccg acattggcac gcaagtgagc gacaacgctc tgcacggcgt     360
gacggccggc tcgacggcgc tgacgtcggt gaccgggctg gttcccgcgg gggccgatga     420
ggtctccgcc caagcggcga cggcgttcac atcggagggc atccaattgc tggcttccaa     480
tgcatcggcc caagaccagc tccaccgtgc gggcgaagcg gtccaggacg tcgcccgcac     540
ctattcgcaa atcgacgacg gcgccgccgg cgtcttcgcc gaataggccc ccaacacatc     600
ggagggagtg atcaccatgc tgtggcacgc aatgccaccg gagctaaata ccgcacggct     660
gatggccggc gcgggtccgg ctccaatgct tgcggcggcc gcgggatggc agacgctttc     720
ggcggctctg gacgctcagg ccgtcgagtt gaccgcgcgc ctgaactctc tgggagaagc     780
ctggactgga ggtggcagcg acaaggcgct tgcggctgca acgccgatgg tggtctggct     840
acaaaccgcg tcaacacagg ccaagacccg tgcgatgcag gcgacggcgc aagccgcggc     900
atacacccag gccatggcca cgacgccgtc gctgccggag atcgccgcca accacatcac     960
ccaggccgtc cttacggcca ccaacttctt cggtatcaac acgatcccga tcgcgttgac    1020
cgagatggat tatttcatcc gtatgtggaa ccaggcagcc ctggcaatgg aggtctacca    1080
ggccgagacc gcggttaaca cgcttttcga aagctcgag ccgatggcgt cgatccttga    1140
tcccggcgcg agccagagca cgacgaaccc gatcttcgga atgccctccc ctggcagctc    1200
aacaccggtt ggccagttgc cgccggcggc tacccagacc ctcggccaac tgggtgagat    1260
gagcggcccg atgcagcagc tgacccagcc gctgcagcag gtgacgtcgt tgttcagcca    1320
ggtgggcggc accggcggcg gcaacccagc cgacgaggaa gccgcgcaga tgggcctgct    1380
cggcaccagt ccgctgtcga accatccgct ggctggtgga tcaggcccca gcgcgggcgc    1440
gggcctgctg cgcgcggagt cgctacctgg cgcaggtggg tcgttgaccc gcacgccgct    1500
gatgtctcag ctgatcgaaa agccggttgc ccccctcggtg atgccggcgg ctgctgccgg    1560
atcgtcggcg acgggtggcg ccgctccggt gggtgcggga gcgatgggcc agggtgcgca    1620
atccggcggc tccaccaggc cgggtctggt cgcgccggca ccgctcgcgc aggagcgtga    1680
agaagacgac gaggacgact gggacgaaga ggacgactgg tgagctcccg taatgacaac    1740
agacttcccg gccacccggg ccggaagact tgccaacatt ttggcgagga aggtaaagag    1800
agaaagtagt ccagcatggc agagatgaag accgatgccg ctaccctcgc gcaggaggca    1860
ggtaatttcg agcggatctc cggcgacctg aaaacccaga tcgaccaggt ggagtcgacg    1920
gcaggttcgt tgcagggcca gtggcgcggc gcggcgggga cggccgccca ggccgcggtg    1980
gtgcgcttcc aagaagcagc caataagcag aagcaggaac tcgacgagat ctcgacgaat    2040
attcgtcagg ccggcgtcca atactcgagg gccgacgagg agcagcagca ggcgctgtcc    2100
tcgcaaatgg gcttctgacc cgctaatacg aaaagaaacg gagcaaaaac atgacagagc    2160
agcagtggaa tttcgcgggt atcgaggccg cggcaagcgc aatccaggga aatgtcacgt    2220
ccattcattc cctccttgac gaggggaagc agtccctgac caagctcgca gcggcctggg    2280
gcggtagcgg ttcggaggcg taccagggtg tccagcaaaa atgggacgcc acggctaccg    2340
agctgaacaa cgcgctgcag aacctggcgc ggacgatcag cgaagccggt caggcaatgg    2400
cttcgaccga aggcaacgtc actgggatgt tcgcataggg caacgccgag ttcgcgtaga    2460
```

```
atagcgaaac acgggatcgg gcgagttcga ccttccgtcg gtctcgccct ttctcgtgtt    2520
tatacgtttg agcgcactct gagaggttgt catggcggcc gactacgaca agctcttccg    2580
gccgcacgaa ggtatggaag ctccggacga tatggcagcg cagccgttct tcgaccccag    2640
tgcttcgttt ccgccggcgc ccgcatcggc aaacctaccg aagcccaacg gccagactcc    2700
gcccccgacg tccgacgacc tgtcggagcg gttcgtgtcg gccccgccgc cgccacccce    2760 accccacct ccgcctccgc caactccgat gccgatcgcc gcaggagagc cgccctcgcc     2820
ggaaccggcc gcatctaaac cacccacacc cccatgccc atcgccggac ccgaaccggc     2880
cccacccaaa ccaccacac cccccatgcc catcgccgga cccgaaccgg ccccacccaa     2940
accacccaca cctccgatgc ccatcgccgg acctgcaccc accccaaccg aatcccagtt    3000
ggcgcccccc agaccaccga caccacaaac gccaaccgga gcgccgcagc aaccggaatc    3060
accggcgccc cacgtacccct cgcacgggcc acatcaaccc cggcgcaccg caccagcacc    3120
gccctgggca aagatgccaa tcggcgaacc cccgccgct ccgtccagac cgtctgcgtc     3180
cccggccgaa ccaccgaccc ggcctgcccc ccaacactcc cgacgtgcgc gccggggtca    3240
ccgctatcgc acagacaccg aacgaaacgt cgggaaggta gcaactggtc catccatcca    3300
ggcgcggctg cgggcagagg aagcatccgg cgcgcagctc gcccccggaa cggagccctc    3360
gccagcgccg ttgggccaac cgagatcgta tctggctccg cccacccgcc ccgcgccgac    3420
agaacctccc cccagcccct cgccgcagcg caactccggt cggcgtgccg agcgacgcgt    3480
ccaccccgat ttagccgccc aacatgccgc ggcgcaacct gattcaatta cggccgcaac    3540
cactggcggt cgtcgccgca agcgtgcagc gccggatctc gacgcgacac agaaatcctt    3600
aaggccggcg gccaagggc cgaaggtgaa gaaggtgaag ccccagaaac cgaaggccac     3660
gaagccgccc aaagtggtgt cgcagcgcgg ctggcgacat gggtgcatg cgttgacgcg     3720 aatcaacctg ggcctgtcac ccgacgagaa gtacgagctg gacctgcacg ctcgagtccg    3780
ccgcaatccc cgcgggtcgt atcagatcgc cgtcgtcggt ctcaaaggtg gggctggcaa    3840
aaccacgctg acagcagcgt tggggtcgac gttggctcag gtgcgggccg accggatcct    3900
ggctctaga                                                            3909

<210> SEQ ID NO 4
<211> LENGTH: 324
<212> TYPE: DNA
<213> ORGANISM: Mycobacterium tuberculosis
<220> FEATURE:
<223> OTHER INFORMATION: DNA sequence Rv3861

<400> SEQUENCE: 4
gtgacctggc tggctgaccc ggtcggcaac agcaggatcg cccgagcgca ggcctgcaaa      60
acgtcaatct cggcgcccat cgtcgaatcc tggcgggcgc aacgcggcgc gcaatgtgga     120
cagcgcgaga atcttgtcg atgttctcgc gctgtccaca tccagggcat ctcaccgcca     180
ctgttccgca gaccctcga accagcggtc caggcggcgg ttgcgtcatg ccgattgggc     240
agacacccgg tggtcgcgca ccgggtaacc gttgcgctcg ccagggatc gcagctggcc     300 caacgcgaat gcccgcgccc ggcc                                            324

<210> SEQ ID NO 5
<211> LENGTH: 348
<212> TYPE: DNA
<213> ORGANISM: Mycobacterium tuberculosis
<220> FEATURE:
<223> OTHER INFORMATION: DNA sequence Rv3862c-whiB6
```

<400> SEQUENCE: 5

```
atgcgatacg ctttcgcggc agaggctaca acctgcaacg ctttctggag gaacgtagac      60
atgacagtaa ccgccctgta tgaggtcccg ctcggcgttt gcacgcaaga tcccgatcgt     120
tggacgacga ctcccgacga cgaggccaag accctgtgcc gggcttgccc gcgccggtgg     180
ctgtgtgcac gcgacgccgt cgagtccgcg ggtgcgaag gctgtgggc aggggtcgta      240
attcccgaat caggccgggc gcgggcattc gcgttgggcc agctgcgatc cctggccgag     300
cgcaacggtt acccggtgcg cgaccaccgg gtgtctgccc aatcggca                 348
```

<210> SEQ ID NO 6
<211> LENGTH: 1176
<212> TYPE: DNA
<213> ORGANISM: Mycobacterium tuberculosis
<220> FEATURE:
<223> OTHER INFORMATION: DNA sequence RV3863

<400> SEQUENCE: 6

```
atggcgggcg agcggaaagt ctgcccaccg tcccggctag tacccgcgaa taagggatca      60
acgcagatgt ctaaagcagg gtcgactgtc ggaccggcgc cgctggtcgc gtgcagcggc     120
ggcacatcag acgtgattga gccccgtcgc ggtgtcgcga tcattggcca ctcgtgccga     180
gtcggcaccc agatcgacga ttctcgaatc tctcagacac atctgcgagc ggtatccgat     240
gatggacggt ggcggatcgt cggcaacatc ccgagaggta tgttcgtcgg cggacgacgc     300
ggcagctcgg tgaccgtcag cgataagacc ctaatccgat cggcgatcc cctggaggc      360
aaggcgttga cgttcgaagt cgtcaggccg tcggattccg ctgcacagca cggccgcgta     420
caaccatcag cggacctgtc ggacgacccg cgcacaacg ctgcgccggt cgcaccggac     480
cccggcgtgg ttcgcgcagg ggcggccgcg gctgcgcgcc gtcgtgaact tgacatcagc     540
caacgcagct tggcggccga cgggatcatc aacgcgggcg cgctcatcgc gttcgagaaa     600
ggccgtagtt ggccccggga acggacccgg gcaaaactcg aagaagtgct gcagtggccc     660
gctggaaccA tcgcgcgaat ccgtcggggc gagcccaccg agcccgcaac aaaccccgac     720
gcgtcccccg gactccggcc tgccgacggc ccggcgtcct tgatcgcgca ggctgtcacc     780
gccgccgtag acggctgcag tctggctatc gcagcgttgc cggcgaccga ggaccccgag     840
ttcaccgaac gtgccgcgcc gatccttgct gatttgcgcc agctcgaggc gattgccgtc     900
caagcaaccc gcatcagccg gattaccccg gaattgatca aggcgttggg cgcggtacgt     960
cgccaccacg acgaattaat gaggctggga gcaaccgccc ctggtgccac actggcgcag    1020
cgcttatatg ccgcacggcg gcgcgcgaac ctttccaccc tggagactgc ccaagcggcc    1080
ggcgtcgcag aagaaatgat cgtcggcgcc gaagccgagg aagagttgcc agccgaggcc    1140
accgaagcga tcgaagcact gatccgtcag atcaat                             1176
```

<210> SEQ ID NO 7
<211> LENGTH: 1206
<212> TYPE: DNA
<213> ORGANISM: Mycobacterium tuberculosis
<220> FEATURE:
<223> OTHER INFORMATION: DNA sequence Rv3864

<400> SEQUENCE: 7

```
atggcatcgg gtagcggtct ttgcaagacg acgagtaact ttatttgggg ccagttactc      60
ttgcttggag agggaatccc cgacccaggc gacattttca acaccggttc gtcgctgttc     120
```

```
aaacaaatca gcgacaaaat gggactcgcc attccgggca ccaactggat cggccaagcg     180
gcggaagctt acctaaacca gaacatcgcg caacaacttc gcgcacaggt gatgggcgat     240
ctcgacaaat taaccggcaa catgatctcg aatcaggcca aatacgtctc cgatacgcgc     300
gacgtcctgc gggccatgaa gaagatgatt gacggtgtct acaaggtttg taagggcctc     360
gaaaagattc cgctgctcgg ccacttgtgg tcgtgggagc tcgcaatccc tatgtccggc     420
atcgcgatgg ccgttgtcgg cggcgcattg ctctatctaa cgattatgac gctgatgaat     480
gcgaccaacc tgagggggaat tctcggcagg ctgatcgaga tgttgacgac cttgccaaag     540
ttccccggcc tgcccgggtt gcccagcctg cccgacatca tcgacggcct ctggccgccg     600
aagttgcccg acattccgat ccccggcctg cccgacatcc cgggcctacc cgacttcaaa     660
tggccgccca cccccggcag cccgttgttc cccgacctcc cgtcgttccc agggttcccc     720
gggttcccgg agttccccgc catccccggg ttccccgcac tgcccgggtt gcccagcatt     780
cccaacttgt tccccggctt gccgggtctg gcgacctgc tgcccggcgt aggcgatttg     840
ggcaagttac ccacctggac tgagctggcc gctttgcctg acttcttggg cggcttcgcc     900
ggcctgccca gctgggtttt tggcaatctg ctcagctttg ccagtttgcc caccgtgggt     960
caggtgaccg ccaccatggg tcagctgcaa cagctcgtgg cggccggcgg tggccccagc    1020
caactggcca gcatgggcag ccaacaagcg caactgatct cgtcgcaggc ccagcaagga    1080
ggccagcagc acgccaccct cgtgagcgac aagaaggaag acgaggaagg cgtggccgag    1140
gcggagcgtg cacccatcga cgctggcacc gcggccagcc aacgggggca ggaggggacc    1200
gtccctt                                                              1206

<210> SEQ ID NO 8
<211> LENGTH: 309
<212> TYPE: DNA
<213> ORGANISM: Mycobacterium tuberculosis
<220> FEATURE:
<223> OTHER INFORMATION: DNA sequence Rv3865

<400> SEQUENCE: 8
atgaccggat ttctcggtgt cgtgccttcg ttcctgaagg tgctggcggg catgcacaac      60
gagatcgtgg gtgatatcaa aagggcgacc gatacggtcg ccgggattag cggacgagtt     120
cagcttaccc atggttcgtt cacgtcgaaa ttcaatgaca cgctgcaaga gtttgagacc     180
acccgtagca gcacgggcac gggttttgcag ggagtcacca gcggactggc caataatctg     240
ctcgcagccg ccgcgccta cctcaaggcc gacgatggcc tagccggtgt tatcgacaag     300
atttttcggt                                                            309

<210> SEQ ID NO 9
<211> LENGTH: 849
<212> TYPE: DNA
<213> ORGANISM: Mycobacterium tuberculosis
<220> FEATURE:
<223> OTHER INFORMATION: DNA sequence Rv3866

<400> SEQUENCE: 9
atgacgggtc cgtccgctgc aggccgcgcg ggcaccgccg acaacgtggt cggcgtcgag      60
gtaaccatcg acggcatgtt ggtgatcgcc gatcggttac acctggttga tttccctgtc     120
acgcttggga ttcggccgaa tatcccgcaa gaggatctgc gagacatcgt ctgggaacag     180
gtgcagcgtg acctcacagc gcaagggggtg ctcgacctcc acggggagcc caaccgacg     240 gtcgcggaga tggtcgaaac cctgggcagg ccagatcgga ccttggaggg tcgctggtgg     300
```

```
cggcgcgaca ttggcggcgt catggtgcgc ttcgtcgtgt gccgcagggg cgaccgccat    360
gtgatcgcgg cgcgcgacgg cgacatgctg gtgctgcagt tggtggcgcc gcaggtcggc    420
ttggcgggca tggtgacagc ggtgctgggg cccgccgaac ccgccaacgt cgaacccctg    480
acgggtgtgg caaccgagct agccgaatgc acaaccgcgt cccaattgac gcaatacggt    540
atcgcaccgg cctcggcccg cgtctatgcc gagatcgtgg gtaacccgac cggctgggtg    600
gagatcgttg ccagccaacg ccaccccggc ggcaccacga cgcagaccga cgccgccgct    660
ggcgtcctgg actccaagct cggtaggctg gtgtcgcttc cccgccgtgt tggaggcgac    720
ctgtacggaa gcttcctgcc cggcactcag cagaacttgg agcgtgcgct ggacggcttg    780
ctagagctgc tccctgcggg cgcttggcta gatcacacct cagatcacgc acaagcctcc    840
tcccgaggc                                                            849

<210> SEQ ID NO 10
<211> LENGTH: 552
<212> TYPE: DNA
<213> ORGANISM: mycobacterium tuberculosis
<220> FEATURE:
<223> OTHER INFORMATION: DNA sequence Rv3867

<400> SEQUENCE: 10
atggtggacc cgccgggcaa cgacgacgac cacggtgatc tcgacgccct cgatttctcc     60
gccgcccaca ccaacgaggc gtcgccgctg gacgccttag cgactatgcc gccggtgcag    120
accgatgacg ccgaaggcga cctggacgcc ctccatgcgc tcaccgaacg cgacgaggag    180
ccggagctgg agttgttcac ggtgaccaac cctcaagggt cggtgtcggt ctcaaccctg    240
atggacggca gaatccagca cgtcgagctg acggacaagg cgaccagcat gtccgaagcg    300
cagctggccg acgagatctt cgttattgcc gatctggccc gccaaaaggc gcgggcgtcg    360
cagtacacgt tcatggtgga gaacatcggt gaactgaccg acgaagacgc agaaggcagc    420
gccctgctgc gggaattcgt ggggatgacc ctgaatctgc cgacgccgga gaggctgcc    480 gcagccgaag ccgaagtgtt cgccacccgc tacgatgtcg actacacctc ccggtacaag    540
gccgatgact ga                                                         552

<210> SEQ ID NO 11
<211> LENGTH: 1722
<212> TYPE: DNA
<213> ORGANISM: mycobacterium tuberculosis
<220> FEATURE:
<223> OTHER INFORMATION: DNA sequence Rv3868

<400> SEQUENCE: 11
atgactgatc gcttggccag tctgttcgaa agcgccgtca gcatgttgcc gatgtcggag     60
gcgcggtcgc tagatctgtt caccgagatc accaactacg acgaatccgc ttgcgacgca    120
tggatcggcc ggatccggtg tggggacacc gaccgggtga cgctgtttcg cgcctggtat    180
tcgcgccgca atttcggaca gttgtcggga tcggtccaga tctcgatgag cacgttaaac    240
gccaggattg ccatcggggg gctgtacggc gatatcacct acccggtcac ctcgccgcta    300
gcgatcacca tgggctttgc cgcatgcgag gcagcgcaag gcaattacgc cgacgccatg    360
gaggccttag aggccgcccc ggtcgcgggt tccgagcacc tggtggcgtg gatgaaggcg    420
gttgtctacg gcgcggccga acgctggacc gacgtgatcg accaggtcaa gagtgctggg    480
aaatggccgg acaagttttt ggccggcgcg gcggtgtgg cgcacggggt tgccgcggca    540
```

```
aacctggcct tgttcaccga agccgaacgc cgactcaccg aggccaacga ctcgcccgcc    600
ggtgaggcgt gtgcgcgcgc catcgcctgg tatctggcga tggcacggcg cagccagggc    660
aacgaaagcg ccgcggtggc gctgctggaa tggttacaga ccactcaccc cgagcccaaa    720
gtggctgcgg cgctgaagga tccctcctac cggctgaaga cgaccaccgc cgaacagatc    780
gcatcccgcg ccgatccctg ggatccgggc agtgtcgtga ccgacaactc cggccgggag    840
cggctgctcg ccgaggccca agccgaactc gaccgccaaa ttgggctcac ccgggttaaa    900
aatcagattg aacgctaccg cgcggcgacg ctgatggccc gggtccgcgc cgccaagggt    960
atgaaggtcg cccagcccag caagcacatg atcttcaccg gaccgcccgg taccggcaag   1020
accacgatcg cgcgggtggt ggccaatatc ctggccggct taggcgtcat tgccgaaccc   1080
aaaactcgtc agacgtcgcg caaggacttc gtcgccgagt acgaggggca atcgcggtc    1140 aagaccgcta agacgatcga tcaggcgctg ggcggggtgc ttttcatcga cgaggcttat   1200
gcgctggtgc aggaaagaga cggccgcacc gatccgttcg gtcaagaggc gctggacacg   1260
ctgctggcgc ggatggagaa cgaccgggac cggctggtgg tgatcatcgc cgggtacagc   1320
tccgacatag atcggctgct ggaaaccaac gagggtctgc ggtcgcggtt cgccactcgc   1380
atcgagttcg acacctattc ccccgaggaa ctcctcgaga tcgccaacgt cattgccgct   1440
gctgatgatt cggcgttgac cgcagaggcg gccgagaact tcttcaggc cgccaagcag   1500 ttggagcagc gcatgttgcg cggccggcgc gccctggacg tcgccggcaa cggtcggtat   1560
gcgcgccagc tggtggaggc cagcgagcaa tgccgggaca tgcgtctagc ccaggtcctc   1620
gatatcgaca ccctcgacga agaccggctt cgcgagatca acggctcaga tatggcggag   1680
gctatcgccg cggtgcacgc acacctcaac atgagagaat ga                       1722

<210> SEQ ID NO 12
<211> LENGTH: 1443
<212> TYPE: DNA
<213> ORGANISM: mycobacterium tuberculosis
<220> FEATURE:
<223> OTHER INFORMATION: DNA sequence Rv3869

<400> SEQUENCE: 12
atggggcttc gcctcaccac caaggttcag gttagcggct ggcgttttct gctgcgccgg     60
ctcgaacacg ccatcgtgcg ccgggacacc cggatgtttg acgacccgct gcagttctac    120
agccgctcga tcgctcttgg catcgtcgtc gcggtcctga ttctggcggg tgccgcgctg    180
ctggcgtact tcaaaccaca aggcaaactc ggcggcacca gcctgttcac cgaccgcgcg    240
accaaccagc tttacgtgct gctgtccgga cagttgcatc cggtctacaa cctgacttcg    300
gcgcggctgg tgctgggcaa tccggccaac ccggccaccg tgaagtcctc cgaactgagc    360
aagctgccga tgggccagac cgttggaatc cccggcgccc cctacgccac gcctgtttcg    420
gcgggcagca cctcgatctg gaccctatgc gacaccgtcg cccgagccga ctccacttcc    480
ccggtagtgc agaccgcggt catcgcgatg ccgttggaga tcgatgcttc gatcgatccg    540
ctccagtcac acgaagcggt gctggtgtcc taccagggcg aaacctggat cgtcacaact    600
aagggacgcc acgccataga tctgaccgac cgcgccctca cctcgtcgat ggggataccg    660
gtgacggcca ggcaaccccc gatctcggag ggcatgttca acgcgctgcc tgatatgggg    720
ccctggcagc tgccgccgat accggcggcg ggcgcgccca attcgcttgg cctacctgat    780
gatctagtga tcggatcggt cttccagatc cacaccgaca agggcccgca atactatgtg    840
gtgctgcccg acggcatcgc gcaggtcaac gcgacaaccg ctgcggcgct gcgcgccacc    900
```

-continued

```
caggcgcacg ggctggtcgc gccaccggca atggtgccca gtctggtcgt cagaatcgcc    960
gaacgggtat acccctcacc gctacccgat gaaccgctca agatcgtgtc ccggccgcag   1020
gatcccgcgc tgtgctggtc atggcaacgc agcgccggcg accagtcgcc gcagtcaacg   1080
gtgctgtccg gccggcatct gccgatatcg ccctcagcga tgaacatggg gatcaagcag   1140
atccacggga cggcgaccgt ttacctcgac ggcggaaaat tcgtggcact gcaatccccc   1200
gatcctcgat acaccgaatc gatgtactac atcgatccac agggcgtgcg ttatggggtg   1260
cctaacgcgg agacagccaa gtcgctgggc ctgagttcac cccaaaacgc gccctgggag   1320
atcgttcgtc tcctggtcga cggtccggtg ctgtcgaaag atgccgcact gctcgagcac   1380
gacacgctgc ccgctgaccc tagcccccga aaagttcccg ccggagcctc cggagccccc   1440
tga                                                                 1443
```

<210> SEQ ID NO 13
<211> LENGTH: 2244
<212> TYPE: DNA
<213> ORGANISM: mycobacterium tuberculosis
<220> FEATURE:
<223> OTHER INFORMATION: DNA sequence Rv3870

<400> SEQUENCE: 13

```
atgacgacca agaagttcac tcccaccatt acccgtggcc cccggttgac cccgggcgag     60
atcagcctca cgccgcccga tgacctgggc atcgacatcc caccgtcggg cgtccaaaag    120
atccttccct acgtgatggg tggcgccatg ctcggcatga tcgccatcat ggtggccggc    180
ggcaccaggc agctgtcgcc gtacatgttg atgatgccgc tgatgatgat cgtgatgatg    240
gtcggcggtc tggccggtag caccggtggt ggcggcaaga aggtgcccga aatcaacgcc    300
gaccgcaagg agtacctgcg gtatttggca ggactacgca cccgagtgac gtcctcggcc    360
acctctcagg tggcgttctt ctcctaccac gcaccgcatc ccgaggatct gttgtcgatc    420
gtcggcaccc aacggcagtg gtcccggccg gccaacgccg acttctatgc ggccacccga    480
atcggtatcg gtgaccagcc ggcggtggat cgattattga agccggccgt cggcggggag    540
ttggccgccg ccagcgcagc acctcagccg ttcctggagc cggtcagtca tatgtgggtg    600
gtcaagtttc tacgaaccca tggattgatc catgactgcc cgaaactgct gcaactccgt    660 accttttccga ctatcgcgat cggcggggac ttggcggggg cagccggcct gatgacggcg    720
atgatctgtc acctagccgt gttccaccca ccggacctgc tgcagatccg ggtgctcacc    780
gaggaacccg acgacccccga ctggtcctgg ctcaaatggc ttccgcacgt acagcaccag    840
accgaaaccg atgcggccgg gtccaccccgg ctgatcttca cgcgccagga aggtctgtcg    900
gacctggccg cgcgcgggcc acacgcaccc gattcgcttc ccggcggccc ctacgtagtc    960
gtcgtcgacc tgaccggcgg caaggctgga ttcccgcccg acgtagggc cggtgtcacg   1020 gtgatcacgt tgggcaacca tcgcggctcg gcctaccgca tcagggtgca cgaggatggg   1080
acggctgatg accggctccc taaccaatcg tttcgccagg tgacatcggt caccgatcgg   1140
atgtcgccgc agcaagccag ccgtatcgcg cgaaagttgg ccggatggtc catcacgggc   1200
accatcctcg acaagacgtc gcgggtccag aagaaggtgg ccaccgactg gcaccagctg   1260
gtcggtgcgc aaagtgtcga ggagataaca ccttcccgct ggaggatgta caccgacacc   1320
gaccgtgacc ggctaaagat cccgtttggt catgaactaa agaccggcaa cgtcatgtac   1380
ctggacatca aagagggcgc ggaattcggc gccggaccgc acggcatgct catcgggacc   1440
```

```
acggggtctg ggaagtccga attcctgcgc accctgatcc tgtcgctggt ggcaatgact   1500
catccagatc aggtgaatct cctgctcacc gacttcaaag gtggttcaac cttcctggga   1560
atggaaaagc ttccgcacac tgccgctgtc gtcaccaaca tggccgagga agccgagctc   1620
gtcagccgga tgggcgaggt gttgaccgga gaactcgatc ggcgccagtc gatcctccga   1680
caggccggga tgaaagtcgg cgcggccgga gccctgtccg gcgtggccga atacgagaag   1740
taccgcgaac gcggtgccga cctacccccg ctgccaacgc ttttcgtcgt cgtcgacgag   1800
ttcgccgagc tgttgcagag tcacccggac ttcatcgggc tgttcgaccg gatctgccgc   1860
gtcgggcggt cgctgagggt ccatctgctg ctggctaccc agtcgctgca gaccggcggt   1920
gttcgcatcg acaaactgga gccaaacctg acatatcgaa tcgcattgcg caccaccagc   1980
tctcatgaat ccaaggcggt aatcggcaca ccggaggcgc agtacatcac caacaaggag   2040
agcggtgtcg ggtttctccg ggtcggcatg aagacccgg tcaagttcag caccttctac    2100
atcagtgggc catacatgcc gccggcggca ggcgtcgaaa ccaatggtga agccggaggg   2160
cccggtcaac agaccactag acaagccgcg cgcattcaca ggttcaccgc ggcaccggtt   2220
ctcgaggagg cgccgacacc gtga                                          2244

<210> SEQ ID NO 14
<211> LENGTH: 1776
<212> TYPE: DNA
<213> ORGANISM: mycobacterium tuberculosis
<220> FEATURE:
<223> OTHER INFORMATION: DNA sequence Rv3871

<400> SEQUENCE: 14
atgactgctg aaccggaagt acggacgctg cgcgaggttg tgctggacca gctcggcact     60
gctgaatcgc gtgcgtacaa gatgtggctg ccgccgttga ccaatccggt cccgctcaac    120
gagctcatcg cccgtgatcg gcgacaaccc ctgcgatttg ccctggggat catggatgaa    180
ccgcgccgcc atctacagga tgtgtgggc gtagacgttt ccggggccgg cggcaacatc     240
ggtattgggg gcgcacctca aaccgggaag tcgacgctac tgcagacgat ggtgatgtcg    300
gccgccgcca cacactcacc gcgcaacgtt cagttctatt gcatcgacct aggtggcggc    360
gggctgatct atctcgaaaa ccttccacac gtcggtgggg tagccaatcg gtccgagccc    420
gacaaggtca accgggtggt cgcagagatg caagccgtca tgcggcaacg ggaaaccacc    480
ttcaaggaac accgagtggg ctcgatcggg atgtaccggc agctgcgtga cgatccaagt    540 caaccgttg cgtccgatcc atacggcgac gtctttctga tcatcgacgg atggcccggt    600
tttgtcggcg agttccccga ccttgagggg caggttcaag atctggccgc ccaggggctg    660
gcgttcggcg tccacgtcat catctccacg ccacgctgga cagagctgaa gtcgcgtgtt    720
cgcgactacc tcggcaccaa gatcgagttc cggcttggtg acgtcaatga aacccagatc    780
gaccggatta cccgcgagat cccggcgaat cgtccgggtc gggcagtgtc gatggaaaag    840
caccatctga tgatcggcgt gcccaggttc gacggcgtgc acagcgccga taacctggtg    900
gaggcgatca ccgcggggt gacgcagatc gcttcccagc acaccgaaca ggcacctccg    960
gtgcgggtcc tgccggagcg tatccacctg cacgaactcg acccgaaccc gccgggacca   1020
gagtccgact accgcactcg ctgggagatt ccgatcggct gcgcgagac ggacctgacg    1080 ccggctcact gccacatgca cacgaacccg cacctactga tcttcggtgc ggccaaatcg   1140
ggcaagacga ccattgccca cgcgatcgcg cgcgccattt gtgcccgaaa cagtccccag   1200
caggtgcggt tcatgctcgc ggactaccgc tcgggcctgc tggacgcggt gccggacacc   1260
```

```
catctgctgg gcgccggcgc gatcaaccgc aacagcgcgt cgctagacga ggccgttcaa    1320
gcactggcgg tcaacctgaa gaagcggttg ccgccgaccg acctgacgac ggcgcagcta    1380
cgctcgcgtt cgtggtggag cggatttgac gtcgtgcttc tggtcgacga ttggcacatg    1440
atcgtgggtg ccgccggggg gatgccgccg atggcaccgc tggccccgtt attgccggcg    1500
gcggcagata tcgggttgca catcattgtc acctgtcaga tgagccaggc ttacaaggca    1560
accatggaca agttcgtcgg cgccgcattc gggtcgggcg ctccgacaat gttcctttcg    1620
ggcgagaagc aggaattccc atccagtgag ttcaaggtca agcggcgccc ccctggccag    1680
gcatttctcg tctcgccaga cggcaaagag gtcatccagg cccctacat cgagcctcca     1740 gaagaagtgt tcgcagcacc cccaagcgcc ggttaa                               1776

<210> SEQ ID NO 15
<211> LENGTH: 297
<212> TYPE: DNA
<213> ORGANISM: Mycobacterium tuberculosis
<220> FEATURE:
<223> OTHER INFORMATION: PE coding sequence (Rv3872)

<400> SEQUENCE: 15
atggaaaaaa tgtcacatga tccgatcgct gccgacattg gcacgcaagt gagcgacaac      60
gctctgcacg gcgtgacggc cggctcgacg gcgctgacgt cggtgaccgg gctggttccc     120 gcggggccg atgaggtctc cgcccaagcg gcgacggcgt tcacatcgga gggcatccaa     180
ttgctggctt ccaatgcatc ggcccaagac cagctccacc gtgcgggcga agcggtccag     240
gacgtcgccc gcacctattc gcaaatcgac gacggcgccg ccggcgtctt cgccgaa       297

<210> SEQ ID NO 16
<211> LENGTH: 1104
<212> TYPE: DNA
<213> ORGANISM: Mycobacterium tuberculosis
<220> FEATURE:
<223> OTHER INFORMATION: PPE coding sequence (Rv3873)

<400> SEQUENCE: 16
atgctgtggc acgcaatgcc accggagcta aataccgcac ggctgatggc cggcgcgggt     60
ccggctccaa tgcttgcggc ggccgcggga tggcagacgc tttcggcggc tctggacgct   120
caggccgtcg agttgaccgc gcgcctgaac tctctgggag aagcctggac tggaggtggc   180
agcgacaagg cgcttgcggc tgcaacgccg atggtggtct ggctacaaac cgcgtcaaca   240
caggccaaga cccgtgcgat gcaggcgacg gcgcaagccg cggcatacac ccaggccatg   300
gccacgacgc cgtcgctgcc ggagatcgcc gccaaccaca tcacccaggc cgtccttacg   360
gccaccaact tcttcggtat caacacgatc ccgatcgcgt tgaccgagat ggattatttc   420
atccgtatgt ggaaccaggc agccctggca atggaggtct accaggccga gaccgcggtt   480
aacacgcttt tcgagaagct cgagccgatg gcgtcgatcc ttgatcccgg cgcgagccag   540
agcacgacga acccgatctt cggaatgccc tcccctggca gctcaacacc ggttggccag   600
ttgccgccgg cggctaccca gaccctcggc caactgggtg agatgagcgg cccgatgcag   660
cagctgaccc agccgctgca gcaggtgacg tcgttgttca gccaggtggg cggcaccggc   720
ggcggcaacc cagccgacga ggaagccgcg cagatgggcc tgctcggcac cagtccgctg   780
tcgaaccatc cgctggctgg tggatcaggc cccagcgcgg gcgcgggcct gctgcgcgcg   840
gagtcgctac ctggcgcagg tgggtcgttg acccgcacgc cgctgatgtc tcagctgatc   900
```

```
gaaaagccgg ttgcccctc ggtgatgccg gcggctgctg ccggatcgtc ggcgacgggt      960
ggcgccgctc cggtgggtgc gggagcgatg ggccaggtg cgcaatccgg cggctccacc     1020
aggccgggtc tggtcgcgcc ggcaccgctc gcgcaggagc gtgaagaaga cgacgaggac    1080
gactgggacg aagaggacga ctgg                                           1104
```

<210> SEQ ID NO 17
<211> LENGTH: 300
<212> TYPE: DNA
<213> ORGANISM: Mycobacterium tuberculosis
<220> FEATURE:
<223> OTHER INFORMATION: CFP-10 coding sequence (Rv3874)

<400> SEQUENCE: 17

```
atggcagaga tgaagaccga tgccgctacc ctcgcgcagg aggcaggtaa tttcgagcgg       60
atctccggcg acctgaaaac ccagatcgac caggtggagt cgacggcagg ttcgttgcag      120
ggccagtggc gcggcgcggc ggggacggcc gcccaggccg cggtggtgcg cttccaagaa      180
gcagccaata gcagaagca ggaactcgac gagatctcga cgaatattcg tcaggccggc      240
gtccaatact cgagggccga cgaggagcag cagcaggcgc tgtcctcgca aatgggcttc      300
```

<210> SEQ ID NO 18
<211> LENGTH: 285
<212> TYPE: DNA
<213> ORGANISM: Mycobacterium tuberculosis
<220> FEATURE:
<223> OTHER INFORMATION: ESAT-6 coding sequence (Rv3875)

<400> SEQUENCE: 18

```
atgacagagc agcagtggaa tttcgcgggt atcgaggccg cggcaagcgc aatccaggga       60
aatgtcacgt ccattcattc cctccttgac gaggggaagc agtccctgac caagctcgca     120
gcggcctggg gcggtagcgg ttcggaggcg taccagggtg tccagcaaaa atgggacgcc     180
acggctaccg agctgaacaa cgcgctgcag aacctggcgc ggacgatcag cgaagccggt     240
caggcaatgg cttcgaccga aggcaacgtc actgggatgt tcgca                     285
```

<210> SEQ ID NO 19
<211> LENGTH: 2001
<212> TYPE: DNA
<213> ORGANISM: mycobacterium tuberculosis
<220> FEATURE:
<223> OTHER INFORMATION: DNA sequence Rv3876

<400> SEQUENCE: 19

```
atggcggccg actacgacaa gctcttccgg ccgcacgaag gtatggaagc tccggacgat       60
atggcagcgc agccgttctt cgaccccagt gcttcgtttc gccggcgcc cgcatcggca      120 aacctaccga agcccaacgg ccagactccg ccccgacgt ccgacgacct gtcggagcgg      180
ttcgtgtcgg ccccgcgcc gccacccca ccccaccctc cgcctccgcc aactccgatg       240
ccgatcgccg caggagagcc gccctcgccg gaaccggccg catctaaacc acccacaccc     300
cccatgccca tcgccggacc cgaaccggcc cacccaaaac cacccacacc cccatgccc      360 atcgccggac ccgaaccggc cccacccaaa ccacccacac ctccgatgcc catcgccgga    420
cctgcaccca ccccaaccga atcccagttg gcgcccccca gaccaccgac accacaaacg    480
ccaaccggag cgccgcagca accggaatca ccggcgcccc acgtaccctc gcacgggca    540 catcaaccc ggcgcaccgc accagcaccg ccctgggcaa agatgccaat cggcgaaccc    600
ccgcccgctc cgtccagacc gtctgcgtcc ccggccgaac caccgaccg gcctgcccc    660
```

```
caacactccc gacgtgcgcg ccggggtcac cgctatcgca cagacaccga acgaaacgtc    720
gggaaggtag caactggtcc atccatccag gcgcggctgc gggcagagga agcatccggc    780
gcgcagctcg cccccggaac ggagccctcg ccagcgccgt tgggccaacc gagatcgtat    840
ctggctccgc ccaccgccc cgcgccgaca gaacctcccc ccagcccctc gccgcagcgc    900
aactccggtc ggcgtgccga gcgacgcgtc caccccgatt tagccgccca acatgccgcg    960
gcgcaacctg attcaattac ggccgcaacc actggcggtc gtcgccgcaa gcgtgcagcg   1020
ccggatctcg acgcgacaca gaaatcctta aggccggcgg ccaaggggcc gaaggtgaag   1080
aaggtgaagc cccagaaacc gaaggccacg aagccgccca aagtggtgtc gcagcgcggc   1140
tggcgacatt gggtgcatgc gttgacgcga atcaacctgg gcctgtcacc cgacgagaag   1200
tacgagctgg acctgcacgc tcgagtccgc cgcaatcccc gcgggtcgta tcagatcgcc   1260
gtcgtcggtc tcaaaggtgg ggctggcaaa accacgctga cagcagcgtt ggggtcgacg   1320
ttggctcagg tgcgggccga ccggatcctg gctctagacg cggatccagg cgccggaaac   1380
ctcgccgatc gggtagggcg acaatcgggc gcgaccatcg ctgatgtgct tgcagaaaaa   1440
gagctgtcgc actacaacga catccgcgca cacactagcg tcaatgcggt caatctggaa   1500
gtgctgccgg caccggaata cagctcggcg cagcgcgcgc tcagcgacgc cgactggcat   1560 tcatcgccg atcctgcgtc gaggttttac aacctcgtct tggctgattg tggggccggc   1620
ttcttcgacc cgctgacccg cggcgtgctg tccacggtgt ccggtgtcgt ggtcgtggca   1680
agtgtctcaa tcgacggcgc acaacaggcg tcggtcgcgt tggactggtt gcgcaacaac   1740
ggttaccaag atttggcgag ccgcgcatgc gtggtcatca atcacatcat gccgggagaa   1800
cccaatgtcg cagttaaaga cctggtgcgg catttcgaac agcaagttca acccggccgg   1860
gtcgtggtca tgccgtggga caggcacatt gcggccggaa ccgagatttc actcgacttg   1920
ctcgacccta tctacaagcg caaggtcctg gaattggccg cagcgctatc cgacgatttc   1980
gagagggctg gacgtcgttg a                                              2001
```

<210> SEQ ID NO 20
<211> LENGTH: 1536
<212> TYPE: DNA
<213> ORGANISM: mycobacterium tuberculosis
<220> FEATURE:
<223> OTHER INFORMATION: DNA sequence Rv3877

<400> SEQUENCE: 20

```
ttgagcgcac ctgctgttgc tgctggtcct accgccgcgg gggcaaccgc tgcgcggcct     60
gccaccaccc gggtgacgat cctgaccggc agacggatga ccgatttggt actgccagcg    120
gcggtgccga tggaaactta tattgacgac accgtcgcgg tgctttccga ggtgttggaa    180
gacacgccgg ctgatgtact cggcggcttc gactttaccg cgcaaggcgt gtgggcgttc    240
gctcgtcccg gatcgccgcc gctgaagctc gaccagtcac tcgatgacgc cggggtggtc    300
gacgggtcac tgctgactct ggtgtcagtc agtcgcaccg agcgctaccg accgttggtc    360
gaggatgtca tcgacgcgat cgccgtgctt gacgagtcac ctgagttcga ccgcacggca    420
ttgaatcgct ttgtgggggc ggcgatcccg cttttgaccg cgcccgtcat cgggatggcg    480
atgcgggcgt ggtgggaaac tgggcgtagc ttgtggtggc cgttgcgat tggcatcctg    540 gggatcgctg tgctggtagg cagcttcgtc gcgaacaggt tctaccagag cggccacctg    600
gccgagtgcc tactggtcac gacgtatctg ctgatcgcaa ccgccgcagc gctggccgtg    660
```

| | |
|---|---|
| ccgttgccgc gcggggtcaa ctcgttgggg gcgccacaag ttgccggcgc cgctacggcc | 720 |
| gtgctgtttt tgaccttgat gacgcgggc ggccctcgga agcgtcatga gttggcgtcg | 780 |
| tttgccgtga tcaccgctat cgcggtcatc gcggccgccg ctgccttcgg ctatggatac | 840 |
| caggactggg tccccgcggg ggggatcgca ttcggctgt tcattgtgac gaatgcggcc | 900 |
| aagctgaccg tcgcggtcgc gcggatcgcg ctgccgccga ttccggtacc cggcgaaacc | 960 |
| gtggacaacg aggagttgct cgatcccgtc gcgaccccgg aggctaccag cgaagaaacc | 1020 |
| ccgacctggc aggccatcat cgcgtcggtg cccgcgtccg cggtccggct caccgagcgc | 1080 |
| agcaaactgg ccaagcaact tctgatcgga tacgtcacgt cgggcaccct gattctggct | 1140 |
| gccggtgcca tcgcggtcgt ggtgcgcggg cacttctttg tacacagcct ggtggtcgcg | 1200 |
| ggtttgatca cgaccgtctg cggatttcgc tcgcggcttt acgccgagcg ctggtgtgcg | 1260 |
| tgggcgttgc tggcggcgac ggtcgcgatt ccgacgggtc tgacggccaa actcatcatc | 1320 |
| tggtacccgc actatgcctg gctgttgttg agcgtctacc tcacggtagc cctggttgcg | 1380 |
| ctcgtggtgg tcgggtcgat ggctcacgtc cggcgcgttt caccggtcgt aaaacgaact | 1440 |
| ctggaattga tcgacggcgc catgatcgct gccatcattc ccatgctgct gtggatcacc | 1500 |
| ggggtgtacg acacggtccg caatatccgg ttctga | 1536 |

<210> SEQ ID NO 21
<211> LENGTH: 840
<212> TYPE: DNA
<213> ORGANISM: Mycobacterium tuberculosis
<220> FEATURE:
<223> OTHER INFORMATION: DNA sequence Rv3878

<400> SEQUENCE: 21

| | |
|---|---|
| atggctgaac cgttggccgt cgatcccacc ggcttgagcg cagcggccgc gaaattggcc | 60 |
| ggcctcgttt ttccgcagcc tccggcgccg atcgcggtca gcggaacgga ttcggtggta | 120 |
| gcagcaatca acgagaccat gccaagcatc gaatcgctgg tcagtgacgg gctgcccggc | 180 |
| gtgaaagccg ccctgactcg aacagcatcc aacatgaacg cggcggcgga cgtctatgcg | 240 |
| aagaccgatc agtcactggg aaccagtttg agccagtatg cattcggctc gtcgggcgaa | 300 |
| ggcctggctg gcgtcgcctc ggtcggtggt cagccaagtc aggctaccca gctgctgagc | 360 |
| acacccgtgt cacaggtcac gacccagctc ggcgagacgg ccgctgagct ggcacccccgt | 420 |
| gttgttgcga cggtgccgca actcgttcag ctggctccgc acgccgttca gatgtcgcaa | 480 |
| aacgcatccc ccatcgctca gacgatcagt caaaccgccc aacaggccgc ccagagcgcg | 540 |
| cagggcggca gcggcccaat gcccgcacag cttgccagcg ctgaaaaacc ggccaccgag | 600 |
| caagcggagc cggtccacga agtgacaaac gacgatcagg gcgaccaggg cgacgtgcag | 660 |
| ccggccgagg tcgttgccgc ggcacgtgac gaaggcgccg gcgcatcacc gggccagcag | 720 |
| cccggcgggg gcgttccgc gcaagccatg gataccggag ccggtgcccg cccagcggcg | 780 |
| agtccgctgg cggccccgt cgatccgtcg actccggcac cctcaacaac cacaacgttg | 840 |

<210> SEQ ID NO 22
<211> LENGTH: 2187
<212> TYPE: DNA
<213> ORGANISM: Mycobacterium tuberculosis
<220> FEATURE:
<223> OTHER INFORMATION: DNA sequence Rv3879c

<400> SEQUENCE: 22

| | |
|---|---|
| atgagtatta ccaggccgac gggcagctat gccagacaga tgctggatcc gggcggctgg | 60 |

-continued

```
gtggaagccg atgaagacac tttctatgac cgggcccagg aatatagcca ggttttgcaa      120
agggtcaccg atgtattgga cacctgccgc cagcagaaag gccacgtctt cgaaggcggc      180
ctatggtccg gcggcgccgc caatgctgcc aacggcgccc tgggtgcaaa catcaatcaa      240
ttgatgacgc tgcaggatta tctcgccacg gtgattacct ggcacaggca tattgccggg      300
ttgattgagc aagctaaatc cgatatcggc aataatgtgg atggcgctca acgggagatc      360
gatatcctgg agaatgaccc tagcctggat gctgatgagc gccataccgc catcaattca      420
ttggtcacgg cgacgcatgg ggccaatgtc agtctggtcg ccagaccgc tgagcgggtg       480
ctggaatcca agaattggaa acctccgaag aacgcactcg aggatttgct tcagcagaag      540
tcgccgccac cccagacgt gcctaccctg gtcgtgccat ccccgggcac accgggcaca      600
ccgggaaccc cgatcacccc gggaaccccg atcaccccgg aaccccaat cacacccatc       660
ccggagcgc cggtaactcc gatcacacca acgcccggca ctcccgtcac gccggtgacc       720
ccgggcaagc cggtcacccc ggtgaccccg gtcaaaccgg gcacaccagg cgagccaacc      780
ccgatcacgc cggtcacccc cccggtcgcc ccggccacac cggcaacccc ggccacgccc      840
gttacccag ctcccgctcc acaccgcag ccggctccgg caccggcgcc atcgcctggg        900
ccccagccgg ttacaccggc cactcccggt ccgtctggtc cagcaacacc gggcacccca     960
gggggcgagc cggcgccgca cgtcaaaccc gcggcgttgg cggagcaacc tggtgtgccg     1020
ggccagcatg cgggcgggg gacgcagtcg gggcctgccc atgcggacga atccgccgcg      1080
tcggtgacgc cggctgcggc gtccggtgtc ccggcgcac gggcggcggc cgccgcgccg      1140
agcggtaccg ccgtgggagc gggcgcgcgt tcgagcgtgg gtacggccgc ggcctcgggc     1200
gcggggtcgc atgctgccac tgggcgggcg ccggtggcta cctcggacaa ggcggcggca     1260
ccgagcacgc gggcggcctc ggcgcggacg gcacctcctg cccgccgcc gtcgaccgat      1320
cacatcgaca aacccgatcg cagcgagtct gcagatgacg gtacgccggt gtcgatgatc     1380
ccggtgtcgg cggctcgggc ggcacgcgac gccgccactg cagctgccag cgcccgccag     1440
cgtggccgcg gtgatgcgct gcggttggcg cgacgcatcg cggcggcgct caacgcgtcc     1500
gacaacaacg cgggcgacta cgggttcttc tggatcaccg cggtgaccac cgacggttcc     1560
atcgtcgtgg ccaacagcta tgggctggcc tacatacccg acgggatgga attgccgaat     1620
aaggtgtact tggccagcgc ggatcacgca atcccggttg acgaaattgc acgctgtgcc     1680
acctacccgg ttttggccgt gcaagcctgg gcggctttcc acgacatgac gctgcgggcg     1740
gtgatcggta ccgcggagca gttggccagt tcggatcccg gtgtggccaa gattgtgctg     1800
gagccagatg acattccgga gagcggcaaa atgacgggcc ggtcgcggct ggaggtcgtc     1860
gaccctcgg cggcggctca gctggccgac actaccgatc agcgtttgct cgacttgttg      1920
ccgccggcgc cggtggatgt caatccaccg ggcgatgagc ggcacatgct gtggttcgag     1980
ctgatgaagc ccatgaccag caccgctacc ggccgcgagg ccgctcatct gcgggcgttc     2040
cgggcctacg ctgcccactc acaggagatt gccctgcacc aagcgcacac tgcgactgac     2100
gcggccgtcc agcgtgtggc cgtcgcggac tggctgtact ggcaatacgt caccgggttg     2160
ctcgaccggg ccctggccgc cgcatgc                                          2187
```

<210> SEQ ID NO 23
<211> LENGTH: 345
<212> TYPE: DNA
<213> ORGANISM: Mycobacterium tuberculosis
<220> FEATURE:

<223> OTHER INFORMATION: DNA sequence Rv3880c

<400> SEQUENCE: 23

```
gtgagcatgg acgaattgga cccgcatgtc gcccgggcgt tgacgctggc ggcgcggttt     60
cagtcggccc tagacgggac gctcaatcag atgaacaacg gatccttccg cgccaccgac   120
gaagccgaga ccgtcgaagt gacgatcaat gggcaccagt ggctcaccgg cctgcgcatc   180
gaagatggtt tgctgaagaa gctgggtgcc gaggcggtgg ctcagcgggt caacgaggcg   240
ctgcacaatg cgcaggccgc ggcgtccgcg tataacgacg cggcgggcga gcagctgacc   300
gctgcgttat cggccatgtc ccgcgcgatg aacgaaggaa tggcc                   345
```

<210> SEQ ID NO 24
<211> LENGTH: 1380
<212> TYPE: DNA
<213> ORGANISM: Mycobacterium tuberculosis
<220> FEATURE:
<223> OTHER INFORMATION: DNA sequence Rv3881c

<400> SEQUENCE: 24

```
atgacgcagt cgcagaccgt gacggtggat cagcaagaga ttttgaacag ggccaacgag     60
gtggaggccc cgatggcgga cccaccgact gatgtcccca tcacaccgtg cgaactcacg   120
gcggctaaaa acgccgccca acagctggta ttgtccgccg acaacatgcg ggaatacctg   180
gcggccggtg ccaaagagcg gcagcgtctg gcgacctcgc tgcgcaacgc ggccaaggcg   240
tatggcgagg ttgatgagga ggctgcgacc gcgctggaca cgacggcga aggaactgtg     300
caggcagaat cggccggggc cgtcggaggg gacagttcgg ccgaactaac cgatacgccg   360
agggtggcca cggccggtga acccaacttc atggatctca agaagcggc aaggaagctc   420
gaaacgggcg accaaggcgc atcgctcgcg cactttgcgg atgggtggaa cactttcaac   480
ctgacgctgc aaggcgacgt caagcggttc cgggggtttg acaactggga aggcgatgcg   540
gctaccgctt gcgaggcttc gctcgatcaa caacggcaat ggatactcca catggccaaa   600
ttgagcgctg cgatggccaa gcaggctcaa tatgtcgcgc agctgcacgt gtgggctagg   660
cgggaacatc cgacttatga agacatagtc gggctcgaac ggctttacgc ggaaaaccct   720
tcggcccgcg accaaattct cccggtgtac gcggagtatc agcagaggtc ggagaaggtg   780
ctgaccgaat acaacaacaa ggcagccctg gaaccggtaa acccgccgaa gcctccccccc  840
gccatcaaga tcgaccccgcc cccgcctccg caagagcagg gattgatccc tggcttcctg   900
atgccgccgt ctgacggctc cggtgtgact cccggtaccg ggatgccagc cgcaccgatg   960
gttccgccta ccggatcgcc gggtggtggc ctcccggctg acacggcggc gcagctgacg   1020
tcggctgggc gggaagccgc agcgctgtcg ggcgacgtgt cggtcaaagc ggcatcgctc   1080
ggtggcggtg gaggcggcgg ggtgccgtcg gcgccgttgg gatccgcgat cggggcgcc   1140
gaatcggtgc ggcccgctgg cgctggtgac attgccggct taggccaggg aagggccggc   1200
ggcggcgccg cgctgggcgg cggtggcatg ggaatgccga tgggtgccgc gcatcaggga   1260
caaggggggcg ccaagtccaa gggttctcag caggaagacg aggcgctcta caccgaggat   1320
cgggcatgga ccgaggccgt cattggtaac cgtcggcgcc aggacagtaa ggagtcgaag   1380
```

<210> SEQ ID NO 25
<211> LENGTH: 1386
<212> TYPE: DNA
<213> ORGANISM: Mycobacterium tuberculosis
<220> FEATURE:
<223> OTHER INFORMATION: DNA sequence Rv3882c

<400> SEQUENCE: 25

```
atgagaaatc ctttagggct gcggttcagc accgggcacg ccttgcttgc ctccgcgttg      60
gccccgccat gcatcatcgc attcttggag acgcgctact ggtgggcggg gattgcgctg     120
gcctcgttgg gcgtcatcgt ggccacggtc actttctacg gccgccggat caccggctgg     180
gtggcggcgt gtacgcgtg gttgcggcgg cgccgacggc ccccggattc ctcgtcagaa      240
cctgtggtcg gggccaccgt gaagccagga gatcacgttg cggtgcgctg gcaaggcgag     300
tttctggtcg cctaatcga gctcattccc cgaccattca cgccgacggt catcgtcgac      360
gggcaagccc acaccgacga catgctggac accggactgg tggaggagct cctgtcggtg     420
cactgtcccg acttggaggc cgatatcgtc tcagccggct accgcgtcgg caataccgca     480
gcgccggacg tggtgagtct gtatcagcag gtgatcggga cagacccggc gccggcgaac     540
cgccggacct ggatcgtgct gcgcgccgac ccggaacgca cccgcaaatc ggcgcagcgc     600
cgcgatgaag gcgtcgcagg actggcccgg tatttggtgg cgtccgcgac gcgcattgcc     660
gatcgactgg ctagccatgg tgtcgacgcg gtgtgtggcc gcagcttcga tgactacgac     720
cacgccaccg acatcggctt tgtgcgggag aaatggtcga tgatcaaggg gcgcgatgcc     780
tacactgccg cctacgcggc gccgggaggt ccggatgtat ggtggtcggc gcgcgcggac     840
cacaccatca ccagagtccg ggtcgcgccg ggatggccc cgcagtccac ggtgttgctg      900
accacggcgg acaagcccaa gacacccagg ggcttcgccc gcctatttgg cgggcagcgg     960
cccgcgctgc aaggccagca tctggtgcc aaccgccact gccagctgcc gatcgggtca     1020
gctggggtac tggtcggcga cgtgaac cgatgcccgg tctacatgcc cttcgacgat     1080
gtcgacatcg ccctcaacct gggtgacgct cagacattca cccagttcgt ggtgcgtgcg     1140
gcggcggcag gtgcgatggt cacagtcggg ccacagttcg aggaatttgc ccggttgatc     1200
ggcgcacaca tcgggcagga ggtaaaggtg gcgtggccga atgcgacgac ctatctcggc     1260
ccgcatcccg gtattgaccg ggtgattctg cggcacaatg tgatcggtac cccgcggcat     1320
cggcagctgc cgattcgccg ggtttcccca cccgaggaaa gccgctacca gatggcgctg     1380
ccgaag                                                                1386
```

<210> SEQ ID NO 26
<211> LENGTH: 1338
<212> TYPE: DNA
<213> ORGANISM: Mycobacterium tuberculosis
<220> FEATURE:
<223> OTHER INFORMATION: DNA sequence Rv3883c

<400> SEQUENCE: 26

```
gtgcaccgta tctttctgat cacggtggcg ctggcgttgc tcaccgcgtc gcccgcatcg      60
gccatcacgc caccgccgat cgatccgggc gcgttgccgc cgacgtgac gggcccggat     120
cagcctaccg aacagcgcgt tttgtgcgcg tcgcccacca cgctgccggg gtccgggttc     180
cacgatccgc cgtggagcaa cacgtatctg ggcgtggccg atgcccacaa gttcgcgacc     240
ggggccgggg tgacggtggc ggtgatcgac accggtgtcg acgcttcgcc acgggtcccg     300
gcggaacctg gcgcgatttt cgtcgaccag gccggtaacg gcctgtctga ctgtgatgcc     360
catgggactc tcacagcatc catcatcgcg ggccggcccc gcccaccga cggttcgtc     420
ggcgtcgcgc ccgacgctcg actgctctcg ctacgtcaga cgtctgaggc cttcgaaccg     480
gtcggctcac aagccaaccc gaatgacccc aacgccaccc cggccgccgg ttccatccgc     540
```

```
agtcttgccc gcgccgtggt gcacgccgcc aacctcggcg tgggtgtgat caacatcagt      600
gaagccgcct gctacaaggt gagcaggccg atcgatgaaa cctcactggg tgcatccatc      660
gactatgcgg tcaacgtcaa aggcgtggtg gtggtggtcg cggccggcaa caccggtggc      720
gattgcgtac agaatccggc gccggacccg tccacacccg cgacccacg cggctggaac       780 aatgtgcaga ccgttgtcac cccgcgtgg tacgcaccgc tggtgttaag cgtcggcggt       840
atcggccaga ccgggatgcc cagctcgttc tcgatgcacg gaccgtgggt ggacgtggcc      900
gcgcccgcag aaaacatcgt cgcgctcggc gacaccggtg aaccggtgaa tgcgctgcaa      960
ggccgggagg ggccggtacc catcgccggc acctcgtttg ccgcggcata tgtgtcgggt     1020
ctggcggccc tgcttcggca gcggttcccc gacctgacgc cggcgcagat catccaccgg     1080
atcaccgcca ccgcgagaca ccccgggggc ggggtcgacg acctggtcgg cgccggcgtc     1140
atcgatgcgg tggccgcgct gacgtgggac attccgcccg ccctgcttc ggcgccatac      1200 aacgtcagac gacttccacc cccggtggtg gagccgggtc ccgatcgtcg cccgattacg     1260
gctgtggcgt tggtggccgt cggccttacg ttggccctgg gcctgggcgc gctggctaga     1320
cgggcgctga gccgccga                                                   1338

<210> SEQ ID NO 27
<211> LENGTH: 1857
<212> TYPE: DNA
<213> ORGANISM: Mycobacterium tuberculosis
<220> FEATURE:
<223> OTHER INFORMATION: DNA sequence Rv3884c

<400> SEQUENCE: 27
atgtcgagaa tggtggacac gatgggtgat ttactcactg cgcgccggca tttcgatcgg       60
gcgatgacga tcaagaatgg ccagggatgc gtggcggcgt tgcctgagtt tgtggctgcc      120
accgaggccg atccgtcgat ggccgacgcg tggctgggtc gtatcgcctg cggtgaccgc      180
gatctggcct cgcttaagca gctcaacgcc catagcgagt ggctgcaccg cgagaccacg      240
cggatcggcc ggacgttggc cgctgaggtc cagctgggac catccatcgg atcacggtg       300 accgacgcat ctcaggtggg gctggcgctg tcgtcggcgt tgacgatcgc ggggagtat      360 gcgaaggccg atgccctgtt agcaaaccgc gagctattgg attcgtggcg caactaccag     420
tggcatcagc tggctcgggc gttcctgatg tacgtcacga agcgatggcc cgacgtgttg     480
tcgacggccg ccgaggatct gccgccacag gcgatcgtca tgccggcggt gaccgcgtcg     540
atttgtgcgc tggcagccca cgccgccgcc catctcgggc aggggcgagt ggccctggac     600
tggctggacc gggtggacgt gatcggacac agcaggtcat cggagcggtt cggcgccgac     660
gtgctcaccg cggcgatcgg accggccgat attccgctgc tggtcgccga cttggcgtat     720
gtgcggggga tggtgtaccg gcaactgcat gaggaggaca aggcccagat ctggctgtcg     780
aaggccacca tcaacggggt gctcaccgac gccgccaaag aagccctggc ggacccgaac     840
ctgcgcttga ttgttaccga tgaacgaacc atcgccagcc gctccgaccg ttgggatgct     900
tcgacggcga aaagccgcga ccagctcgat gacgacaatg cagcgcagcg gcgcggcgag     960
ctgctagccg agggccggga actgctggcc aaacaggtgg gcctggcggc ggtcaagcaa    1020
gcggtatcgg cgctggaaga ccaactcgag gtgcgcatga tgcgcctaga gcacggccta    1080
ccggtggagg ggcagaccaa ccacatgttg ctggtggggc caccaggcac aggtaagaca    1140
accaccgctg aagcgctcgg caagatctac gccggcatgg ggatcgtgcg tcaccccgaa    1200
attcgagaag ttcgccgatc ggacttctgt gggcactaca tcggggagtc aggacccaag    1260
```

| | |
|---|---|
| acgaacgagc tgatcgaaaa gtcactcggg cgaatcattt tcatggacga gttctactcg | 1320 |
| ctgatcgaac gtcatcaaga cggaacaccg gacatgatcg gcatggaggc ggtcaatcaa | 1380 |
| ctcctggttc aattggaaac acaccgattc gacttctgtt tcatcgggc cggctatgag | 1440 |
| gatcaggtgg atgaattcct caccgtgaac ccgggtttgg ctggccggtt caaccgaaag | 1500 |
| ctgcggttcg agtcttattc gccggtggag atcgtcgaga ttggacaccg ctacgctaca | 1560 |
| ccgcgcgcca gccagctcga tgacgccgca cgggaggtat tcctcgacgc ggtcaccacc | 1620 |
| atccgtaact acaccacccc tagtgggcag cacggtatcg acgctatgca aaacggtcgg | 1680 |
| ttcgcccgca acgtgatcga acgcgccgaa gggttccggg cacccgggt ggttgcgcaa | 1740 |
| aaacgtgcgg gccaaccggt atcggttcag gatctgcaga tcatcaccgc caccgacatc | 1800 |
| gatgccgcga tacgcagcgt gtgctcagac aaccgagaca tggccgcgat cgtttgg | 1857 |

<210> SEQ ID NO 28
<211> LENGTH: 1611
<212> TYPE: DNA
<213> ORGANISM: Mycobacterium tuberculosis
<220> FEATURE:
<223> OTHER INFORMATION: DNA sequence Rv3885c

<400> SEQUENCE: 28

| | |
|---|---|
| ttgacgtcca agctgaccgg gttcagcccg cgcagtgcga ggcgggtcgc cggggtgtgg | 60 |
| acagtgttcg tgctcgcgtc ggcgggctgg gcgctgggcg ccagctagg tgcggtcatg | 120 |
| gctgtcgtgg tcggcgtcgc cttggtgttc gtacagtggt ggggtcagcc ggcgtggtcg | 180 |
| tgggcggtac tggggctgcg gggtcggcgt cccgtcaaat ggaatgaccc aattaccttg | 240 |
| gccaacaacc gatccggggg tggcgtccgc gtgcaagacg tgtcgcggt ggtggcggtg | 300 |
| caacttctcg gccgagcgca ccgggcgact acggtcaccg ggtcggtgac cgtagaaagc | 360 |
| gacaacgtga ttgacgtcgt tgagctcgcg ccgttgctgc gccacccgct ggacctggaa | 420 |
| ctcgattcaa tcagcgtcgt caccttcggc tcgcgaaccg gcaccgtcgg cgattacccg | 480 |
| cgggtgtatg acgcggagat cggtacgccg ccgtatgccg gcggcgcga aacgtggctg | 540 |
| atcatgcggc ttccggtgat cggcaacacc caagctttac gctggcgtac cagcgttggg | 600 |
| gccgctgcca tttcggtcgc ccaacgcgtt gccagctccc tgcgctgtca gggcttgcgc | 660 |
| gccaaactgg ccaccgcaac agacttggct gagcttgatc gccggctggg gtcggacgcg | 720 |
| gtagccggga gtgcgcagcg ctggaaagct atccgcggtg aagccgggtg gatgacgacg | 780 |
| tatgcgtacc cggctgaggc gatttcgtcg cgggttctct cgcaagcctg gacgctgcgt | 840 |
| gccgatgagg tcatccagaa cgtaacggtg tatccggacg cgacgtgcac cgcgaccatc | 900 |
| accgtgcgca caccgacgcc ggcgcctacc ccgcccagtg tgatcttgcg tcggctcaat | 960 |
| ggtgagcaag ccgccgcggc tgcggccaac atgtgcgggc cacgtccaca cctacgcgga | 1020 |
| cagcggcgct gcccgttgcc ggcgcagcta gtcaccgaga tcggaccgtc gggggtgttg | 1080 |
| attggcaagc tgagcaacgg ggaccggctg atgattcccg ttaccgacgc cggtgagctg | 1140 |
| tcgcgcgtct tcgtggccgc ggacgacacg atcgccaaga ggatcgtgat tcgcgtcgtc | 1200 |
| ggtgccggtg agcgggtgtg tgtgcacact cgcgaccaag agcgttgggc cagcgtacgc | 1260 |
| atgccgcagt tgagcatcgt cggcacacca cggcccgcgc gcgcaccac tgtcggcgtc | 1320 |
| gtggagtacg tgcggcggcg caagaacggc gatgacggca aatctgaagg cagcggtgtc | 1380 |
| gatgtcgcga tttcgcccac gccacggcca gccagtgtca tcaccattgc ccgacccggt | 1440 |

```
acctcgctgt ccgagagcga tcggcatggc ttcgaggtga ccatcgaaca aatcgatcgg      1500
gcaacggtga aagtcggtgc ggcaggacaa aactggctgg ttgagatgga aatgttccgt      1560
gcggagaacc gctatgtcag ccttgagccg gtcacgatgt cgataggccg g               1611

<210> SEQ ID NO 29
<211> LENGTH: 620
<212> TYPE: DNA
<213> ORGANISM: Mycobacterium tuberculosis
<220> FEATURE:
<223> OTHER INFORMATION: CFP-10 + ESAT-6

<400> SEQUENCE: 29
atggcagaga tgaagaccga tgccgctacc ctcgcgcagg aggcaggtaa tttcgagcgg        60
atctccggcg acctgaaaac ccagatcgac caggtggagt cgacggcagg ttcgttgcag       120
ggccagtggc gcggcgcggc ggggacggcc gcccaggccg cggtggtgcg cttccaagaa       180
gcagccaata agcagaagca ggaactcgac gagatctcga cgaatattcg tcaggccggc       240
gtccaatact cgagggccga cgaggagcag cagcaggcgc tgtcctcgca aatgggcttc       300
tgacccgcta atacgaaaag aaacggagca aaaacatgac agagcagcag tggaatttcg       360
cgggtatcga ggccgcggca agcgcaatcc agggaaatgt cacgtccatt cattccctcc       420
ttgacgaggg gaagcagtcc ctgaccaagc tcgcagcggc ctgggcggt agcggttcgg        480 aggcgtacca gggtgtccag caaaaatggg acgccacggc taccgagctg aacaacgcgc       540
tgcagaacct ggcgcggacg atcagcgaag ccggtcaggc aatggcttcg accgaaggca       600
acgtcactgg gatgttcgca                                                   620

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Primer
      SP6-BAC1

<400> SEQUENCE: 30
agttagctca ctcattaggc a                                                  21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Primer
      T7-BAC1

<400> SEQUENCE: 31
ggatgtgctg caaggcgatt a                                                  21

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Primer
      esat-6F

<400> SEQUENCE: 32
gtcacgtcca ttcattccct                                                    20

<210> SEQ ID NO 33
```

```
<211> LENGTH: 19
<212> TYPE: DNA
<213> ORGANISM: Artificial Sequence
<220> FEATURE:
<223> OTHER INFORMATION: Description of Artificial Sequence: Primer
      esat-6R

<400> SEQUENCE: 33
atcccagtga cgttgcctt                                                  19

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Primer
      RD1mic flanking region F

<400> SEQUENCE: 34
gcagtgcaaa ggtgcagata                                                 20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Primer
      RD1mic flanking region R

<400> SEQUENCE: 35
gattgagaca cttgccacga                                                 20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Primer
      plcA.int.F

<400> SEQUENCE: 36
caagtttggt ctggtcgaat                                                 20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Primer
      plcA.int.R

<400> SEQUENCE: 37
gctacccaag gtctcctggt                                                 20

<210> SEQ ID NO 38
<211> LENGTH: 153
<212> TYPE: DNA
<213> ORGANISM: Mycobacterium tuberculosis
<220> FEATURE:
<223> OTHER INFORMATION: Sequences at the junction RD1mic

<400> SEQUENCE: 38
caagacgagg ttgtaaaacc tcgacgcagg atcggcgatg aaatgccagt cggcgtcgct     60
gagcgcgcgc tgcgccgagt cccatttttgt cgctgatttg tttgaacagc gacgaaccgg   120
tgttgaaaat gtcgcctggg tcggggattc cct                                 153
```

```
<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Primer
      RD5mic flanking region F

<400> SEQUENCE: 39
gaatgccgac gtcatatcg                                             19

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Primer
      RD5mic flanking region R

<400> SEQUENCE: 40
cggccactga gttcgattat                                            20

<210> SEQ ID NO 41
<211> LENGTH: 152
<212> TYPE: DNA
<213> ORGANISM: Mycobacterium tuberculosis
<220> FEATURE:
<223> OTHER INFORMATION: Sequence at the junction RD5mic

<400> SEQUENCE: 41
cctcgatgaa ccacctgaca tgaccccatc ctttccaaga actggagtct ccggacatgc    60
cggggcggtt cactgcccca ggtgtcctgg gtcgttccgt tgaccgtcga gtccgaacat   120
ccgtcattcc cggtggcagt cggtgcggtg ac                                152

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Primer
      MiD1 flanking region F

<400> SEQUENCE: 42
cagccaacac caagtagacg                                            20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Primer
      MiD1 flanking region R

<400> SEQUENCE: 43
tctacctgca gtcgcttgtg                                            20

<210> SEQ ID NO 44
<211> LENGTH: 123
<212> TYPE: DNA
<213> ORGANISM: Mycobacterium tuberculosis
<220> FEATURE:
<223> OTHER INFORMATION: Sequence at the junction MiD1

<400> SEQUENCE: 44
cacctgacat gaccccatcc tttccaagaa ctggagtctc cggacatgcc ggggcggttc    60
```

```
agggacattc atgtccatct tctggcagat cagcagatcg cttgttctca gtgcaggtga    120
gtc                                                                  123

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Primer
      MiD2 flanking region R

<400> SEQUENCE: 45
gtccatcgag gatgtcgagt                                                 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Primer
      MiD2 flanking region L

<400> SEQUENCE: 46
ctaggccatt ccgttgtctg                                                 20

<210> SEQ ID NO 47
<211> LENGTH: 151
<212> TYPE: DNA
<213> ORGANISM: Mycobacterium tuberculosis
<220> FEATURE:
<223> OTHER INFORMATION: Sequence at the junction MiD2

<400> SEQUENCE: 47
gctgcctact acgctcaacg ccagagacca gccgccggct gaggtctcag atcagagagt    60
ctccggactc accggggcgg ttcataaagg cttcgagacc ggacgggctg taggttcctc   120
aactgtgtgg cggatggtct gagcacttaa c                                  151

<210> SEQ ID NO 48
<211> LENGTH: 15
<212> TYPE: DNA
<213> ORGANISM: Artificial Sequence
<220> FEATURE:
<223> OTHER INFORMATION: Description of Artificial Sequence: Primer
      MiD3 flanking region R

<400> SEQUENCE: 48
ggcgacgcca tttcc                                                      15

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Primer
      MiD3 flanking region L

<400> SEQUENCE: 49
aactgtcggg cttgctctt                                                  19

<210> SEQ ID NO 50
<211> LENGTH: 181
<212> TYPE: DNA
<213> ORGANISM: Mycobacterium tuberculosis
<220> FEATURE:
```

<223> OTHER INFORMATION: Sequence at the junction MiD3

<400> SEQUENCE: 50

```
tggcgccggc acctccgttg ccaccgttgc cgccgctggt gggcgcggtg ccgttcgccc      60
cggccgaacc gttcagggcc gggttcgccc tcagccgcta acacgccga ccaagatcaa     120
cgagctacct gcccggtcaa ggttgaagag ccccatatc agcaagggcc cggtgtcggc     180
g                                                                    181
```

<210> SEQ ID NO 51
<211> LENGTH: 108
<212> TYPE: PRT
<213> ORGANISM: Mycobacterium tuberculosis
<220> FEATURE:
<223> OTHER INFORMATION: RV3861 - hypothetical protein

<400> SEQUENCE: 51

```
Val Thr Trp Leu Ala Asp Pro Val Gly Asn Ser Arg Ile Ala Arg Ala
  1               5                  10                  15

Gln Ala Cys Lys Thr Ser Ile Ser Ala Pro Ile Val Glu Ser Trp Arg
             20                  25                  30

Ala Gln Arg Gly Ala Gln Cys Gly Gln Arg Glu Lys Ser Cys Arg Cys
         35                  40                  45

Ser Arg Ala Val His Ile Gln Gly Ile Ser Pro Leu Phe Arg Arg
     50                  55                  60

Pro Leu Glu Pro Ala Val Gln Ala Ala Val Ala Ser Cys Arg Leu Gly
 65                  70                  75                  80

Arg His Pro Val Val Ala His Arg Val Thr Val Ala Leu Gly Gln Gly
                 85                  90                  95

Ser Gln Leu Ala Gln Arg Glu Cys Pro Arg Pro Ala
            100                 105
```

<210> SEQ ID NO 52
<211> LENGTH: 116
<212> TYPE: PRT
<213> ORGANISM: Mycobacterium tuberculosis
<220> FEATURE:
<223> OTHER INFORMATION: WHIB6 - Possible transcriptional regulatory
      protein WHIB-like WHIB6

<400> SEQUENCE: 52

```
Met Arg Tyr Ala Phe Ala Ala Glu Ala Thr Thr Cys Asn Ala Phe Trp
  1               5                  10                  15

Arg Asn Val Asp Met Thr Val Thr Ala Leu Tyr Glu Val Pro Leu Gly
             20                  25                  30

Val Cys Thr Gln Asp Pro Asp Arg Trp Thr Thr Thr Pro Asp Asp Glu
         35                  40                  45

Ala Lys Thr Leu Cys Arg Ala Cys Pro Arg Arg Trp Leu Cys Ala Arg
     50                  55                  60

Asp Ala Val Glu Ser Ala Gly Ala Glu Gly Leu Trp Ala Gly Val Val
 65                  70                  75                  80

Ile Pro Glu Ser Gly Arg Ala Arg Ala Phe Ala Leu Gly Gln Leu Arg
                 85                  90                  95

Ser Leu Ala Glu Arg Asn Gly Tyr Pro Val Arg Asp His Arg Val Ser
            100                 105                 110

Ala Gln Ser Ala
        115
```

-continued

```
<210> SEQ ID NO 53
<211> LENGTH: 392
<212> TYPE: PRT
<213> ORGANISM: Mycobacterium tuberculosis
<220> FEATURE:
<223> OTHER INFORMATION: Rv3863 - hypothetical alanine rich protein

<400> SEQUENCE: 53

Met Ala Gly Glu Arg Lys Val Cys Pro Pro Ser Arg Leu Val Pro Ala
  1               5                  10                  15

Asn Lys Gly Ser Thr Gln Met Ser Lys Ala Gly Ser Thr Val Gly Pro
             20                  25                  30

Ala Pro Leu Val Ala Cys Ser Gly Thr Ser Asp Val Ile Glu Pro
         35                  40                  45

Arg Arg Gly Val Ala Ile Ile Gly His Ser Cys Arg Val Gly Thr Gln
     50                  55                  60

Ile Asp Asp Ser Arg Ile Ser Gln Thr His Leu Arg Ala Val Ser Asp
 65                  70                  75                  80

Asp Gly Arg Trp Arg Ile Val Gly Asn Ile Pro Arg Gly Met Phe Val
                 85                  90                  95

Gly Gly Arg Arg Gly Ser Ser Val Thr Val Ser Asp Lys Thr Leu Ile
            100                 105                 110

Arg Phe Gly Asp Pro Pro Gly Gly Lys Ala Leu Thr Phe Glu Val Val
        115                 120                 125

Arg Pro Ser Asp Ser Ala Ala Gln His Gly Arg Val Gln Pro Ser Ala
    130                 135                 140

Asp Leu Ser Asp Asp Pro Ala His Asn Ala Ala Pro Val Ala Pro Asp
145                 150                 155                 160

Pro Gly Val Val Arg Ala Gly Ala Ala Ala Ala Arg Arg Arg Glu
                165                 170                 175

Leu Asp Ile Ser Gln Arg Ser Leu Ala Ala Asp Gly Ile Ile Asn Ala
            180                 185                 190

Gly Ala Leu Ile Ala Phe Glu Lys Gly Arg Ser Trp Pro Arg Glu Arg
        195                 200                 205

Thr Arg Ala Lys Leu Glu Glu Val Leu Gln Trp Pro Ala Gly Thr Ile
    210                 215                 220

Ala Arg Ile Arg Arg Gly Glu Pro Thr Glu Pro Ala Thr Asn Pro Asp
225                 230                 235                 240

Ala Ser Pro Gly Leu Arg Pro Ala Asp Gly Pro Ala Ser Leu Ile Ala
                245                 250                 255

Gln Ala Val Thr Ala Ala Val Asp Gly Cys Ser Leu Ala Ile Ala Ala
            260                 265                 270

Leu Pro Ala Thr Glu Asp Pro Glu Phe Thr Glu Arg Ala Ala Pro Ile
        275                 280                 285

Leu Ala Asp Leu Arg Gln Leu Glu Ala Ile Ala Val Gln Ala Thr Arg
    290                 295                 300

Ile Ser Arg Ile Thr Pro Glu Leu Ile Lys Ala Leu Gly Ala Val Arg
305                 310                 315                 320

Arg His His Asp Glu Leu Met Arg Leu Gly Ala Thr Ala Pro Gly Ala
                325                 330                 335

Thr Leu Ala Gln Arg Leu Tyr Ala Ala Arg Arg Ala Asn Leu Ser
            340                 345                 350

Thr Leu Glu Thr Ala Gln Ala Ala Gly Val Ala Glu Glu Met Ile Val
        355                 360                 365

Gly Ala Glu Ala Glu Glu Glu Leu Pro Ala Glu Ala Thr Glu Ala Ile
```

```
                    370                 375                 380
Glu Ala Leu Ile Arg Gln Ile Asn
385                 390

<210> SEQ ID NO 54
<211> LENGTH: 402
<212> TYPE: PRT
<213> ORGANISM: Mycobacterium tuberculosis
<220> FEATURE:
<223> OTHER INFORMATION: Rv3864 - conserved hypothetical protein

<400> SEQUENCE: 54

Met Ala Ser Gly Ser Gly Leu Cys Lys Thr Thr Ser Asn Phe Ile Trp
  1               5                  10                  15

Gly Gln Leu Leu Leu Gly Glu Gly Ile Pro Asp Pro Gly Asp Ile
                 20                  25                  30

Phe Asn Thr Gly Ser Ser Leu Phe Lys Gln Ile Ser Asp Lys Met Gly
             35                  40                  45

Leu Ala Ile Pro Gly Thr Asn Trp Ile Gly Gln Ala Ala Glu Ala Tyr
         50                  55                  60

Leu Asn Gln Asn Ile Ala Gln Gln Leu Arg Ala Gln Val Met Gly Asp
 65                  70                  75                  80

Leu Asp Lys Leu Thr Gly Asn Met Ile Ser Asn Gln Ala Lys Tyr Val
                 85                  90                  95

Ser Asp Thr Arg Asp Val Leu Arg Ala Met Lys Lys Met Ile Asp Gly
            100                 105                 110

Val Tyr Lys Val Cys Lys Gly Leu Glu Lys Ile Pro Leu Leu Gly His
        115                 120                 125

Leu Trp Ser Trp Glu Leu Ala Ile Pro Met Ser Gly Ile Ala Met Ala
    130                 135                 140

Val Val Gly Gly Ala Leu Leu Tyr Leu Thr Ile Met Thr Leu Met Asn
145                 150                 155                 160

Ala Thr Asn Leu Arg Gly Ile Leu Gly Arg Leu Ile Glu Met Leu Thr
                165                 170                 175

Thr Leu Pro Lys Phe Pro Gly Leu Pro Gly Leu Pro Ser Leu Pro Asp
            180                 185                 190

Ile Ile Asp Gly Leu Trp Pro Pro Lys Leu Pro Asp Ile Pro Ile Pro
        195                 200                 205

Gly Leu Pro Asp Ile Pro Gly Leu Pro Asp Phe Lys Trp Pro Pro Thr
    210                 215                 220

Pro Gly Ser Pro Leu Phe Pro Asp Leu Pro Ser Phe Pro Gly Phe Pro
225                 230                 235                 240

Gly Phe Pro Glu Phe Pro Ala Ile Pro Gly Phe Pro Ala Leu Pro Gly
                245                 250                 255

Leu Pro Ser Ile Pro Asn Leu Phe Pro Gly Leu Pro Gly Leu Gly Asp
            260                 265                 270

Leu Leu Pro Gly Val Gly Asp Leu Gly Lys Leu Pro Thr Trp Thr Glu
        275                 280                 285

Leu Ala Ala Leu Pro Asp Phe Leu Gly Gly Phe Ala Gly Leu Pro Ser
    290                 295                 300

Leu Gly Phe Gly Asn Leu Leu Ser Phe Ala Ser Leu Pro Thr Val Gly
305                 310                 315                 320

Gln Val Thr Ala Thr Met Gly Gln Leu Gln Gln Leu Val Ala Ala Gly
                325                 330                 335

Gly Gly Pro Ser Gln Leu Ala Ser Met Gly Ser Gln Gln Ala Gln Leu
```

```
                    340                 345                 350
Ile Ser Ser Gln Ala Gln Gln Gly Gly Gln Gln His Ala Thr Leu Val
            355                 360                 365

Ser Asp Lys Lys Glu Asp Glu Glu Gly Val Ala Glu Ala Glu Arg Ala
        370                 375                 380

Pro Ile Asp Ala Gly Thr Ala Ala Ser Gln Arg Gly Gln Glu Gly Thr
385                 390                 395                 400

Val Leu

<210> SEQ ID NO 55
<211> LENGTH: 103
<212> TYPE: PRT
<213> ORGANISM: Mycobacterium tuberculosis
<220> FEATURE:
<223> OTHER INFORMATION: Rv3865 - conserved hypothetical protein

<400> SEQUENCE: 55

Met Thr Gly Phe Leu Gly Val Val Pro Ser Phe Leu Lys Val Leu Ala
  1               5                  10                  15

Gly Met His Asn Glu Ile Val Gly Asp Ile Lys Arg Ala Thr Asp Thr
             20                  25                  30

Val Ala Gly Ile Ser Gly Arg Val Gln Leu Thr His Gly Ser Phe Thr
         35                  40                  45

Ser Lys Phe Asn Asp Thr Leu Gln Glu Phe Glu Thr Thr Arg Ser Ser
     50                  55                  60

Thr Gly Thr Gly Leu Gln Gly Val Thr Ser Gly Leu Ala Asn Asn Leu
 65                  70                  75                  80

Leu Ala Ala Ala Gly Ala Tyr Leu Lys Ala Asp Asp Gly Leu Ala Gly
                 85                  90                  95

Val Ile Asp Lys Ile Phe Gly
            100

<210> SEQ ID NO 56
<211> LENGTH: 283
<212> TYPE: PRT
<213> ORGANISM: Mycobacterium tuberculosis
<220> FEATURE:
<223> OTHER INFORMATION: Rv3866 - conserved hypothetical protein

<400> SEQUENCE: 56

Met Thr Gly Pro Ser Ala Ala Gly Arg Ala Gly Thr Ala Asp Asn Val
  1               5                  10                  15

Val Gly Val Glu Val Thr Ile Asp Gly Met Leu Val Ile Ala Asp Arg
             20                  25                  30

Leu His Leu Val Asp Phe Pro Val Thr Leu Gly Ile Arg Pro Asn Ile
         35                  40                  45

Pro Gln Glu Asp Leu Arg Asp Ile Val Trp Glu Gln Val Gln Arg Asp
     50                  55                  60

Leu Thr Ala Gln Gly Val Leu Asp Leu His Gly Glu Pro Gln Pro Thr
 65                  70                  75                  80

Val Ala Glu Met Val Glu Thr Leu Gly Arg Pro Asp Arg Thr Leu Glu
                 85                  90                  95

Gly Arg Trp Trp Arg Arg Asp Ile Gly Gly Val Met Val Arg Phe Val
                100                 105                 110

Val Cys Arg Arg Gly Asp Arg His Val Ile Ala Ala Arg Asp Gly Asp
            115                 120                 125

Met Leu Val Leu Gln Leu Val Ala Pro Gln Val Gly Leu Ala Gly Met
```

```
                130                 135                 140
Val Thr Ala Val Leu Gly Pro Ala Glu Pro Ala Asn Val Glu Pro Leu
145                 150                 155                 160

Thr Gly Val Ala Thr Glu Leu Ala Glu Cys Thr Thr Ala Ser Gln Leu
                165                 170                 175

Thr Gln Tyr Gly Ile Ala Pro Ala Ser Ala Arg Val Tyr Ala Glu Ile
            180                 185                 190

Val Gly Asn Pro Thr Gly Trp Val Glu Ile Val Ala Ser Gln Arg His
        195                 200                 205

Pro Gly Gly Thr Thr Thr Gln Thr Asp Ala Ala Ala Gly Val Leu Asp
    210                 215                 220

Ser Lys Leu Gly Arg Leu Val Ser Leu Pro Arg Arg Val Gly Gly Asp
225                 230                 235                 240

Leu Tyr Gly Ser Phe Leu Pro Gly Thr Gln Gln Asn Leu Glu Arg Ala
                245                 250                 255

Leu Asp Gly Leu Leu Glu Leu Leu Pro Ala Gly Ala Trp Leu Asp His
            260                 265                 270

Thr Ser Asp His Ala Gln Ala Ser Ser Arg Gly
        275                 280
```

<210> SEQ ID NO 57
<211> LENGTH: 183
<212> TYPE: PRT
<213> ORGANISM: mycobacterium tuberculosis
<220> FEATURE:
<223> OTHER INFORMATION: Protein sequence Rv3867

<400> SEQUENCE: 57

```
Met Val Asp Pro Pro Gly Asn Asp Asp His Gly Asp Leu Asp Ala
1               5                   10                  15

Leu Asp Phe Ser Ala Ala His Thr Asn Glu Ala Ser Pro Leu Asp Ala
                20                  25                  30

Leu Asp Asp Tyr Ala Pro Val Gln Thr Asp Asp Ala Glu Gly Asp Leu
            35                  40                  45

Asp Ala Leu His Ala Leu Thr Glu Arg Asp Glu Glu Pro Glu Leu Glu
    50                  55                  60

Leu Phe Thr Val Thr Asn Pro Gln Gly Ser Val Ser Val Ser Thr Leu
65                  70                  75                  80

Met Asp Gly Arg Ile Gln His Val Glu Leu Thr Asp Lys Ala Thr Ser
                85                  90                  95

Met Ser Glu Ala Gln Leu Ala Asp Glu Ile Phe Val Ile Ala Asp Leu
            100                 105                 110

Ala Arg Gln Lys Ala Arg Ala Ser Gln Tyr Thr Phe Met Val Glu Asn
        115                 120                 125

Ile Gly Glu Leu Thr Asp Glu Asp Ala Glu Gly Ser Ala Leu Leu Arg
    130                 135                 140

Glu Phe Val Gly Met Thr Leu Asn Leu Pro Thr Pro Glu Glu Ala Ala
145                 150                 155                 160

Ala Ala Glu Ala Glu Val Phe Ala Thr Arg Tyr Asp Val Asp Tyr Thr
                165                 170                 175

Ser Arg Tyr Lys Ala Asp Asp
            180
```

<210> SEQ ID NO 58
<211> LENGTH: 573
<212> TYPE: PRT

<213> ORGANISM: mycobacterium tuberculosis
<220> FEATURE:
<223> OTHER INFORMATION: Protein sequence Rv3868

<400> SEQUENCE: 58

```
Met Thr Asp Arg Leu Ala Ser Leu Phe Glu Ser Ala Val Ser Met Leu
1               5                   10                  15

Pro Met Ser Glu Ala Arg Ser Leu Asp Leu Phe Thr Glu Ile Thr Asn
            20                  25                  30

Tyr Asp Glu Ser Ala Cys Asp Ala Trp Ile Gly Arg Ile Arg Cys Gly
        35                  40                  45

Asp Thr Asp Arg Val Thr Leu Phe Arg Ala Trp Tyr Ser Arg Arg Asn
    50                  55                  60

Phe Gly Gln Leu Ser Gly Ser Val Gln Ile Ser Met Ser Thr Leu Asn
65                  70                  75                  80

Ala Arg Ile Ala Ile Gly Gly Leu Tyr Gly Asp Ile Thr Tyr Pro Val
                85                  90                  95

Thr Ser Pro Leu Ala Ile Thr Met Gly Phe Ala Ala Cys Glu Ala Ala
            100                 105                 110

Gln Gly Asn Tyr Ala Asp Ala Met Glu Ala Leu Glu Ala Ala Pro Val
        115                 120                 125

Ala Gly Ser Glu His Leu Val Ala Trp Met Lys Ala Val Val Tyr Gly
    130                 135                 140

Ala Ala Glu Arg Trp Thr Asp Val Ile Asp Gln Val Lys Ser Ala Gly
145                 150                 155                 160

Lys Trp Pro Asp Lys Phe Leu Ala Gly Ala Gly Val Ala His Gly
                165                 170                 175

Val Ala Ala Ala Asn Leu Ala Leu Phe Thr Glu Ala Glu Arg Arg Leu
            180                 185                 190

Thr Glu Ala Asn Asp Ser Pro Ala Gly Glu Ala Cys Ala Arg Ala Ile
        195                 200                 205

Ala Trp Tyr Leu Ala Met Ala Arg Ser Gln Gly Asn Glu Ser Ala
    210                 215                 220

Ala Val Ala Leu Leu Glu Trp Leu Gln Thr Thr His Pro Glu Pro Lys
225                 230                 235                 240

Val Ala Ala Ala Leu Lys Asp Pro Ser Tyr Arg Leu Lys Thr Thr Thr
                245                 250                 255

Ala Glu Gln Ile Ala Ser Arg Ala Asp Pro Trp Asp Pro Gly Ser Val
            260                 265                 270

Val Thr Asp Asn Ser Gly Arg Glu Arg Leu Leu Ala Glu Ala Gln Ala
        275                 280                 285

Glu Leu Asp Arg Gln Ile Gly Leu Thr Arg Val Lys Asn Gln Ile Glu
    290                 295                 300

Arg Tyr Arg Ala Ala Thr Leu Met Ala Arg Val Arg Ala Ala Lys Gly
305                 310                 315                 320

Met Lys Val Ala Gln Pro Ser Lys His Met Ile Phe Thr Gly Pro Pro
                325                 330                 335

Gly Thr Gly Lys Thr Thr Ile Ala Arg Val Val Ala Asn Ile Leu Ala
            340                 345                 350

Gly Leu Gly Val Ile Ala Glu Pro Lys Leu Val Glu Thr Ser Arg Lys
        355                 360                 365

Asp Phe Val Ala Glu Tyr Glu Gly Gln Ser Ala Val Lys Thr Ala Lys
    370                 375                 380

Thr Ile Asp Gln Ala Leu Gly Gly Val Leu Phe Ile Asp Glu Ala Tyr
```

```
                385                 390                 395                 400

Ala Leu Val Gln Glu Arg Asp Gly Arg Thr Asp Pro Phe Gly Gln Glu
                405                 410                 415

Ala Leu Asp Thr Leu Leu Ala Arg Met Glu Asn Asp Arg Asp Arg Leu
                420                 425                 430

Val Val Ile Ile Ala Gly Tyr Ser Ser Asp Ile Asp Arg Leu Leu Glu
                435                 440                 445

Thr Asn Glu Gly Leu Arg Ser Arg Phe Ala Thr Arg Ile Glu Phe Asp
                450                 455                 460

Thr Tyr Ser Pro Glu Glu Leu Leu Glu Ile Ala Asn Val Ile Ala Ala
465                 470                 475                 480

Ala Asp Asp Ser Ala Leu Thr Ala Glu Ala Glu Asn Phe Leu Gln
                485                 490                 495

Ala Ala Lys Gln Leu Glu Gln Arg Met Leu Arg Gly Arg Arg Ala Leu
                500                 505                 510

Asp Val Ala Gly Asn Gly Arg Tyr Ala Arg Gln Leu Val Glu Ala Ser
                515                 520                 525

Glu Gln Cys Arg Asp Met Arg Leu Ala Gln Val Leu Asp Ile Asp Thr
                530                 535                 540

Leu Asp Glu Asp Arg Leu Arg Glu Ile Asn Gly Ser Asp Met Ala Glu
545                 550                 555                 560

Ala Ile Ala Ala Val His Ala His Leu Asn Met Arg Glu
                565                 570

<210> SEQ ID NO 59
<211> LENGTH: 480
<212> TYPE: PRT
<213> ORGANISM: mycobacterium tuberculosis
<220> FEATURE:
<223> OTHER INFORMATION: Protein sequence Rv3869

<400> SEQUENCE: 59

Met Gly Leu Arg Leu Thr Thr Lys Val Gln Val Ser Gly Trp Arg Phe
1               5                   10                  15

Leu Leu Arg Arg Leu Glu His Ala Ile Val Arg Asp Thr Arg Met
                20                  25                  30

Phe Asp Asp Pro Leu Gln Phe Tyr Ser Arg Ser Ile Ala Leu Gly Ile
                35                  40                  45

Val Val Ala Val Leu Ile Leu Ala Gly Ala Ala Leu Leu Ala Tyr Phe
                50                  55                  60

Lys Pro Gln Gly Lys Leu Gly Gly Thr Ser Leu Phe Thr Asp Arg Ala
65                  70                  75                  80

Thr Asn Gln Leu Tyr Val Leu Leu Ser Gly Gln Leu His Pro Val Tyr
                85                  90                  95

Asn Leu Thr Ser Ala Arg Leu Val Leu Gly Asn Pro Ala Asn Pro Ala
                100                 105                 110

Thr Val Lys Ser Ser Glu Leu Ser Lys Leu Pro Met Gly Gln Thr Val
                115                 120                 125

Gly Ile Pro Gly Ala Pro Tyr Ala Thr Pro Val Ser Ala Gly Ser Thr
                130                 135                 140

Ser Ile Trp Thr Leu Cys Asp Thr Val Ala Arg Ala Asp Ser Thr Ser
145                 150                 155                 160

Pro Val Val Gln Thr Ala Val Ile Ala Met Pro Leu Glu Ile Asp Ala
                165                 170                 175

Ser Ile Asp Pro Leu Gln Ser His Glu Ala Val Leu Val Ser Tyr Gln
```

-continued

```
                180                 185                 190
Gly Glu Thr Trp Ile Val Thr Thr Lys Gly Arg His Ala Ile Asp Leu
            195                 200                 205
Thr Asp Arg Ala Leu Thr Ser Ser Met Gly Ile Pro Val Thr Ala Arg
        210                 215                 220
Pro Thr Pro Ile Ser Glu Gly Met Phe Asn Ala Leu Pro Asp Met Gly
225                 230                 235                 240
Pro Trp Gln Leu Pro Pro Ile Pro Ala Ala Gly Ala Pro Asn Ser Leu
                245                 250                 255
Gly Leu Pro Asp Asp Leu Val Ile Gly Ser Val Phe Gln Ile His Thr
            260                 265                 270
Asp Lys Gly Pro Gln Tyr Tyr Val Val Leu Pro Asp Gly Ile Ala Gln
        275                 280                 285
Val Asn Ala Thr Thr Ala Ala Leu Arg Ala Thr Gln Ala His Gly
    290                 295                 300
Leu Val Ala Pro Pro Ala Met Val Pro Ser Leu Val Arg Ile Ala
305                 310                 315                 320
Glu Arg Val Tyr Pro Ser Pro Leu Pro Asp Glu Pro Leu Lys Ile Val
                325                 330                 335
Ser Arg Pro Gln Asp Pro Ala Leu Cys Trp Ser Trp Gln Arg Ser Ala
            340                 345                 350
Gly Asp Gln Ser Pro Gln Ser Thr Val Leu Ser Gly Arg His Leu Pro
        355                 360                 365
Ile Ser Pro Ser Ala Met Asn Met Gly Ile Lys Gln Ile His Gly Thr
    370                 375                 380
Ala Thr Val Tyr Leu Asp Gly Gly Lys Phe Val Ala Leu Gln Ser Pro
385                 390                 395                 400
Asp Pro Arg Tyr Thr Glu Ser Met Tyr Tyr Ile Asp Pro Gln Gly Val
                405                 410                 415
Arg Tyr Gly Val Pro Asn Ala Glu Thr Ala Lys Ser Leu Gly Leu Ser
            420                 425                 430
Ser Pro Gln Asn Ala Pro Trp Glu Ile Val Arg Leu Leu Val Asp Gly
        435                 440                 445
Pro Val Leu Ser Lys Asp Ala Ala Leu Leu Glu His Asp Thr Leu Pro
    450                 455                 460
Ala Asp Pro Ser Pro Arg Lys Val Pro Ala Gly Ala Ser Gly Ala Pro
465                 470                 475                 480
```

<210> SEQ ID NO 60
<211> LENGTH: 747
<212> TYPE: PRT
<213> ORGANISM: mycobacterium tuberculosis
<220> FEATURE:
<223> OTHER INFORMATION: Protein sequence Rv3870

<400> SEQUENCE: 60

```
Met Thr Thr Lys Lys Phe Thr Pro Thr Ile Thr Arg Gly Pro Arg Leu
1               5                   10                  15
Thr Pro Gly Glu Ile Ser Leu Thr Pro Pro Asp Asp Leu Gly Ile Asp
                20                  25                  30
Ile Pro Pro Ser Gly Val Gln Lys Ile Leu Pro Tyr Val Met Gly Gly
            35                  40                  45
Ala Met Leu Gly Met Ile Ala Ile Met Val Ala Gly Gly Thr Arg Gln
        50                  55                  60
Leu Ser Pro Tyr Met Leu Met Met Pro Leu Met Met Ile Val Met Met
```

```
             65                  70                  75                  80
Val Gly Gly Leu Ala Gly Ser Thr Gly Gly Gly Lys Lys Val Pro
                 85                  90                  95
Glu Ile Asn Ala Asp Arg Lys Glu Tyr Leu Arg Tyr Leu Ala Gly Leu
                100                 105                 110
Arg Thr Arg Val Thr Ser Ser Ala Thr Ser Gln Val Ala Phe Phe Ser
                115                 120                 125
Tyr His Ala Pro His Pro Glu Asp Leu Leu Ser Ile Val Gly Thr Gln
                130                 135                 140
Arg Gln Trp Ser Arg Pro Ala Asn Ala Asp Phe Tyr Ala Ala Thr Arg
145                 150                 155                 160
Ile Gly Ile Gly Asp Gln Pro Ala Val Asp Arg Leu Leu Lys Pro Ala
                165                 170                 175
Val Gly Gly Glu Leu Ala Ala Ala Ser Ala Ala Pro Gln Pro Phe Leu
                180                 185                 190
Glu Pro Val Ser His Met Trp Val Val Lys Phe Leu Arg Thr His Gly
                195                 200                 205
Leu Ile His Asp Cys Pro Lys Leu Leu Gln Leu Arg Thr Phe Pro Thr
                210                 215                 220
Ile Ala Ile Gly Gly Asp Leu Ala Gly Ala Ala Gly Leu Met Thr Ala
225                 230                 235                 240
Met Ile Cys His Leu Ala Val Phe His Pro Pro Asp Leu Leu Gln Ile
                245                 250                 255
Arg Val Leu Thr Glu Glu Pro Asp Asp Pro Asp Trp Ser Trp Leu Lys
                260                 265                 270
Trp Leu Pro His Val Gln His Gln Thr Glu Thr Asp Ala Ala Gly Ser
                275                 280                 285
Thr Arg Leu Ile Phe Thr Arg Gln Glu Gly Leu Ser Asp Leu Ala Ala
                290                 295                 300
Arg Gly Pro His Ala Pro Asp Ser Leu Pro Gly Gly Pro Tyr Val Val
305                 310                 315                 320
Val Val Asp Leu Thr Gly Gly Lys Ala Gly Phe Pro Pro Asp Gly Arg
                325                 330                 335
Ala Gly Val Thr Val Ile Thr Leu Gly Asn His Arg Gly Ser Ala Tyr
                340                 345                 350
Arg Ile Arg Val His Glu Asp Gly Thr Ala Asp Asp Arg Leu Pro Asn
                355                 360                 365
Gln Ser Phe Arg Gln Val Thr Ser Val Thr Asp Arg Met Ser Pro Gln
                370                 375                 380
Gln Ala Ser Arg Ile Ala Arg Lys Leu Ala Gly Trp Ser Ile Thr Gly
385                 390                 395                 400
Thr Ile Leu Asp Lys Thr Ser Arg Val Gln Lys Lys Val Ala Thr Asp
                405                 410                 415
Trp His Gln Leu Val Gly Ala Gln Ser Val Glu Ile Thr Pro Ser
                420                 425                 430
Arg Trp Arg Met Tyr Thr Asp Thr Asp Arg Asp Arg Leu Lys Ile Pro
                435                 440                 445
Phe Gly His Glu Leu Lys Thr Gly Asn Val Met Tyr Leu Asp Ile Lys
                450                 455                 460
Glu Gly Ala Glu Phe Gly Ala Gly Pro His Gly Met Leu Ile Gly Thr
465                 470                 475                 480
Thr Gly Ser Gly Lys Ser Glu Phe Leu Arg Thr Leu Ile Leu Ser Leu
                485                 490                 495
```

```
Val Ala Met Thr His Pro Asp Gln Val Asn Leu Leu Thr Asp Phe
            500                 505                 510

Lys Gly Gly Ser Thr Phe Leu Gly Met Glu Lys Leu Pro His Thr Ala
            515                 520                 525

Ala Val Val Thr Asn Met Ala Glu Glu Ala Glu Leu Val Ser Arg Met
            530                 535                 540

Gly Glu Val Leu Thr Gly Glu Leu Asp Arg Arg Gln Ser Ile Leu Arg
545                 550                 555                 560

Gln Ala Gly Met Lys Val Gly Ala Ala Gly Ala Leu Ser Gly Val Ala
                565                 570                 575

Glu Tyr Glu Lys Tyr Arg Glu Arg Gly Ala Asp Leu Pro Pro Leu Pro
            580                 585                 590

Thr Leu Phe Val Val Asp Glu Phe Ala Glu Leu Leu Gln Ser His
            595                 600                 605

Pro Asp Phe Ile Gly Leu Phe Asp Arg Ile Cys Arg Val Gly Arg Ser
            610                 615                 620

Leu Arg Val His Leu Leu Ala Thr Gln Ser Leu Gln Thr Gly Gly
625                 630                 635                 640

Val Arg Ile Asp Lys Leu Glu Pro Asn Leu Thr Tyr Arg Ile Ala Leu
                645                 650                 655

Arg Thr Thr Ser Ser His Glu Ser Lys Ala Val Ile Gly Thr Pro Glu
                660                 665                 670

Ala Gln Tyr Ile Thr Asn Lys Glu Ser Gly Val Gly Phe Leu Arg Val
                675                 680                 685

Gly Met Glu Asp Pro Val Lys Phe Ser Thr Phe Tyr Ile Ser Gly Pro
690                 695                 700

Tyr Met Pro Pro Ala Ala Gly Val Glu Thr Asn Gly Glu Ala Gly Gly
705                 710                 715                 720

Pro Gly Gln Gln Thr Thr Arg Gln Ala Ala Arg Ile His Arg Phe Thr
                725                 730                 735

Ala Ala Pro Val Leu Glu Glu Ala Pro Thr Pro
            740                 745

<210> SEQ ID NO 61
<211> LENGTH: 591
<212> TYPE: PRT
<213> ORGANISM: mycobacterium tuberculosis
<220> FEATURE:
<223> OTHER INFORMATION: Protein sequence Rv3871

<400> SEQUENCE: 61

Met Thr Ala Glu Pro Glu Val Arg Thr Leu Arg Glu Val Val Leu Asp
1               5                   10                  15

Gln Leu Gly Thr Ala Glu Ser Arg Ala Tyr Lys Met Trp Leu Pro Pro
            20                  25                  30

Leu Thr Asn Pro Val Pro Leu Asn Glu Leu Ile Ala Arg Asp Arg Arg
        35                  40                  45

Gln Pro Leu Arg Phe Ala Leu Gly Ile Met Asp Glu Pro Arg Arg His
    50                  55                  60

Leu Gln Asp Val Trp Gly Val Asp Val Ser Gly Ala Gly Gly Asn Ile
65                  70                  75                  80

Gly Ile Gly Gly Ala Pro Gln Thr Gly Lys Ser Thr Leu Leu Gln Thr
                85                  90                  95

Met Val Met Ser Ala Ala Ala Thr His Ser Pro Arg Asn Val Gln Phe
            100                 105                 110
```

-continued

```
Tyr Cys Ile Asp Leu Gly Gly Gly Leu Ile Tyr Leu Glu Asn Leu
            115                 120                 125

Pro His Val Gly Gly Val Ala Asn Arg Ser Glu Pro Asp Lys Val Asn
        130                 135                 140

Arg Val Val Ala Glu Met Gln Ala Val Met Arg Gln Arg Glu Thr Thr
145                 150                 155                 160

Phe Lys Glu His Arg Val Gly Ser Ile Gly Met Tyr Arg Gln Leu Arg
                165                 170                 175

Asp Asp Pro Ser Gln Pro Val Ala Ser Asp Pro Tyr Gly Asp Val Phe
            180                 185                 190

Leu Ile Ile Asp Gly Trp Pro Gly Phe Val Gly Glu Phe Pro Asp Leu
        195                 200                 205

Glu Gly Gln Val Gln Asp Leu Ala Ala Gln Gly Leu Ala Phe Gly Val
    210                 215                 220

His Val Ile Ile Ser Thr Pro Arg Trp Thr Glu Leu Lys Ser Arg Val
225                 230                 235                 240

Arg Asp Tyr Leu Gly Thr Lys Ile Glu Phe Arg Leu Gly Asp Val Asn
                245                 250                 255

Glu Thr Gln Ile Asp Arg Ile Thr Arg Glu Ile Pro Ala Asn Arg Pro
            260                 265                 270

Gly Arg Ala Val Ser Met Glu Lys His His Leu Met Ile Gly Val Pro
        275                 280                 285

Arg Phe Asp Gly Val His Ser Ala Asp Asn Leu Val Glu Ala Ile Thr
    290                 295                 300

Ala Gly Val Thr Gln Ile Ala Ser Gln His Thr Glu Gln Ala Pro Pro
305                 310                 315                 320

Val Arg Val Leu Pro Glu Arg Ile His Leu His Glu Leu Asp Pro Asn
                325                 330                 335

Pro Pro Gly Pro Glu Ser Asp Tyr Arg Thr Arg Trp Glu Ile Pro Ile
            340                 345                 350

Gly Leu Arg Glu Thr Asp Leu Thr Pro Ala His Cys His Met His Thr
        355                 360                 365

Asn Pro His Leu Leu Ile Phe Gly Ala Ala Lys Ser Gly Lys Thr Thr
    370                 375                 380

Ile Ala His Ala Ile Ala Arg Ala Ile Cys Ala Arg Asn Ser Pro Gln
385                 390                 395                 400

Gln Val Arg Phe Met Leu Ala Asp Tyr Arg Ser Gly Leu Leu Asp Ala
                405                 410                 415

Val Pro Asp Thr His Leu Leu Gly Ala Gly Ala Ile Asn Arg Asn Ser
            420                 425                 430

Ala Ser Leu Asp Glu Ala Val Gln Ala Leu Ala Val Asn Leu Lys Lys
        435                 440                 445

Arg Leu Pro Pro Thr Asp Leu Thr Thr Ala Gln Leu Arg Ser Arg Ser
    450                 455                 460

Trp Trp Ser Gly Phe Asp Val Val Leu Leu Val Asp Asp Trp His Met
465                 470                 475                 480

Ile Val Gly Ala Ala Gly Gly Met Pro Pro Met Ala Pro Leu Ala Pro
                485                 490                 495

Leu Leu Pro Ala Ala Ala Asp Ile Gly Leu His Ile Ile Val Thr Cys
            500                 505                 510

Gln Met Ser Gln Ala Tyr Lys Ala Thr Met Asp Lys Phe Val Gly Ala
        515                 520                 525
```

-continued

```
Ala Phe Gly Ser Gly Ala Pro Thr Met Phe Leu Ser Gly Glu Lys Gln
    530                 535                 540

Glu Phe Pro Ser Ser Glu Phe Lys Val Lys Arg Arg Pro Pro Gly Gln
545                 550                 555                 560

Ala Phe Leu Val Ser Pro Asp Gly Lys Glu Val Ile Gln Ala Pro Tyr
                565                 570                 575

Ile Glu Pro Pro Glu Glu Val Phe Ala Ala Pro Pro Ser Ala Gly
            580                 585                 590

<210> SEQ ID NO 62
<211> LENGTH: 99
<212> TYPE: PRT
<213> ORGANISM: Mycobacterium tuberculosis
<220> FEATURE:
<223> OTHER INFORMATION: Rv3872-PE35 - PE family-related protein

<400> SEQUENCE: 62

Met Glu Lys Met Ser His Asp Pro Ile Ala Ala Asp Ile Gly Thr Gln
  1               5                  10                  15

Val Ser Asp Asn Ala Leu His Gly Val Thr Ala Gly Ser Thr Ala Leu
                 20                  25                  30

Thr Ser Val Thr Gly Leu Val Pro Ala Gly Ala Asp Glu Val Ser Ala
             35                  40                  45

Gln Ala Ala Thr Ala Phe Thr Ser Glu Gly Ile Gln Leu Leu Ala Ser
         50                  55                  60

Asn Ala Ser Ala Gln Asp Gln Leu His Arg Ala Gly Glu Ala Val Gln
 65                  70                  75                  80

Asp Val Ala Arg Thr Tyr Ser Gln Ile Asp Asp Gly Ala Ala Gly Val
                 85                  90                  95

Phe Ala Glu

<210> SEQ ID NO 63
<211> LENGTH: 368
<212> TYPE: PRT
<213> ORGANISM: Mycobacterium tuberculosis
<220> FEATURE:
<223> OTHER INFORMATION: Rv3873-PPE68 - PPE family protein

<400> SEQUENCE: 63

Met Leu Trp His Ala Met Pro Pro Glu Leu Asn Thr Ala Arg Leu Met
  1               5                  10                  15

Ala Gly Ala Gly Pro Ala Pro Met Leu Ala Ala Ala Gly Trp Gln
                 20                  25                  30

Thr Leu Ser Ala Ala Leu Asp Ala Gln Ala Val Glu Leu Thr Ala Arg
             35                  40                  45

Leu Asn Ser Leu Gly Glu Ala Trp Thr Gly Gly Ser Asp Lys Ala
         50                  55                  60

Leu Ala Ala Ala Thr Pro Met Val Val Trp Leu Gln Thr Ala Ser Thr
 65                  70                  75                  80

Gln Ala Lys Thr Arg Ala Met Gln Ala Thr Gln Ala Ala Tyr
                 85                  90                  95

Thr Gln Ala Met Ala Thr Thr Pro Ser Leu Pro Glu Ile Ala Ala Asn
                100                 105                 110

His Ile Thr Gln Ala Val Leu Thr Ala Thr Asn Phe Phe Gly Ile Asn
            115                 120                 125

Thr Ile Pro Ile Ala Leu Thr Glu Met Asp Tyr Phe Ile Arg Met Trp
        130                 135                 140
```

-continued

Asn Gln Ala Ala Leu Ala Met Glu Val Tyr Gln Ala Glu Thr Ala Val
145                 150                 155                 160

Asn Thr Leu Phe Glu Lys Leu Glu Pro Met Ala Ser Ile Leu Asp Pro
            165                 170                 175

Gly Ala Ser Gln Ser Thr Thr Asn Pro Ile Phe Gly Met Pro Ser Pro
        180                 185                 190

Gly Ser Ser Thr Pro Val Gly Gln Leu Pro Pro Ala Thr Gln Thr
    195                 200                 205

Leu Gly Gln Leu Gly Glu Met Ser Gly Pro Met Gln Gln Leu Thr Gln
    210                 215                 220

Pro Leu Gln Gln Val Thr Ser Leu Phe Ser Gln Val Gly Gly Thr Gly
225                 230                 235                 240

Gly Gly Asn Pro Ala Asp Glu Glu Ala Gln Met Gly Leu Leu Gly
                245                 250                 255

Thr Ser Pro Leu Ser Asn His Pro Leu Ala Gly Gly Ser Gly Pro Ser
            260                 265                 270

Ala Gly Ala Gly Leu Leu Arg Ala Glu Ser Leu Pro Gly Ala Gly Gly
        275                 280                 285

Ser Leu Thr Arg Thr Pro Leu Met Ser Gln Leu Ile Glu Lys Pro Val
    290                 295                 300

Ala Pro Ser Val Met Pro Ala Ala Ala Gly Ser Ser Ala Thr Gly
305                 310                 315                 320

Gly Ala Ala Pro Val Gly Ala Gly Ala Met Gly Gln Gly Ala Gln Ser
                325                 330                 335

Gly Gly Ser Thr Arg Pro Gly Leu Val Ala Pro Ala Pro Leu Ala Gln
            340                 345                 350

Glu Arg Glu Glu Asp Glu Asp Asp Trp Asp Glu Glu Asp Asp Trp
        355                 360                 365

<210> SEQ ID NO 64
<211> LENGTH: 100
<212> TYPE: PRT
<213> ORGANISM: Mycobacterium tuberculosis
<220> FEATURE:
<223> OTHER INFORMATION: Rv3874-esxB - 10kDa culture filtrate
      antigen CFP10

<400> SEQUENCE: 64

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
            20                  25                  30

Glu Ser Thr Ala Gly Ser Leu Gln Gly Gln Trp Arg Gly Ala Ala Gly
        35                  40                  45

Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe
            100

<210> SEQ ID NO 65
<211> LENGTH: 95
<212> TYPE: PRT
<213> ORGANISM: Mycobacterium tuberculosis

```
<220> FEATURE:
<223> OTHER INFORMATION: Rv3875-Esat6 - 6 kDa early secretory
      antigenic target Esat6 (Esat-6)

<400> SEQUENCE: 65

Met Thr Glu Gln Gln Trp Asn Phe Ala Gly Ile Glu Ala Ala Ser
  1               5                  10                  15

Ala Ile Gln Gly Asn Val Thr Ser Ile His Ser Leu Leu Asp Glu Gly
             20                  25                  30

Lys Gln Ser Leu Thr Lys Leu Ala Ala Ala Trp Gly Gly Ser Gly Ser
         35                  40                  45

Glu Ala Tyr Gln Gly Val Gln Gln Lys Trp Asp Ala Thr Ala Thr Glu
     50                  55                  60

Leu Asn Asn Ala Leu Gln Asn Leu Ala Arg Thr Ile Ser Glu Ala Gly
 65                  70                  75                  80

Gln Ala Met Ala Ser Thr Glu Gly Asn Val Thr Gly Met Phe Ala
                 85                  90                  95

<210> SEQ ID NO 66
<211> LENGTH: 666
<212> TYPE: PRT
<213> ORGANISM: mycobacterium tuberculosis
<220> FEATURE:
<223> OTHER INFORMATION: Protein sequence Rv3876

<400> SEQUENCE: 66

Met Ala Ala Asp Tyr Asp Lys Leu Phe Arg Pro His Glu Gly Met Glu
  1               5                  10                  15

Ala Pro Asp Asp Met Ala Ala Gln Pro Phe Phe Asp Pro Ser Ala Ser
             20                  25                  30

Phe Pro Pro Ala Pro Ala Ser Ala Asn Leu Pro Lys Pro Asn Gly Gln
         35                  40                  45

Thr Pro Pro Pro Thr Ser Asp Asp Leu Ser Glu Arg Phe Val Ser Ala
     50                  55                  60

Pro Pro Pro Pro Pro Pro Pro Pro Pro Pro Pro Pro Thr Pro Met
 65                  70                  75                  80

Pro Ile Ala Ala Gly Glu Pro Pro Ser Pro Glu Pro Ala Ala Ser Lys
                 85                  90                  95

Pro Pro Thr Pro Pro Met Pro Ile Ala Gly Pro Glu Pro Ala Pro Pro
                100                 105                 110

Lys Pro Pro Thr Pro Pro Met Pro Ile Ala Gly Pro Glu Pro Ala Pro
            115                 120                 125

Pro Lys Pro Pro Thr Pro Pro Met Pro Ile Ala Gly Pro Ala Pro Thr
        130                 135                 140

Pro Thr Glu Ser Gln Leu Ala Pro Pro Arg Pro Pro Thr Pro Gln Thr
145                 150                 155                 160

Pro Thr Gly Ala Pro Gln Gln Pro Glu Ser Pro Ala Pro His Val Pro
                165                 170                 175

Ser His Gly Pro His Gln Pro Arg Arg Thr Ala Pro Ala Pro Pro Trp
            180                 185                 190

Ala Lys Met Pro Ile Gly Glu Pro Pro Ala Pro Ser Arg Pro Ser
        195                 200                 205

Ala Ser Pro Ala Glu Pro Pro Thr Arg Pro Ala Pro Gln His Ser Arg
    210                 215                 220

Arg Ala Arg Arg Gly His Arg Tyr Arg Thr Asp Thr Glu Arg Asn Val
225                 230                 235                 240
```

-continued

```
Gly Lys Val Ala Thr Gly Pro Ser Ile Gln Ala Arg Leu Arg Ala Glu
            245                 250                 255

Glu Ala Ser Gly Ala Gln Leu Ala Pro Gly Thr Glu Pro Ser Pro Ala
        260                 265                 270

Pro Leu Gly Gln Pro Arg Ser Tyr Leu Ala Pro Thr Arg Pro Ala
        275                 280                 285

Pro Thr Glu Pro Pro Pro Ser Pro Ser Pro Gln Arg Asn Ser Gly Arg
290                 295                 300

Arg Ala Glu Arg Arg Val His Pro Asp Leu Ala Ala Gln His Ala Ala
305                 310                 315                 320

Ala Gln Pro Asp Ser Ile Thr Ala Ala Thr Thr Gly Gly Arg Arg Arg
                325                 330                 335

Lys Arg Ala Ala Pro Asp Leu Asp Ala Thr Gln Lys Ser Leu Arg Pro
                340                 345                 350

Ala Ala Lys Gly Pro Lys Val Lys Lys Val Lys Pro Gln Lys Pro Lys
            355                 360                 365

Ala Thr Lys Pro Pro Lys Val Val Ser Gln Arg Gly Trp Arg His Trp
        370                 375                 380

Val His Ala Leu Thr Arg Ile Asn Leu Gly Leu Ser Pro Asp Glu Lys
385                 390                 395                 400

Tyr Glu Leu Asp Leu His Ala Arg Val Arg Arg Asn Pro Arg Gly Ser
                405                 410                 415

Tyr Gln Ile Ala Val Val Gly Leu Lys Gly Ala Gly Lys Thr Thr
                420                 425                 430

Leu Thr Ala Ala Leu Gly Ser Thr Leu Ala Gln Val Arg Ala Asp Arg
            435                 440                 445

Ile Leu Ala Leu Asp Ala Asp Pro Gly Ala Gly Asn Leu Ala Asp Arg
        450                 455                 460

Val Gly Arg Gln Ser Gly Ala Thr Ile Ala Asp Val Leu Ala Glu Lys
465                 470                 475                 480

Glu Leu Ser His Tyr Asn Asp Ile Arg Ala His Thr Ser Val Asn Ala
                485                 490                 495

Val Asn Leu Glu Val Leu Pro Ala Pro Glu Tyr Ser Ser Ala Gln Arg
            500                 505                 510

Ala Leu Ser Asp Ala Asp Trp His Phe Ile Ala Asp Pro Ala Ser Arg
        515                 520                 525

Phe Tyr Asn Leu Val Leu Ala Asp Cys Gly Ala Gly Phe Phe Asp Pro
530                 535                 540

Leu Thr Arg Gly Val Leu Ser Thr Val Ser Gly Val Val Val Ala
545                 550                 555                 560

Ser Val Ser Ile Asp Gly Ala Gln Gln Ala Ser Val Ala Leu Asp Trp
                565                 570                 575

Leu Arg Asn Asn Gly Tyr Gln Asp Leu Ala Ser Arg Ala Cys Val Val
            580                 585                 590

Ile Asn His Ile Met Pro Gly Glu Pro Asn Val Ala Val Lys Asp Leu
        595                 600                 605

Val Arg His Phe Glu Gln Val Gln Pro Gly Arg Val Val Met
610                 615                 620

Pro Trp Asp Arg His Ile Ala Ala Gly Thr Glu Ile Ser Leu Asp Leu
625                 630                 635                 640

Leu Asp Pro Ile Tyr Lys Arg Lys Val Leu Glu Leu Ala Ala Ala Leu
                645                 650                 655

Ser Asp Asp Phe Glu Arg Ala Gly Arg Arg
```

<210> SEQ ID NO 67
<211> LENGTH: 511
<212> TYPE: PRT
<213> ORGANISM: mycobacterium tuberculosis
<220> FEATURE:
<223> OTHER INFORMATION: Protein sequence Rv3877

<400> SEQUENCE: 67

```
Met Ser Ala Pro Ala Val Ala Gly Pro Thr Ala Gly Ala Thr
1               5                   10                  15

Ala Ala Arg Pro Ala Thr Thr Arg Val Thr Ile Leu Thr Gly Arg Arg
            20                  25                  30

Met Thr Asp Leu Val Leu Pro Ala Ala Val Pro Met Glu Thr Tyr Ile
        35                  40                  45

Asp Asp Thr Val Ala Val Leu Ser Glu Val Leu Glu Asp Thr Pro Ala
    50                  55                  60

Asp Val Leu Gly Gly Phe Asp Phe Thr Ala Gln Gly Val Trp Ala Phe
65                  70                  75                  80

Ala Arg Pro Gly Ser Pro Pro Leu Lys Leu Asp Gln Ser Leu Asp Asp
                85                  90                  95

Ala Gly Val Val Asp Gly Ser Leu Leu Thr Leu Val Ser Val Ser Arg
            100                 105                 110

Thr Glu Arg Tyr Arg Pro Leu Val Glu Asp Val Ile Asp Ala Ile Ala
        115                 120                 125

Val Leu Asp Glu Ser Pro Glu Phe Asp Arg Thr Ala Leu Asn Arg Phe
    130                 135                 140

Val Gly Ala Ala Ile Pro Leu Leu Thr Ala Pro Val Ile Gly Met Ala
145                 150                 155                 160

Met Arg Ala Trp Trp Glu Thr Gly Arg Ser Leu Trp Trp Pro Leu Ala
                165                 170                 175

Ile Gly Ile Leu Gly Ile Ala Val Leu Val Gly Ser Phe Val Ala Asn
            180                 185                 190

Arg Phe Tyr Gln Ser Gly His Leu Ala Glu Cys Leu Leu Val Thr Thr
        195                 200                 205

Tyr Leu Leu Ile Ala Thr Ala Ala Ala Leu Ala Val Pro Leu Pro Arg
    210                 215                 220

Gly Val Asn Ser Leu Gly Ala Pro Gln Val Ala Gly Ala Thr Ala
225                 230                 235                 240

Val Leu Phe Leu Thr Leu Met Thr Arg Gly Gly Pro Arg Lys Arg His
                245                 250                 255

Glu Leu Ala Ser Phe Ala Val Ile Thr Ala Ile Ala Val Ile Ala Ala
            260                 265                 270

Ala Ala Ala Phe Gly Tyr Gly Tyr Gln Asp Trp Val Pro Ala Gly Gly
        275                 280                 285

Ile Ala Phe Gly Leu Phe Ile Val Thr Asn Ala Ala Lys Leu Thr Val
    290                 295                 300

Ala Val Ala Arg Ile Ala Leu Pro Pro Ile Pro Val Pro Gly Glu Thr
305                 310                 315                 320

Val Asp Asn Glu Glu Leu Leu Asp Pro Val Ala Thr Pro Glu Ala Thr
                325                 330                 335

Ser Glu Glu Thr Pro Thr Trp Gln Ala Ile Ile Ala Ser Val Pro Ala
            340                 345                 350

Ser Ala Val Arg Leu Thr Glu Arg Ser Lys Leu Ala Lys Gln Leu Leu
```

```
                355                 360                 365
Ile Gly Tyr Val Thr Ser Gly Thr Leu Ile Leu Ala Ala Gly Ala Ile
        370                 375                 380

Ala Val Val Arg Gly His Phe Phe Val His Ser Leu Val Val Ala
385                 390                 395                 400

Gly Leu Ile Thr Thr Val Cys Gly Phe Arg Ser Arg Leu Tyr Ala Glu
                405                 410                 415

Arg Trp Cys Ala Trp Ala Leu Leu Ala Ala Thr Val Ala Ile Pro Thr
            420                 425                 430

Gly Leu Thr Ala Lys Leu Ile Ile Trp Tyr Pro His Tyr Ala Trp Leu
            435                 440                 445

Leu Leu Ser Val Tyr Leu Thr Val Ala Leu Val Ala Leu Val Val Val
        450                 455                 460

Gly Ser Met Ala His Val Arg Arg Val Ser Pro Val Val Lys Arg Thr
465                 470                 475                 480

Leu Glu Leu Ile Asp Gly Ala Met Ile Ala Ala Ile Ile Pro Met Leu
                485                 490                 495

Leu Trp Ile Thr Gly Val Tyr Asp Thr Val Arg Asn Ile Arg Phe
                500                 505                 510

<210> SEQ ID NO 68
<211> LENGTH: 280
<212> TYPE: PRT
<213> ORGANISM: Mycobacterium tuberculosis
<220> FEATURE:
<223> OTHER INFORMATION: Rv3878 - conserved hypothetical alanine
      rich protein

<400> SEQUENCE: 68

Met Ala Glu Pro Leu Ala Val Asp Pro Thr Gly Leu Ser Ala Ala Ala
 1               5                  10                  15

Ala Lys Leu Ala Gly Leu Val Phe Pro Gln Pro Pro Ala Pro Ile Ala
                20                  25                  30

Val Ser Gly Thr Asp Ser Val Val Ala Ala Ile Asn Glu Thr Met Pro
            35                  40                  45

Ser Ile Glu Ser Leu Val Ser Asp Gly Leu Pro Gly Val Lys Ala Ala
        50                  55                  60

Leu Thr Arg Thr Ala Ser Asn Met Asn Ala Ala Ala Asp Val Tyr Ala
65                  70                  75                  80

Lys Thr Asp Gln Ser Leu Gly Thr Ser Leu Ser Gln Tyr Ala Phe Gly
                85                  90                  95

Ser Ser Gly Glu Gly Leu Ala Gly Val Ala Ser Val Gly Gly Gln Pro
            100                 105                 110

Ser Gln Ala Thr Gln Leu Leu Ser Thr Pro Val Ser Gln Val Thr Thr
        115                 120                 125

Gln Leu Gly Glu Thr Ala Ala Glu Leu Ala Pro Arg Val Val Ala Thr
    130                 135                 140

Val Pro Gln Leu Val Gln Leu Ala Pro His Ala Val Gln Met Ser Gln
145                 150                 155                 160

Asn Ala Ser Pro Ile Ala Gln Thr Ile Ser Gln Thr Ala Gln Gln Ala
                165                 170                 175

Ala Gln Ser Ala Gln Gly Gly Ser Gly Pro Met Pro Ala Gln Leu Ala
            180                 185                 190

Ser Ala Glu Lys Pro Ala Thr Glu Gln Ala Glu Pro Val His Glu Val
        195                 200                 205
```

```
Thr Asn Asp Asp Gln Gly Asp Gln Gly Asp Val Gln Pro Ala Glu Val
    210                 215                 220

Val Ala Ala Ala Arg Asp Glu Gly Ala Gly Ala Ser Pro Gly Gln Gln
225                 230                 235                 240

Pro Gly Gly Gly Val Pro Ala Gln Ala Met Asp Thr Gly Ala Gly Ala
                245                 250                 255

Arg Pro Ala Ala Ser Pro Leu Ala Ala Pro Val Asp Pro Ser Thr Pro
                260                 265                 270

Ala Pro Ser Thr Thr Thr Thr Leu
        275                 280

<210> SEQ ID NO 69
<211> LENGTH: 729
<212> TYPE: PRT
<213> ORGANISM: Mycobacterium tuberculosis
<220> FEATURE:
<223> OTHER INFORMATION: Rv3879c - hypothetical alanine and proline
      rich protein

<400> SEQUENCE: 69

Met Ser Ile Thr Arg Pro Thr Gly Ser Tyr Ala Arg Gln Met Leu Asp
 1               5                  10                  15

Pro Gly Gly Trp Val Glu Ala Asp Glu Asp Thr Phe Tyr Asp Arg Ala
                20                  25                  30

Gln Glu Tyr Ser Gln Val Leu Gln Arg Val Thr Asp Val Leu Asp Thr
            35                  40                  45

Cys Arg Gln Gln Lys Gly His Val Phe Glu Gly Gly Leu Trp Ser Gly
    50                  55                  60

Gly Ala Ala Asn Ala Ala Asn Gly Ala Leu Gly Ala Asn Ile Asn Gln
65                  70                  75                  80

Leu Met Thr Leu Gln Asp Tyr Leu Ala Thr Val Ile Thr Trp His Arg
                85                  90                  95

His Ile Ala Gly Leu Ile Glu Gln Ala Lys Ser Asp Ile Gly Asn Asn
            100                 105                 110

Val Asp Gly Ala Gln Arg Glu Ile Asp Ile Leu Glu Asn Asp Pro Ser
        115                 120                 125

Leu Asp Ala Asp Glu Arg His Thr Ala Ile Asn Ser Leu Val Thr Ala
    130                 135                 140

Thr His Gly Ala Asn Val Ser Leu Val Ala Glu Thr Ala Glu Arg Val
145                 150                 155                 160

Leu Glu Ser Lys Asn Trp Lys Pro Pro Lys Asn Ala Leu Glu Asp Leu
                165                 170                 175

Leu Gln Gln Lys Ser Pro Pro Pro Asp Val Pro Thr Leu Val Val
            180                 185                 190

Pro Ser Pro Gly Thr Pro Gly Thr Pro Gly Thr Pro Ile Thr Pro Gly
        195                 200                 205

Thr Pro Ile Thr Pro Gly Thr Pro Ile Thr Pro Ile Pro Gly Ala Pro
    210                 215                 220

Val Thr Pro Ile Thr Pro Thr Pro Gly Thr Pro Val Thr Pro Val Thr
225                 230                 235                 240

Pro Gly Lys Pro Val Thr Pro Val Thr Pro Val Lys Pro Gly Thr Pro
                245                 250                 255

Gly Glu Pro Thr Pro Ile Thr Pro Val Thr Pro Pro Val Ala Pro Ala
            260                 265                 270

Thr Pro Ala Thr Pro Ala Thr Pro Val Thr Pro Ala Pro Ala Pro His
        275                 280                 285
```

```
Pro Gln Pro Ala Pro Ala Pro Ser Pro Gly Pro Gln Pro Val
    290                 295                 300
Thr Pro Ala Thr Pro Gly Pro Ser Gly Pro Ala Thr Pro Gly Thr Pro
305                 310                 315                 320
Gly Gly Glu Pro Ala Pro His Val Lys Pro Ala Ala Leu Ala Glu Gln
                325                 330                 335
Pro Gly Val Pro Gly Gln His Ala Gly Gly Thr Gln Ser Gly Pro
            340                 345                 350
Ala His Ala Asp Glu Ser Ala Ala Ser Val Thr Pro Ala Ala Ala Ser
                355                 360                 365
Gly Val Pro Gly Ala Arg Ala Ala Ala Ala Pro Ser Gly Thr Ala
    370                 375                 380
Val Gly Ala Gly Ala Arg Ser Ser Val Gly Thr Ala Ala Ala Ser Gly
385                 390                 395                 400
Ala Gly Ser His Ala Ala Thr Gly Arg Ala Pro Val Ala Thr Ser Asp
                405                 410                 415
Lys Ala Ala Ala Pro Ser Thr Arg Ala Ala Ser Ala Arg Thr Ala Pro
                420                 425                 430
Pro Ala Arg Pro Pro Ser Thr Asp His Ile Asp Lys Pro Asp Arg Ser
            435                 440                 445
Glu Ser Ala Asp Asp Gly Thr Pro Val Ser Met Ile Pro Val Ser Ala
    450                 455                 460
Ala Arg Ala Ala Arg Asp Ala Ala Thr Ala Ala Ala Ser Ala Arg Gln
465                 470                 475                 480
Arg Gly Arg Gly Asp Ala Leu Arg Leu Ala Arg Arg Ile Ala Ala Ala
                485                 490                 495
Leu Asn Ala Ser Asp Asn Asn Ala Gly Asp Tyr Gly Phe Phe Trp Ile
                500                 505                 510
Thr Ala Val Thr Thr Asp Gly Ser Ile Val Val Ala Asn Ser Tyr Gly
                515                 520                 525
Leu Ala Tyr Ile Pro Asp Gly Met Glu Leu Pro Asn Lys Val Tyr Leu
    530                 535                 540
Ala Ser Ala Asp His Ala Ile Pro Val Asp Glu Ile Ala Arg Cys Ala
545                 550                 555                 560
Thr Tyr Pro Val Leu Ala Val Gln Ala Trp Ala Ala Phe His Asp Met
                565                 570                 575
Thr Leu Arg Ala Val Ile Gly Thr Ala Glu Gln Leu Ala Ser Ser Asp
            580                 585                 590
Pro Gly Val Ala Lys Ile Val Leu Glu Pro Asp Asp Ile Pro Glu Ser
            595                 600                 605
Gly Lys Met Thr Gly Arg Ser Arg Leu Glu Val Val Asp Pro Ser Ala
    610                 615                 620
Ala Ala Gln Leu Ala Asp Thr Thr Asp Gln Arg Leu Leu Asp Leu Leu
625                 630                 635                 640
Pro Pro Ala Pro Val Asp Val Asn Pro Pro Gly Asp Glu Arg His Met
                645                 650                 655
Leu Trp Phe Glu Leu Met Lys Pro Met Thr Ser Thr Ala Thr Gly Arg
            660                 665                 670
Glu Ala Ala His Leu Arg Ala Phe Arg Ala Tyr Ala Ala His Ser Gln
                675                 680                 685
Glu Ile Ala Leu His Gln Ala His Thr Ala Thr Asp Ala Ala Val Gln
    690                 695                 700
```

-continued

Arg Val Ala Val Ala Asp Trp Leu Tyr Trp Gln Tyr Val Thr Gly Leu
705                 710                 715                 720

Leu Asp Arg Ala Leu Ala Ala Ala Cys
            725

<210> SEQ ID NO 70
<211> LENGTH: 115
<212> TYPE: PRT
<213> ORGANISM: Mycobacterium tuberculosis
<220> FEATURE:
<223> OTHER INFORMATION: Rv3880c - conserved hypothetical protein

<400> SEQUENCE: 70

Val Ser Met Asp Glu Leu Asp Pro His Val Ala Arg Ala Leu Thr Leu
 1               5                  10                  15

Ala Ala Arg Phe Gln Ser Ala Leu Asp Gly Thr Leu Asn Gln Met Asn
            20                  25                  30

Asn Gly Ser Phe Arg Ala Thr Asp Glu Ala Glu Thr Val Glu Val Thr
         35                 40                  45

Ile Asn Gly His Gln Trp Leu Thr Gly Leu Arg Ile Glu Asp Gly Leu
  50                 55                  60

Leu Lys Lys Leu Gly Ala Glu Ala Val Ala Gln Arg Val Asn Glu Ala
 65                 70                  75                  80

Leu His Asn Ala Gln Ala Ala Ser Ala Tyr Asn Asp Ala Ala Gly
            85                  90                  95

Glu Gln Leu Thr Ala Ala Leu Ser Ala Met Ser Arg Ala Met Asn Glu
            100                 105                 110

Gly Met Ala
        115

<210> SEQ ID NO 71
<211> LENGTH: 460
<212> TYPE: PRT
<213> ORGANISM: Mycobacterium tuberculosis
<220> FEATURE:
<223> OTHER INFORMATION: Rv3881c - conserved hypothetical alanine
      and glycine rich protein

<400> SEQUENCE: 71

Met Thr Gln Ser Gln Thr Val Thr Val Asp Gln Gln Glu Ile Leu Asn
 1               5                  10                  15

Arg Ala Asn Glu Val Glu Ala Pro Met Ala Asp Pro Thr Asp Val
            20                  25                  30

Pro Ile Thr Pro Cys Glu Leu Thr Ala Ala Lys Asn Ala Ala Gln Gln
         35                 40                  45

Leu Val Leu Ser Ala Asp Asn Met Arg Glu Tyr Leu Ala Ala Gly Ala
  50                 55                  60

Lys Glu Arg Gln Arg Leu Ala Thr Ser Leu Arg Asn Ala Ala Lys Ala
 65                 70                  75                  80

Tyr Gly Glu Val Asp Glu Glu Ala Ala Thr Ala Leu Asp Asn Asp Gly
            85                  90                  95

Glu Gly Thr Val Gln Ala Glu Ser Gly Ala Val Gly Gly Asp Ser
            100                 105                 110

Ser Ala Glu Leu Thr Asp Thr Pro Arg Val Ala Thr Ala Gly Glu Pro
        115                 120                 125

Asn Phe Met Asp Leu Lys Glu Ala Ala Arg Lys Leu Glu Thr Gly Asp
    130                 135                 140

Gln Gly Ala Ser Leu Ala His Phe Ala Asp Gly Trp Asn Thr Phe Asn

```
                145                 150                 155                 160
Leu Thr Leu Gln Gly Asp Val Lys Arg Phe Arg Gly Phe Asp Asn Trp
                165                 170                 175

Glu Gly Asp Ala Ala Thr Ala Cys Glu Ala Ser Leu Asp Gln Gln Arg
                180                 185                 190

Gln Trp Ile Leu His Met Ala Lys Leu Ser Ala Ala Met Ala Lys Gln
                195                 200                 205

Ala Gln Tyr Val Ala Gln Leu His Val Trp Ala Arg Arg Glu His Pro
                210                 215                 220

Thr Tyr Glu Asp Ile Val Gly Leu Glu Arg Leu Tyr Ala Glu Asn Pro
225                 230                 235                 240

Ser Ala Arg Asp Gln Ile Leu Pro Val Tyr Ala Glu Tyr Gln Gln Arg
                245                 250                 255

Ser Glu Lys Val Leu Thr Glu Tyr Asn Asn Lys Ala Ala Leu Glu Pro
                260                 265                 270

Val Asn Pro Pro Lys Pro Pro Ala Ile Lys Ile Asp Pro Pro Pro
                275                 280                 285

Pro Pro Gln Glu Gln Gly Leu Ile Pro Gly Phe Leu Met Pro Pro Ser
                290                 295                 300

Asp Gly Ser Gly Val Thr Pro Gly Thr Gly Met Pro Ala Ala Pro Met
305                 310                 315                 320

Val Pro Pro Thr Gly Ser Pro Gly Gly Gly Leu Pro Ala Asp Thr Ala
                325                 330                 335

Ala Gln Leu Thr Ser Ala Gly Arg Glu Ala Ala Leu Ser Gly Asp
                340                 345                 350

Val Ala Val Lys Ala Ala Ser Leu Gly Gly Gly Gly Gly Gly Val
                355                 360                 365

Pro Ser Ala Pro Leu Gly Ser Ala Ile Gly Gly Ala Glu Ser Val Arg
                370                 375                 380

Pro Ala Gly Ala Gly Asp Ile Ala Gly Leu Gly Gln Gly Arg Ala Gly
385                 390                 395                 400

Gly Gly Ala Ala Leu Gly Gly Gly Gly Met Gly Met Pro Met Gly Ala
                405                 410                 415

Ala His Gln Gly Gln Gly Gly Ala Lys Ser Lys Gly Ser Gln Gln Glu
                420                 425                 430

Asp Glu Ala Leu Tyr Thr Glu Asp Arg Ala Trp Thr Glu Ala Val Ile
                435                 440                 445

Gly Asn Arg Arg Arg Gln Asp Ser Lys Glu Ser Lys
450                 455                 460

<210> SEQ ID NO 72
<211> LENGTH: 462
<212> TYPE: PRT
<213> ORGANISM: Mycobacterium tuberculosis
<220> FEATURE:
<223> OTHER INFORMATION: Rv3882c - possible conserved membrane
      protein

<400> SEQUENCE: 72

Met Arg Asn Pro Leu Gly Leu Arg Phe Ser Thr Gly His Ala Leu Leu
 1               5                  10                  15

Ala Ser Ala Leu Ala Pro Pro Cys Ile Ile Ala Phe Leu Glu Thr Arg
                20                  25                  30

Tyr Trp Trp Ala Gly Ile Ala Leu Ala Ser Leu Gly Val Ile Val Ala
                35                  40                  45
```

```
Thr Val Thr Phe Tyr Gly Arg Arg Ile Thr Gly Trp Val Ala Ala Val
 50                  55                  60

Tyr Ala Trp Leu Arg Arg Arg Arg Pro Pro Asp Ser Ser Ser Glu
 65                  70                  75                  80

Pro Val Val Gly Ala Thr Val Lys Pro Gly Asp His Val Ala Val Arg
                 85                  90                  95

Trp Gln Gly Glu Phe Leu Val Ala Val Ile Glu Leu Ile Pro Arg Pro
                100                 105                 110

Phe Thr Pro Thr Val Ile Val Asp Gly Gln Ala His Thr Asp Asp Met
            115                 120                 125

Leu Asp Thr Gly Leu Val Glu Glu Leu Leu Ser Val His Cys Pro Asp
130                 135                 140

Leu Glu Ala Asp Ile Val Ser Ala Gly Tyr Arg Val Gly Asn Thr Ala
145                 150                 155                 160

Ala Pro Asp Val Val Ser Leu Tyr Gln Gln Val Ile Gly Thr Asp Pro
                165                 170                 175

Ala Pro Ala Asn Arg Arg Thr Trp Ile Val Leu Arg Ala Asp Pro Glu
                180                 185                 190

Arg Thr Arg Lys Ser Ala Gln Arg Arg Asp Glu Gly Val Ala Gly Leu
            195                 200                 205

Ala Arg Tyr Leu Val Ala Ser Ala Thr Arg Ile Ala Asp Arg Leu Ala
210                 215                 220

Ser His Gly Val Asp Ala Val Cys Gly Arg Ser Phe Asp Asp Tyr Asp
225                 230                 235                 240

His Ala Thr Asp Ile Gly Phe Val Arg Glu Lys Trp Ser Met Ile Lys
                245                 250                 255

Gly Arg Asp Ala Tyr Thr Ala Ala Tyr Ala Ala Pro Gly Gly Pro Asp
                260                 265                 270

Val Trp Trp Ser Ala Arg Ala Asp His Thr Ile Thr Arg Val Arg Val
            275                 280                 285

Ala Pro Gly Met Ala Pro Gln Ser Thr Val Leu Leu Thr Thr Ala Asp
290                 295                 300

Lys Pro Lys Thr Pro Arg Gly Phe Ala Arg Leu Phe Gly Gly Gln Arg
305                 310                 315                 320

Pro Ala Leu Gln Gly Gln His Leu Val Ala Asn Arg His Cys Gln Leu
                325                 330                 335

Pro Ile Gly Ser Ala Gly Val Leu Val Gly Glu Thr Val Asn Arg Cys
                340                 345                 350

Pro Val Tyr Met Pro Phe Asp Asp Val Asp Ile Ala Leu Asn Leu Gly
            355                 360                 365

Asp Ala Gln Thr Phe Thr Gln Phe Val Val Arg Ala Ala Ala Ala Gly
            370                 375                 380

Ala Met Val Thr Val Gly Pro Gln Phe Glu Glu Phe Ala Arg Leu Ile
385                 390                 395                 400

Gly Ala His Ile Gly Gln Glu Val Lys Val Ala Trp Pro Asn Ala Thr
                405                 410                 415

Thr Tyr Leu Gly Pro His Pro Gly Ile Asp Arg Val Ile Leu Arg His
                420                 425                 430

Asn Val Ile Gly Thr Pro Arg His Arg Gln Leu Pro Ile Arg Arg Val
                435                 440                 445

Ser Pro Pro Glu Glu Ser Arg Tyr Gln Met Ala Leu Pro Lys
450                 455                 460
```

-continued

<210> SEQ ID NO 73
<211> LENGTH: 446
<212> TYPE: PRT
<213> ORGANISM: Mycobacterium tuberculosis
<220> FEATURE:
<223> OTHER INFORMATION: Rv3883c - possible secreted protease

<400> SEQUENCE: 73

```
Val His Arg Ile Phe Leu Ile Thr Val Ala Leu Ala Leu Leu Thr Ala
  1               5                  10                  15

Ser Pro Ala Ser Ala Ile Thr Pro Pro Ile Asp Pro Gly Ala Leu
             20                  25                  30

Pro Pro Asp Val Thr Gly Pro Asp Gln Pro Thr Glu Gln Arg Val Leu
             35                  40                  45

Cys Ala Ser Pro Thr Thr Leu Pro Gly Ser Gly Phe His Asp Pro Pro
         50                  55                  60

Trp Ser Asn Thr Tyr Leu Gly Val Ala Asp Ala His Lys Phe Ala Thr
 65                  70                  75                  80

Gly Ala Gly Val Thr Val Ala Val Ile Asp Thr Gly Val Asp Ala Ser
                 85                  90                  95

Pro Arg Val Pro Ala Glu Pro Gly Gly Asp Phe Val Asp Gln Ala Gly
            100                 105                 110

Asn Gly Leu Ser Asp Cys Asp Ala His Gly Thr Leu Thr Ala Ser Ile
            115                 120                 125

Ile Ala Gly Arg Pro Ala Pro Thr Asp Gly Phe Val Gly Val Ala Pro
        130                 135                 140

Asp Ala Arg Leu Leu Ser Leu Arg Gln Thr Ser Glu Ala Phe Glu Pro
145                 150                 155                 160

Val Gly Ser Gln Ala Asn Pro Asn Asp Pro Asn Ala Thr Pro Ala Ala
                165                 170                 175

Gly Ser Ile Arg Ser Leu Ala Arg Ala Val Val His Ala Ala Asn Leu
            180                 185                 190

Gly Val Gly Val Ile Asn Ile Ser Glu Ala Ala Cys Tyr Lys Val Ser
            195                 200                 205

Arg Pro Ile Asp Glu Thr Ser Leu Gly Ala Ser Ile Asp Tyr Ala Val
        210                 215                 220

Asn Val Lys Gly Val Val Val Val Ala Ala Gly Asn Thr Gly Gly
225                 230                 235                 240

Asp Cys Val Gln Asn Pro Ala Pro Asp Pro Ser Thr Pro Gly Asp Pro
                245                 250                 255

Arg Gly Trp Asn Asn Val Gln Thr Val Val Thr Pro Ala Trp Tyr Ala
            260                 265                 270

Pro Leu Val Leu Ser Val Gly Ile Gly Gln Thr Gly Met Pro Ser
            275                 280                 285

Ser Phe Ser Met His Gly Pro Trp Val Asp Val Ala Ala Pro Ala Glu
    290                 295                 300

Asn Ile Val Ala Leu Gly Asp Thr Gly Glu Pro Val Asn Ala Leu Gln
305                 310                 315                 320

Gly Arg Glu Gly Pro Val Pro Ile Ala Gly Thr Ser Phe Ala Ala Ala
                325                 330                 335

Tyr Val Ser Gly Leu Ala Ala Leu Leu Arg Gln Arg Phe Pro Asp Leu
            340                 345                 350

Thr Pro Ala Gln Ile Ile His Arg Ile Thr Ala Thr Ala Arg His Pro
        355                 360                 365

Gly Gly Gly Val Asp Asp Leu Val Gly Ala Gly Val Ile Asp Ala Val
```

```
                    370                 375                 380
Ala Ala Leu Thr Trp Asp Ile Pro Pro Gly Pro Ala Ser Ala Pro Tyr
385                 390                 395                 400

Asn Val Arg Arg Leu Pro Pro Val Val Glu Pro Gly Pro Asp Arg
                405                 410                 415

Arg Pro Ile Thr Ala Val Ala Leu Val Ala Val Gly Leu Thr Leu Ala
                420                 425                 430

Leu Gly Leu Gly Ala Leu Ala Arg Arg Ala Leu Ser Arg Arg
                435                 440                 445

<210> SEQ ID NO 74
<211> LENGTH: 619
<212> TYPE: PRT
<213> ORGANISM: Mycobacterium tuberculosis
<220> FEATURE:
<223> OTHER INFORMATION: Rv3884c - probable CBXX/CFQX family protein

<400> SEQUENCE: 74

Met Ser Arg Met Val Asp Thr Met Gly Asp Leu Leu Thr Ala Arg Arg
  1               5                  10                  15

His Phe Asp Arg Ala Met Thr Ile Lys Asn Gly Gln Gly Cys Val Ala
                 20                  25                  30

Ala Leu Pro Glu Phe Val Ala Thr Glu Ala Asp Pro Ser Met Ala
             35                  40                  45

Asp Ala Trp Leu Gly Arg Ile Ala Cys Gly Asp Arg Asp Leu Ala Ser
         50                  55                  60

Leu Lys Gln Leu Asn Ala His Ser Glu Trp Leu His Arg Glu Thr Thr
 65                  70                  75                  80

Arg Ile Gly Arg Thr Leu Ala Ala Glu Val Gln Leu Gly Pro Ser Ile
                 85                  90                  95

Gly Ile Thr Val Thr Asp Ala Ser Gln Val Gly Leu Ala Leu Ser Ser
                100                 105                 110

Ala Leu Thr Ile Ala Gly Glu Tyr Ala Lys Ala Asp Ala Leu Leu Ala
            115                 120                 125

Asn Arg Glu Leu Leu Asp Ser Trp Arg Asn Tyr Gln Trp His Gln Leu
130                 135                 140

Ala Arg Ala Phe Leu Met Tyr Val Thr Gln Arg Trp Pro Asp Val Leu
145                 150                 155                 160

Ser Thr Ala Ala Glu Asp Leu Pro Pro Gln Ala Ile Val Met Pro Ala
                165                 170                 175

Val Thr Ala Ser Ile Cys Ala Leu Ala Ala His Ala Ala His Leu
                180                 185                 190

Gly Gln Gly Arg Val Ala Leu Asp Trp Leu Asp Arg Val Asp Val Ile
            195                 200                 205

Gly His Ser Arg Ser Glu Arg Phe Gly Ala Asp Val Leu Thr Ala
        210                 215                 220

Ala Ile Gly Pro Ala Asp Ile Pro Leu Leu Val Ala Asp Leu Ala Tyr
225                 230                 235                 240

Val Arg Gly Met Val Tyr Arg Gln Leu His Glu Glu Asp Lys Ala Gln
                245                 250                 255

Ile Trp Leu Ser Lys Ala Thr Ile Asn Gly Val Leu Thr Asp Ala Ala
            260                 265                 270

Lys Glu Ala Leu Ala Asp Pro Asn Leu Arg Leu Ile Val Thr Asp Glu
            275                 280                 285

Arg Thr Ile Ala Ser Arg Ser Asp Arg Trp Asp Ala Ser Thr Ala Lys
```

```
            290                 295                 300
Ser Arg Asp Gln Leu Asp Asp Asn Ala Ala Gln Arg Arg Gly Glu
305                 310                 315                 320

Leu Leu Ala Glu Gly Arg Glu Leu Leu Ala Lys Gln Val Gly Leu Ala
                325                 330                 335

Ala Val Lys Gln Ala Val Ser Ala Leu Glu Asp Gln Leu Glu Val Arg
                340                 345                 350

Met Met Arg Leu Glu His Gly Leu Pro Val Glu Gly Gln Thr Asn His
                355                 360                 365

Met Leu Leu Val Gly Pro Gly Thr Gly Lys Thr Thr Ala Glu
370                 375                 380

Ala Leu Gly Lys Ile Tyr Ala Gly Met Gly Ile Val Arg His Pro Glu
385                 390                 395                 400

Ile Arg Glu Val Arg Arg Ser Asp Phe Cys Gly His Tyr Ile Gly Glu
                405                 410                 415

Ser Gly Pro Lys Thr Asn Glu Leu Ile Glu Lys Ser Leu Gly Arg Ile
                420                 425                 430

Ile Phe Met Asp Glu Phe Tyr Ser Leu Ile Glu Arg His Gln Asp Gly
                435                 440                 445

Thr Pro Asp Met Ile Gly Met Glu Ala Val Asn Gln Leu Leu Val Gln
450                 455                 460

Leu Glu Thr His Arg Phe Asp Phe Cys Phe Ile Gly Ala Gly Tyr Glu
465                 470                 475                 480

Asp Gln Val Asp Glu Phe Leu Thr Val Asn Pro Gly Leu Ala Gly Arg
                485                 490                 495

Phe Asn Arg Lys Leu Arg Phe Glu Ser Tyr Ser Pro Val Glu Ile Val
                500                 505                 510

Glu Ile Gly His Arg Tyr Ala Thr Pro Arg Ala Ser Gln Leu Asp Asp
                515                 520                 525

Ala Ala Arg Glu Val Phe Leu Asp Ala Val Thr Thr Ile Arg Asn Tyr
                530                 535                 540

Thr Thr Pro Ser Gly Gln His Gly Ile Asp Ala Met Gln Asn Gly Arg
545                 550                 555                 560

Phe Ala Arg Asn Val Ile Glu Arg Ala Glu Gly Phe Arg Asp Thr Arg
                565                 570                 575

Val Val Ala Gln Lys Arg Ala Gly Gln Pro Val Ser Val Gln Asp Leu
                580                 585                 590

Gln Ile Ile Thr Ala Thr Asp Ile Asp Ala Ala Ile Arg Ser Val Cys
                595                 600                 605

Ser Asp Asn Arg Asp Met Ala Ala Ile Val Trp
610                 615
```

<210> SEQ ID NO 75
<211> LENGTH: 537
<212> TYPE: PRT
<213> ORGANISM: Mycobacterium tuberculosis
<220> FEATURE:
<223> OTHER INFORMATION: Rv3885c - possible conserved membrane protein

<400> SEQUENCE: 75

```
Leu Thr Ser Lys Leu Thr Gly Phe Ser Pro Arg Ser Ala Arg Arg Val
  1               5                  10                  15

Ala Gly Val Trp Thr Val Phe Val Leu Ala Ser Ala Gly Trp Ala Leu
                 20                  25                  30
```

-continued

```
Gly Gly Gln Leu Gly Ala Val Met Ala Val Val Gly Val Ala Leu
            35                  40                  45

Val Phe Val Gln Trp Trp Gly Gln Pro Ala Trp Ser Trp Ala Val Leu
        50                  55                  60

Gly Leu Arg Gly Arg Arg Pro Val Lys Trp Asn Asp Pro Ile Thr Leu
 65                  70                  75                  80

Ala Asn Asn Arg Ser Gly Gly Val Arg Val Gln Asp Gly Val Ala
                85                  90                  95

Val Val Ala Val Gln Leu Leu Gly Arg Ala His Arg Ala Thr Thr Val
            100                 105                 110

Thr Gly Ser Val Thr Val Glu Ser Asp Asn Val Ile Asp Val Val Glu
            115                 120                 125

Leu Ala Pro Leu Leu Arg His Pro Leu Asp Leu Glu Leu Asp Ser Ile
            130                 135                 140

Ser Val Val Thr Phe Gly Ser Arg Thr Gly Thr Val Gly Asp Tyr Pro
145                 150                 155                 160

Arg Val Tyr Asp Ala Glu Ile Gly Thr Pro Pro Tyr Ala Gly Arg Arg
                165                 170                 175

Glu Thr Trp Leu Ile Met Arg Leu Pro Val Ile Gly Asn Thr Gln Ala
            180                 185                 190

Leu Arg Trp Arg Thr Ser Val Gly Ala Ala Ile Ser Val Ala Gln
            195                 200                 205

Arg Val Ala Ser Ser Leu Arg Cys Gln Gly Leu Arg Ala Lys Leu Ala
            210                 215                 220

Thr Ala Thr Asp Leu Ala Glu Leu Asp Arg Arg Leu Gly Ser Asp Ala
225                 230                 235                 240

Val Ala Gly Ser Ala Gln Arg Trp Lys Ala Ile Arg Gly Glu Ala Gly
                245                 250                 255

Trp Met Thr Thr Tyr Ala Tyr Pro Ala Glu Ala Ile Ser Ser Arg Val
            260                 265                 270

Leu Ser Gln Ala Trp Thr Leu Arg Ala Asp Glu Val Ile Gln Asn Val
            275                 280                 285

Thr Val Tyr Pro Asp Ala Thr Cys Thr Ala Thr Ile Thr Val Arg Thr
            290                 295                 300

Pro Thr Pro Ala Pro Thr Pro Pro Ser Val Ile Leu Arg Arg Leu Asn
305                 310                 315                 320

Gly Glu Gln Ala Ala Ala Ala Ala Asn Met Cys Gly Pro Arg Pro
                325                 330                 335

His Leu Arg Gly Gln Arg Arg Cys Pro Leu Pro Ala Gln Leu Val Thr
            340                 345                 350

Glu Ile Gly Pro Ser Gly Val Leu Ile Gly Lys Leu Ser Asn Gly Asp
            355                 360                 365

Arg Leu Met Ile Pro Val Thr Asp Ala Gly Glu Leu Ser Arg Val Phe
370                 375                 380

Val Ala Ala Asp Asp Thr Ile Ala Lys Arg Ile Val Ile Arg Val Val
385                 390                 395                 400

Gly Ala Gly Glu Arg Val Cys Val His Thr Arg Asp Gln Glu Arg Trp
                405                 410                 415

Ala Ser Val Arg Met Pro Gln Leu Ser Ile Val Gly Thr Pro Arg Pro
            420                 425                 430

Ala Pro Arg Thr Thr Val Gly Val Val Glu Tyr Val Arg Arg Arg Lys
            435                 440                 445

Asn Gly Asp Asp Gly Lys Ser Glu Gly Ser Gly Val Asp Val Ala Ile
```

```
                    450                 455                 460
Ser Pro Thr Pro Arg Pro Ala Ser Val Ile Thr Ile Ala Arg Pro Gly
465                 470                 475                 480

Thr Ser Leu Ser Glu Ser Asp Arg His Gly Phe Glu Val Thr Ile Glu
            485                 490                 495

Gln Ile Asp Arg Ala Thr Val Lys Val Gly Ala Ala Gly Gln Asn Trp
            500                 505                 510

Leu Val Glu Met Glu Met Phe Arg Ala Glu Asn Arg Tyr Val Ser Leu
        515                 520                 525

Glu Pro Val Thr Met Ser Ile Gly Arg
    530                 535
```

IDENTIFICATION OF VIRULENCE ASSOCIATED REGIONS RD1 AND RD5 LEADING TO IMPROVE VACCINE OF M. BOVIS BCG AND M. MICROTI

This application is a National stage of International Application No. PCT/IB03/01789, filed Apr. 1, 2003, which claims the benefit of the filing date of European Application EP 02290864.4, filed Apr. 5, 2002. Applicant claims the benefit of the filing date of each of these applications.

Virulence associated regions have been sought for a long time in *Mycobacterium*. The present invention concerns the identification of 2 genomic regions which are shown to be associated with a virulent phenotype in *Mycobacteria* and particularly in *M. tuberculosis*. It concerns also the fragments of said regions.

One of these two regions are known as RD5, as disclosed in Molecular Microbiology (1999), vol. 32, pages 643 to 655 (Gordon S. V. et al.). The other region named RD1-2F9 spans the known region RD1, as disclosed in Molecular Microbiology (1999), vol. 32, pages 643 to 655 (Gordon S. V. et al.). Both of the regions RD1 and RD5, or at least one of them, are absent from the vaccine strains of *M. bovis* BCG and in *M. microti*, strains found involved and used as live vaccines in the 1960's.

Other applications which are encompassed by the present invention are related to the use of all or part of the said regions to detect virulent strains of *Mycobacteria* and particularly *M. tuberculosis* in humans and animals. The region RD1-2F9 and RD5 are considered as virulence markers under the present invention. The recombinant *Mycobacteria* and particularly *M. bovis* BCG, after modification of their genome by introduction of all or part of RD1-2F9 region and/or RD5 region in said genome, can be used for the immune system of patients affected with a cancer as for example a bladder cancer.

The recombinant *Mycobacteria* and particularly *M. bovis* BCG after modification of their genome by introduction of all or part of RD1-2F9 region and/or RD5 region in said genome can be used for the immune system of patients affected with a cancer as for example a bladder cancer.

The present invention relates to a strain of *M. bovis* BCG or *M. microti*, wherein said strain has integrated all or part of the region RD1-2F9 responsible for enhanced immunogenicity to the tubercle bacilli, especially the genes incoding the ESAT-6 and CFP-10 antigens. These strains will be referred to as the *M. bovis* BCG::RD1 or *M. microti*::RD1 strains and are useful as a new improved vaccined for prevention of tuberculosis infections and for treating superficial bladder cancer.

*Mycobacterium bovis* BCG (bacille Calmette-Guérin) has been used since 1921 to prevent tuberculosis although it is of limited efficacy against adult pulmonary disease in highly endemic areas. *Mycobacterium microti*, another member of the *Mycobacterium tuberculosis* complex, was originally described as the infective agent of a tuberculosis-like disease in voles (*Microtus agrestis*) in the 1930's (Wells, A. Q. 1937. Tuberculosis in wild voles. Lancet 1221 and Wells, A. Q. 1946. The murine type of tubercle bacillus. Medical Research council special report series 259:1-42.). Until recently, *M. microti* strains were thought to be pathogenic only for voles, but not for humans and some were even used as a live-vaccine. In fact, the vole bacillus proved to be safe and effective in preventing clinical tuberculosis in a trial involving roughly 10,000 adolescents in the UK in the 1950's (Hart, P. D. a., and I. Sutherland. 1977. BCG and vole bacillus vaccines in the prevention of tuberculosis in adolescence and early adult life. British Medical Journal 2:293-295). At about the same time, another strain, OV166, was successfully administered to half a million newborns in Prague, former Czechoslovakia, without any serious complications (Sula, L., and I. Radkovsky. 1976. Protective effects of *M. microti* vaccine against tuberculosis. J. Hyg. Epid. Microbiol. Immunol. 20:1-6). *M. microti* vaccination has since been discontinued because it was no more effective than the frequently employed BCG vaccine. As a result, improved vaccines are needed for preventing and treating tuberculosis.

The problem for attempting to ameliorate this live vaccine is that the molecular mechanism of both the attenuation and the immunogenicity of BCG is still poorly understood. Comparative genomic studies of all six members of the *M. tuberculosis* complex have identified more than 140 genes, whose presence is facultative, that may confer differences in phenotype, host range and virulence. Relative to the genome of the paradigm strain, *M. tuberculosis* H37Rv (S. T. Cole, et al., *Nature* 393, 537 (1998)), many of these genes occur in chromosomal regions that have been deleted from certain species (RD1-16, RvD1-5), M. A. Behr, et al., Science 284, 1520 (1999); R. Brosch, et al., Infection Immun. 66, 2221 (1998); S. V. Gordon, et al., Molec Microbiol 32, 643 (1999); H. Salamon, et al, Genome Res 10, 2044 (2000), G. G. Mahairas et al, J. Bacteriol. 178, 1274 (1996) and R. Brosch, et al., Proc Natl Acad Sci USA 99, 3684 (2002).

In connection with the invention and based on their distribution among tubercle bacilli and potential to encode virulence functions, RD1, RD3-5, RD7 and RD9 (FIGS. 1A, B) were accorded highest priority for functional genomic analysis using "knock-ins" of *M. bovis* BCG to assess their potential contribution to the attenuation process. Clones spanning these RD regions were selected from an ordered *M. tuberculosis* H37Rv library of integrating shuttle cosmids (S. T. Cole, et al, *Nature* 393, 537 (1998) and W. R. Bange, et al, *Tuber. Lung Dis.* 79, 171 (1999)), and individually electroporated into BCG Pasteur, where they inserted stably into the attB site (M. H. Lee, et al, *Proc. Natl. Acad. Sci. USA* 88, 3111 (1991)).

We have uncovered that only reintroduction of all or part of RD1-2F9 led to profound phenotypic alteration. Strikingly, the BCG::RD1 "knock-in" grew more vigorously than BCG controls in immuno-deficient mice, inducing extensive splenomegaly and granuloma formation.

RD1 is restricted to the avirulent strains *M. bovis* BCG and *M. microti*. Although the endpoints are not identical, the deletions have removed from both vaccine strains a cluster of six genes (Rv3871-Rv3876) that are part of the ESAT-6 locus (FIG. 1A (S. T. Cole, et al., *Nature* 393, 537 (1998) and F. Tekaia, et al., *Tubercle Lung Disease* 79, 329 (1999)).

Among the missing products are members of the mycobacterial PE (Rv3872), PPE (Rv3873), and ESAT-6 (Rv3874, Rv3875) protein families. Despite lacking obvious secretion signals, ESAT-6 (Rv3875) and the related protein CFP-10 (kv3874), are abundant components of short-term culture filtrate, acting as immunodominant T-cell antigens that induce potent Th1 responses (F. Tekaia, et al., Tubercle Lung Disease 79, 329 (1999); A. L. Sorensen, et al, Infect. Immun. 63, 1710 (1995) and R. Colangelli, et al., Infect. Immun. 68, 990 (2000)).

In summary, we have discovered that the restoration of RD1-2F9 to *M. bovis* BCG leads to increased persistence in immunocompetent mice. The *M. bovis* BCG::RD1 strain induces RD1-specific immune responses of the Th1-type, has enhanced immunogenicity and confers better protection than *M. bovis* BCG alone in animal models of tuberculosis. The *M.*

*bovis* BCG::RD1 vaccine is significantly more virulent than *M. bovis* BCG in immunodeficient mice but considerably less virulent than *M. tuberculosis*.

In addition, we show that *M. microti* lacks a different but overlapping part of the RD1 region (RD1$^{mic}$) to *M. bovis* BCG and our results indicate that reintroduction of RD1-2F9 confers increased virulence of BCG::RD1 in immunodeficient mice. The rare strains of *M. microti* that are associated with human disease contain a region referred to as RD5$^{mic}$ whereas those from voles do not.

*M. bovis* BCG vaccine could be improved by reintroducing other genes encoding ESAT-6 family members that have been lost, notably, those found in the RD8 and RD5 loci of *M. tuberculosis*. These regions also code for additional T-cell antigens.

*M. bovis* BCG::RD1 could be improved by reintroducing the RD8 and RD5 loci of *M. tuberculosis*.

*M. bovis* BCG vaccine could be improved by reintroducing and overexpressing the genes contained in the RD1, RD5 and RD8 regions.

Accordingly, these new strains, showing greater persistence and enhanced immunogenicity, represent an improved vaccine for preventing tuberculosis and treating bladder cancer.

In addition, the greater persistence of these recombinant strains is an advantage for the presentation of other antigens, for instance from HIV in humans and in order to induce protection immune responses. Those improved strains may also be of use in veterinary medicine, for instance in preventing bovine tuberculosis.

DESCRIPTION

Therefore, the present invention is aimed at a strain of *M. bovis* BCG or *M. microti*, wherein said strain has integrated all or part of the RD1-2F9 region as shown in SEQ ID No 1 responsible for enhanced immunogenicity to the tubercle bacilli. These strains will be referred to as the *M. bovis* BCG::RD1 or *M. microti*::RD1 strains.

In connection with the invention, "part or all of the RD1-2F9 region" means that the strain has integrated a portion of DNA originating from *Mycobacterium tuberculosis* or any virulent member of the *Mycobacterium tuberculosis* complex (*M. africanum, M. bovis, M. canettii*), which comprises at least one, two, three, four, five, or more gene(s) selected from Rv3861 (SEQ ID No 4), Rv3862 (SEQ ID No 5), Rv3863 (SEQ ID No 6), Rv3864 (SEQ ID No 7), Rv3865 (SEQ ID No 8), Rv3866 (SEQ ID No 9), Rv3867 (SEQ ID No 10), Rv3868 (SEQ ID No 11), Rv3869 (SEQ ID No 12), Rv3870 (SEQ ID No 13), Rv3871 (SEQ ID No 14), Rv3872 (SEQ ID No 15, mycobacterial PE), Rv3873 (SEQ ID No 16, PPE), Rv3874 (SEQ ID No 17, CFP-10), Rv3875 (SEQ ID No 18, ESAT-6), Rv3876 (SEQ ID No 19), Rv3877 (SEQ ID No 20), Rv3878 (SEQ ID No 21), Rv3879 (SEQ ID No 22), Rv3880 (SEQ ID No 23), Rv3881 (SEQ ID No 24), Rv3882 (SEQ ID No 25), Rv3883 (SEQ ID No 26), Rv3884 (SEQ ID No 27) and Rv3885 (SEQ ID No 28). The expression "a portion of DNA" means also a nucleotide sequence or a nucleic acid or a polynucleotide. The expression "gene" is referred herein as the coding sequence in frame with its natural promoter as well as the coding sequence which has been isolated and framed with an exogenous promoter, for example a promoter capable of directing high level of expression of said coding sequence.

In a specific aspect, the invention relates to a strain of *M. bovis* BCG or *M. microti* wherein said strain has integrated at least one, two, three or more gene(s) selected from Rv3867 (SEQ ID No 10), Rv3868 (SEQ ID No 11), Rv3869 (SEQ ID No 12), Rv3870 (SEQ ID No 13), Rv3871 (SEQ ID No 14), Rv3872 (SEQ ID No 15, mycobacterial PE), Rv3873 (SEQ ID No 16, PPE), Rv3874 (SEQ ID No 17, CFP-10), Rv3875 (SEQ ID No 18, ESAT-6), Rv3876 (SEQ ID No 19) and Rv3877 (SEQ ID No 20). In another specific aspect, the invention relates to a strain of *M. bovis* BCG or *M. microti* wherein said strain has integrated at least one, two, three or more gene(s) selected from Rv3871 (SEQ ID No 14), Rv3872 (SEQ ID No 15, mycobacterial PE), Rv3873 (SEQ ID No 16, PPE), Rv3874 (SEQ ID No 17, CFP-10), Rv3875 (SEQ ID No 18, ESAT-6) and Rv3876 (SEQ ID No 19).

Preferably, a strain according to the invention is one which has integrated a portion of DNA originating from *Mycobacterium tuberculosis* or any virulent member of the *Mycobacterium tuberculosis* complex (*M. africanum, M. bovis, M. canettii*), which comprises at least four genes selected from Rv3861 (SEQ ID No 4), Rv3862 (SEQ ID No 5), Rv3863 (SEQ ID No 6), Rv3864 (SEQ ID No 7), Rv3865 (SEQ ID No 8), Rv3866 (SEQ ID No 9), Rv3867 (SEQ ID No 10), Rv3868 (SEQ ID No 11), Rv3869 (SEQ ID No 12), Rv3870 (SEQ ID No 13), Rv3871 (SEQ ID No 14), Rv3872 (SEQ ID No 15, mycobacterial PE), Rv3873 (SEQ ID No 16, PPE), Rv3814 (SEQ ID No 17, CFP-10), Rv3875 (SEQ ID No 18, ESAT-6), Rv3876 (SEQ ID No 19), Rv3877 (SEQ ID No 20), Rv3878 (SEQ ID No 21), Rv3879 (SEQ ID No 22), Rv3880 (SEQ ID No 23), Rv3881 (SEQ ID No 24), Rv3882 (SEQ ID No 25), Rv3883 (SEQ ID No 26), Rv3884 (SEQ ID No 27) and Rv3885 (SEQ ID No 28), provided that it comprises Rv3874 (SEQ ID No 17, CFP-10) and/or Rv3875 (SEQ ID No 18, ESAT-6).

Strains which have integrated a portion of DNA originating from *Mycobacterium tuberculosis* or any virulent member of the *Mycobacterium tuberculosis* complex (*M. Africanum, M. bovis, M. canettii*) comprising at least Rv3871 (SEQ ID No 14), Rv3875 (SEQ ID No 18, ESAT-6) and Rv3876 (SEQ ID No 19) or at least Rv3871 (SEQ ID No 14), Rv3875 (SEQ ID No 18, ESAT-6) and Rv3877 (SEQ ID No 20) or at least Rv3871 (SEQ ID No 14), Rv3875 (SEQ ID No 18, ESAT-6), Rv3876 (SEQ ID No 19) and Rv3877 (SEQ ID No 20) are of particular interest.

The above strains according to the invention may further comprise Rv3874 (SEQ ID No 17, CFP-10), Rv3872 (SEQ ID No 15, mycobacterial PE) and/or Rv3873 (SEQ ID No 16, PPE). In addition, it may further comprise at least one, two, three or four gene(s) selected from Rv3861 (SEQ ID No 4), Rv3862 (SEQ ID No 5), Rv3863 (SEQ ID No 6), Rv3864 (SEQ ID No 7), Rv3865 (SEQ ID No 8), Rv3866 (SEQ ID No 9), Rv3867 (SEQ ID No 10), Rv3868 (SEQ ID No 11), Rv3869 (SEQ ID No 12), Rv3870 (SEQ ID No 13), Rv3878 (SEQ ID No 21), Rv3879 (SEQ ID No 22), Rv3880 (SEQ ID No 23), Rv3881 (SEQ ID No 24), Rv3882 (SEQ ID No 25), Rv3883 (SEQ ID No 26), Rv3884 (SEQ ID No 27) and Rv3885 (SEQ ID No 28).

The invention encompasses strains which have integrated a portion of DNA originating from *Mycobacterium tuberculosis* or any virulent member of the *Mycobacterium tuberculosis* complex (*M. africanum, M. bovis, M. canettii*), which comprises Rv3875 (SEQ ID No 18, ESAT-6) or Rv3874 (SEQ ID No 17, CFP-10) or both Rv3875 (SEQ ID No 18, ESAT-6) and Rv3874 (SEQ ID No 17, CFP-10).

These genes can be mutated (deletion, insertion or base modification) so as to maintain the improved immunogenicity while decreasing the virulence of the strains. Using routine procedure, the man skilled in the art can select the *M. bovis* BCG::RD1 or *M. microti*::RD1 strains, in which a mutated gene has been integrated, showing improved immunogenicity and lower virulence.

We have shown here that introduction of the RD 1-2F9 region makes the vaccine strains induce a more effective immune response against a challenge with *M. tuberculosis*. However, this first generation of constructs can be followed by other, more fine-tuned generations of constructs, as the complemented BCG::RD1 vaccine strain also showed a more virulent phenotype in severely immuno-compromised (SCID) mice. Therefore, the BCG::RD1 constructs may be modified so as to be applicable as vaccine strains while being safe for immuno-compromised individuals. The term "construct" means an engineered gene unit, usually involving a gene of interest that has been fused to a promoter.

In this perspective, the man skilled in the art can adapt the BCG::RD1 strain by the conception of BCG vaccine strains that only carry parts of the genes coding for ESAT-6 or CFP-10 in a mycobacterial expression vector (for example pSM81) tinder the control of a promoter, more particularly an hsp60 promoter. For example, at least one portion of the esat-6 gene that codes for immunogenic 20-mer peptides of ESAT-6 active as T-cell epitopes (Mustafa A S, Oftung F, Amoudy H A, Madi N M, Abal A T, Shabant F, Rosen Krands I, & Andersen P. (2000) Multiple epitopes from the *Mycobacterium tuberculosis* ESAT-6 antigen are recognized by antigen-specific human T cell lines. Clin Infect Dis. 30 Suppl 3:S201-5, peptides P1 to P8 are incorporated herein in the description) could be cloned into this vector and electroporated into BCG, resulting in a BCG strain that produces these epitopes.

Alternatively, the ESAT-6 and CFP-10 encoding genes (for example on plasmid RD1-AP34 and or RD1-2F9) could be altered by directed mutagenesis (using for example QuikChange Site-Directed Mutagenesis Kit from Stratagen) in a way that most of the immunogenic peptides of ESAT-6 remain intact, but the biological functionality of ESAT-6 is lost.

This approach could result in a more protective BCG vaccine without increasing the virulence of the recombinant BCG strain.

Therefore, the invention is also aimed at a method for preparing and selecting *M. bovis* BCG or *M. microti* recombinant strains comprising a step consisting of modifying the *M. bovis* BCG::RD1 or *M. microti*::RD1 strains as defined above by insertion, deletion or mutation in the integrated RD1 region, more particularly in the esat-6 or CFP-10 gene, said method leading to strains that are less virulent for immuno-depressed individuals. Together, these methods would allow to explain what causes the effect that we see with our BCG::RD1 strain (the presence of additional T-cell epitopes from ESAT-6 and CFP10 resulting in increased immunogenicity) or whether the effect is caused by better fitness of the recombinant BCG::RD1 clones resulting in longer exposure time of the immune system to the vaccine—or—by a combinatorial effect of both factors.

In a preferred embodiment, the invention is aimed at the *M. bovis* BCG::RD1 strains, which have integrated a cosmid herein referred to as the RD1-2F9 and RD1-AP34 contained in the *E. coli* strains deposited on Apr. 2, 2002 at the CNCM. (Institut Pasteur, 25, rue du Docteur Roux, 75724 Paris cedex 15, France) under the accession number I-2831 and I-2832 respectively. The RD1-2F9 is a cosmid comprising the portion of the *Mycobacterium tuberculosis* H37Rv genome previously named RD1-2F9 that spans the RD1 region and contains a gene conferring resistance to Kanamycin. The RD1-AP34 is a cosmid comprising a portion of the *Mycobacterium tuberculosis* H37Rv genome containing two genes coding for ESAT-6 and CFP-10 as well as a gene conferring resistance to Kanamycin.

The cosmid RD1-AP34 contains a 3909 bp fragment of the *M. tuberculosis* H37Rv genome from region 4350459 bp to 4354367 bp that has been cloned into an integrating vector pKint in order to be integrated in the genome of *Mycobacterium bovis* BCG and *Mycobacterium microti* strains (SEQ ID No 3). The Accession No. of the segment 160 of the *M. tuberculosis* H37Rv genome that contains this region is AL022120.

```
                                                               SEQ ID No 3:
  1 gaattccat ccagtgagtt caaggtcaag cggcgccccc ctggccaggc atttctcgtc 61 tcgccagacg gcaaagaggt catccaggcc ccctacatcg agcctccaga agaagtgttc 121 gcagcacccc caagcgccgg ttaagattat ttcattgccg gtgtagcagg acccgagctc 181 agcccggtaa tcgagttcgg gcaatgctga ccatcgggtt tgtttccggc tataaccgaa 241 cggtttgtgt acgggataca aatacaggga gggaagaagt aggcaaatgg aaaaaatgtc 301 acatgatccg atcgctgccg acattggcac gcaagtgagc gacaacgctc tgcacggcgt 361 gacggccggc tcgacggcgc tgacgtcggt gaccgggctg gttcccgcgg gggccgatga 421 ggtctccgcc caagcggcga cggcgttcac atcggagggc atccaattgc tggcttccaa 481 tgcatcggcc caagaccagc tccaccgtgc gggcgaagcg gtccaggacg tcgcccgcac 541 ctattcgcaa atcgacgacg gcgccgccgg cgtcttcgcc gaataggccc ccaacacatc 601 ggagggagtg atcaccatgc tgtggcacgt aatgccaccg gagctaaata ccgcacggct 661 gatggccggc gcgggtccgg ctccaatgct tgcggcggcc gcgggatggc agacgctttc 721 ggcggctctg gacgctcagg ccgtcgagtt gaccgcgcgc ctgaactctc tgggagaagc 781 ctggactgga ggtggcagcg acaaggcgct tgcggctgca acgccgatgg tggtctggct 841 acaaaccgcg tcaacacagg ccaagacccg tgcgatgcag gcgacggcgc aagccgcggc
```

-continued

```
 901 atacacccag gccatggcca cgacgccgtc gctgccggag atcgccgcca accacatcac
 961 ccaggccgtc cttacggcca ccaacttctt cggtatcaac acgatcccga tcgcgttgac
1021 cgagatggat tatttcatcc gtatgtggaa ccaggcagcc ctggcaatgg aggtctacca
1081 ggccgagacc gcggttaaca cgcttttcga agagctcgag ccgatggcgt cgatccttga
1141 tcccggcgcg agccagagca cgacgaaccc gatcttcgga atgccctccc ctggcagctc
1201 aacaccggtt ggccagttgc cgccggcggc tacccagacc ctcggccaac tgggtgagat
1261 gagcggcccg atgcagcagc tgacccagcc gctgcagcag gtgacgtcgt tgttcagcca
1321 ggtgggcggc accggcggcg gcaacccagc cgacgaggaa gccgcgcaga tgggcctgct
1381 cggcaccagt acgctgtcga accatccgct ggctggtgga tcaggcccca gcgcgggcgc
1441 gggcctgctg cgcgcggagt cgctacctgg cgcaggtggg tcgttgaccc gcacgccgct
1501 gatgtctcag ctgatcgaaa agccggttgc ccctcggtg atgccggcgg ctgctgccgg
1561 atcgtcggcg acgggtggcg ccgctccggt gggtgcggga gcgatgggcc agggtgcgca
1621 atccggcggc tccaccaggc cgggtctggt cgcgccggca ccgctcgcgc aggagcgtga
1681 agaagacgac gaggacgact gggacgaaga ggacgactgg tgagctcccg taatgacaac
1741 agacttcccg gccacccggg ccggaagact tgccaacatt ttggcgagga aggtaaagag
1801 agaaagtagt ccagc**atggc agagatgaag accgatgccg ctaccctcgc gcaggaggca
1861 ggtaatttcg agcggatctc cggcgacctg aaaacccaga tcgaccaggt ggagtcgacg
1921 gcaggttcgt tgcagggcca gtggcgcggc gcggcgggga cggccgccca ggccgcggtg
1981 gtgcgcttcc aagaagcagc caataagcag aagcaggaac tcgacgagat ctcgacgaat
2041 attcgtcagg ccggcgtcca atactcgagg gccgacgagg agcagcagca ggcgctgtcc
2101 tcgcaaatgg gcttc**tgacc cgctaatacg aaaagaaacg gagcaaaaac atgacagagc
2161 agcagtggaa tttcgcgggt atcgaggccg cggcaagcgc aatccaggga aatgtcacgt
2221 ccattcattc cctccttgac gagggggaagc agtccctgac caagctcgca gcggcctggg
2281 gcggtagcgg ttcggaggcg taccagggtg tccagcaaaa atgggacgcc acggctaccg
2341 agctgaacaa cgcgctgcag aacctggcgc ggacgatcag cgaagccggt caggcaatgg
2401 cttcgaccga aggcaacgtc actgggatgt tcgcataggg caacgccgag ttcgcgtaga
2461 atagcgaaac acgggatcgg gcgagttcga ccttccgtcg gtctcgccct ttctcgtgtt
2521 tatacgtttg agcgcactct gagaggttgt catggcggcc gactacgaca agctcttccg
2581 gccgcacgaa ggtatggaag ctccggacga tatggcagcg cagccgttct tcgaccccag
2641 tgcttcgttt ccgccggcgc ccgcatcggc aaacctaccg aagcccaacg gccagactcc
2701 gcccccgacg tccgacgacc tgtcggagcg gttcgtgtcg gccccgccgc cgccaccccc
2761 acccccacct ccgcctccgc caactccgat gccgatcgcc gcaggagagc cgccctcgcc
2821 ggaaccggcc gcatctaaac cacccacacc ccccatgccc atcgcggac ccgaaccggc
2881 cccacccaaa ccacccacac ccccatgcc atcgccgga cccgaaccgg ccccacccaa
2941 accacccaca cctccgatgc ccatcgccgg acctgcaccc accccaaccg aatcccagtt
3001 ggcgcccccc agaccaccga caccacaaac gccaaccgga gcgccgcagc aaccggaatc
3061 accggcgccc cacgtaccct cgcacgggcc acatcaaccc cggcgcaccg caccagcacc
3121 gccctgggca aagatgccaa tcggcgaacc cccgcccgct ccgtccagac cgtctgcgtc
3181 cccggccgaa ccaccgaccc ggcctgcccc caacactcc cgacgtgcgc gccggggtca
3241 ccgctatcgc acagacaccg aacgaaacgt cgggaaggta gcaactggtc catccatcca
```

```
-continued
3301 ggcgcggctg cgggcagagg aagcatccgg cgcgcagctc gccccggaa cggagccctc 3361 gccagcgccg ttgggccaac cgagatcgta tctggctccg cccacccgcc ccgcgccgac 3421 agaacctccc cccagcccct cgccgcagcg caactccggt cggcgtgccg agcgacgcgt 3481 ccaccccgat ttagccgccc aacatgccgc ggcgcaacct gattcaatta cggccgcaac 3541 cactggcggt cgtcgccgca agcgtgcagc gccggatctc gacgcgacac agaaatcctt 3601 aaggccggcg gccaagggc cgaaggtgaa gaaggtgaag ccccagaaac cgaaggccac 3661 gaagccgccc aaagtggtgt cgcagcgcgg ctggcgacat tgggtgcatg cgttgacgcg 3721 aatcaacctg ggcctgtcac ccgacgagaa gtacgagctg gacctgcacg ctcgagtccg 3781 ccgcaatccc cgcgggtcgt atcagatcgc cgtcgtcggt ctcaaaggtg gggctggcaa 3841 aaccacgctg acagcagcgt tggggtcgac gttggctcag gtgcgggccg accggatcct 3901 ggctctaga
``` pos. 0001-0006 EcoRI-restriction site
pos. 0286-0583 Rv3872 coding for a PE-Protein (SEQ ID No 15)
pos. 0616-1720 Rv3873 coding for a PPE-Protein (SEQ ID No 16)
pos. 1816-2115 Rv3874 coding for Culture Filtrat protein 10kD (CFP10) (SEQ ID No 17)
pos. 2151-2435 Rv3875 coding for Early Secreted Antigen Target 6kD (ESAT6) (SEQ ID No 18)
pos. 3903-3609 XbaI-restriction site
pos. 1816-2435 CFP-10 gene+esat-6 gene (SEQ ID No 29).

These sequences can be completed with the Rv3861 to Rv3871, and Rv3876 to Rv3885 as referred in Table 1 below.

| Gene Name | Gene length | Protein length | Gene type | Accesion number in NCBI Bank NC = gene NP = protein | Loc (kb) in M. tuberculosis H37Rv | Coordinates in Mycobacterium tuberculosis H37Rv | Molecular mass of protein (Dalton) | Description |
|---|---|---|---|---|---|---|---|---|
| Rv3861 | 324 | 108 | CDS | | 4337.95 | 4337946 . . . 4338269 | 11643.42 | hypothetical protein |
| Rv3862 c-whiB6 | 348 | 116 | CDS | | 4338.52 | compl 4338174 . . . 4338521 | 12792.38 | possible transcriptional regulatory protein whiB-like WhiB6 |
| Rv3863 | 1176 | 392 | CDS | | 4338.85 | 4338849 . . . 4340024 | 41087.44 | hypothetical alanine rich protein |
| Rv3864 | 1206 | 402 | CDS | | 4340.27 | 4340270 . . . 4341475 | 42068.66 | conserved hypothetical protein |
| Rv3865 | 309 | 103 | CDS | | 4341.57 | 4341566 . . . 4341874 | 10618.01 | conserved hypothetical protein |
| Rv3866 | 849 | 283 | CDS | | 4341.88 | 4341880 . . . 4342728 | 30064.04 | conserved hypothetical protein |
| Rv3867 | 549 | 183 | CDS | NC_000962 NP_218384 | 4342.77 | 4342767 . . . 4343318 | 19945.52 | conserved protein |
| Rv3868 | 1719 | 573 | CDS | NC_000962 NP_218385 | 4343.3 | 4343311 . . . 4345032 | 62425.40 | conserved protein |
| Rv3869 | 1440 | 480 | CDS | NC_000962 NP_218386 | 4345.04 | 4345036 . . . 4346478 | 51092.58 | possible conserved membrane protein |
| Rv3870 | 2241 | 747 | CDS | NC_000962 NP_218387 | 4346.48 | 4346478 . . . 4348721 | 80912.76 | possible conserved membrane protein |
| Rv3871 | 1773 | 591 | CDS | NC_000962 NP_218388 | 4348.83 | 4348824 . . . 4350599 | 64560.65 | conserved protein |

-continued

| Gene Name | Gene length | Protein length | Gene type | Accesion number in NCBI Bank NC = gene NP = protein | Loc (kb) in M. tuberculosis H37Rv | Coordinates in Mycobacterium tuberculosis H37Rv | Molecular mass of protein (Dalton) | Description |
|---|---|---|---|---|---|---|---|---|
| Rv3876 | 1998 | 666 | CDS | NC_000962 NP_218393 | 4353.01 | 4353007 ... 4355007 | 70644.92 | conserved proline and alanine rich protein |
| Rv3877 | 1533 | 511 | CDS | NC_000962 NP_218394 | 4355.01 | 4355004 ... 4356539 | 53981.12 | probable conserved transmembrane protein |
| Rv3878 | 840 | 280 | CDS | NC_000962 | 4356.69 | 4356693 ... 4357532 | 27395.23 | conserved hypothetical alanine rich protein |
| Rv3879c | 2187 | 729 | CDS | NC_000962 | 4359.78 | compl. 4357596 ... 4359782 | 74492.13 | hypothetical alanine and proline rich protein |
| Rv3880c | 345 | 115 | CDS | NC_000962 | 4360.55 | compl. 4360202 ... 4360546 | 12167.51 | conserved hypothetical protein |
| Rv3881c | 1380 | 460 | CDS | NC_000962 | 4361.92 | compl. 4360546 ... 4361925 | 47593.62 | conserved hypothetical alanine and glycine rich protein |
| Rv3882c | 1386 | 462 | CDS | NC_000962 | 4363.42 | compl. 4362035 ... 4363420 | 50396.58 | possible conserved membrane protein |
| Rv3883c | 1338 | 446 | CDS | NC_000962 | 4364.76 | compl. 4363420 ... 4364757 | 45085.89 | possible secreted protease |
| Rv3884c | 1857 | 619 | CDS | NC_000962 | 4366.84 | compl. 4364982 ... 4366838 | 68040.97 | probable CBXX/CFQX family protein |
| Rv3885c | 1611 | 537 | CDS | NC_000962 | 4368.52 | compl. 4366911 ... 4368521 | 57637.95 | possible conserved membrane protein |

The sequence of the fragment RD1-2F9 (~32 kb) covers the region of the *M. tuberculosis* genome AL123456 from ca 4337 kb to ca. 4369 kb, and also contains the sequence described in SEQ ID No 1. Therefore, the invention also embraces *M. bovis* BCG::RD1 strain and *M. microtri*::RD1 strain which have integrated the sequence as shown in SEQ ID No 1.

The above described strains fulfill the aim of the invention which is to provide an improved tuberculosis vaccine or *M. bovis* BCG-based prophylactic or therapeutic agent, or a recombinant *M. microti* derivative for these purposes.

The above described *M. bovis* BCG::RD1 strains are better tuberculosis vaccines than *M. bovis* BCG. These strains can also be improved by reintroducing other genes found in the RD8 and RD5 loci of *M. tubercluosis* or any virulent member of the *Mycobacterium tuberculosis* complex (*M. africanum, M. bovis M. canettii*). These regions code for additional T-cell antigens.

As indicated, overexpressing the genes contained in the RD1, RD5 and RD8 regions by means of exogenous promoters is encompassed by the invention. The same applies regarding *M. microti*::RD1 strains. *M. microti* strains could also be improved by reintroducing the RD8 locus of *M. tuberculosis* or any virulent member of the *Mycobacterium tuberculosis* complex (*M. africanum, M. bovis, M. canettii*).

In a second embodiment, the invention is directed to a cosmid or a plasmid, more commonly named vectors, comprising all or part of the RD1-2F9 region originating from *Mycobacterium tuberculosis* or any virulent member of the *Mycobacterium tuberculosis* complex (*M. africanum, M. bovis, M. canettii*), said region comprising at least ones two, three or more gene(s) selected from Rv3861 (SEQ ID No 4), Rv3862 (SEQ ID No 5), Rv3863 (SEQ ID No 6), Rv3864 (SEQ ID No 7), Rv3865 (SEQ ID No 8), Rv3866 (SEQ ID No 9), Rv3867 (SEQ ID No 10), Rv3868 (SEQ ID No 11), Rv3869 (SEQ ID No 12), Rv3870 (SEQ ID No 13), Rv3871 (SEQ ID No 14), Rv3872 (SEQ ID No 15, mycobacterial PE), Rv3873 (SEQ ID No 16, PPE), Rv3874 (SEQ ID No 17, CFP-10), Rv3875 (SEQ ID No 18, ESAT-6), Rv3876 (SEQ ID No 19), Rv3877 (SEQ ID No 20), Rv3878 (SEQ ID No 21), Rv3879 (SEQ ID No 22), Rv3880 (SEQ ID No 23), Rv3881 (SEQ ID No 24), Rv3882 (SEQ ID No 25), Rv3883 (SEQ ID No 26), Rv3884 (SEQ ID No 27) and Rv3885 (SEQ ID No 28). The term "vector" refers to a DNA molecule originating from a virus a bacteria, or the cell of a higher organism into which another DNA fragment of appropriate size can be integrated without loss of the vectors capacity for self-replication; a vector introduces foreign DNA into host cells, where it can be reproduced in large quantities. Examples are plasmids, cosmids, and yeast artificial chromosomes; vectors are often recombinant molecules containing DNA sequences from several sources.

Preferably, a cosmid or a plasmid of the invention comprises a part of the RD1-2F9 region originating from *Mycobacterium tuberculosis* or any virulent member of the *Mycobacterium tuberculosis* complex (*M. africanum, M. bovis, M. canettii*), said part comprising at least one, two, three or more gene(s) selected from Rv3867 (SEQ ID No 10), Rv3868 (SEQ ID No 11), Rv3869 (SEQ ID No 12), Rv3870 (SEQ ID No 13), Rv3871 (SEQ ID No 14), Rv3872 (SEQ ID No 15, mycobacterial PE), Rv3873 (SEQ ID No 16, PPE), Rv3874 (SEQ ID No 17, CFP-10), Rv3875 (SEQ ID No 18, ESAT6), Rv3876 (SEQ ID No 19) and Rv3877 (SEQ ID No 20).

Preferably, a cosmid or a plasmid of the invention comprises a part of the RD1-2F9 region originating from *Mycobacterium tuberculosis* or any virulent member of the *Mycobacterium tuberculosis* complex (*M. africanum, M. bovis, M. canettii*), said part comprising at least one, two, three or more gene(s) selected from Rv3872 (SEQ ID No 15, mycobacterial PE), Rv3873 (SEQ ID No 16, PPE), Rv3874 (SEQ ID No 17, CFP-10), Rv3875 (SEQ ID No 18, ESAT-6) and Rv3876 (SEQ ID No 19).

Preferably, a cosmid or a plasmid of the invention comprises CFP-10, ESAT-6 or both or a part of them. It may also comprise a mutated gene selected CFP-10, ESAT-6 or both, said mutated gene being responsible for the improved immunogenicity and decreased virulence.

A cosmid or a plasmid as mentioned above may comprise at least four genes selected from Rv3861 (SEQ ID No 4), Rv3862 (SEQ ID No 5), Rv3863 (SEQ ID No 6), Rv3864 (SEQ ID No 7), Rv3865 (SEQ ID No 8), Rv3866 (SEQ ID No 9), Rv3867 (SEQ ID No 10), Rv3868 (SEQ ID No 11), Rv3869 (SEQ ID No 12), Rv3870 (SEQ ID No 13), Rv3871 (SEQ ID No 14), Rv3872 (SEQ ID No 15, mycobacterial PE), Rv3873 (SEQ ID No 16, PPE), Rv3874 (SEQ ID No 17, CFP-10), Rv3875 (SEQ ID No 18, ESAT-6), Rv3876 (SEQ ID No 19), Rv3877 (SEQ ID No 20), Rv3878 (SEQ ID No 21), Rv3879 (SEQ ID No 22), Rv3880 (SEQ ID No 23), Rv3881 (SEQ ID No 24), Rv3882 (SEQ ID No 25), Rv3883 (SEQ ID No 26), Rv3884 (SEQ ID No 27) and Rv3885 (SEQ ID No 28), provided that it comprises Rv3874 (SEQ ID No 17, CFP-10) and/or Rv3875 (SEQ ID No 18, ESAT-6)

Advantageously, a cosmid or a plasmid of the invention comprises a portion of DNA originating from *Mycobacterium tuberculosis* or any virulent member of the *Mycobacterium tuberculosis* complex (*M. africanum, M. bovis, M. canettii*), which comprises at least Rv3871 (SEQ ID No 14), Rv3875 (SEQ ID No 18, ESAT-6) and Rv3876 (SEQ ID No 19) or at least Rv3871 (SEQ ID No 14), Rv3875 (SEQ ID No 18, ESAT-6) and Rv3877 (SEQ ID No 20) or at least Rv3871 (SEQ ID No 14), Rv3875 (SEQ ID No 18, ESAT-6), Rv3876 (SEQ ID No 19) and Rv3877 (SEQ ID No 20).

The above cosmids or plasmids may further comprise Rv3872 (SEQ ID No 15, mycobacterial PE) Rv3873 (SEQ ID No 16, PPE) Rv3874 (SEQ ID No 17, CFP-10). It may also further comprise at least one, two, three or four gene(s) selected from Rv3861 (SEQ ID No 4), Rv3862 (SEQ ID No 5), Rv3863 (SEQ ID No 6), Rv3864 (SEQ ID No 7), Rv3865 (SEQ ID No 8), Rv3866 (SEQ ID No 9), Rv3867 (SEQ ID No 10), Rv3868 (SEQ ID No 11), Rv3869 (SEQ ID No 12), Rv3870 (SEQ ID No 13), Rv3878 (SEQ ID No 21), Rv3879 (SEQ ID No 22), Rv3880 (SEQ ID No 23), Rv3881 (SEQ ID No 24), Rv3882 (SEQ ID No 25), Rv3883 (SEQ ID No 26), Rv3884 (SEQ ID No 27) and Rv3885 (SEQ ID No 28).

Two particular cosmids of the invention are the cosmids herein referred as RD1-2F9 and RD1-AP34 contained in the *E. coli* strains deposited at the CNCM (Institut Pasteur, 25, rue du Docteur Roux, 75724 Paris cedex 15, France) under the accession number I-2831 and I-2832 respectively.

A particular plasmid or cosmid of the invention is one which has integrated the complete RD1-2F9 region as shown in SEQ ID No 1.

The invention also relates to the use of these cosmids or plasmids for transforming *M. bovis* BCG or *M. microti* strains.

As indicated above, these cosmids or plasmids may comprise a mutated gene selected from Rv3861 to Rv3885, said mutated gene being responsible for the improved immunogenicity and decreased virulence.

In another embodiment, the invention embraces a pharmaceutical composition comprising a strain as depicted above and a pharmaceutically acceptable carrier.

In addition to the strains, these pharmaceutical compositions may contain suitable pharmaceutically-acceptable carriers comprising excipients and auxiliaries which facilitate processing of the living vaccine into preparations which can be used pharmaceutically. Further details on techniques for formulation and administration may be found in the latest edition of Remington's Pharmaceutical Sciences (Maack Publishing Co., Easton, Pa.).

Preferably, such composition is suitable for oral, intravenous or subcutaneous administration.

The determination of the effective dose is well within the capability of those skilled in the art. A therapeutically effective dose refers to that amount of active ingredient, i.e the number of strains administered, which ameliorates the symptoms or condition. Therapeutic efficacy and toxicity may be determined by standard pharmaceutical procedures in experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions which exhibit large therapeutic indices are preferred. Of course, ED50 is to be modulated according to the mammal to be treated or vaccinated. In this regard, the invention contemplates a composition suitable for human administration as well as veterinary composition.

The invention is also aimed at a vaccine comprising a *M. bovis* BCG::RD1 or *M. microti*::RD1 strain as depicted above and a suitable carrier. This vaccine is especially useful for preventing tuberculosis. It can also be used for treating bladder cancer.

The *M. bovis* BCG::RD1 or *M. microti*::RD1 strains are also useful as a carrier for the expression and presentation of foreign antigens or molecules of interest that are of therapeutic or prophylactic interest. Owing to its greater persistence, BCG::RD1 will present antigens to the immune system over a longer period thereby inducing stronger, more robust immune responses and notably protective responses. Examples of such foreign antigens can be found in patents and patent applications U.S. Pat. No. 6,191,270 for antigen LSA3, U.S. Pat. Nos. 6,096,879 and 5,314,808 for HBV antigens, EP 201,540 for HIV-1 antigens, U.S. Pat. No. 5,986, 051 for *H. pylori* antigens and FR 2,744,724 for *P. falciparum* MSP-1 antigen.

The invention also concerns a product comprising a strain as depicted above and at least one protein selected from ESAT-6 and CFP-10 or epitope derived thereof for a separate, simultaneous or sequential use for treating tuberculosis.

In still another embodiment, the invention concerns the use of a *M. bovis* BCG::RD1 or *M. microti*::RD1 strain as depicted above for preventing or treating tuberculosis. It also concerns the use of a *M. bovis* BCG::RD1 or *M. microti*::RD1 strain as a powerful adjuvant/immunomodulator used in the treatment of superficial bladder cancer.

The invention also contemplates the identification at the species level of members of the *M. tuberculosis* complex by means of an RD-based molecular diagnostic test. Inclusion of markers for RD1$^{mic}$ and RD5$^{mic}$ would improve the tests and act as predictors of virulence, especially in humans.

In this regard, the invention concerns a diagnostic kit for the identification at the species level of members of the *M. tuberculosis* complex comprising DNA probes and primers specifically hybridizing to a DNA portion of the RD1 or RD5 region of *M. tuberculosis*, more particularly probes hybridizing under stringent conditions to a gene selected from Rv3871 (SEQ ID No 14), Rv3872 (SEQ ID No 15, mycobacterial PE), Rv3873 (SEQ ID No 16, PPE), Rv3874 (SEQ ID No 17, CFP-10), Rv3875 (SEQ ID No 18, ESAT-6), and Rv3876 (SEQ ID No 19), preferably CFP-10 and ESAT-6.

As used herein, the term "stringent conditions" refers to conditions which permit hybridization between the probe sequences and the polynucleotide sequence to be detected. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature. The temperature range corresponding to a particular level of stringency can be further narrowed by calculating the purine to pyrimidine ratio of the nucleic acid of interest and adjusting the temperature accordingly. Variations on the above ranges and conditions are well known in the art.

Among the preferred primers, we can cite:

```
primer esat-6F
GTCACGTCCATTCATTCCCT,     (SEQ ID No 32)

primer esat-6R
ATCCCAGTGACGTTGCCTT),     (SEQ ID No 33)

primer RD1mic flanking region F
GCAGTGCAAAGGTGCAGATA,     (SEQ ID No 34)

primer RD1mic flanking region R
GATTGAGACACTTGCCACGA,     (SEQ ID No 35)

primer RD5mic flanking region F
GAATGCCGACGTCATATCG,      (SEQ ID No 39)

primer RD5mic flanking region R
CGGCCACTGAGTTCGATTAT.     (SEQ ID No 40)
```

The present invention covers also the complementary nucleotide sequences of said above primers as well as the nucleotide sequences hybridizing under stringent conditions with them and having at least 20 nucleotides and less than 500 nucleotides.

Diagnostic kits for the identification at the species level of members of the *M. tuberculosis* complex comprising at least one, two, three or more antibodies directed to mycobacterial PE, PPE, CFP-10, ESAT-6, are also embraced by the invention.

Preferably, such kit comprises antibodies directed to CFP-10 and ESAT-6.

As used herein, the term "antibody" refers to intact molecules as well as fragments thereof, such as Fab, F(ab').sub.2, and Fv, which are capable of binding the epitopic determinant. Probes or antibodies can be labeled with isotopes, fluorescent or phosphorescent molecules or by any other means known in the art.

The invention also relates to virulence markers associated with RD1 and/or RD5 regions of the genome of *M. tuberculosis* or a part of these regions.

The invention is further detailed below and will be illustrated with the following figures.

FIGURE LEGENDS

FIG. 1: *M. bovis* BCG and *M. microti* have a chromosomal deletion, RD1, spanning the cfp10-esat6 locus.

(A) Map of the cfp10-esat6 region showing the six possible reading frames and the *M. tuberculosis* H37Rv gene predictions.

The deleted regions are shown for BCG and *M. microti* with their respective H37Rv genome coordinates, and the extent of the conserved ESAT-6 locus (F. Tekaia, et al., *Tubercle Lung Disease* 79, 329 (1999)), is indicated by the gray bar.

(B) Table showing characteristics of deleted regions selected for complementation analysis. Potential virulence factors and their putative functions disrupted by each deletion are shown. The coordinates are for the *M. tuberculosis* H37Rv genome.

(C) Clones used to complement BCG. Individual clones spanning RD1 regions (RD1-I106 and RD1-2F9) were selected from an ordered *M. tuberculosis* genomic library (R.B. unpublished) in pYUB412 (S. T. Cole, et al., *Nature* 393, 537 (1998) and W. R. Bange, F. M. Collins, W. R. Jacobs, Jr., *Tuber. Lung Dis.* 79, 171 (1999)) and electroporated into *M. bovis* BCG strains, or *M. microti*. Hygromycin-resistant transformants were verified using PCR specific for the corresponding genes. pAP35 was derived from RD1-2F9 by excision of an AflII fragment. pAP34 was constructed by subcloning an EcoRI-XbaI fragment into the integrative vector pKINT. The ends of each fragment are related to the BCG RD1 deletion (shaded box) with black lines and the H37Rv coordinates for the other fragment ends given in kilobases.

(D) Immunoblot analysis, using an ESAT-6 monoclonal antibody, of whole cell protein extracts from log-phase cultures of (well n° 1) H37Rv (S. T. Cole, et al., *Nature* 393, 537 (1998)), (n° 2) BCG::pYUB412 (M. A. Behr, et al., *Science* 284, 1520 (1999)), (n° 3) BCG::RD1-I106 (R. Brosch, et al., *Infection Immun.* 66, 2221 (1998)), (n° 4) BCG::RD1-2F9 (S. V. Gordon, et al., *Molec Microbiol* 32, 643 (1999)), (n° 5) *M. bovis* (H. Salamon et al, *Genome Res* 10, 2044 (2000)), (n° 6) *Mycobacterium smegmatis* (G. G. Mahairas, et al, *J. Bacteriol.* 178, 1274 (1996)), (n° 7) *M. smegmatis*::pYUB412, and (n° 8) *M. smegmatis*::RD1-2F9 (R. Brosch, et al., *Proc Natl Acad Sci USA* 99, 3684 (2002)).

FIG. 2: Complementation of BCG Pasteur with the RD1 region alters the colony morphology and leads to accumulation of Rv3873 and ESAT-6 in the cell wall.

(A) Serial dilutions of 3 week old cultures of BCG::pYUB412, BCG::I106 or BCG::RD1-2F9 growing on Middlebrook 7H10 agar plates. The white square shows the area of the plate magnified in the image to the right.

(B) Light microscope image at fifty fold magnification of BCG::pYUB412 and BCG::RD1-2F9 colonies. 5 μl drops of bacterial suspensions of each strain were spotted adjacently onto 7H10 plates and imaged after 10 days growth, illuminating the colonies through the agar.

(C) Immunoblot analysis of different cell fractions of H37Rv using either an anti-ESAT-6 antibody or (D) anti-Rv3873 (PPE) rabbit serum. H37Rv and BCG signify whole cell extracts from the respective bacteria and Cyt, Mem and CW correspond to the cytosolic, membrane and cell wall fractions of *M. tuberculosis* H37Rv.

FIG. 3: Complementation of BCG Pasteur with the RD1 region increases bacterial persistence and pathogenicity in mice.

(A) Bacteria in the spleen and lungs of BALB/c mice following intravenous (i.v.) infection via the lateral tail vein with $10^6$ colony forming units (cfu) of *M. tuberculosis* H37Rv (black) or $10^7$ cfu of either BCG::pYUB412 (light grey) or BCG::RD1-I106 (grey).

(B) Bacterial persistence in the spleen and lungs of C57BL/6 mice following i.v. infection with $10^5$ cfu of BCG::pYUB412 (light grey), BCG::RD1-I106 (middle grey) or BCG::RD1-2F9 (dark grey).

(C) Bacterial multiplication after i.v. infection with $10^6$ cfu of BCG::pYUB412 (light grey) and BCG::RD1-2F9 (grey) in severe combined immunodeficiency mice (SCID). For A, B, and C each timepoint is the mean of 3 to 4 mice and the error bars represent standard deviations.

(D) Spleens from SCID mice three weeks after i.v. infection with $10^6$ cfu of either BCG::pYUB412, BCG::RD1-2F9 or BCG::I301 (an RD3 "knock-in", FIG. 1B). The scale is in cm.

FIG. 4: Immunization of mice with BCG::RD1 generates marked ESAT-6 specific T-cell responses and enhanced protection to a challenge with *M. tuberculosis*.

(A) Proliferative response of splenocytes of C57BL/6 mice immunized subcutaneously (s.c.) with $10^6$ CFU of BCG::pYUB412 (open squares) or BCG::RD1-2F9 (solid squares) to in vitro stimulation with various concentrations of synthetic peptides from poliovirus type 1 capsid protein VP I, ESAT-6 or Ag85A (K. Huygen, et al., *Infect. Immun.* 62, 363 (1994), L. Brandt, *J. Immunol.* 157, 3527 (1996) and C. Leclerc et al, *J. Virol.* 65, 711 (1991)).

(B) Proliferation of splenocytes from BCG::RD1-2F9-immunised mice in the absence or presence of 10 μg/ml of ESAT-6 1-20 peptide, with or without 1 μg/ml of anti-CD4 (GK1.5) or anti-CD8 (H35-17-2) monoclonal antibody. Results are expressed as mean and standard deviation of $^3$H-thymidine incorporation from duplicate wells.

(C) Concentration of IFN-γ in culture supernatants of splenocytes of C57BL/6 mice stimulated for 72 h with peptides or PPD after s.c. or i.v. immunization with either BCG::pYUB412 (middle grey and white) or BCG::RDI-2F9 (light grey and black). Mice were inoculated with either $10^6$ (white and light grey) or $10^7$ (middle grey and black) cfu. Levels of IFN-γ were quantified using a sandwich ELISA (detection limit of 500 pg/ml) with the mAbs R4-6A2 and biotin-conjugated XMG1.2. Results are expressed as the mean and standard deviation of duplicate culture wells.

(D) Bacterial counts in the spleen and lungs of vaccinated and unvaccinated BALB/c mice 2 months after an i.v. challenge with *M. tuberculosis* H37Rv. The mice were challenged 2 months after i.v. inoculation with $10^6$ cfu of either BCG::pYUB412 or BCG::RDI-2F9. Organ homogenates for bacterial enumeration were plated on 7H11 medium, with or without hygromycin, to differentiate *M. tuberculosis* from residual BCG colonies. Results are expressed as the mean and standard deviation of 4 to 5 mice and the levels of significance derived using the Wilcoxon rank-sum test.

Figure 5:
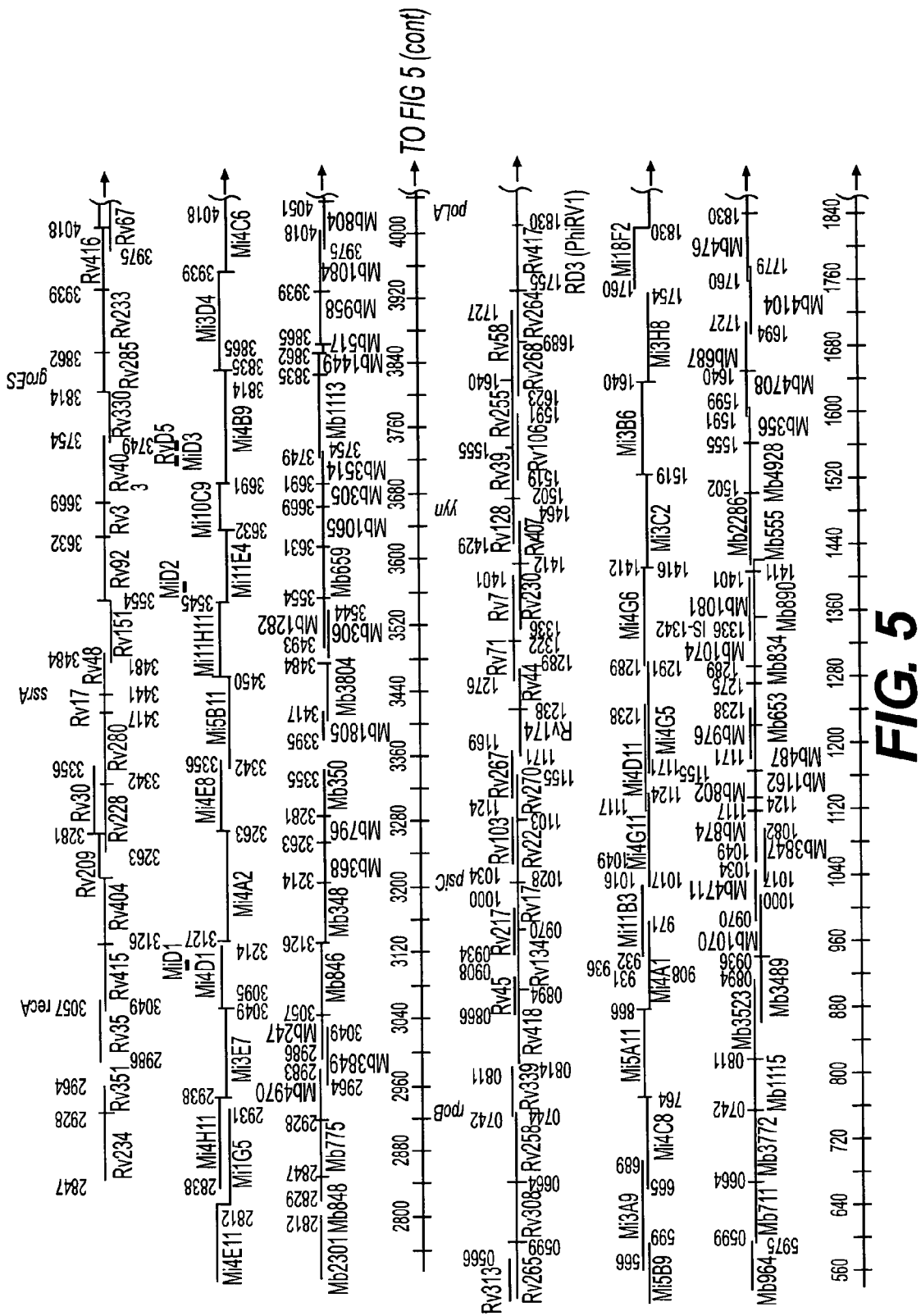
Figure 5:
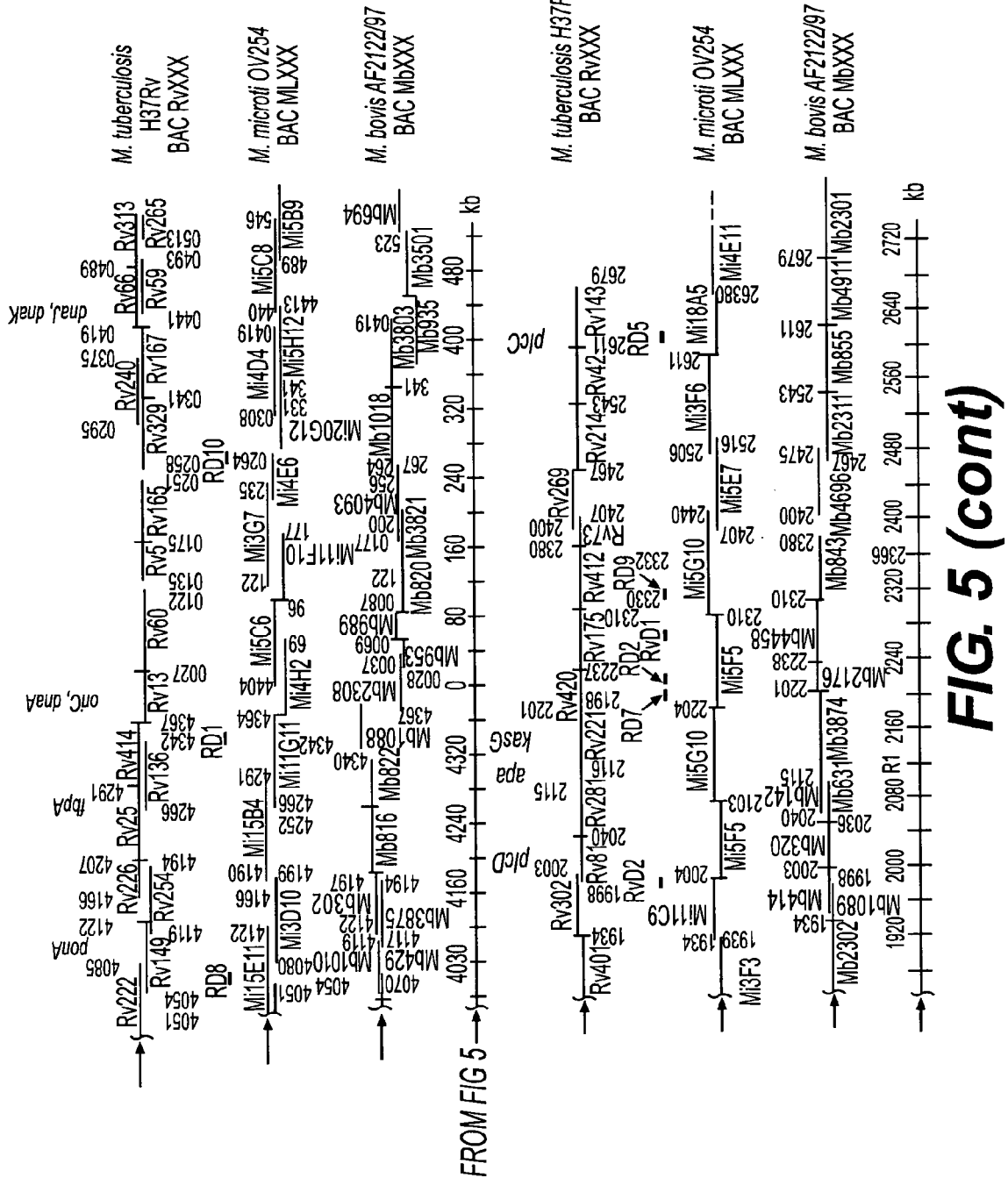

FIG. 5: *Mycobacterium microti* strain OV254 BAC map (BAC clones named MiXXX, where XXX is the identification number of the clone), overlaid on the *M. tuberculosis* H37Rv (BAC clones named RvXXX, where XXX is the identification number of the clone) and *M. bovis* AF2122/97 (BAC clones named MbXXX, where XXX is the identification number of the clone) BAC maps. The scale bars indicate the position on the *M. tuberculosis* genome.

FIG. 6: Difference in the region 4340-4360 kb between the deletion in BCG RD1$^{beg}$ (A) and in *M. microti* RD1$^{mic}$ (C) relative to *M. tuberculosis* H37Rv (B).

FIG. 7: Difference in the region 3121-3127 kb between *M. tuberculosis* H37Rv (A) and *M. microti* OV254 (B). Gray boxes picture the direct repeats (DR), black ones the unique numbered spacer sequences. * spacer sequence identical to the one of spacer 58 reported by van Embden et al. (42). Note that spacers 33-36 and 20-22 are not shown because H37Rv lacks these spacers.

FIG. 8: A) AseI PFGE profiles of various *M. microti* strains; Hybridization with a radiolabeled B) esat-6 probe; C) probe of the RD1$^{mic}$ flanking region; D) plcA probe. 1. *M. bovis* AF2122/97, 2. *M. canetti*, 3. *M. bovis* BCG Pasteur, 4. *M. tuberculosis* H37Rv, 5. *M. microti* OV254, 6. *M. microti* Myc 94-2272, 7. *M. microti* B3 type mouse, 8. *M. microti* B4 type mouse, 9. *M. microti* B2 type llama, 10. *M. microti* B1 type llama, 11. *M. microti* ATCC 35782. M: Low range PFGE marker (NEB).

Figure 9:
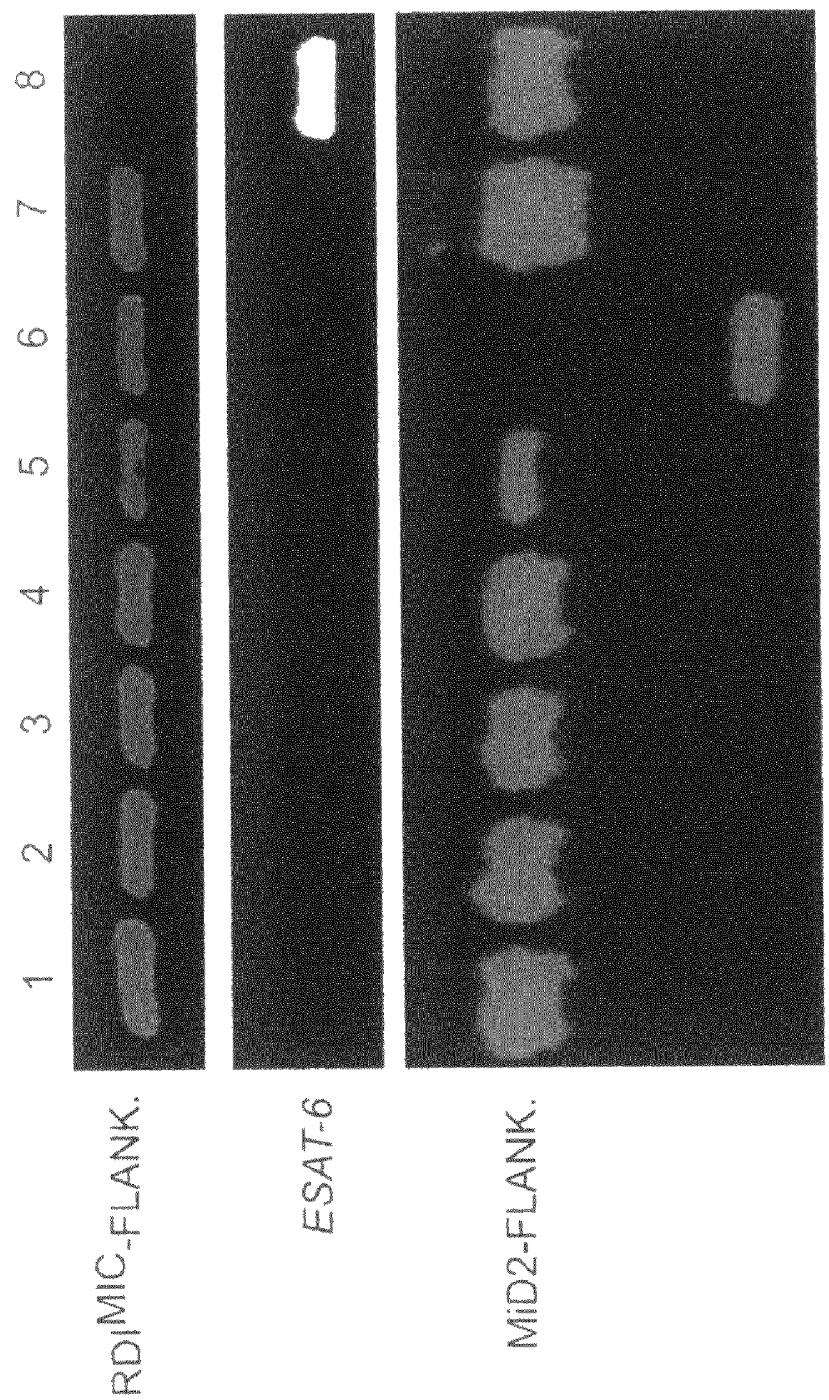

FIG. 9: PCR products obtained from various *M. microti* strains using primers that flank the RD1$^{mic}$ region, for amplifying ESAT-6 antigen, that flank the MiD2 region. 1. *M. microti* B1 type llama, 2. *M. microti* B4 type mouse, 3. *M. microti* B3 type mouse, 4. *M. microti* B2 type llama, 5. *M. microti* ATCC 35782, 6. *M. microti* OV254, 7. *M. microti* Myc 94-2272, 8. *M. tuberculosis* H37Rv.

Figure 10:
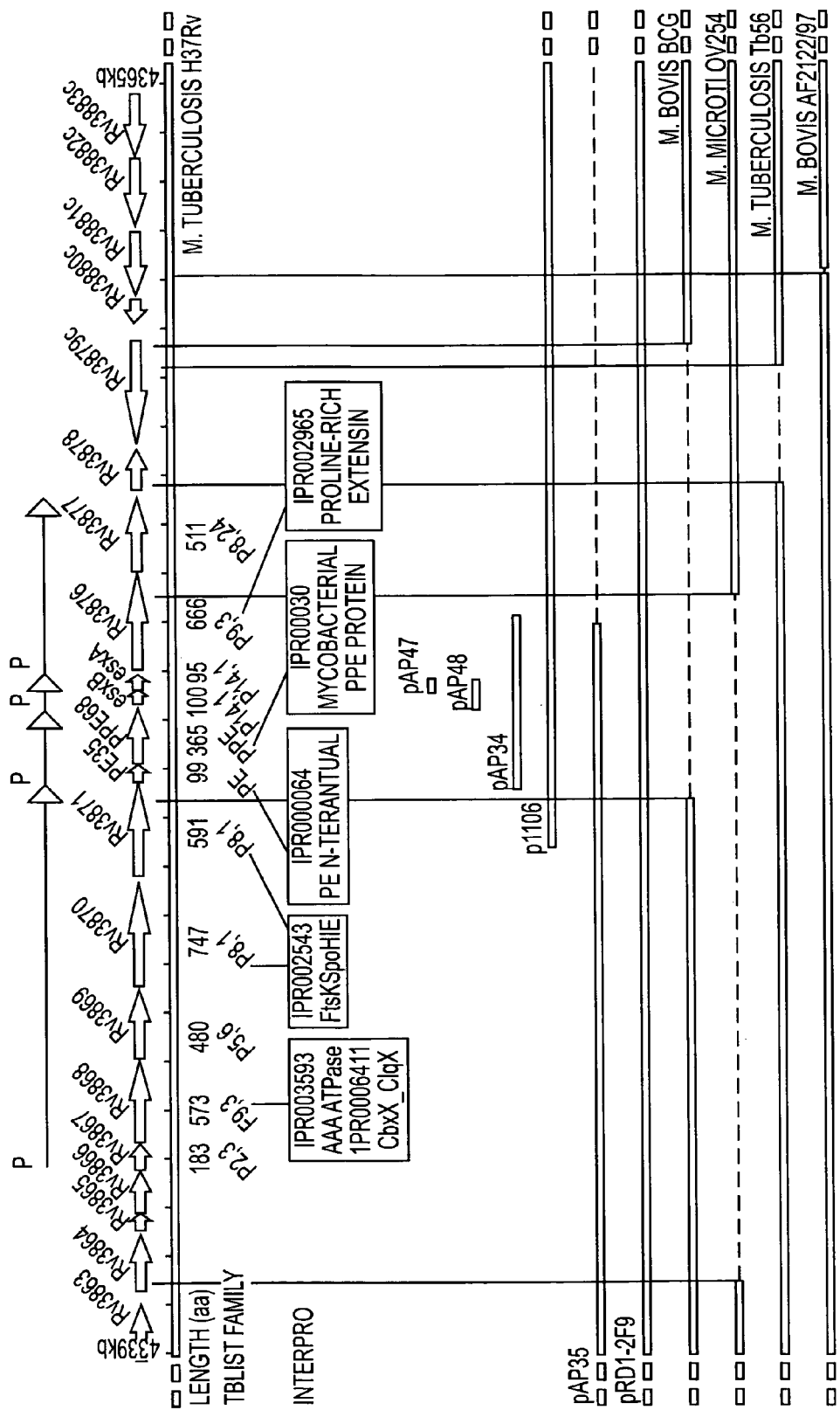

FIG. 10: Map of the *M. tuberculosis* H37Rv RD1 genomic region. Map of the fragments used to complement BCG and *M. microti* (black) and the genomic regions deleted from different mycobacterial strains (grey). The middle part shows key genes, putative promoters (P) and transcripts, the various proteins from the RD1 region, their sizes (number of amino acid residues), InterPro domains, and membership of *M. tuberculosis* protein families from TubercuList. The dashed lines mark the extent of the RD1 deletion in BCG, *M. microti* and *M. tuberculosis* clinical isolate MT56 (Brosch, R, et al. A new evolutionary scenario for the *Mycobacterium tuberculosis* complex. *Proc Natl Acad Sci USA* 99, 3684-9. (2002)). *M. bovis* AF2122197 is shown because it contains a frameshift mutation in Rv3881, a gene flanking the RD1 region of BCG. The fragments are drawn to show their ends in relation to the genetic map, unless they extend beyond the genomic region indicated. pRDI-2F9, pRD1-I106 and pAP35 are based on pYUB412; pAP34 on pKINT; pAP47 and pAP48 on pSM81.

Figure 11:
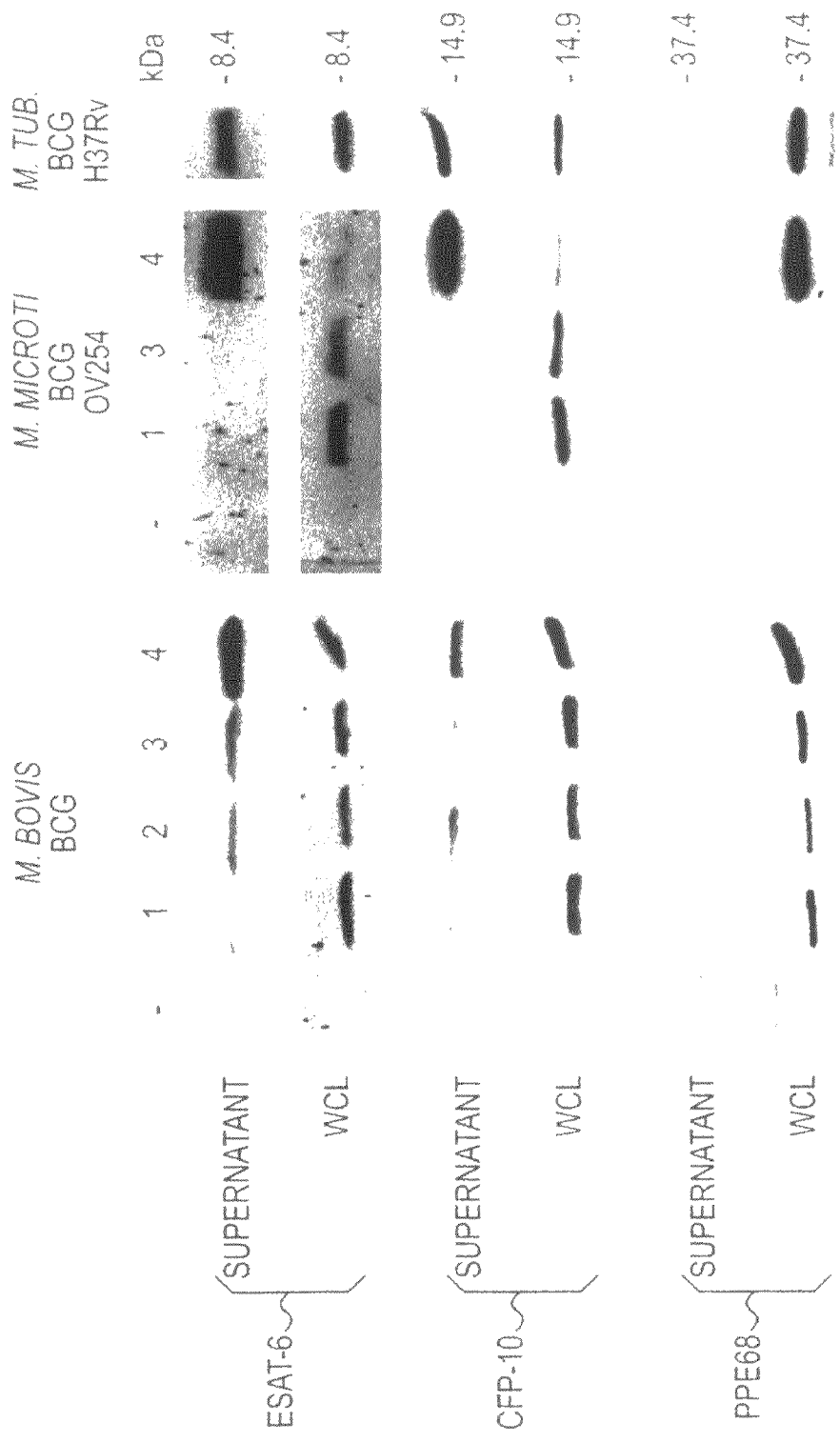

FIG. 11: Western blot analysis of various RD1 knock-ins of *M. bovis* BCG and *M. microti*. The left panel shows results of immunodetection of ESAT-6, CFP-10 and PPE68 (Rv3873) in whole cell lysates (WCL) and culture supernatants of BCG; the center panel displays the equivalent findings from *M. microti*, and the right panel contains *M. tuberculosis* H37Rv control samples. Samples from mycobacteria transformed with the following plasmids were present in lanes: -, pYUB412 vector control; 1, pAP34; 2, pAP35; 3, RD1-I106; 4, RD1-2F9. The positions of the nearest molecular weight markers are indicated.

FIG. 12: Analysis of immune responses induced by BCG recombinants. A, The upper three panels display the results of splenocyte proliferation assays in response to stimulation in vitro with a peptide from MalE (negative control), to PPD or to a peptide containing an immunodominant CD4-epitope from ESAT-6. B, The lower panel shows IFN-γ production by splenocytes in response to the same antigens. Symbols indicate the nature of the various BCG transformants. Samples were taken from C57BL/6 mice immunised subcutaneously.

FIG. 13: Further immunological characterization of responses to BCG::RD1-2F9 A, Proliferative response of splenocytes of C57BL/6 mice immunized subcutaneously (s.c.) with $10^6$ CFU of BCG::PYUB412 or BCG::RD1-2F9 to in vitro stimulation with various concentrations of synthetic peptides from poliovirus type 1 capsid protein VP1 (negative control), ESAT-6 or Ag85A (see Methods for details). B, Proliferation of splenocytes from BCG::RD1-2F9-immunised mice in the absence or presence of ESAT-6 1-20 peptide, with or without anti-CD4 or anti-CD8 monoclonal antibody. Results are expressed as mean and standard deviation of $^3$H-thymidine incorporation from duplicate wells. C, Concentration of IFN-γ in culture supernatants of splenocytes of C57BL/6 mice stimulated for 72 h with peptides or PPD after s.c. or i.v. immunization with either BCG::pYUB412 or BCG::RD1-2F9. Mice were inoculated with either $10^6$ or $10^7$ CFU. Results are expressed as the mean and standard deviation of duplicate culture wells.

FIG. 14: Mouse protection studies. A, Bacterial counts in the spleen and lungs of vaccinated and unvaccinated C57BL/6 mice 2 months after an i.v. challenge with *M. tuberculosis* H37Rv. The mice were challenged 2 months after i.v. inoculation with $10^6$ cfu of either BCG::pYUB412 or BCG::RD1-2F9. Organ homogenates for bacterial enumeration were plated on 7H11 medium, with or without hygromycin, to differentiate *M. tuberculosis* from residual BCG colonies. Results are expressed as the mean and standard deviation of 4 mice. Hatched columns correspond to the cohort of unvaccinated mice, while white and black columns correspond to mice vaccinated with BCG::pYUB412 and BCG::RD1-2F9, respectively. B, Bacterial counts in the spleen and lungs of vaccinated and unvaccinated C57BL6 mice after an aerosol challenge with 1000 CFUs of *M. tuberculosis*. All mice were treated with antibiotics for three weeks prior to infection with *M. tuberculosis*. Data are the mean and SE measured on groups of three animals, and differences between groups were analysed analyzed using ANOVA (*p<0.05, **p<0.01).

FIG. 15: Guinea pig protection studies. A, Mean weight gain of vaccinated and unvaccinated guinea pigs following aerosol infection with *M. tuberculosis* H37Rv. Guinea pigs were vaccinated with either saline (triangles), BCG (squares) or BCG::RD1-2F9 (filled circles). The error bars are the standard error of the mean. Each time point represents the mean weight of six guinea pigs. For the saline vaccinated group the last live weight was used for calculating the means as the animals were killed on signs of severe tuberculosis which occurred after 50, 59, 71, 72, 93 and 93 days. B, Mean bacterial counts in the spleen and lungs of vaccinated and unvaccinated guinea pigs after an aerosol challenge with *M. tuberculosis* H37Rv. Groups of 6 guinea pigs were vaccinated subcutaneously with either saline, BCG or BCG::RD1-2F9 and infected 56 days later. Vaccinated animals were killed 120 days following infection and unvaccinated ones on signs of suffering or significant weight loss. The error bars represent the standard error of the mean of six observations. C, Spleens of vaccinated guinea pigs 120 days after infection with *M. tuberculosis* H37Rv; left, animal immunized with BCG; right, animal immunized with BCG::RD1-2F9.

Figure 16:
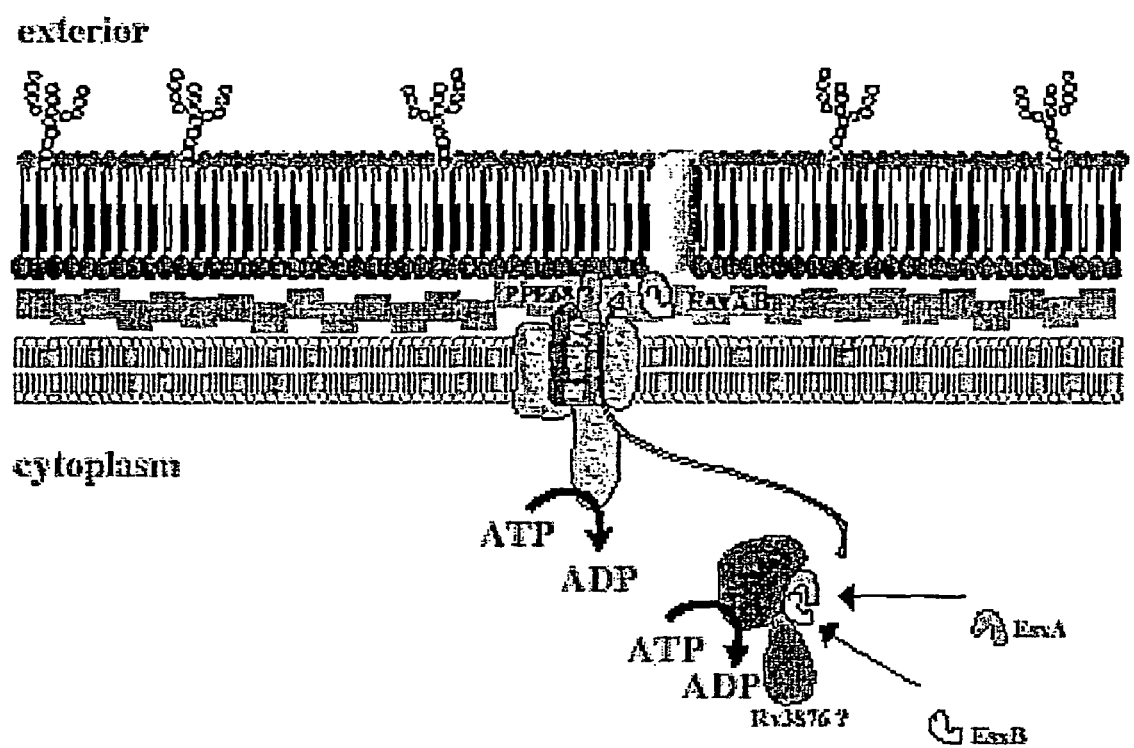

FIG. 16: Diagram of the *M. tuberculosis* H37Rv genomic region showing a working model for biogenesis and export of ESAT-6 proteins. It presents a possible functional model indicating predicted subcellular localization and potential interactions within the mycobacterial cell envelope. Rosetta stone analysis indicates direct interaction between proteins Rv3870 and Rv3871, and the sequence similarity between the N-terminal domains of Rv3868 and Rv3876 suggests that these putative chaperones might also interact. Rv3868 is a member of the AAA-family of ATPases that perform chaperone-like functions by assisting in the assembly, and disassembly of protein complexes (Neuwald, A. F., Aravind, L., Spouge, J. L. & Koonin, E. V. AAA+: A class of chaperone-like ATPases associated with the assembly, operation, and disassembly of protein complexes. *Genome Res* 9, 27-43. (1999).). It is striking that many type III secretion systems require chaperones for stabilization of the effector proteins that they secrete and for prevention of premature protein-protein interactions (Page, A. L. & Parsot, C. Chaperones of the type III secretion pathway: jacks of all trades. *Mol Mcrobiol* 46, 1-11. (2002).). Thus, Rv3868, and possibly Rv3876, may be required for the folding and/or dimerization of ESAT-6/CFP-10 proteins (Renshaw, P. S., et al. Conclusive evidence that the major T-cell antigens of the *M. tuberculosis* complex ESAT-6 and CFP-10 form a tight, 1:1 complex and characterisation of the structural properties of ESAT-6, CFP-10 and the ESAT-6-CFP-10 complex: implications for pathogenesis and virulence. *J Biol Chem* 8, 8 (2002).), or even to prevent premature dimerization. ESAT-6/CFP-10 are predicted to be exported through a transmembrane channel, consisting of at least Rv3870, Rv3871, and Rv3877, and possibly Rv3869, in a process catalysed by ATP-hydrolysis. Rv3873 (PPE 68) is known to occur in the cell envelope and may also be involved as shown herein.

EXAMPLE 1

Figures 1C, 1D:
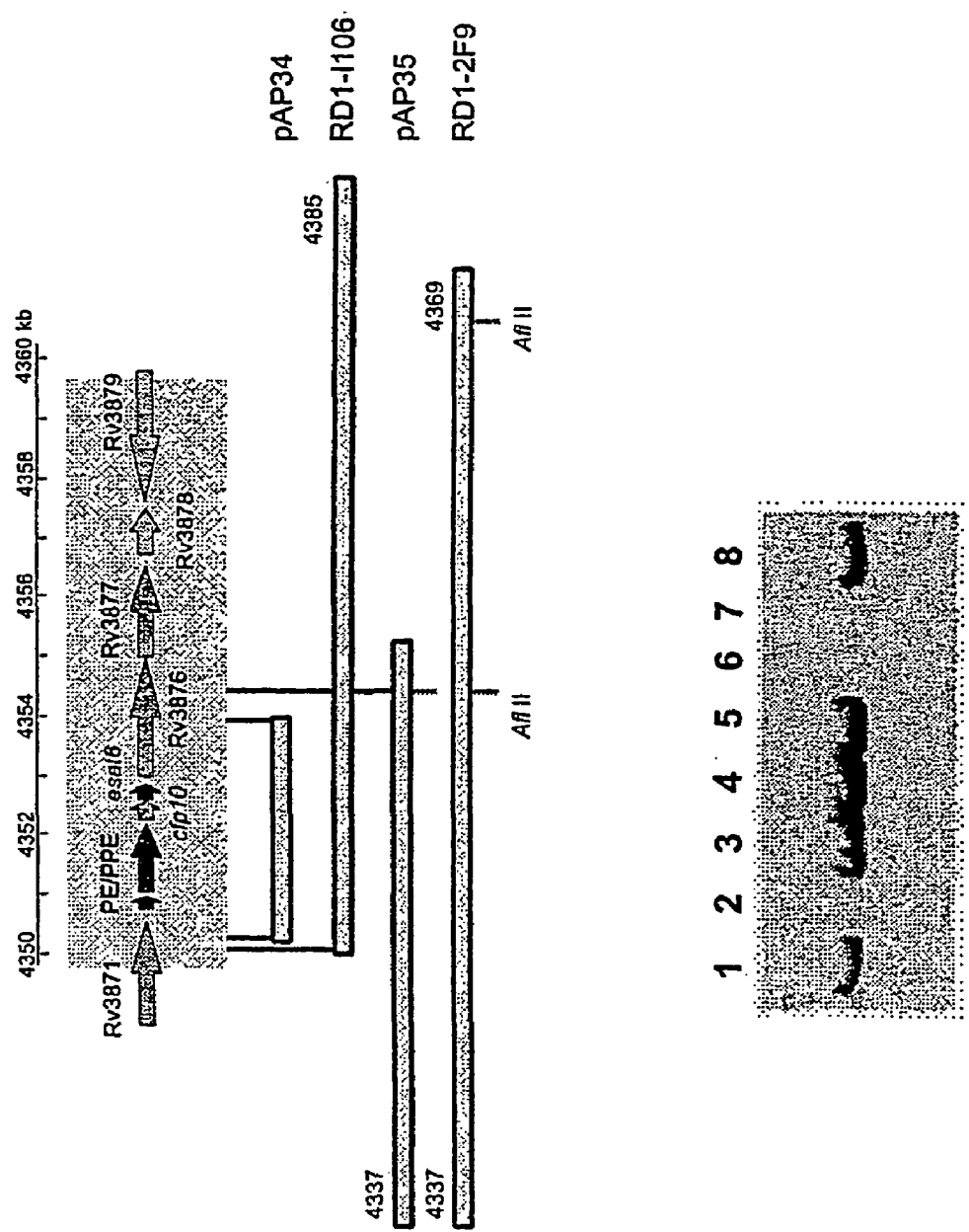
Figure 2A:
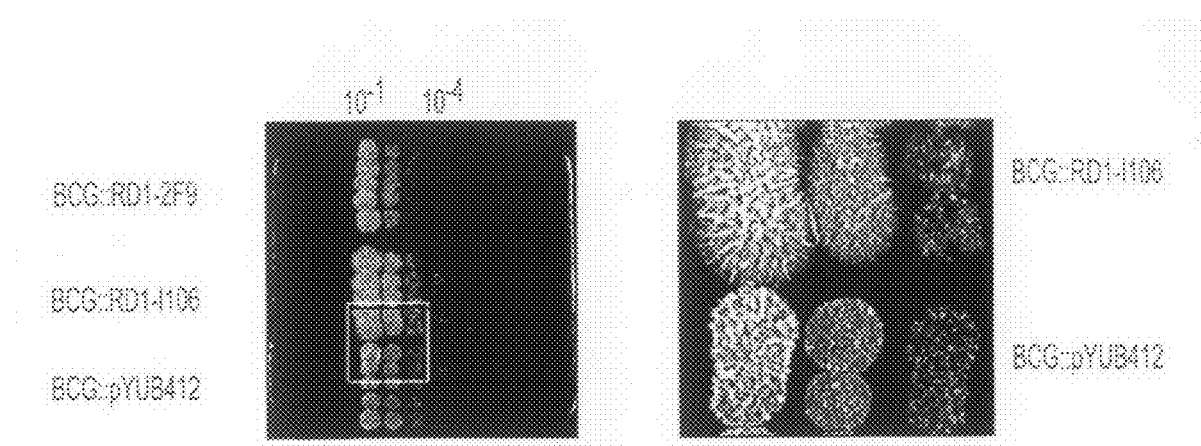
Figure 2B:
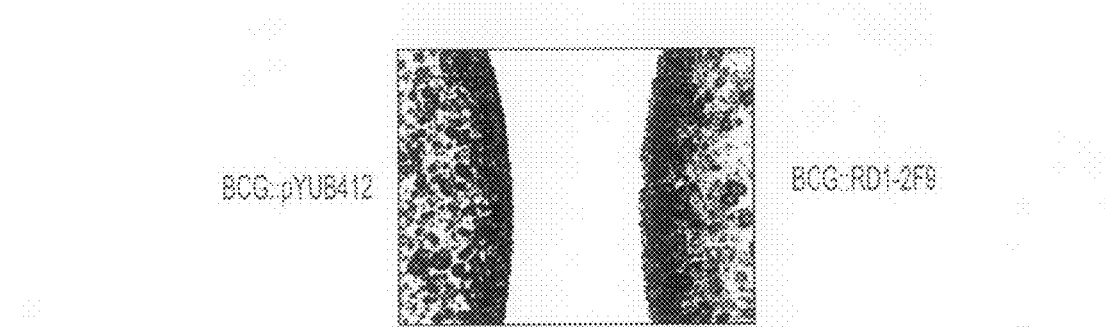

Preparation and Assessment of *M. bovis* BCG::RD1 Strains as a Vaccine for Treating or Preventing Tuberculosis As mentioned above, we have found that complementation with RD1 was accompanied by a change in colonial appearance as the BCG Pasteur "knock-in" strains developed a strikingly different morphotype (FIG. 2A). The RD1 complemented strains adopted a spreading, less-rugose morphology, that is characteristic of *M. bovis*, and this was more apparent when the colonies were inspected by light microscopy (FIG. 2B). Maps of the clones used are shown (FIG. 1C). These changes were seen following complementation with all of the RD1 constructs (FIG. 1C) and on complementing *M. microti* (data not shown). Pertinently, Calmette and Guérin (A. Calmette, *La vaccination preventive contre la tuberculose*. (Masson et cie., Paris, 1927)) observed a change in colony morphology during their initial passaging of *M. bovis*, and our experiments now demonstrate that this change, corresponding to loss of RD1, directly contributed to attenuating this virulent strain. The integrity of the cell wall is known to be a key virulence determinant for *M. tuberculosis* (C. E. Barry, *Trends Microbiol* 9, 237 (2001)), and changes in both cell wall lipids (M. S. Glickman, J. S. Cox, W. R. Jacobs, Jr., *Mol Cell* 5, 717 (2000)) and protein (F. X. Berthet, et al., *Science* 282, 759 (1998)) have been shown to alter colony morphology and diminish persistence in animal models.

Figure 2C:
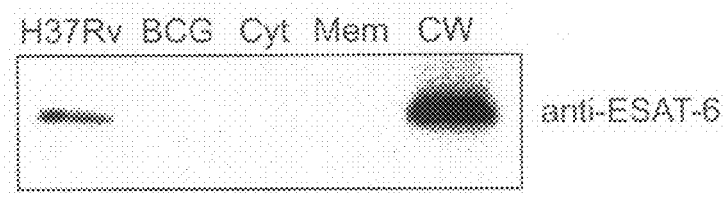
Figure 2D:
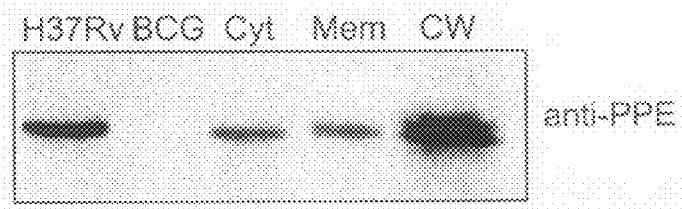

To determine which genes were implicated in these morphological changes, antibodies recognising three RD1 proteins (Rv3873, CFP10 and ESAT-6) were used in immunocytological and subcellular fractionation analysis. When the different cell fractions from *M. tuberculosis* were immunoblotted all three proteins were localized in the cell wall fraction (FIG. 2C) though significant quantities of Rv3873, a PPE protein, were also detected in the membrane and cytosolic fractions (FIG. 2D). Using immunogold staining and electron microscopy the presence of ESAT-6 in the envelope of *M. tuberculosis* was confirmed but no alteration in capsular ultrastructure could be detected (data not shown). Previously, CFP-10 and ESAT-6 have been considered as secreted proteins (F. X. Berthet et al, *Microbiology* 144, 3195 (1998)) but our results suggest that their biological functions are linked directly with the cell wall.

Figure 3A:
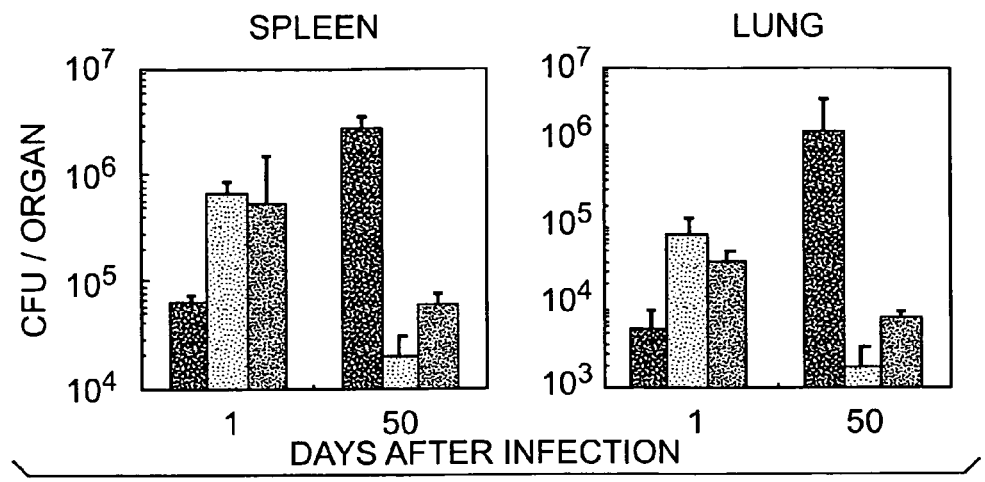
Figure 3B:
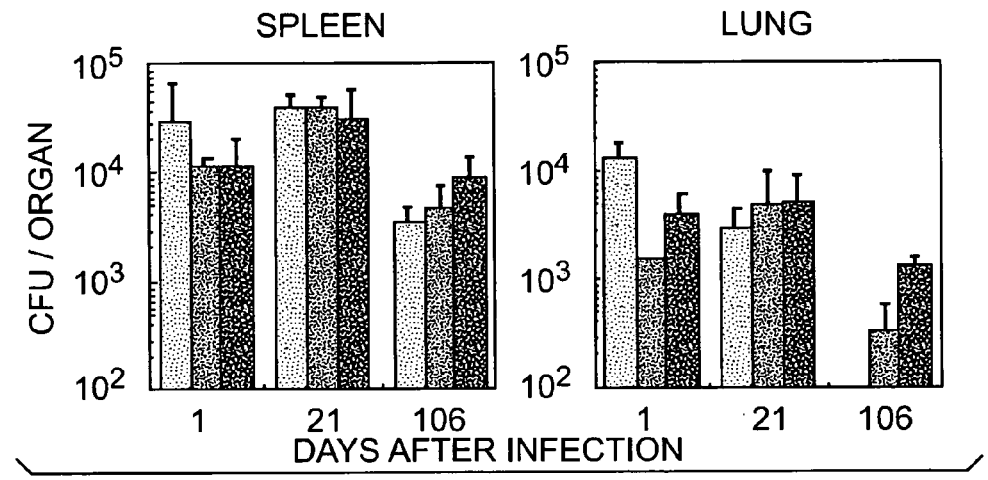
Figure 3C:
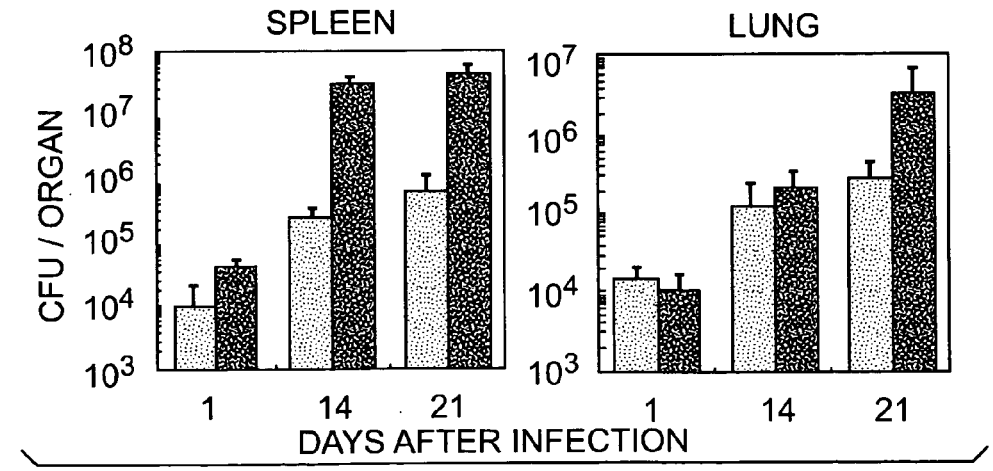
Figure 3D:
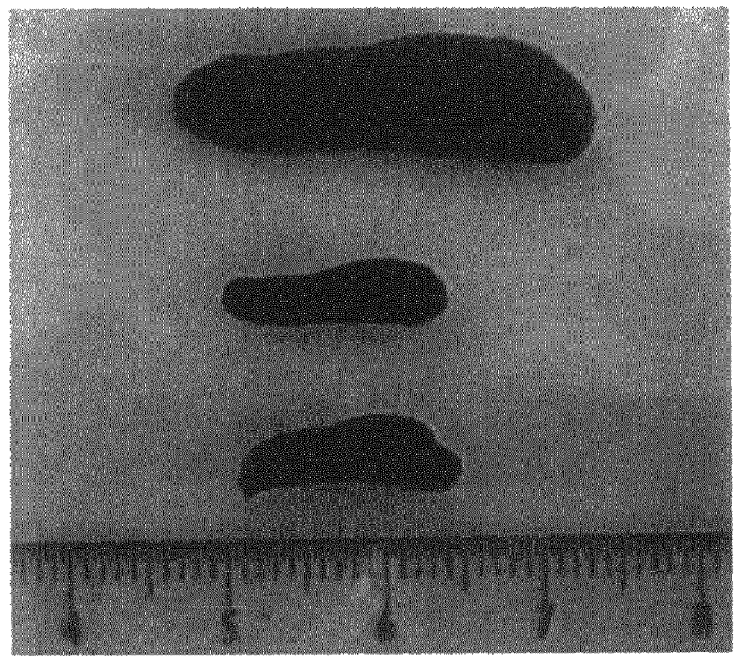

Changes in colonial morphology are often accompanied by altered bacterial virulence. Initial assessment of the growth of different BCG::RD1 "knock-ins" in C57BL/6 or BALB/c mice following intravenous infection revealed that complementation did not restore levels of virulence to those of the reference strain *M. tubercluosis* H37Rv (FIG. 3A). In longer-term experiments, modest yet significant differences were detected in the persistence of the BCG::RD1 "knock-ins" in comparison to BCG controls. Following intravenous infection of C57BL/6 mice, only the RD1 "knock-ins" were still detectable in the lungs after 106 days (FIG. 3B). This difference in virulence between the RD1 recombinants and the BCG vector control was more pronounced in severe combined immunodeficiency (SCID) mice (FIG. 3C). The BCG::RD1-2F9 "knock-in" was markedly more virulent, as evidenced by the growth rate in lungs and spleen and also by an increased degree of splenomegaly (FIG. 3D). Cytological examination revealed numerous bacilli, extensive cellular infiltration and granuloma formation. These increases in virulence following complementation with the RD1 region, demonstrate that the loss of this genomic locus contributed to the attenuation of BCG.

The inability to restore full virulence to BCG Pasteur was not due to instability of our constructs nor to the strain used (data not shown). Essentially identical results were obtained on complementing BCG Russia, a strain less passaged than BCG Pasteur and presumed, therefore, to be closer to the original ancestor (M. A. Behr, et al., *Science* 284, 1520 (1999)). This indicates that the attenuation of BCG was a polymutational process and loss of residual virulence for animals was documented in the late 1920s (T. Oettinger, et al, *Tuber Lung Dis* 79, 243 (1999)). Using the same experimental strategy, we also tested the effects of complementing with RD3-5, RD7 and RD9 (S. T. Cole, et al., *Nature* 393, 537 (1998); M. A. Behr, et al., *Science* 284, 1520 (1999); R. Brosch, et al., *Infection Immun.* 66, 2221 (1998) and S. V. Gordon et al., *Molec Microbiol* 32, 643 (1999)) encoding putative virulence factors (FIG. 1B). Reintroduction of these regions, which are not restricted to avirulent strains, did not affect virulence in immuno-competent mice. Although it is possible that deletion effects act synergistically it seems more plausible that other attenuating mechanisms are at play.

Figure 4A:
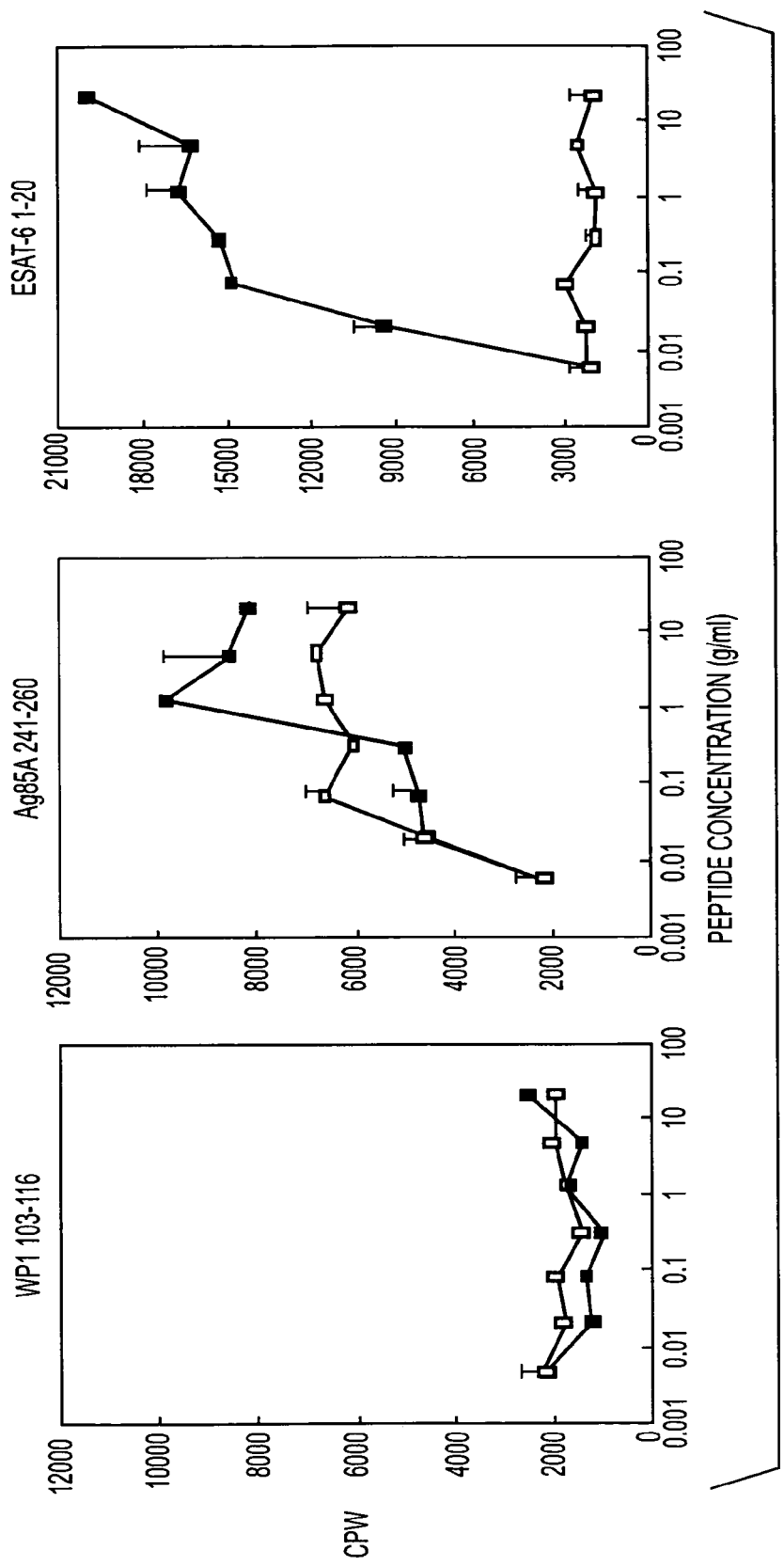
Figure 4B:
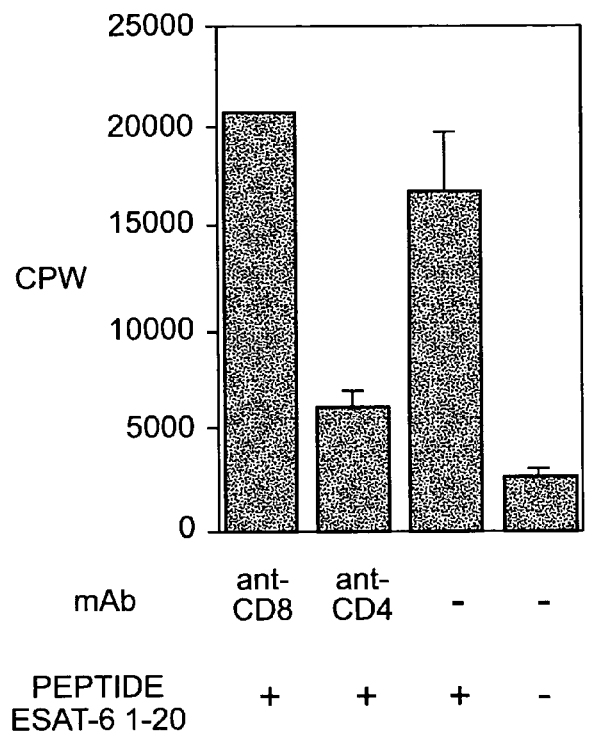
Figure 4C:
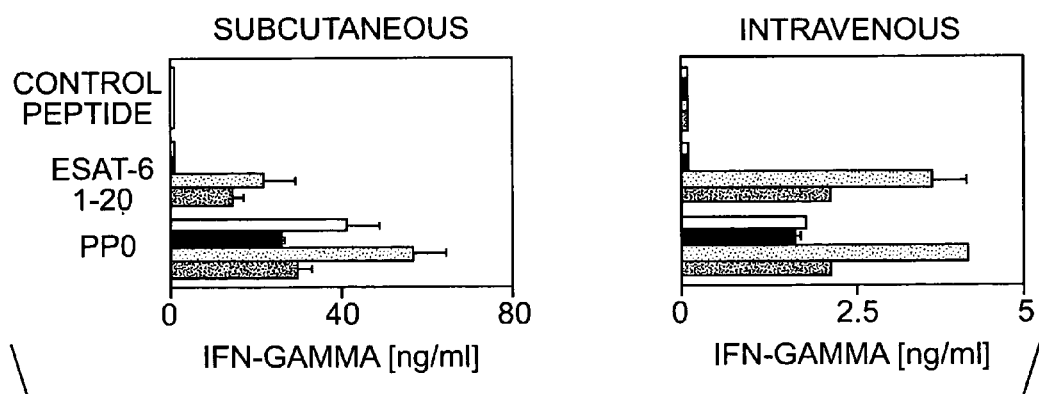
Figure 4D:
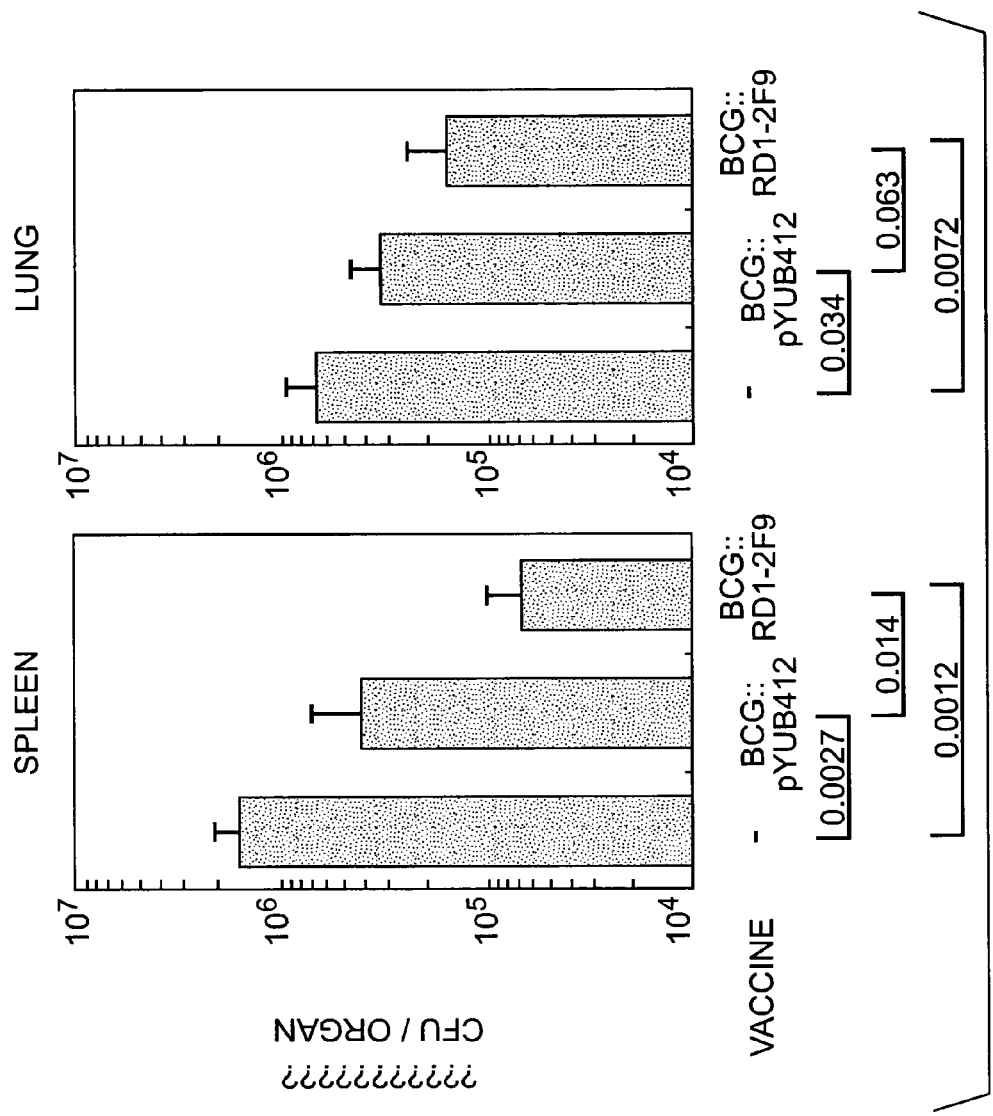

Since RD1 encodes at least two potent T-cell antigens (R. Colangelli, et al., *Infect. Immun.* 68, 990 (2000), M. Harboe, et al., *Infect. Immun.* 66, 717 (1998) and R. L. V. SkjØt et al., *Infect. Inmun.* 68, 214 (2000)), we investigated whether its restoration induced immune responses to these antigens or even improved the protective capacity of BCG. Three weeks following either intravenous or subcutaneous inoculation with BCG::RD1 or BCG controls, we observed similar proliferation of splenocytes to an Ag85A (an antigenic BCG protein) peptide (K. Huygen, et al., *Infect. Immun.* 62, 363 (1994)), but not against a control viral peptide (FIG. 4A). Moreover, BCG::RD1 generated powerful $CD4^+$ T-cell responses against the ESAT-6 peptide as shown by splenocyte proliferation (FIGS. 4A, B) and strong IFN-γ production (FIG. 4C). In contrast, the BCG::pYUB412 control did not stimulate ESAT-6 specific T-cell responses thus indicating that these were mediated by the RD1 locus. ESAT-6 is, therefore, highly immunogenic in mice in the context of recombinant BCG.

When used as a subunit vaccine, ESAT-6 elicits T-cell responses and induces levels of protection weaker than but akin to those of BCG (L. Brandt et al, *Infect. Immun.* 68, 791 (2000)). Challenge experiments were conducted to determine if induction of immune responses to BCG::RD1-encoded antigens, such as ESAT-6, could improve protection against infection with *M. tuberculosis*. Groups of mice inoculated with either BCG::pYUB412 or BCG::RD1 were subsequently infected intravenously with *M. tuberculosis* H37Rv. These experiments showed that immunization with the BCG::RD1 "knock-in" inhibited the growth of *M. tuberculosis* within both BALB/c (FIG. 4D) and C57BL/6 mice when compared to inoculation with BCG alone.

Although the increases in protection induced by BCG::RD1 and the BCG control are modest they demonstrate convincingly that genetic differences have developed between the live vaccine and the pathogen which have weakened the protective capacity of BCG. This study therefore defines the genetic basis of a compromise that has occurred, during the attenuation process, between loss of virulence and reduced protection (M. A. Behr, P. M. Small, *Nature* 389, 133 (1997)). The strategy of reintroducing, or even overproducing (M. A. Horwitz et al, *Proc Natl Acad Sci USA* 97, 13853 (2000)), the missing immunodominant antigens of *M. tuberculosis* in BCG, could be combined with an immuno-neutral attenuating mutation to create a more efficacious tuberculosis vaccine.

EXAMPLE 2

BAC Based Comparative Genomics Identifies *Mycobacterium microti* as a Natural ESAT-6 Deletion Mutant We searched for any genetic differences between human and vole isolates that might explain their different degree of virulence and host preference and what makes the vole isolates harmless for humans. In this regard, comparative genomics methods were employed in connection with the present invention to identify major differences that may exist between the *M. microti* reference strain OV254 and the entirely sequenced strains of *M. tuberculosis* H37Rv (10) or *M. bovis* AF2122/97 (14). An ordered Bacterial Artificial Chromosome (BAC) library of *M. microti* OV254 was constructed and individual BAC to BAC comparison of a minimal set of these clones with BAC clones from previously constructed libraries of *M. tuberculosis* H37Rv and *M. bovis* AF2122/97 was undertaken.

Ten regions were detected in *M. microti* that were different to the corresponding genomic regions in *M. tuberculosis* and *M. bovis*. To investigate if these regions were associated with the ability of *M. microti* strains to infect humans, their genetic organization was studied in 8 additional *M. microti* strains; including those isolated recently from patients with pulmonary tuberculosis. This analysis identified some regions that were specifically absent from all tested *M. microti* strains, but present in all other members of the *M. tuberculosis* complex and other regions that were only absent from vole isolates of *M. microti*.

2.1 Material and Methods

Bacterial strains and plasmids. *M. microti* OV254 which was originally isolated from voles in the UK in the 1930's was kindly supplied by M J Colston (45). DNA from *M. microti* OV216 and OV183 were included in a set of strains used during a multicenter study (26). *M. microti* Myc 94-2272 was isolated in 1988 from the perfusion fluid of a 41-year-old dialysis patient (43) and was kindly provided by L. M. Parsons. *M. microti* 35782 was purchased from American Type Culture Collection (designation TMC 1608 (M. P. Prague)). *M. microti* B1 type llama, B2 type llama, B3 type mouse and B4 type mouse were obtained from the collection of the National Reference Center for Mycobacteria, Forschungszentrum Borstel, Germany. *M. bovis* strain AF2122/97, spoligotype 9 was responsible for a herd outbreak in Devon in the UK and has been isolated from lesions in both cattle and badgers. Typically, mycobacteria were grown on 7H9 Middlebrook liquid medium (Difco) containing 10% oleic-acid-dextrose-catalase (Difco), 0.2% pyruvic acid and 0.05% Tween 80.

Library construction, preparation of BAC DNA and sequencing reactions. Preparation of agarose-embedded genomic DNA from *M. microti* strain OV254, *M. tuberculosis* H37Rv, *M. bovis* BCG was performed as described by Brosch et al. (5). The *M. microti* library was constructed by ligation of partially digested HindIII fragments (50-125 kb) into pBeloBAC11. From the 10,000 clones that were obtained, 2,000 were picked into 96 well plates and stored at −80° C. Plasmid preparations of recombinant clones for sequencing reactions were obtained by pooling eight copies of 96 well plates, with each well containing an overnight culture in 250 µl 2YT medium with 12.5 µg·ml$^{-1}$ chloramphenicol. After 5 min centrifugation at 3000 rpm, the bacterial pellets were resuspended in 25 µl of solution A (25 mM Tris, pH 8.0, 50 mM glucose and 10 mM EDTA), cells were lysed by adding 25 µl of buffer B (NaOH 0.2 M, SDS 0.2%). Then 20 µl of cold 3 M sodium acetate pH 4.8 were added and kept on ice for 30 min. After centrifugation at 3000 rpm for 30 min, the pooled supernatants (140 µl) were transferred to new plates. 130 µl of isopropanol were added, and after 30 min on ice, DNA was pelleted by centrifugation at 3500 rpm for 15 min. The supernatant was discarded and the pellet resuspended in 50 µl of a 10 µg/ml RNAse A solution (in Tris 10 mM pH 7.5/EDTA 10 mM) and incubated at 64° C. for 15 min. After precipitation (2.5 µl of sodium acetate 3 M pH 7 and 200 µl of absolute ethanol) pellets were rinsed with 200 µl of 70% ethanol, air dried and finally suspended in 20 µl of TE buffer.

End-sequencing reactions were performed with a Taq DyeDeoxy Terminator cycle sequencing kit (Applied Biosystems) using a mixture of 13:1 of DNA solution, 2:1 of Primer (2 M) (SP6-BAC1, AGTTAGCTCACTCATTAGGCA (SEQ ID No 15), or T7-BAC1, GGATGTGCTGCAAGGCGATTA (SEQ ID No 16)), 2.5:1 of Big Dye and 2.5:1 of a 5× buffer (50 mM MgCl$_2$, 50 mM Tris). Thermal cycling was performed on a PTC-100 amplifier (MJ Inc.) with an initial denaturation step of 60 s at 95° C., followed by 90 cycles of 15 s at 95° C., 15 s at 56° C., 4 min at 60° C. DNA was then precipitated with 80:1 of 76% ethanol and centrifuged at 3000 rpm for 30 min. After discarding the supernatant, DNA was finally rinsed with 80 µl of 70% ethanol and resuspended in appropriate buffers depending on the type of automated sequencer used (ABI 377 or ABI 3700). Sequence data were transferred to Digital workstations and edited using the TED software from the Staden package (37). Edited sequences were compared against the *M. tuberculosis* H37Rv database the *M. bovis* BLAST server, and in-house databases to determine the relative positions of the *M. microti* OV254 BAC end-sequences.

Preparation of BAC DNA from recombinants and BAC digestion profile comparison. DNA for digestion was prepared as previously described (4). DNA (1 µg) was digested with HindIII (Boehringer) and restriction products separated by pulsed-field gel electrophoresis (PFGE) on a Biorad CHEF-DR III system using a 1% (w/v) agarose gel and a pulse of 3.5 s for 17 h at 6 V·cm$^{-1}$. Low-range PFGE markers (NEB) were used as size standards. Insert sizes were estimated after ethidium bromide staining and visualization with UV light. Different comparisons were made with overlapping clones from the *M. microti* OV254, *M. bovis* AF2122/97, and *M. tuberculosis* H37Rv pBeloBAC11 libraries.

PCR analysis to determine presence of genes in different *M. microti* strains. Reactions contained 5 µl of 10×PCR buffer (100 mM β-mercaptoethanol, 600 mM Tris-HCl, pH 8.8, 20 mM MgCl$_2$, 170 mM (NH$_4$)$_2$SO$_4$, 20 mM nucleotide mix dNTP), 2.5 µl of each primer at 2 µM, 10 ng of template DNA, 10% DMSO and 0.5 unit pf Taq polymerase in a final volume of 12.5 µl. Thermal cycling was performed on a PTC-100 amplifier (MJ Inc.) with an initial denaturation step of 90 s at 95° C., followed by 35 cycles of 45 s at 95° C., 1 min at 60° C. and 2 min at 72° C.

RFLP analysis. In brief, agarose plugs of genomic DNA prepared as previously described (5) were digested with either AseI, DraI or XbaI (NEB), then electrophoresed on a 1% agarose gel, and finally transferred to Hybond-C extra nitrocellulose membranes (Amersham). Different probes were amplified by PCR from the *M. microti* strain OV254 or *M. tuberculosis* H37Rv using primers for:

esat-6 (esat-6F GTCACGTCCATTCATTCCCT (SEQ ID No 17);

esat-6R ATCCCAGTGACGTTGCCTT) (SEQ ID No 18), the RD1$^{mic}$ flanking region (4340, 209F GCAGTGCAAAG-GTGCAGATA (SEQ ID No 19); 4354,701R GATTGAGA-CACTTGCCACGA (SEQ ID No 20)), or plcA (plcA.int.F CAAGTTGGGTCTGGTCGAAT (SEQ ID No 21); plcA.int.R GCTACCCAAGGTCTCCTGGT (SEQ ID No 22)). Amplification products were radio-labeled by using the Stratagene Prime-It II kit (Stratagene). Hybridizations were performed at 65° C. in a solution containing NaCl 0.8 M, EDTA pH 8, 5 mM, sodium phosphate 50 mM pH 8, 2% SDS, 1×Denhardt's reagent and 100 µg/ml salmon sperm DNA (Genaxis). Membranes were exposed to phosphorimager screens and images were digitalized by using a STORM phospho-imager.

DNA sequence accession numbers. The nucleotide sequences that flank MiD1, MiD2, MiD3 as well as the junction sequence of RD1$^{mic}$ have been deposited in the EMBL database. Accession numbers are AJ345005, AJ345006, AJ315556 and AJ315557, respectively.

2.2 Results

Establishment of a complete ordered BAC library of *M. microti* OV254. Electroporation of pBeloBAC11 containing partial HindIII digests of *M. microti* OV254 DNA into *Escherichia coli* DH10B yielded about 10,000 recombinant clones, from which 2,000 were isolated and stored in 96-well plates. Using the complete sequence of the *M. tuberculosis* H37Rv genome as a scaffold, end-sequencing of 384 randomly chosen *M. microti* BAC clones allowed us to select enough clones to cover almost all of the 4.4 Mb chromosome. A few rare clones that spanned regions that were not covered by this approach were identified by PCR screening of pools as previously described (4). This resulted in a minimal set of 50 BACs, covering over 99.9% of the *M. microti* OV254 genome, whose positions relative to *M. tuberculosis* H37Rv are shown in FIG. 5. The insert size ranged between 50 and 125 kb, and the recombinant clones were stable. Compared with other BAC libraries from tubercle bacilli (4, 13) the *M. microti* OV254 BAC library contained clones that were generally larger than those obtained previously, which facilitated the comparative genomics approach, described below.

Identification of DNA deletions in *M. microti* OV254 relative to *M. tuberculosis* H37Rv by comparative genomics. The minimal overlapping set of 50 BAC clones, together with the availability of three other ordered BAC libraries from *M. tuberculosis* H37Rv, *M. bovis* BCG Pasteur 1173P2 (5, 13) and *M. bovis* AF2122/97 (14) allowed us to carry out direct BAC to BAC comparison of clones spanning the same genomic regions. Size differences of PFGE-separated HindIII restriction fragments from *M. microti* OV254 BACs, relative to restriction fragments from *M. bovis* and/or *M. tuberculosis* BAC clones, identified loci that differed among the tested strains. Size variations of at least 2 kb were easily detectable and 10 deleted regions, evenly distributed around the genome, and containing more than 60 open reading frames (ORFs), were identified. These regions represent over 60 kb that are missing from *M. microti* OV254 strain compared to *M. tuberculosis* H37Rv. First, it was found that phiRv2 (RD11), one of the two *M. tuberculosis* H37Rv prophages was present in *M. microti* OV254, whereas phiRv1, also referred to as RD3 (29) was absent. Second, it was found that *M. microti* lacks four of the genomic regions that were also absent from *M. bovis* BCG. In fact, these four regions of difference named RD7, RD8, RD9 and RD10 are absent from all members of the *M. tuberculosis* complex with the exception of *M. tuberculosis* and *M. canettii*, and seem to have been lost from a common progenitor strain of *M. africanum*, *M. microti* and *M. bovis* (3). As such, our results obtained with individual BAC to BAC comparisons show that *M. microti* is part of this non-*M. tuberculosis* lineage of the tubercle bacilli, and this assumption was further confirmed by sequencing the junction regions of RD7-RD10 in *M. microti* OV254. The sequences obtained were identical to those from *M. africanum*, *M. bovis* and *M. bovis* BCG strains. Apart from these four conserved regions of difference, and phiRv1 (RD3) *M. microti* OV254 did not show any other RDs with identical junction regions to *M. bovis* BCG Pasteur, which misses at least 17 RDs relative to *M. tuberculosis* H37Rv (1, 13, 35). However, five other regions missing from the genome of *M. microti* OV254 relative to *M. tuberculosis* H37Rv were identified (RD1$^{mic}$, RD5$^{mic}$, MiD1, MiD2, MiD3). Such regions are specific either for strain OV254 or for *M. microti* strains in general. Interestingly, two of these regions, RD1$^{mic}$, RD5$^{mic}$ partially overlap RDs from the *M. bovis* BCG.

Antigens ESAT-6 and CFP-10 are absent from *M. microti*. One of the most interesting findings of the BAC to BAC comparison was a novel deletion in a genomic region close to the origin of replication (FIG. 5). Detailed PCR and sequence analysis of this region in *M. microti* OV254 showed a segment of 14 kb to be missing (equivalent to *M. tuberculosis* H37Rv from 4340.4 to 4354.5 kb) that partly overlapped RD1$^{bcg}$ absent from *M. bovis* BCG. More precisely, ORFs Rv3864 and Rv3876 are truncated in *M. microti* OV254 and ORFs Rv3865 to Rv3875 are absent (FIG. 6). This observation is particularly interesting as previous comparative genomic analysis identified RD1$^{bcg}$ as the only RD region that is specifically absent from all BCG sub-strains but present in all other members of the *M. tuberculosis* complex (1, 4, 13, 29, 35). As shown in FIG. 6, in *M. microti* OV254 the RD1$^{mic}$ deletion is responsible for the loss of a large portion of the conserved ESAT-6 family core region (40) including the genes coding for the major T-cell antigens ESAT-6 and CFP-10 (2, 15). The fact that previous deletion screening protocols employed primer sequences that were designed for the right hand portion of the RD1$^{bcg}$ region (i.e. gene Rv3878) (6, 39) explains why the RD1$^{mic}$ deletion was not detected earlier by these investigations. FIG. 6 shows that RD1$^{mic}$ does not affect genes Rv3877, Rv3878 and Rv3879 which are part of the RD1$^{bcg}$ deletion.

Deletion of phospholipase-C genes in *M. microti* OV254. RD5$^{mic}$, the other region absent from *M. microti* OV254, that partially overlapped an RD region from BCG, was revealed by comparison of BAC clone Mi18A5 with BAC Rv143 (FIG. 5). PCR analysis and sequencing of the junction region revealed that RD5$^{mic}$ was smaller than the RD5 deletion in BCG (Table 2 and 3 below).

TABLE 2

Description of the putative function of the deleted and truncated ORFs in *M. microti* OV254

| Region | Start-End | overlapping ORF | Putative Function or family |
|---|---|---|---|
| RD 10 | 264,5-266,5 | Rv0221-Rv0223 | echA1 |
| RD 3 | 1779,5-1788,5 | Rv1573-Rv1586 | bacteriophage proteins |
| RD 7 | 2207,5-2220,5 | Rv1964-Rv1977 | yrbE3A-3B; mce3A-F; unknown |
| RD 9 | 2330-2332 | Rv2072-Rv2075 | cobL; probable oxidoreductase; unknown |
| RD 5$^{mic}$ | 2627,6-2633,4 | Rv2348-Rv2352 | plc A-C; member of PPE family |
| MiD1 | 3121,8-3126,6 | Rv2816-Rv2819 | IS6110 transposase; unknown |
| MiD2 | 3554,0-3755,2 | Rv3187-Rv3190 | IS6110 transposase; unknown |
| MiD3 | 3741,1-3755,7 | Rv3345-Rv3349 | members of the PE-PGRS and PPE families; insertion elements |
| RD 8 | 4056,8-4062,7 | Rv3617-Rv3618 | ephA; lpqG; member of the PE-PGRS family |
| RD 1$^{mic}$ | 4340,4-4354,5 | Rv3864-Rv3876 | member of the CBXX/CF QX family; member of the PE and PPE families; ESAT-6; CFP 10; unknown |

TABLE 3

Sequence at the junction of the deleted regions in M. microti OV254

| Junction | Position | ORFs | Sequences at the junction | Flanking primers |
|---|---|---|---|---|
| RD1$^{mic}$ (SEQ ID No 23) | 4340, 421-<br>4354, 533 | Rv3864-<br>Rv3876 | CAAGACGAGGTTGTAAAACCTCGACG<br>CAGGATCGGCGATGAAATGCCAGTCG<br>GCGTCGCTGAGCGCGCGCTGCGCCGA<br>GTCCCATTTTGTCGCTGATTTGTTTGAACA<br>GGGTCGGGGATTCCCT | 4340, 209F (SEQ ID No 19)<br>GCAGTGCAAAGGTGCAGATA<br>4354, 701R (SEQ ID No 20)<br>GATTGAGACACTTGCCACGA |
| RD5$^{mic}$ (SEQ ID No 26) | 2626, 831-<br>2635, 581 | Rv2349-<br>Rv2355 | CCTCGATGAACCACCTGACATGACCC<br>CATCCTTTCCAAGAACTGGAGTCTCC<br>GGACATGCCGGGGCGGTTCACTGCCC<br>CAGGTGTCCTGGGTCGTTCCGTTGACCGT<br>CGAGTCCGAACATCCGTCATTCCCGGTGG<br>CAGTCGGTGCGGTGAC | 2627, 370F (SEQ ID No 24)<br>GAATGCCGACGTCATATCG<br>2633, 692R (SEQ ID No 25)<br>CGGCCACTGAGTTCGATTAT |

TABLE 3-continued

Sequence at the junction of the deleted regions in M. microti OV254

| Junction | Position | ORFs | Sequences at the junction | Flanking primers |
|---|---|---|---|---|
| MiD1 (SEQ ID No 29) | 3121, 880- 3126, 684 | Rv2815c- Rv2818c | CACCTGACATGACCCCATCCTTTCCA AGAACTGGAGTCTCCGGACATGCCGG GGCGGTTCAG*GG*ACATTCATGTCCATCTT *CTGGCAGATCAGCAGATCGCTTGTTCTCAG TGCAGGTGAGTC* | 3121, 690F (SEQ ID No 27) CAGCCAACACCAAGTAGACG 3126, 924R (SEQ ID No 28) TCTACCTGCAGTCGCTTGTG |
| MiD2 (SEQ ID No 32) | 3554, 066- 3555, 259 | Rv3188- Rv3189 | GCTGCCTACTACGCTCAACGCCAGAG ACCAGCCGCCGGCTGAGGTCTCAGAT CAGAGAGTCTCCGGACTCACCGGGGC GGTTCA*TAAAGGCTTCGAGACCGGACGG GCTGTAGGTTCCTCAACTGTGTGGCGGAT GGTCTGAGCACTTAAC* | 3553, 880F (SEQ ID No 30) GTCCATCGAGGATGTCTGAGT 3555, 385R (SEQ ID No 31) CTAGGCCATTCCGTTGTCTG |
| MiD3 (SEQ ID No 35) | 3741, 139- 3755, 777 | Rv3345c- Rv3349c | TGGCGCCGGCACCTCCGTTGCCACCG TTGCCGCCGCTGGTGGGCGCGGTGCC GTTCGCCCCGGCCCGAACCGTTCAGGG CCGGGTTC*GCCCTCAGCCGCTAAACACG CCGACCAAGATCAACGAGCTACCTGCCCG GTCAAGGTTGAAGAGCCCCCATATCAGCA AGGGCCCGGTGTCGGCG* | 3740, 950F (SEQ ID No 33) GGCGACGCCATTTCC 3755, 988R (SEQ ID No 34) AACTGTCGGGCTTGCTCTT |

In fact, *M. microti* OV254 lacks the genes plcA, plcB, plcC and one specific PPE-protein encoding gene (Rv2352). This was confirmed by the absence of a clear band on a Southern blot of AseI digested genomic DNA from *M. microti* OV254 hybridized with a plcA probe. However, the genes Rv2346c and Rv2347c, members of the esat-6 family, and Rv2348c, that are missing from *M. bovis* and BCG strains (3) are still present in *M. microti* OV254. The presence of an IS6110 element in this segment suggests that recombination between two IS6110 elements could have been involved in the loss of RD5$^{mic}$, and this is supported by the finding that the remaining copy of IS6110 does not show a 3 base-pair direct repeat in strain OV254 (Table 3).

Lack of MiD1 provides genomic clue for *M. microti* OV254 characteristic spoligotype. MiD1 encompasses the three ORFs Rv2816, Rv2817 and Rv2818 that encode putative proteins whose functions are yet unknown, and has occurred in the direct repeat region (DR), a polymorphic locus in the genomes of the tubercle bacilli that contains a cluster of direct repeats of 36 bp, separated by unique spacer sequences of 36 to 41 by (17), (FIG. 7). The presence or absence of 43 unique spacer sequences that intercalate the DR sequences is the basis of spacer-oligo typing, a powerful typing method for strains from the *M. tuberculosis* complex (23). *M. microti* isolates exhibit a characteristic spoligotype with an unusually small DR cluster, due to the presence of only spacers 37 and 38 (43). In *M. microti* OV254, the absence of spacers 1 to 36, which are present in many other *M. tuberculosis* complex strains, appears to result from an IS6110 mediated deletion of 636 by of the DR region. Amplification and PvuII restriction analysis of a 2.8 kb fragment obtained with primers located in the genes that flank the DR region (Rv2813c and Rv2819) showed that there is only one copy of IS6110 remaining in this region (FIG. 7). This IS6110 element is inserted into ORF Rv2819 at position 3,119,932 relative to the *M. tuberculosis* H37Rv genome. As for other IS6110 elements that result from homologous recombination between two copies (7), no 3 base-pair direct repeat was found for this copy of IS6110 in the DR region. Concerning the absence of spacers 39-43 (FIG. 7), it was found that *M. microti* showed a slightly different organization of this locus than *M. bovis* strains, which also characteristically lack spacers 39-43. In *M. microti* OV254 an extra spacer of 36 by was found that was not present in *M. bovis* no in *M. tuberculosis* H37Rv. The sequence of this specific spacer was identical to that of spacer 58 reported by van Embden and colleagues (42). In their study of the DR region, in many strains from the *M. tuberculosis* complex, this spacer was only found in *M. microti* strain NLA000016240 (AF189828) and in some ancestral *M. tuberculosis* strains (3, 42). Like MiD1, MiD2 most probably results from an IS6110 mediated deletion of two genes (Rv3188, Rv3189) that encode putative proteins whose function is unknown (Table 3 above and Table 4 below).

TABLE 4

Presence of the RD and MiD regions in different *M. microti* strains

| HOST Strain | VOLES OV 254 | OV 183 | OV 216 | ATCC 35782 | HUMAN Myc 94-2272 | B3 type mouse | B4 type mouse | B1 type llama | B2 type llama |
|---|---|---|---|---|---|---|---|---|---|
| RD1$^{mic}$ | absent | absent | absent | absent | absent | absent | absent | absent | absent |
| RD3 | absent | absent | absent | absent | absent | absent | absent | absent | absent |
| RD7 | absent | absent | absent | absent | absent | absent | absent | absent | absent |
| RD8 | absent | absent | absent | absent | absent | absent | absent | absent | absent |
| RD9 | absent | absent | absent | absent | absent | absent | absent | absent | absent |
| RD10 | absent | absent | absent | absent | absent | absent | absent | absent | absent |
| MiD3 | absent | ND | ND | absent | absent | absent | absent | absent | absent |
| MiD1 | absent | ND | ND | present | partial | partial | partial | present | present |

TABLE 4-continued

Presence of the RD and MiD regions in different *M. microti* strains

| HOST Strain | VOLES OV 254 | OV 183 | OV 216 | ATCC 35782 | HUMAN Myc 94-2272 | B3 type mouse | B4 type mouse | B1 type llama | B2 type llama |
|---|---|---|---|---|---|---|---|---|---|
| RD5$^{mic}$ | absent | absent | absent | present | present | present | present | present | present |
| MiD2 | absent | ND | ND | present | present | present | present | present | present |

ND, not determined

Absence of some members of the PPE family in *M. microti*. MiD3 was identified by the absence of two HindIII sites in BAC Mi4B9 that exist at positions 3749 kb and 3754 kb in the *M. tuberculosis* H37Rv chromosome. By PCR and sequence analysis, it was determined that MiD3 corresponds to a 12 kb deletion that has truncated or removed five genes orthologous to Rv3345c-Rv3349c. Rv3347c encodes a protein of 3157 amino-acids that belongs to the PPE family and Rv3346c a conserved protein that is also present in *M. leprae*. The function of both these putative proteins is unknown while Rv3348 and Rv3349 are part of an insertion element (Table 2). At present, the consequences of the MiD3 deletions for the biology of *M. microti* remains entirely unknown.

Extra-DNA in *M. microti* OV254 relative to *M. tuberculosis* H37Rv. *M. microti* OV254 possesses the 6 regions RvD1 to RvD5 and TBD1 that are absent from the sequenced strain *M. tuberculosis* H37Rv, but which have been shown to be present in other members of the *M. tuberculosis* complex, like *M. canettii*, *M. africanum*, *M. bovis*, and *M. bovis* BCG (3, 7, 13). In *M. tuberculosis* H37Rv, four of these regions (RvD2-5) contain a copy of IS6110 which is not flanked by a direct repeat, suggesting that recombination of two IS6110 elements was involved in the deletion of the intervening genomic regions (7). In consequence, it seems plausible that these regions were deleted from the *M. tuberculosis* H37Rv genome rather than specifically acquired by *M. microti*. In addition, three other small insertions have also been found and they are due to the presence of an IS6110 element in a different location than in *M. tuberculosis* H37Rv and *M. bovis* AF2122/97. Indeed, PvuII RFLP analysis of *M. microti* OV254 reveals 13 IS6110 elements (data not shown).

Genomic diversity of *M. microti* strains. In order to obtain a more global picture of the genetic organization of the taxon *M. microti* we evaluated the presence or absence of the variable regions found in strain OV254 in eight other *M. microti* strains. These strains which were isolated from humans and voles have been designated as *M. microti* mainly on the basis of their specific spoligotype (26, 32, 43) and can be further divided into subgroups according to the host such as voles, llama and humans (Table 3). As stated in the introduction, *M. microti* is rarely found in humans unlike *M. tuberculosis*. So the availability of 9 strains from variable sources for genetic characterization is an exceptional resource. Among them was one strain (Myc 94-2272) from a severely immuno-compromised individual (43), and four strains were isolated from HIV-positive or HV-negative humans with spoligotypes typical of llama and mouse isolates. For one strain, ATCC 35872/M. P. Prague, we could not identify with certainty the original host from which the strain was isolated, nor if this strain corresponds to *M. microti* OV166, that was received by Dr. Sula from Dr. Wells and used thereafter for the vaccination program in Prague in the 1960's (38).

Figure 8A:
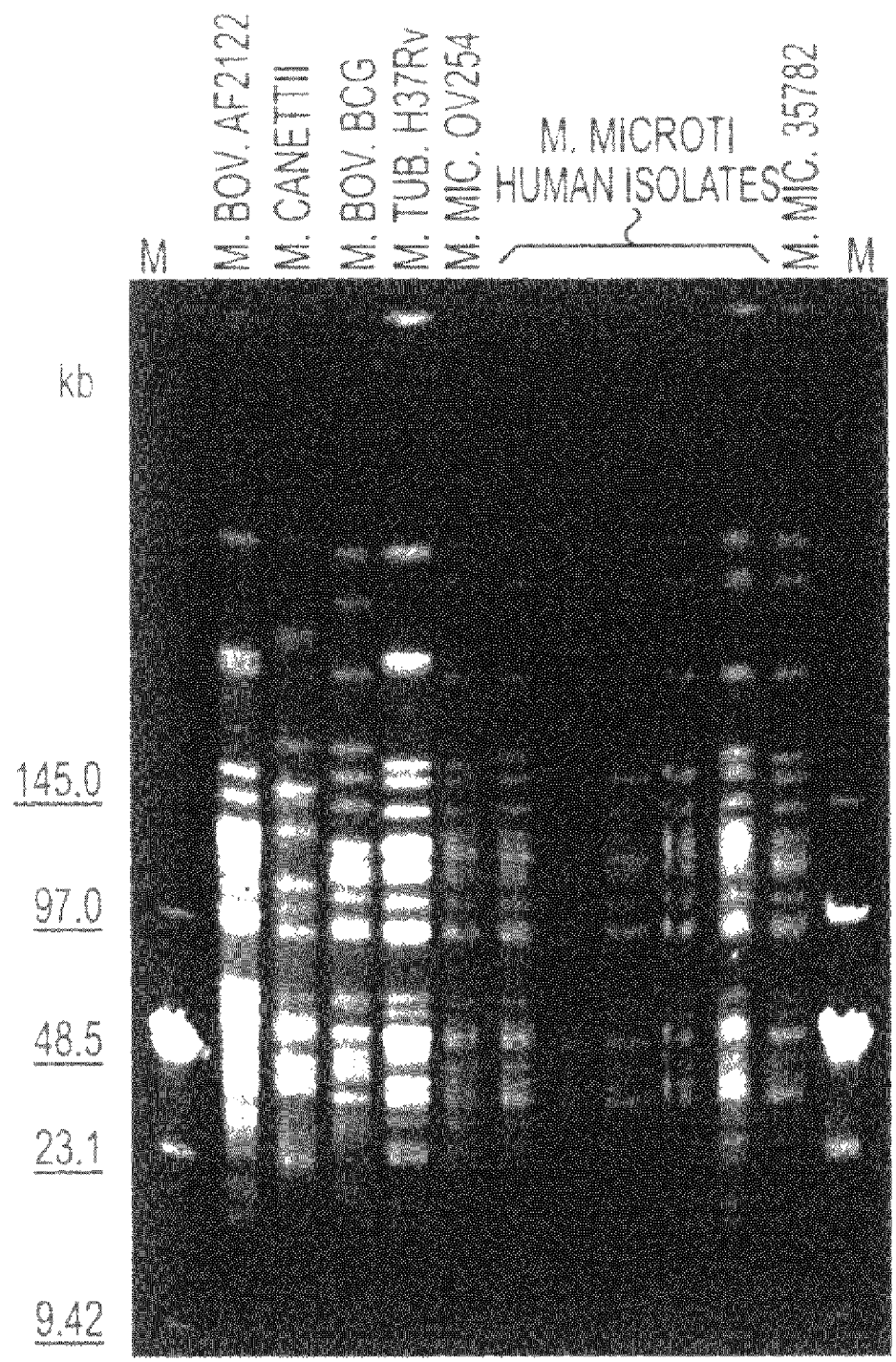
Figure 8B:
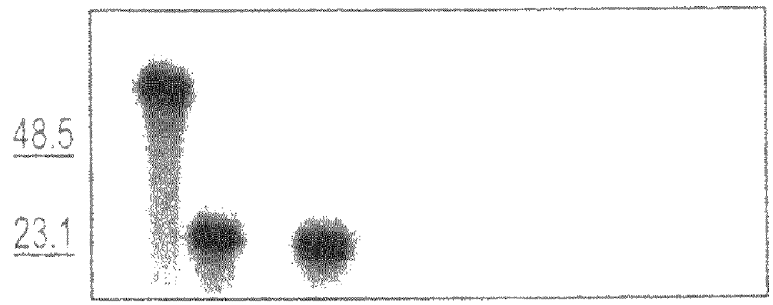

First, we were interested if these nine strains designated as *M. microti* on the basis of their spoligotypes also resembled each other by other molecular typing criteria. As RFLP of pulsed-field gel separated chromosomal DNA represents probably the most accurate molecular typing strategy for bacterial isolates, we determined the AseI profiles of the available *M. microti* strains, and found that the profiles resembled each other closely but differed significantly from the macro-restriction patterns of *M. tuberculosis*, *M. bovis* and *M. bovis* BCG strains used as controls. However, as depicted in FIG. 8A, the patterns were not identical to each other and each *M. microti* strain showed subtle differences, suggesting that they were not epidemiologically related. A similar observation was made with other rare cutting restriction enzymes, like DraI or XbaI (data not shown).

Common and diverging features of *M. microti* strains. Two strategies were used to test for the presence or absence of variable regions in these strains for which we do not have ordered BAC libraries. First, PCRs using internal and flanking primers of the variable regions were employed and amplification products of the junction regions were sequenced. Second, probes from the internal portion of variable regions absent from *M. microti* OV254 were obtained by amplification of *M. tuberculosis* H37Rv DNA using specific primers. Hybridization with these radio-labeled probes was carried out on blots from PFGE separated AseI restriction digests of the *M. microti* strains. In addition, we confirmed the findings obtained by these two techniques by using a focused macroarray, containing some of the genes identified in variable regions of the tubercle bacilli to date (data not shown).

This led to the finding that the RD1$^{mic}$ deletion is specific for all *M. microti* strains tested.

Figure 8C:
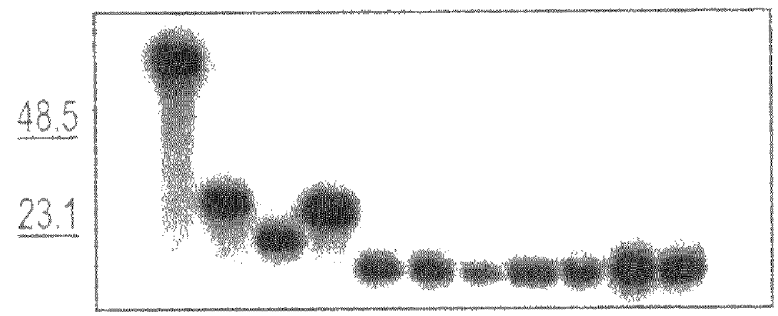

Indeed, none of the *M. microti* DNA-digests hybridized with the radio-labeled esat-6 probe (FIG. 8B) but with the RD1$^{mic}$ flanking region (FIG. 8C). In addition, PCR amplification using primers flanking the RD1$^{mic}$ region (Table 2) yielded fragments of the same size for *M. microti* strains whereas no products were obtained for *M. tuberculosis*, *M. bovis* and *M. bovis* BCG strains (FIG. 9). Furthermore, the sequence of the junction region was found identical among the strains which confirms that the genomic organization of the RD1$^{mic}$ locus was the same in all tested *M. microti* strains (Table 3). This clearly demonstrates that *M. microti* lacks the conserved ESAT-6 family core region stretching in other members of the *M. tuberculosis* complex from Rv3864 to Rv3876 and, as such, represents a taxon of naturally occurring ESAT-6/CFP-10 deletion mutants.

Figure 8D:
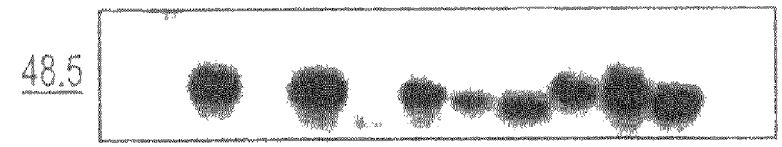

Like RD1$^{mic}$, MiD3 was found to be absent from all nine *M. microti* strains tested and, therefore, appears to be a specific genetic marker that is restricted to *M. microti* strains (Table 3). However, PCR amplification showed that RD5$^{mic}$ is absent only from the vole isolates OV254, OV216 and OV183, but present in the *M. microti* strains isolated from human and other origins (Table 3). This was confirmed by the presence of single bands but of differing sizes on a Southern blot hybridized with a plcA probe for all *M. microti* tested strains except OV254 (FIG. 8D). Interestingly, the presence or absence of RD5$^{mic}$ correlated with the similarity of IS6110 RFLP profiles. The profiles of the three *M. microti* strains isolated from voles in the UK differed considerably from the IS6110 RFLP patterns of humans isolates (43). Taken together, these results underline the proposed involvement of IS6110 mediated deletion of the RD5 region and further suggest that RD5 may be involved in the variable potential of *M. microti* strains to cause disease in humans. Similarly, it was found that MiD1 was missing only from the vole isolates OV254, OV216 and OV183, which display the same spoligotype (43), confirming the observations that MiD1 confers the particular spoligotype of a group of *M. microti* strains isolated from voles. In contrast, PCR analysis revealed that MiD1 is only partially deleted from strains B3 and B4 both characterized by the mouse spoligotype and the human isolate *M. microti* Myc 94-2272 (Table 3). For strain ATCC 35782 deletion of the MiD1 region was not observed. These findings correlate with the described spoligotypes of the different isolates, as strains that had intact or partially deleted MiD1 regions had more spacers present than the vole isolates that only showed spacers 37 and 38.

2.3 Comments and Discussion

We have searched for major genomic variations, due to insertion-deletion events, between the vole pathogen, *M. microti*, and the human pathogen, *M. tuberculosis*. BAC based comparative genomics led to the identification of 10 regions absent from the genome of the vole bacillus *M. microti* OV254 and several insertions due to IS6110. Seven of these deletion regions were also absent from eight other *M. microti* strains, isolated from voles or humans, and they account for more than 60 kb of genomic DNA. Of these regions, RD1$^{mic}$ is of particular interest, because absence of part of this region has been found to be restricted to the BCG vaccine strains to date. As *M. microti* was originally described as non pathogenic for humans, it is proposed here that RD1 genes are involved in the pathogenicity for humans. This is reinforced by the fact that RD1$^{bcg}$ (29) has lost putative ORFs belonging to the esat-6 gene cluster including the genes encoding ESAT-6 and CFP-10 (FIG. 6) (40). Both polypeptides have been shown to act as potent stimulators of the immune system and are antigens recognized during the early stages of infection (8, 12, 20, 34). Moreover, the biological importance of this RD1 region for mycobacteria is underlined by the fact that it is also conserved in *M. leprae*, where genes ML0047-ML0056 show high similarities in their sequence and operon organization to the genes in the esat-6 core region of the tubercle bacilli (11). In spite of the radical gene decay observed in *M. leprae*, the esat-6 operon apparently has kept its functionality in this organism.

However, the RD1 deletion may not be the only reason why the vole bacillus is attenuated for humans. Indeed, it remains unclear why certain *M. microti* strains included in the present study that show exactly the same RD1$^{mic}$ deletion as vole isolates, have been found as causative agents of human tuberculosis. As human *M. microti* cases are extremely rare, the most plausible explanation for this phenomenon would be that the infected people were particularly susceptible for mycobacterial infections in general. This could have been due to an immunodeficiency (32, 43) or to a rare genetic host predisposition such as interferon gamma- or IL-12 receptor modification (22).

In addition, the finding that human *M. microti* isolates differed from vole isolates by the presence of region RD5$^{mic}$ may also have an impact on the increased potential of human *M. microti* isolates to cause disease. Intriguingly, BCG and the vole bacillus lack overlapping portions of this chromosomal region that encompasses three (plcA, plcB, plcC) of the four genes encoding phospholipase C (PLC) in *M. tuberculosis*. PLC has been recognized as an important virulence factor in numerous bacteria, including *Clostridium perfringens*, *Listeria monocytogenes* and *Pseudomonas aeruginosa*, where it plays a role in cell to cell spread of bacteria, intracellular survival, and cytolysis (36, 41). To date, the exact role of PLC for the tubercle bacilli remains unclear. plcA encodes the antigen mtp40 which has previously been shown to be absent from seven tested vole and hyrax isolates (28). Phospholipase C activity in *M. tuberculosis*, *M. microti* and *M. bovis*, but not in *M. bovis* BCG, has been reported (21, 47). However, PLC and sphingomyelinase activities have been found associated with the most virulent mycobacterial species (21). The levels of phospholipase C activity detected in *M. bovis* were much lower than those seen in *M. tuberculosis* consistent with the loss of plcABC. It is likely, that plcD is responsible for the residual phospholipase C activity in strains lacking RD5, such as *M. bovis* and *M. microti* OV254. Indeed, the plcD gene is located in region RvD2 which is present in some but not all tubercle bacilli (13, 18). Phospholipase encoding genes have been recognized as hotspots for integration of IS6110 and it appears that the regions RD5 and RvD2 undergo independent deletion processes more frequently than any other genomic regions (44). Thus, the virulence of some *M. microti* strains may be due to a combination of functional phospholipase C encoding genes (7, 25, 26, 29).

Another intriguing detail revealed by this study is that among the deleted genes seven code for members of the PPE family of Gly-, Ala-, Asn-rich proteins. A closer look at the sequences of these genes showed that in some cases they were small proteins with unique sequences, like for example Rv3873, located in the RD1$^{mic}$ region, or Rv2352c and Rv2353c located in the RD5$^{mic}$ region. Others, like Rv3347c, located in the MiD3 region code for a much larger PPE protein (3157 aa). In this case a neighboring gene (Rv3345c), belonging to another multigene family, the PE-PGRS family, was partly affected by the MiD3 deletion. While the function of the PE/PPE proteins is currently unknown, their predicted abundance in the proteome of *M. tuberculosis* suggests that they may play an important role in the life cycle of the tubercle bacilli. Indeed, recently some of them were shown to be involved in the pathogenicity of *M. tuberculosis* strains (9). Complementation of such genomic regions in *M. microti* OV254 should enable us to carry out proteomics and virulence studies in animals in order to understand the role of such ORFs in pathogenesis.

In conclusion, this study has shown that *M. microti*, a taxon originally named after its major host *Microtus agrestis*, the common vole, represents a relatively homogenous group of tubercle bacilli. Although all tested strains showed unique PFGE macro-restriction patterns that differed slightly among each other, deletions that were common to all *M. microti* isolates (RD7-RD10, MiD3, RD1$^{mic}$) have been identified. The conserved nature of these deletions suggests that these strains are derived from a common precursor that has lost these regions, and their loss may account for some of the observed common phenotypic properties of *M. microti*, like the very slow growth on solid media and the formation of tiny colonies. This finding is consistent with results from a recent study that showed that *M. microti* strains carry a particular mutation in the gyrB gene (31).

Of particular interest, some of these common features (e.g. the flanking regions of RD1$^{mic}$, or MiD3) could be exploited for an easy-to-perform PCR identification test, similar to the one proposed for a range of tubercle bacilli (33). This test enables unambiguous and rapid identification of *M. microti* isolates in order to obtain a better estimate of the overall rate of *M. microti* infections in humans and other mammalian species.

EXAMPLE 3

Recombinant BCG Exporting ESAT-6 Confers Enhanced Protection Against Tuberculosis 3.1 Complementation of the RD1 Locus of BCG Pasteur and *M. microti*

To construct a recombinant vaccine that secretes both ESAT-6 and CFP-10, we complemented BCG Pasteur for the RD1 region using genomic fragments spanning variable sections of the esxBA (or ESAT-6) locus from *M. tuberculosis* (FIG. 10). The RD1 deletion in BCG interrupts or removes nine CDS and affects all four transcriptional units: three are removed entirely while the fourth (Rv3867-Rv3871) is largely intact apart from the loss of 112 codons from the 3'-end of Rv3871 (FIG. 10). Transcriptome analysis of BCG, performed using cDNA probes obtained from early log phase cultures with oligonucleotide-based microarrays, was able to detect signals at least two fold greater than background for the probes corresponding to Rv3867 to 3871 inclusive, but not for the RD1-deleted genes Rv3872 to Rv3879. This suggests that the Rv3867-3871 transcriptional unit is still active in BCG which, like *M. bovis*, also has frameshifts in the neighbouring gene, Rv3881 (FIG. 10). The RD1$^{mic}$ deletion of *M. microti* removes three transcriptional units completely with only gene Rv3877 remaining from the fourth. The *M. tuberculosis* clinical isolate MT56 has lost genes Rv3878-Rv3879 (Brosch, R., et al. A new evolutionary scenario for the *Mycobacterium tuberculosis* complex. *Proc Natl Acad Sci USA* 99, 36849. (2002)) but still secretes ESAT-6 and CFP-10 (FIG. 10).

To test the hypothesis that a dedicated export machinery exists and to establish which genes were essential for creating an ESAT-6-CFP-10 secreting vaccine we assembled a series of integrating vectors carrying fragments spanning different portions of the RD1 esx gene cluster (FIG. 10). These integrating vectors stably insert into the attB site of the genome of tubercle bacilli. pAP34 was designed to carry only the antigenic core region encoding ESAT-6 and CFP-10, and the upstream PE and PPE genes, whereas RD1-I106 and RD1-pAP35 were selected to include the core region and either the downstream or upstream portion of the gene cluster, respectively. The fourth construct RD1-2F9 contains a ~32 kb segment from *M. tuberculosis* that stretches from Rv3861 to Rv3885 covering the entire RD1 gene cluster. We adopted this strategy of complementation with large genomic fragments to avoid polar effects that might be expected if a putative protein complex is only partially complemented in trans. In addition, a set of smaller expression constructs (pAP47, pAP48) was established in which individual genes are transcribed from a heat shock promoter (FIG. 10). Using appropriate antibodies all of these constructs were found to produce the corresponding proteins after transformation of BCG or *M. microti* (see below).

3.2 Several Genes of the esx Cluster are Required for Export of ESAT-6 and CFP-10

The four BCG::RD1 recombinants BCG::RD1-pAP34, BCG::RD1-pAP35, BCG::RD1-2F9 and BCG::RD1-I106) (FIG. 11) were initially tested to ensure that ESAT-6 and CFP-10 were being appropriately expressed from the respective integrated constructs. Immunoblotting of whole cell protein extracts from mid-log phase cultures of the various BCG::RD1 recombinants using an ESAT-6 monoclonal antibody or polyclonal sera for CFP-10 and the PPE68 protein Rv3873 demonstrated that all three proteins were expressed from the four constructs at levels comparable to those of *M. tuberculosis* (FIG. 11). However, striking differences were seen when the supernatants from early log-phase cultures of each recombinant were screened by Western blot for the two antigens. Although low levels of ESAT-6 and CFP-10 could be detected in the concentrated supernatant protein fractions of BCG::RD1-pAP34, BCG::RD1-pAP35 and BCG::RD1-I106 it was only with the integrated construct encompassing the entire esx gene cluster (BCG::RD1-2F9) that the two antigens accumulated in significant amounts. The high concentrations of ESAT-6 and CFP-10 seen in the supernatant of the recombinant BCG::RD1-2F9 were not due to a non-specific increase in permeability, or loss of cell wall material, because when the same whole cell and supernatant protein fractions were immunoblotted with serum raised against Rv3873, this protein was only localized in the cell wall of the various recombinants. As expected, when constructs were used containing esxA or esxBA alone, ESAT-6 did not accumulate in the culture supernatant (data not shown).

To assess the effect of the RD1$^{mic}$ deletion of *M. microti* on the export of ESAT-6 and CFP-10 and subsequent antigen handling, the experiments were replicated in this genomic background. As with BCG, ESAT-6 and CFP-10 were only exported into the supernatant fraction in significant amounts if expressed in conjunction with the entire esx cluster (FIG. 11). The combined findings demonstrate that complementation with esxA or esxB alone is insufficient to produce a recombinant vaccine that secretes these two antigens. Rather, secretion requires expression of genes located both upstream and downstream of the antigenic core region confirming our hypothesis that the conserved esx gene cluster does indeed encode functions essential for the export of ESAT-6 and CFP-10.

3.3 Secretion of ESAT-6 is Needed to Induce Antigen Specific T-Cell Responses

Figure 12A:
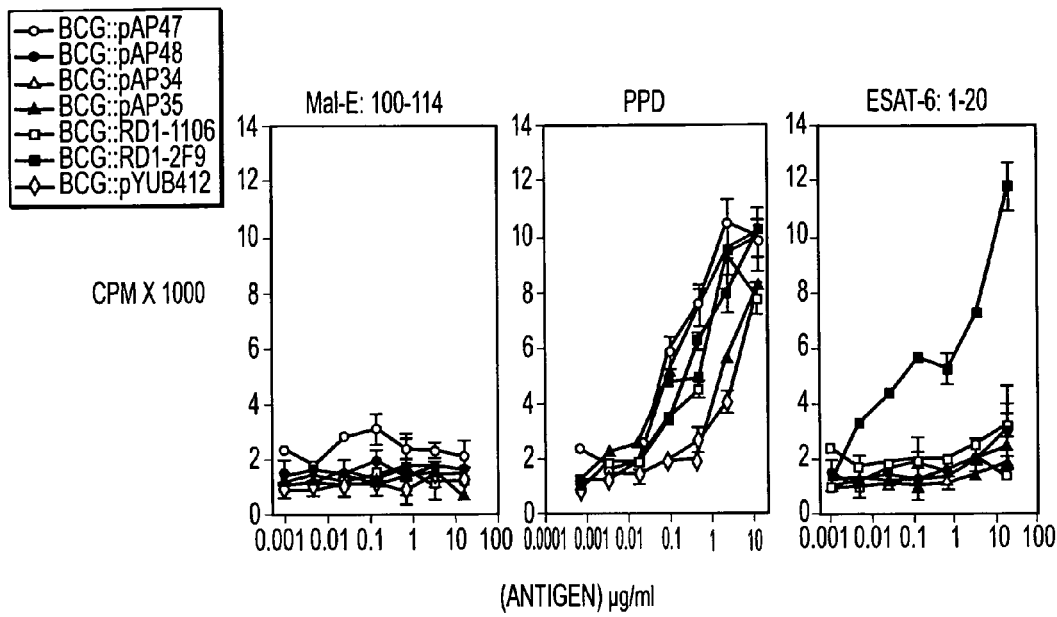
Figure 12B:
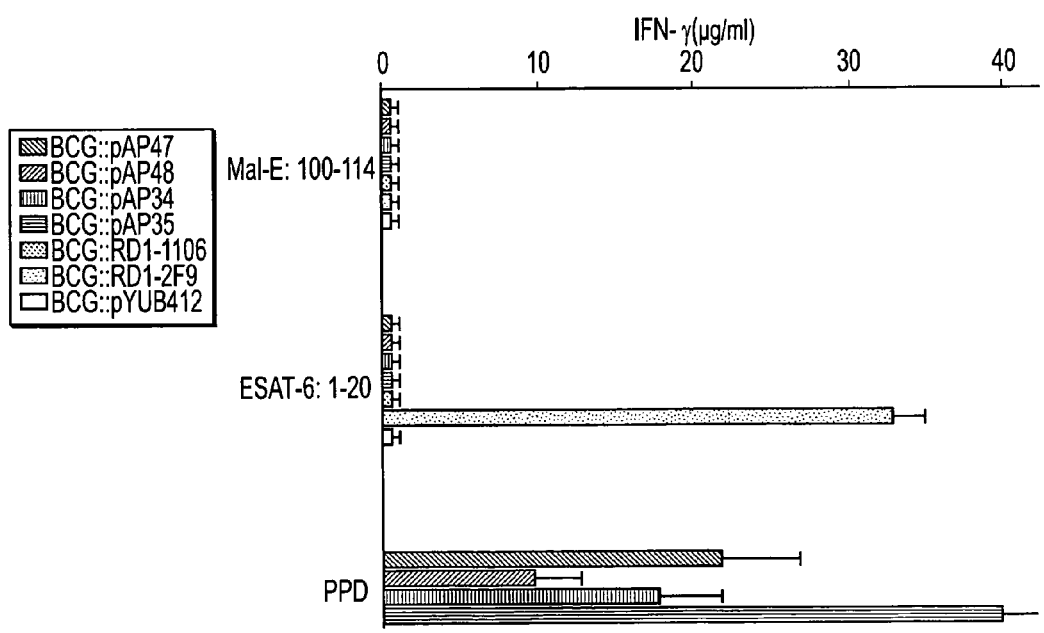

Since the classical observation that inoculation with live, but not dead BCG, confers protection against tuberculosis in animal models it has been considered that secretion of antigens is critical for maximizing protective T-cell immunity. Using our panel of recombinant vaccines we were able to test if antigen secretion was indeed essential for eliciting ESAT-6 specific T-cell responses. Groups of C57/BL6 mice were inoculated subcutaneously with one of six recombinant vaccines (BCG-pAP47, BCG-pAP48, BCG::RD1-pAP34, BCG::RD1-pAP35, BCG::RD1-I106, BCG::RD1-2F9) or with BCG transformed with the empty vector pYUB412. Three weeks following vaccination, T-cell immune responses to the seven vaccines were assessed by comparing antigen-specific splenocyte proliferation and gamma interferon (IFN-γ) production (FIG. 12A). As anticipated, all of the vaccines generated splenocyte proliferation and IFN-γ production in response to PPD (partially purified protein derivative) but not against an unrelated MalE control peptide, indicating successful vaccination in each case. However, only splenocytes from the mice inoculated with BCG::RD1-2F9 proliferated markedly in response to the immunodominant ESAT-6 peptide (FIG. 12A). Furthermore, IFN-γ was only detected in culture supernatants of splenocytes from mice immunized with BCG::RD1-2F9 following incubation with the ESAT-6 peptide (FIG. 12B) or recombinant CFP-10 protein (data not shown). These data demonstrate that export of the antigens is essential for stimulating specific Th1-oriented T-cells.

Figure 13A:
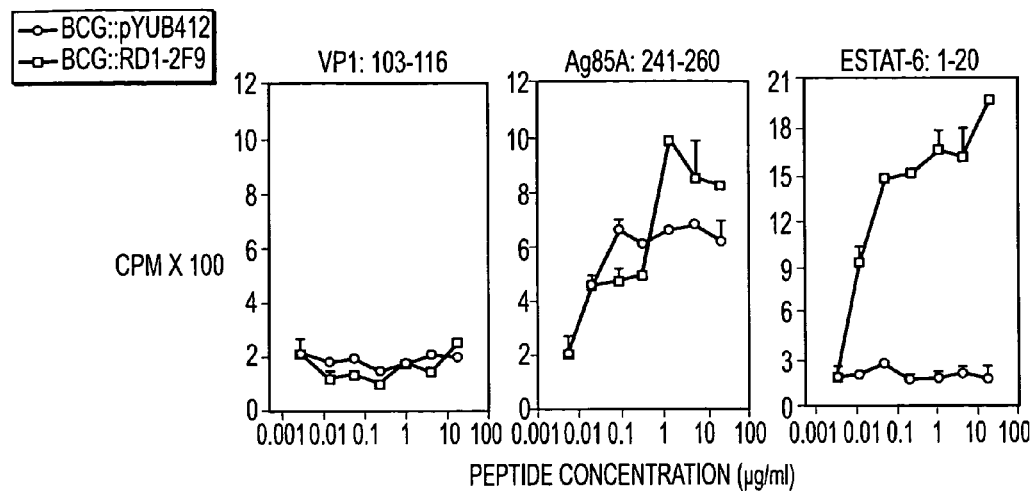
Figure 13B:
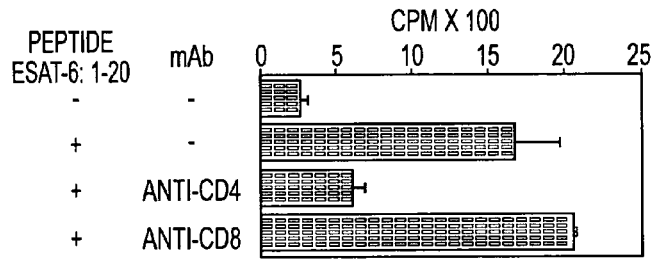
Figure 13C:
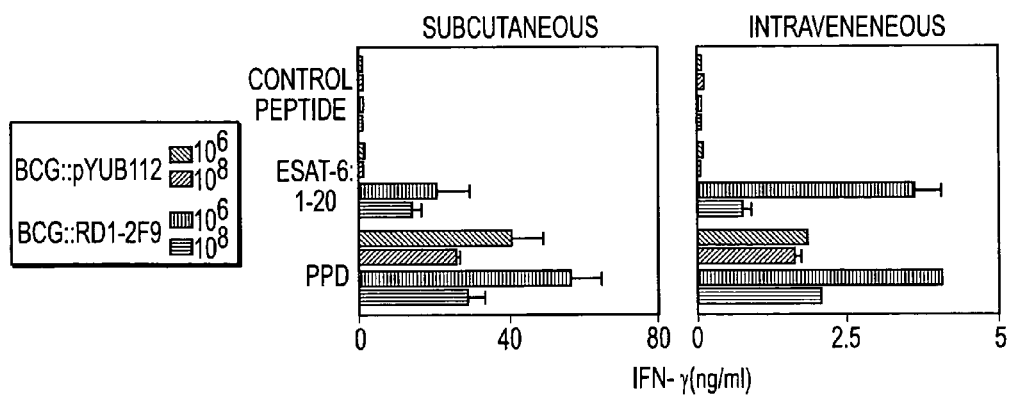

Further characterization of the immune responses was carried out. Splenocytes from mice immunized with BCG::RD1-2F9 or control BCG both proliferated in response to the immunodominant antigen 85A peptide (FIG. 13A). The strong splenocyte proliferation in the presence of ESAT-6 was abolished by an anti-CD4 monoclonal antibody but not by anti-CD8 indicating that the CD4+ T-cell subset was involved (FIG. 13B). Interestingly, as judged by in vitro IFN-γ response to PPD and the ESAT peptide, subcutaneous immunization generated much stronger T-cell responses (FIG. 13C) compared to intravenous injection. After subcutaneous immunization with BCG::RD1-2F9, strong ESAT-6 specific responses were also detected in inguinal lymph nodes (data not shown). These experiments demonstrated that the ESAT-6 T-cell immune responses to vaccination with BCG::RD1-2F9 were potent, reproducible and robust, making this recombinant an excellent candidate for protection studies.

3.4 Protective Efficacy of BCG::RD1-2F9 in Immuno-Competent Mice

Figure 14A:
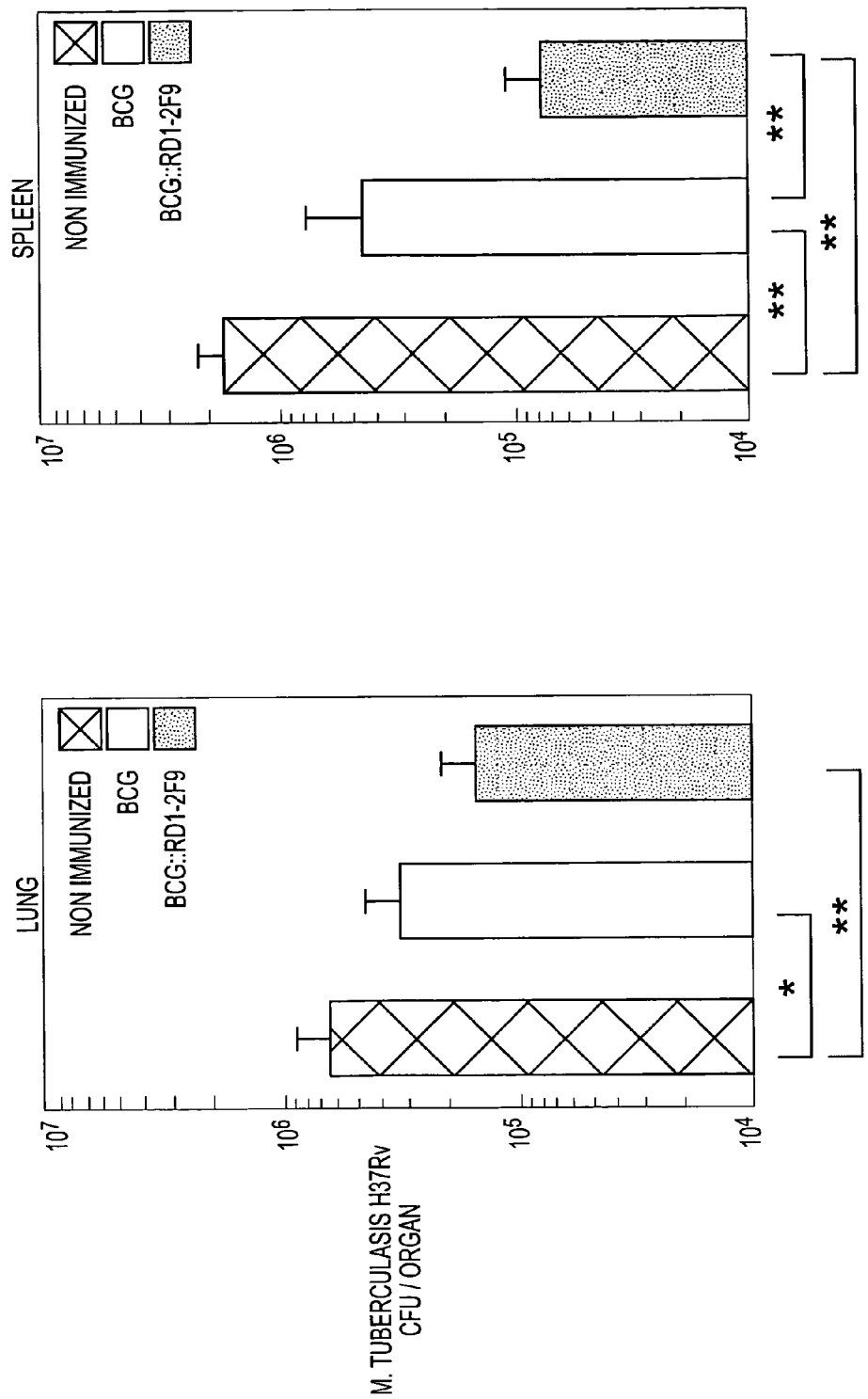

When used alone as a subunit or DNA vaccine, ESAT-6 induces levels of protection weaker than but akin to those of BCG (Brandt, L., Elhay, M., Rosenkrands, I., Lindblad, E B. & Andersen, P. ESAT-6 subunit vaccination against *Mycobacterium tuberculosis. Infect Immun.* 68, 791-795 (2000)). Thus, it was of interest to determine if the presentation to the immune system of ESAT-6 and/or CFP-10 in the context of recombinant BCG, mimicking the presentation of the antigens during natural infection, could increase the protective efficiency of BCG. The BCG::RD1-2F9 recombinant was therefore selected for testing as a vaccine, since it was the only ESAT-6 exporting BCG that elicited vigorous antigen specific T-cell immune responses. Groups of C57BL/6 mice were inoculated intravenously with either BCG::RD1-2F9 or BCG::pYUB412 and challenged intravenously after eight weeks with *M. tuberculosis* H37Rv. Growth of *M. tuberculosis* H37Rv in spleens and lungs of each vaccinated cohort was compared with that of unvaccinated controls two months after infection (FIG. 14A). This demonstrated that, compared to vaccination with BCG, the BCG::RD1-2F9 vaccine inhibited growth of *M. tuberculosis* H37Rv in the spleens by 0.4 log 10 CFU and was of comparable efficacy at protecting the lungs.

Figure 14B:
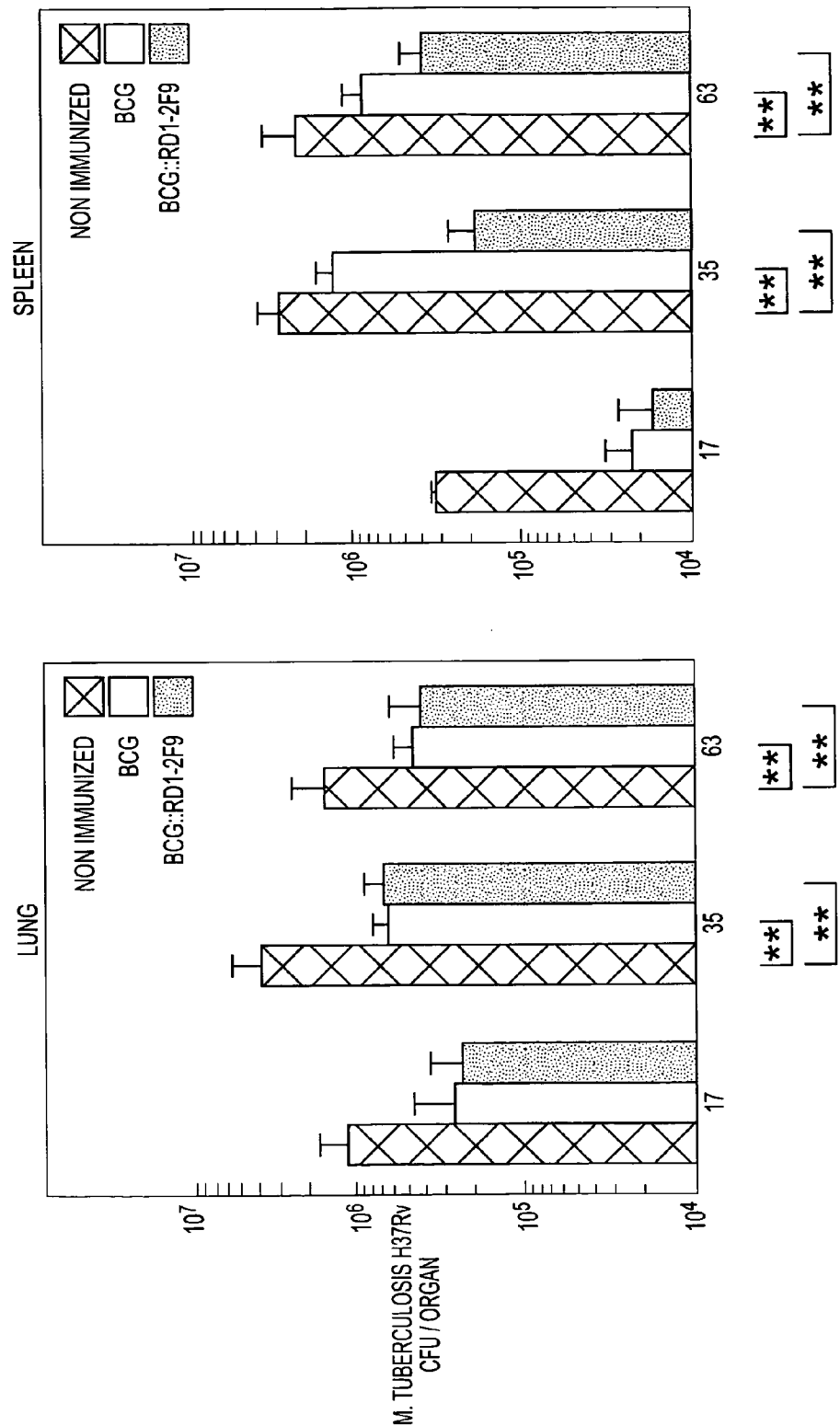

To investigate this enhanced protective effect against tuberculosis further we repeated the challenge experiment using the aerosol route. In this experiment antibiotic treatment was employed to clear persisting BCG from mouse organs prior to infection with *M. tuberculosis*. Two months following vaccination C57BL/6 mice were treated with daily rifampicin/izoniazid for three weeks and then infected with 1000 CFU of *M. tuberculosis* H37Rv by the respiratory route. Mice were then sacrificed after 17, 35 and 63 days and bacterial enumeration carried out on the lungs and spleen. This demonstrated that, even following respiratory infection, vaccination with BCG::RD1-2F9 was superior to vaccination with the control strain of BCG (FIG. 14B). However, growth of *M. tuberculosis* was again only inhibited strongly in the mouse spleens.

EXAMPLE 4

Protective Efficacy of BCG::RD1-2F9 in Guinea Pigs 4.1 Animal models *M. tuberculosis* H37Rv and the different recombinant vaccines were prepared in the same manner as for the immunological assays. For the guinea pig assays, groups of outbred female Dunkin-Hartley guinea pigs (David Hall, UK) were inoculated with $5 \times 10^4$ CFUs by the subcutaneous route. Aerosol challenge was performed 8 weeks after vaccination using a contained Henderson apparatus and an H37Rv (NCTC 7416) suspension in order to obtain an estimated retained inhaled dose of approximately 1000 CFU/lung (Williams, A., Davies, A, Marsh, P. D., Chambers, M. A & Hewinson, R. G. Comparison of the protective efficacy of bacille calmette-Guerin vaccination against aerosol challenge with *Mycobacterium tuberculosis* and *Mycobacterium bovis. Clin Infect Dis* 30 Suppl 3, S299-301. (2000)). Organs were homogenized and dilutions plated out on 7H11 agar, as for the mice experiments. Guinea pig experiments were carried out in the framework of the European Union TB vaccine development program.

Figure 15A:
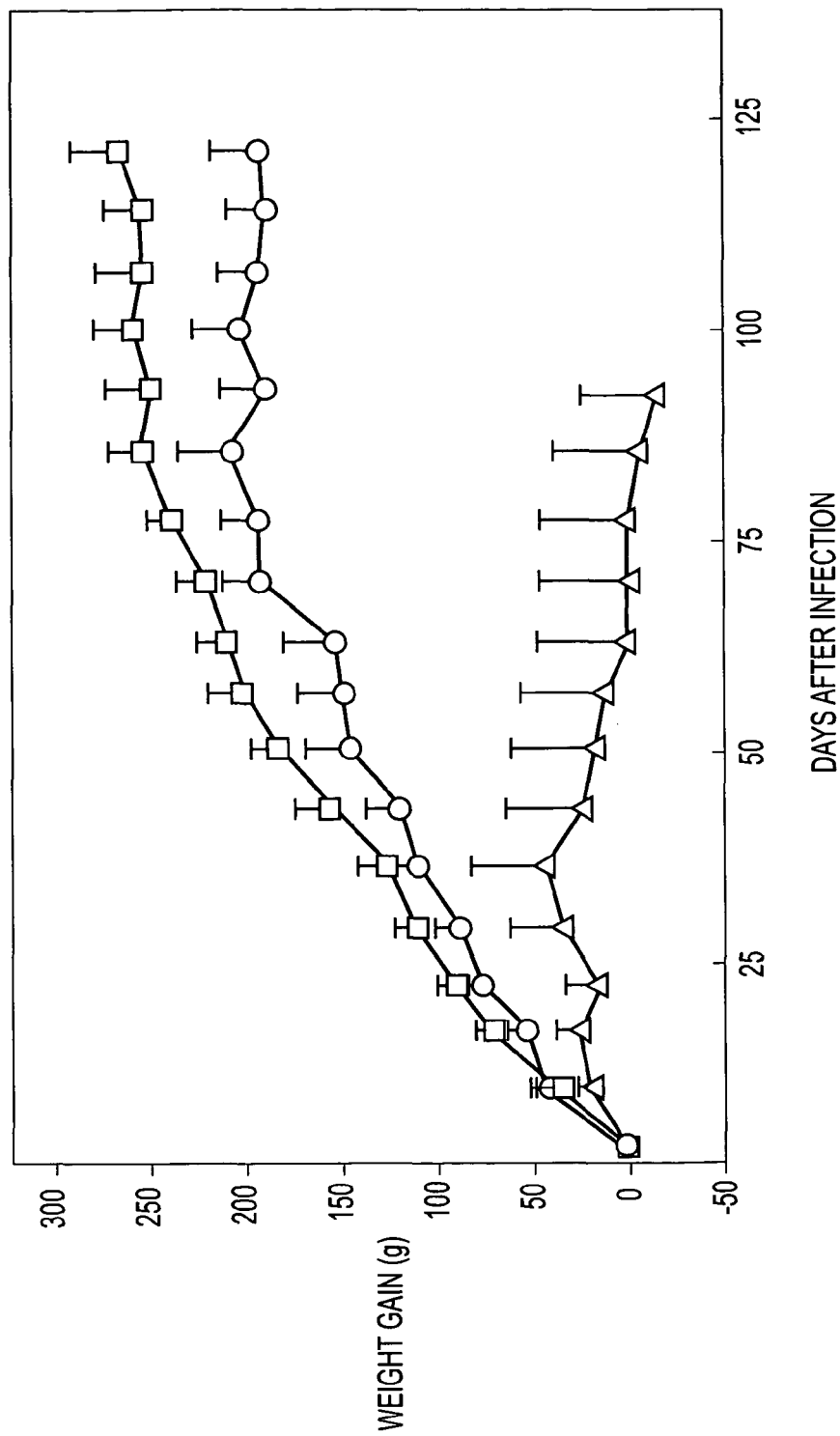
Figure 15B:
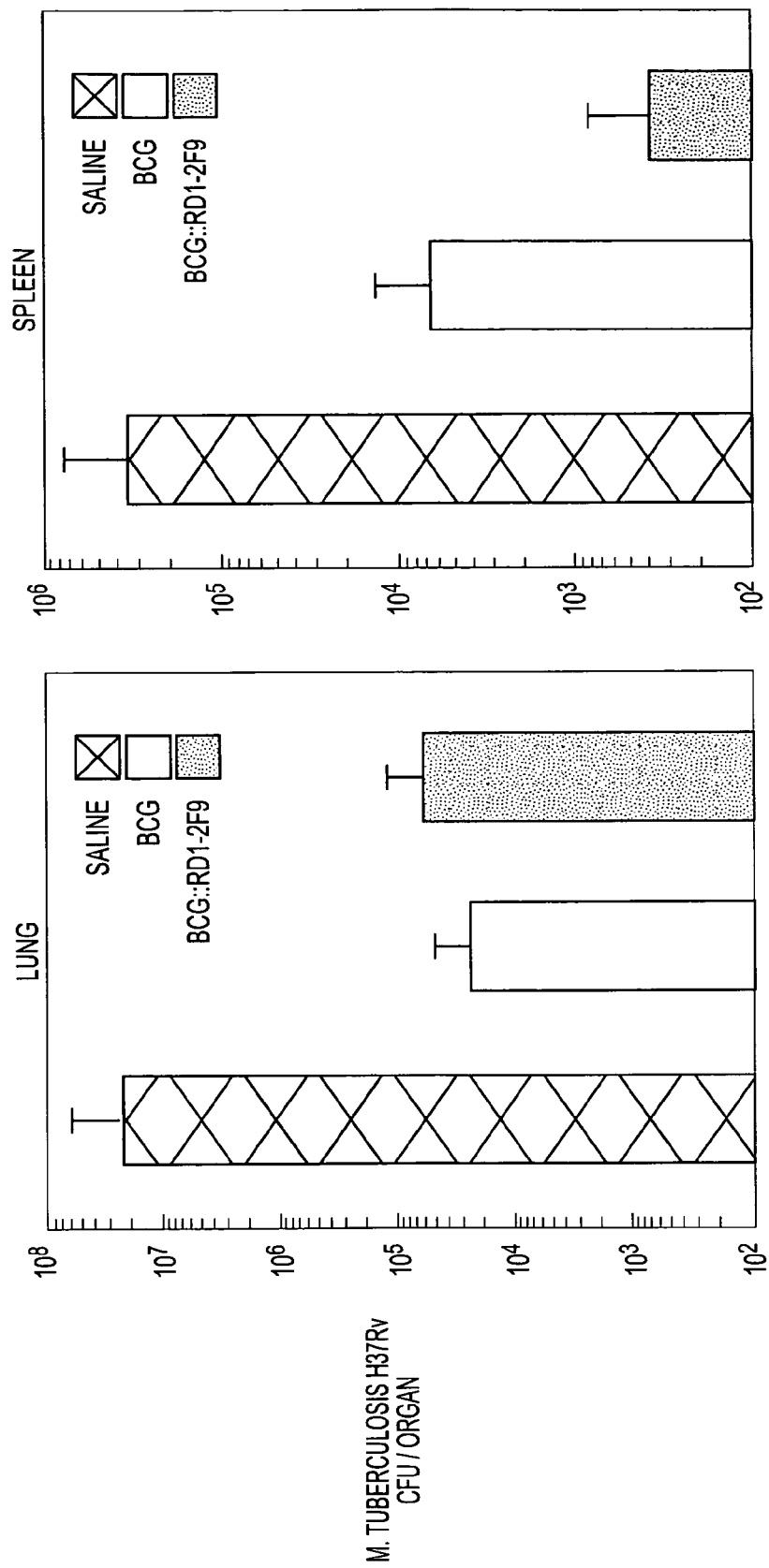
Figure 15C:
Figure 15C:
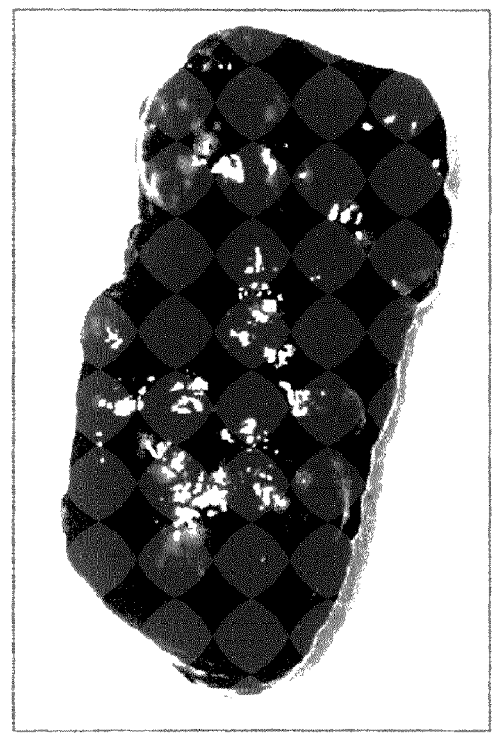

4.2 Results. Although experiments in mice convincingly demonstrated a superior protective efficacy of BCG::RD1 over BCG it was important to establish a similar effect in the guinea pig model of tuberculosis. Guinea pigs are exquisitely sensitive to tuberculosis, succumbing rapidly to low dose infection with *M. tuberculosis*, and develop a necrotic granulomatous pathology closer to that of human tuberculosis. Immunization of guinea pigs with BCG::RD1-2F9 was therefore compared to conventional BCG vaccination. Groups of six guinea pigs were inoculated subcutaneously with saline, BCG or BCG::RD1-2F9. Eight weeks following inoculation the three guinea pig cohorts were challenged with *M. tuberculosis* H37Rv via the aerosol route. Individual animals were weighed weekly and were killed 17 weeks after challenge or earlier if they developed signs of severe tuberculosis. Whereas all unvaccinated guinea pigs failed to thrive and were euthanised before the last time-point because of overwhelming disease, both the BCG- and recombinant BCG::RD1-2F9-vaccinated animals progressively gained weight and were clinically well when killed on termination of the experiment (FIG. 15A). This indicated that although the BCG::RD1-2F9 recombinant is more virulent in severely immunodeficient mice (Pym, A. S., Brodin, P., Brosch, R, Huerre, M. & Cole, S. T. Loss of RD1 contributed to the attenuation of the live tuberculosis vaccines *Mycobacterium bovis* BCG and *Mycobacterium micron. Mol. Microbiol.* 46, 709-717 (2002)), there is no increased pathogenesis in the highly susceptible guinea pig model of tuberculosis. Moreover, when the bacterial loads in the spleens of the vaccinated animals were compared there was a greater than ten-fold reduction in the number of CFU recovered from the animals immunised with BCG::RD1-2F9 when compared to BCG (FIG. 15B). Interestingly, there was no significant difference between the number of CFU obtained from the lungs of the two vaccinated groups indicating that the organ-specific enhanced protection observed in mice vaccinated with BCG::RD1-2F9 was also seen with guinea pigs. This marked reduction of bacterial loads in the spleens of BCG::RD1-2F9 immunized animals was also reflected in the gross pathology. Visual examination of the spleens showed that tubercules were much larger and more numerous on the surface of the BCG-vaccinated guinea pigs (FIG. 15C). These results demonstrate that the recombinant vaccine BCG::RD1-2F9 conveys enhanced protection to an aerosol challenge with *M. tuberculosis* in two distinct animal models.

GENERAL CONCLUSION

Tuberculosis is still one of the leading infectious causes of death in the world despite a decade of improving delivery of treatment and control strategies (Dye, C., Scheele, S., Dolin, P., Pathania, V. & Raviglione, M. C. Consensus statement. Global burden of tuberculosis: estimated incidence, prevalence, and mortality by country. WHO Global Surveillance and Monitoring Project. *Jama* 282, 677-86. (1999)). Reasons for the recalcitrance of this pandemic are multi-factorial but include the modest efficacy of the widely used vaccine, BCG. Two broad approaches can be distinguished for the development of improved tuberculosis vaccines (Baldwin, S. L., et al. Evaluation of new vaccines in the mouse and guinea pig model of tuberculosis. *Infection & Immunity* 66, 2951-9 (1998), Kaufmann, S. H. How can immunology contribute to the control of tuberculosis *Nature Rev Immunol* 1, 20-30. (2001), and Young, D. B. & Fruth, U. in *New Generation Vaccines* (eds. Levine, M., Woodrow, G., Kaper, J. & Cobon G S) 631-645 (Marcel Dekker, 1997)). These are the development of subunit vaccines based on purified protein antigens or new live vaccines that stimulate a broader range of immune responses. Although a growing list of individual or combination subunit vaccines, and hybrid proteins, have been tested, none has yet proved superior to BCG in animal models (Baldwin, S. L., et al., 1998). Similarly, new attenuated vaccines derived from virulent *M. tuberculosis* have yet to out-perform BCG (Jackson, M., et al. Persistence and protective efficacy of a *Mycobacterium tuberculosis* auxotroph vaccine. *Infect Immun* 67, 2867-73. (1999) and Hondalus, M. K, et al. Attenuation of and protection induced by a leucine auxotroph of *Mycobacterium tuberculosis*. *Infect Immun* 68, 2888-98. (2000)). Interestingly, the only vaccine that appears to surpass BCG is a BCG recombinant over expressing antigen 85A (Horwitz, M. A., Harth, G., Dillon, B. J. & Maslesa-Galic, S. Recombinant *bacillus* calmette-guerin (BCG) vaccines expressing the *Mycobacterium tuberculosis* 30-kDa major secretory protein induce greater protective immunity against tuberculosis than conventional BCG vaccines in a highly susceptible animal model. *Proc Natl Acad Sci USA* 97, 13853-8. (2000)). The basis for this vaccine was the notion that over-expression of an immunodominant T-cell antigen could quantitatively enhance the BCG-elicited immune response.

In frame with the invention, we were able to show that restoration of the RD1 locus did indeed improve the protective efficacy of BCG and defines a genetic modification that should be included in new recombinant BCG vaccines. Moreover, we were able to demonstrate two further findings that will be crucial for the development of a live vaccine against tuberculosis. First, we have identified the genetic basis of secretion for the ESAT-6 family of immunodominant T-cell antigens, and second, we show that export of these antigens from the cytosol is essential for maximizing their antigenicity.

The extra-cellular proteins of *M. tuberculosis* have been extensively studied and shown to be a rich source of protective antigens (Sorensen, A. L., Nagai, S., Houen, G., Andersen, P. & Andersen, A. B. Purification and characterization of a low-molecular-mass T-cell antigen secreted by *Mycobacterium tuberculosis. Infect Immun* 63, 1710-7 (1995), SkjØt, R. L. V., et al. Comparative evaluation of low-molecular-mass proteins from *Mycobacterium tuberculosis* identifies members of the ESAT-6 family as immunodominant T-cell antigens. *Infect. Immun* 68, 214-220 (2000), Horwitz, M. A., Lee, B. W., Dillon, B. J. & Harth, G. Protective immunity against tuberculosis induced by vaccination with major extracellular proteins of *Mycobacterium tuberculosis*. Proc Natl Acad Sci USA 92, 1530-4 (1995) and Boesen, H., Jensen, B. N., Wilcke, T. & Andersen, P. Human T-cell responses to secreted antigen fractions of *Mycobacterium tuberculosis. Infect Immun* 63, 1491-7 (1995)). Despite this it remains a mystery how some of these proteins, that lack conventional secretion signals, are exported from the cytosol, a unique problem in *M. tuberculosis* given the impermeability and waxy nature of the mycobacterial cell envelope. Although two secA orthologues were identified in the genome sequence of *M. tuberculosis* (Cole, S. T., et al. Deciphering the biology of *Mycobacterium tuberculosis* from the complete genome sequence. *Nature* 393, 537-544 (1998)), no genes for obvious type I, II, or III protein secretion systems were detected, like those that mediate the virulence of many Gram-negative bacterial pathogens (Finlay, B. B. & Falkow, S. Common themes in microbial pathogenicity revisited. *Microbiol. Mol. Biol. Rev.* 61, 136-169 (1997)). This suggested that novel secretion systems might exist. An in silico analysis of the *M. tuberculosis* proteome identified a set of proteins and genes whose inferred functions, genomic organisation and strict association with the esx gene family suggested that they could constitute such a system (Tekaia, F., et al. Analysis of the proteome of *Mycobacterium tuberculosis* in silico. *Tubercle Lung Disease* 79, 329-342 (1999)). Our results provide the first empirical evidence that this gene cluster is essential for the normal export of ESAT-6 and CFP-10.

The antigen genes, esxBA, lie at the center of the conserved gene cluster. Bioinformatics and comparative genomics predicted that both the conserved upstream genes Rv3868-Rv3871, as well as the downstream genes Rv3876-Rv3877, would be required for secretion (FIG. 1) and strong experimental support for this prediction is provided here. Our experiments show that only when BCG or *M. microti* are complemented with the entire cluster is maximal export of ESAT-6 and CFP-10 obtained. This suggests that at least Rv3871 and either Rv3876 or Rv3877 are indeed essential for the normal secretion of ESAT-6 as these are the only conserved genes absent or disrupted in BCG which are not complemented by RD1-I106 or RD1-pAP35. These genes encode a large transmembrane protein with ATPase activity, an ATP-dependent chaperone and an integral membrane protein, functional predictions compatible with them being part of a multi-protein complex involved in the translocation of polypeptides. Amongst the proteins encoded by the esx cluster, Rv3871 and Rv3877 are highly conserved, as orthologues have been identified in the more streamlined clusters found in other actinomycetes, further supporting their direct role in secretion (Gey Van Pittius, N. C., et al. The ESAT-6 gene cluster of *Mycobacterium tuberculosis* and other high G+C Gram-positive bacteria. *Genome Biol* 2, 44.1-44.18 (2001)). It has been shown recently that ESAT-6 and CFP-10 form a heterodimer in vitro (Renshaw, P. S.; et al. Conclusive evidence that the major T-cell antigens of the *M. tuberculosis* complex ESAT-6 and CFP-10 form a tight, 1:1 complex and characterisation of the structural properties of ESAT-6, CFP-10 and the ESAT-6-CFP-10 complex: implications for pathogenesis and virulence. *J Biol Chem* 8, 8 (2002)) but it is not known whether dimerization precedes translocation across the cell membrane or occurs at a later stage in vivo. In either case, chaperone or protein clamp activity is likely to be required to assist dimer formation or to prevent premature complexes arising as is well documented for type III secretion systems (Page, A. L. & Parsot, C. Chaperones of the type III secretion pathway: jacks of all trades. *Mol Microbiol* 46, 1-11. (2002)). These, and other questions concerning the precise roles of the individual components of the ESAT-6 secretory apparatus, can now be addressed experimentally using the tools developed here.

The second major finding of the invention is that the secretion of ESAT-6 (and probably CFP-10) is critical for inducing maximal T-cell responses although other RD1-encoded proteins may also contribute such as the PPE68 protein (Rv3873) which is located in the cell envelope. We show that even though whole cell expression levels of ESAT-6 are comparable amongst our vaccines (FIG. 2); only the vaccine strain exporting ESAT-6, via an intact secretory apparatus, elicits powerful T-cell responses. Surprisingly, even the recombinants RD1-pAP47 and RD1-pAP48, that overexpress ESAT-6 intracellularly, did not generate detectable ESAT-6 specific T-cell responses. Although antigen secretion has long been recognized as important for inducing immunity against *M. tuberculosis*, and is often used to explain why killed BCG offers no protection, this is one of the first formal demonstrations of its importance. BCG, like *M. tuberculosis* resides in the phagosome, where secreted antigens have ready access to the MHC class II antigen processing pathway, essential for inducing IFN-γ producing CD4 T-cells considered critical for protection against tuberculosis. Further understanding of the mechanism of ESAT-6 secretion could allow the development of BCG recombinants that deliver other antigens in the same way.

The main aim of the present invention was to qualitatively enhance the antigenicity of BCG. So, having assembled a recombinant vaccine that secreted the T-cell antigens ESAT-6 and CFP-10, and shown that it elicited powerful CD4 T-cell immunity against at least ESAT-6 and CFP-10, the next step was to rigorously test its efficacy in animal models of tuberculosis. In three distinct models, including two involving respiratory challenge, we were able to demonstrate that the ESAT-6-CFP-10 secreting recombinant improved protection when compared to a BCG control, although this effect was restricted to the spleen. This is probably due to the fact that the enhanced immunity induced by the two additional antigens is insufficient to abort the primary infection but does significantly reduce the dissemination of bacteria from the lung. The lack of protection afforded to the lung, the portal of entry for *M. tuberculosis*, does not prevent BCG::RD1-2F9 from being a promising vaccine candidate. Primary tuberculosis occurs in the middle and lower lobes and is rarely symptomatic (Garay, S. M. in *Tuberculosis* (eds. Rom, W. N. & Garay, S. M.) 373-413 (Little, Brown and Company, Boston, 1996)). The bacteria need to reach the upper lobes, the commonest site of disease, by haematogenous spread. Therefore, a vaccine that inhibits dissemination of *M. tuberculosis* from the primary site of infection would probably have major impact on the outcome of tuberculosis.

Recombinant BCG vaccines have definite advantages over other vaccination strategies in that they are inexpensive, easy to produce and convenient to store. However, despite an unrivalled and enviable safety record, concerns remain, and BCG is currently not administered to individuals with HIV infection. As shown above, the recombinant BCG::RD1-2F9 grows more rapidly in Severe Combined Immunodeficiency (SCID) mice, an extreme model of immunodeficiency, than its parental BCG strain. However, in both immunocompetent mice and guinea pigs we have not observed any increased pathology, only a slight increase in persistence which may be beneficial, since the declining efficacy of BCG with serial passage has been attributed to an inadvertent increase in its attenuation (Behr, M. A. & Small, P.M. Has BCG attenuated to impotence? *Nature* 389, 133-4. (1977)).

Ultimately, the robust enhancement in protection we have observed with the reincorporation of the RD1 locus is a compelling reason to include this genetic modification in any recombinant BCG vaccine, even if this may require the need for a balancing attenuating mutation.

In summary, the data presented here show that, in addition to its increased persistence, BCG::RD1-2F9 induces specific T-cell memory and enhances immune responses to other endogenous Th1 antigens such as the mycoloyl transferase, antigen 85A.

REFERENCES

1. Behr, M. A., M. A. Wilson, W. P. Gill, H. Salamon, G. K Schoolnik, S. Rane, and P. M. Small. 1999. Comparative genomics of BCG vaccines by whole-genome DNA microarray. Science 284:1520-1523.
2. Berthet, F.-X., P. B. Rasmusse, I. Rosenkrands, P. Andersen, and B. Gicquel. 1998. A *Mycobacterium tuberculosis* operon encoding ESAT-6 and a novel low-molecular-mass culture filtrate protein (CFP-10). Microbiology 144:3195-3203.
3. Brosch, R., S. V. Gordon, M. Marmiesse, P. Brodin, C. Buchrieser, K. Eiglmeier, T. Garnier, C. Gutierrez, G. Hewinson, K. Kremer, L. M. Parsons, A. S. Pym, S. Samper, D. van Soolingen, and S. T. Cole. 2002. A new evolutionary scenario for the *Mycobacterium tuberculosis* complex. Proc. Natl. Acad. Sci. USA 99:3684-3689.
4. Brosch, R., S. V. Gordon, A. Billault, T. Garnier, K. Eiglmeier, C. Soravito, B. G. Barrell, and S. T. Cole. 1998. Use of a *Mycobacterium tuberculosis* H37Rv bacterial artificial chromosome library for genome mapping, sequencing, and comparative genomics. Infect. Immun. 66:2221-2229.
5. Brosch, R., S. V. Gordon, C. Buchrieser, A. S. Pym, T. Garnier, and S. T. Cole. 2000. Comparative genomics uncovers large tandem chromosomal duplications in *Mycobacterium bovis* BCG Pasteur. Comp. Funct. Genom. (Yeast) 17:111-123.
6. Brosch, R, S. V. Gordon, A. Pym, K. Eiglmeier, T. Garnier, and S. T. Cole. 2000. Comparative genomics of the mycobacteria. Int. J. Med. Microbiol. 290:143-152.
7. Brosch, R., W. J. Philipp, E. Stavropoulos, M. J. Colston, S. T. Cole, and S. V. Gordon. 1999. Genomic analysis reveals variation between *Mycobacterium tuberculosis* H37Rv and the attenuated *M. tuberculosis* H37Ra strain. Infect Immun. 67:5768-5774.
8. Brusasca, P. N., R. Colangeli, K. P. Lyashchenko, X. Zhao, M. Vogelstein, J. S. Spencer, D. N. McMurray, and M. L. Gennaro. 2001. Immunological characterization of antigens encoded by the RD1 region of the *Mycobacterium tuberculosis* genome. Scand. J. Immunol. 54:448-452.
9. Camacho, L. R., D. Ensergueix, E. Perez, B. Gicquel, and C. Guilhot. 1999. Identification of a virulence gene cluster of *Mycobacterium tuberculosis* by signature-tagged transposon mutagenesis. Mol. Microbiol. 34:257-267.
10. Cole, S. T., R. Brosch, J. Parkhill, T. Garnier, C. Churcher, D. Harris, S. V. Gordon, K. Eiglmeier, S. Gas, Barry C E, III, F. Tekaia, K. Badcock, D. Basham, D. Brown, T. Chillingworth, R. Connor, R. Davies, K. Devlin, T. Feltwell, S. Gentles, N. Hamlin, S. Holroyd, T. Hornsby, K. Jagels, A. Krogh, J. McLeah, S. Moule, L. Murphy, K. Oliver, J. Osborne, M. A. Quail, M. A. Rajandream, J. Rogers, S. Rutter, K. Soeger, J. Skelton, R. Squares, S. Squares, J. E. Sulston, K. Taylor, S. Whitehead, and B. G. Barrell. 1998. Deciphering the biology of *Mycobacterium tuberculosis* from the complete genome sequence. Nature 393:537-544.
11. Cole, S. T., K. Eiglmeier, J. Parkhill, K. D. James, N. R. Thomson, P. R. Wheeler, N. Honore, T. Garnier, C. Churcher, D). Harris, K. Mungall, D. Basham, D. Brown, T. Chillingworth, R. Connor, R. M. Davies, K. Devlin, S. Duthoy, T. Feltwell, A. Fraser, N. Hamlin, S. Holroyd, T. Hornsby, K Jagels, C. Lacroix, J. Maclean, S. Moule, L. Murphy, K. Oliver, M. A. Quail, M. A. Rajandream, K. M.

Rutherford, S. Rutter, K. Seeger, S. Simon, M. Simmonds, J. Skelton, R. Squares, S. Squares, K. Stevens, K. Taylor, S. Whitehead, J. R. Woodward, and B. G. Barrell. 2001. Massive gene decay in the leprosy bacillus. Nature 409:1007-1011.

12. Elhay, M. J., T. Oettinger, and P. Andersen. 1998. Delayed-type hypersensitivity responses to ESAT-6 and MPT64 from *Mycobacterium tuberculosis* in the guinea pig. Infect. Immun. 66:3454-3456.

13. Gordon, S. V., R. Brosch, A. Billault, T. Garnier, K. Eiglmeier, and S. T. Cole. 1999. Identification of variable regions in the genomes of tubercle bacilli using bacterial artificial chromosome arrays. Mol. Microbiol. 32:643-655.

14. Gordon, S. V., K. Eiglmeier, T. Garnier, R. Brosch, J. Parkhill, B. Barrell, S. T. Cole, and R. G. Hewinson. 2001. Genomics of *Mycobacterium bovis*. Tuberculosis (Edinb) 81:157-163.

15. Harboe, M., A. S. Malin, H. S. Dockrell, H. G. Wiker, G. Ulvund, A. Holm, M. C. Jorgensen, and P. Andersen. 1998. B-cell epitopes and quantification of the ESAT-6 protein of *Mycobacterium tuberculosis*. Infect. Immun. 66:717-723.

16. Hart, P. D. a., and I. Sutherland. 1977. BCG and vole bacillus vaccines in the prevention of tuberculosis in adolescence and early adult life. British Medical Journal 2:293-295.

17. Hermans, P. W. M., D. Van Soolingen, E. M. Bik, P. E. W. De Haas, J. W. Dale, and J. D. A. van Embden. 1991. Insertion element IS987 from *Mycobacterium bovis* BCG is located in a hot-spot integration region for insertion elements in *Mycobacterium tuberculosis* complex strains. Infect. Immun. 59:2695-2705.

18. Ho, T. B., B. D. Robertson, G. M. Taylor, R. J. Shaw, and D. B. Young. 2000. Comparison of *Mycobacterium tuberculosis* genomes reveals frequent deletions in a 20 kb variable region in clinical isolates. Comp. Funct. Genom. (Yeast) 17:272-282.

19. Horstkotte, M. A., I. Sobottka, K. Schewe Carl, P. Schaefer, R. Laufs, S. Rutesch-Gerdes, and S. Niemann. 2001. *Mycobacterium microti* llama-type infection presenting as pulmonary tuberculosis in a human immunodeficiency virus-positive patient. J. Clin. Microbiol. 39:406-407.

20. Horwitz, M. A., B. W. Lee, B. J. Dillon, and G. Harth. 1995. Protective immunity against tuberculosis induced by vaccination with major extracellular proteins of *Mycobacterium tuberculosis*. Proc. Natl. Acad. Sci. USA 92:1530-1534.

21. Johansen, K. A., R. E. Gill, and M. L. Vasin. 1996. Biochemical and molecular analysis of phospholipase C and phospholipase D activity in mycobacteria. Infect. Immun. 64:3259-3266.

22. Jouanguy, E., R. Doffinger, S. Dupuis, A. Pallier, F. Altare, and J. L. Casanova. 1999. IL-12 and IFN-gamma in host defense against mycobacteria and salmonella in mice and men. Curr. Opin. Immunol. 11:346-351.

23. Kamerbeek, J., L. Schouls, A. Kolk, M. Van Agterveld, D. Van Soolingen, S. Kuijper, A. Bunschoten, H. Molhuizen, R. Shaw, M. Goyal, and J. Van Embden. 1997. Simultaneous detection and strain differentiation of *Mycobacterium tuberculosis* for diagnosis and epidemiology. J. Clin. Microbiol. 35:907-914.

24. Kato-Maeda, M., J. T. Rhee, T. R. Gingeras, H. Salamon, J. Drenkow, N. Smittipat, and P. M. Small. 2001. Comparing genomes within the species *Mycobacterium tuberculosis*. Genome Res. 11:547-554.

25. Kremer, K., van Soolingen, D., van Embden, J., Hughes, S., Inwald, J., and G. Hewinson. 1998. *Mycobacterium microti*: more widespread than previously thought. J. Clin. Microbiol. 36:2793-2794.

26. Kremer, K., D. van Soolingen, R. Frothingham, W. H. Haas, P. W. Hermans, C. Martin, P. Palittapongarnpim, B. B. Plikaytis, L. W. Riley, M. A. Yakrus, J. M. Musser, and J. D. van Embden. 1999. Comparison of methods based on different molecular epidemiological markers for typing of *Mycobacterium tuberculosis* complex strains: interlaboratory study of discriminatory power and reproducibility. J. Clin. Microbiol. 37:2607-2618.

27. Levy Frebault, V., and F. Portaels. 1992. Proposed minimal standards for the genus *Mycobacterium* and for description of new slowly growing *Mycobacterium* spp. Int. J. Syst. Bact. 42:315-323.

28. Liebana, E., A. Aranaz, B. Francis, and D. Cousins. 1996. Assessment of genetic markers for species differentiation within the *Mycobacterium tuberculosis* complex. J. Clin. Microbiol. 34:933-938.

29. Mahairas, G. G., P. J. Sabo, M. J. Hickey, D. C. Singh, and C. K. Stover. 1996. Molecular analysis of genetic differences between *Mycobacterium bovis* BCG and virulent *M. bovis*. J. Bact. 178:1274-1282.

30. Manabe, Y. C., Scott, C. P., and W. R. Bishai. 2002 Naturally attenuated, orally administered *Mycobacterium microti* as a tuberculosis vaccine is better than subcutaneous *Mycobacterium bovis* BCG. Infect Immun. 70:1566-1570.

31. Niemann, S., Harmsen, D., Rusch-Gerdes, S., and E. Richter. 2000. Differentiation of clinical *Mycobacterium tuberculosis* complex isolates by gyrB DNA sequence polymorphism analysis. J. Clin. Microbiol. 38:3231-3234.

32. Niemann, S., E. Richter, H. Daluegge-Tamm, H. Schlesinger, D. Graupner, B. Koenigstein, G. Gurath, U. Greinert, and S. Ruesch-Gerdes. 2000. Two cases of *Mycobacterium microti*-derived tuberculosis in HIV-negative immunocompetent patients. Emerg. Infect. Dis. 6:539-542.

33. Parsons, L. M., Brosch, R., Cole, S. T., Somoskovi, A., Loder, A., Britzel, G., van Soolingen, D., Hale, Y., Salfinger, M. 2002. Rapid and easy-to-perform identification of *Mycobacterium tuberculosis* complex isolates using PCR-based genomic deletion analysis. J. Clin. Microbiol. submitted and disclosure of the European Patent Application N° 02 290 458.2 filed on Feb. 25, 2002 (Irstitut Pasteur).

34. Rosenkrands, I., P. B. Rasmussen, M. Carnio, S. Jacobsen, M. Theisen, and P. Andersen. 1998. Identification and characterization of a 29-kilodalton protein from *Mycobacterium tuberculosis* culture filtrate recognized by mouse memory effector cells. Infect. Immun. 66:2728-2735.

35. Salamon, H., M. Kato-Maeda, P. M. Small, J. Drenkow, and T. R. Gingeras. 2000. Detection of deleted genomic DNA using a semiautomated computational analysis of GeneChip data. Genome Res. 10:2044-2054.

36. Songer, J. G., 1997. Bacterial phospholipases and their role in virulence. Trends Microbiol. 5:156-161.

37. Staden, R. 1996. The Staden sequence analysis package. Mol. Biotechnol. 5:233-241.

38. Sula, L., and I. Radkovsky. 1976. Protective effects of *M. microti* vaccine against tuberculosis. J. Hyg. Epid. Microbiol. Immunol. 20:1-6.

39. Talbot, E. A., D. L. Williams, and R. Frothingham. 1997. PCR identification of *Mycobacterium bovis* BCG. J. Clin. Microbiol. 35:566-569.

40. Tekaia, F., S. V. Gordon, T. Garnier, R. Brosch, B. G. Barrell, and S. T. Cole. 1999. Analysis of the proteome of *Mycobacterium tuberculosis* in silico. Tubercle & Lung Disease 79:329-342.
41. Titball, R. W. 1998. Bacterial phospholipases. Soc. Appl. Bacteriol. Symp. Ser. 27:127-137.
42. van Embden, J. D., T. van Gorkom, K. Kremer, R. Jansen, B. A. van Der Zeijst, and L. M. Schouls. 2000. Genetic variation and evolutionary origin of the direct repeat locus of *Mycobacterium tuberculosis* complex bacteria. J. Bacteriol. 182:2393-2401.
43. van Soolingen, D., A. G. M. Van Der Zanden, P. E. W. De Haas, G. T. Noordhoek, A. Kiers, N. A. Foudraine, F. Portaels, A. H. J. Kolk, K. Kremer, and J. D. A. Van Embden. 1998. Diagnosis of *Mycobacterium microti* infections among humans by using novel genetic markers. J. Clin. Microbiol. 36:1840-1845.
44. Vera-Cabrera, L., M. A. Hernandez-Vera, O. Welsh, W. M. Johnson, and J. Castro-Garza. 2001. Phospholipase region of *Mycobacterium tuberculosis* is a preferential locus for IS6110 transposition. J. Clin. Microbiol. 39:3499-3504.
45. Wells, A. Q. 1937. Tuberculosis in wild voles. Lancet 1221.
46. Wells, A. Q. 1946. The murine type of tubercle bacillus. Medical Research council special report series 259:1-42.
47. Wheeler, P. R., and C. Ratledge. 1992. Control and location of acyl-hydrolysing phospholipase activity in pathogenic mycobacteria. J. Gen. Microbiol. 138:825-830.

The invention claimed is:

1. A strain of M. bovis BCG, wherein said strain has integrated the DNA fragment RD1-2F9, which comprises 31808 bp of DNA originating from Mycobacterium tuberculosis or any virulent member of the Mycobacterium tuberculosis complex (M. africanum, M. bovis, M. canettii), and having SEQ ID NO:1, and which is responsible for enhanced immunogenicity and increased persistence of BCG to the tubercle bacilli.

2. A cosmid which is contained in the E. coli strain deposited at the CNCM under the accession number I-2831.

3. A transformed M. bovis BCG strain, wherein the strain has integrated a portion of DNA originating from Mycobacterium tuberculosis or any virulent member of the Mycobacterium tuberculosis complex (M. africanum, M. bovis, M. canettii), wherein the integrated DNA comprises the genes Rv3874 (SEQ ID NO:17, CFP-10), Rv3875 (SEQ ID NO:18, ESAT-6), Rv3868 (SEQ ID NO:11), Rv3869 (SEQ ID NO:12), Rv3870 (SEQ ID NO:13), Rv3871 (SEQ ID NO:14), Rv3876 (SEQ ID NO:19), and Rv3877 (SEQ ID NO:20).

4. A strain according to claim 3, wherein said strain has integrated a portion of DNA originating from Mycobacterium tuberculosis or any virulent member of the Mycobacterium tuberculosis complex (M. africanum, M. bovis, M. canettii), wherein the integrated DNA further comprises at least nine genes selected from the group consisting of Rv3861 (SEQ ID NO:4), Rv3862 (SEQ ID NO:5), Rv3863 (SEQ ID NO:6), Rv3864 (SEQ ID NO:7), Rv3865 (SEQ ID NO:8), Rv3866 (SEQ ID NO:9), Rv3867 (SEQ ID NO:10), Rv3872 (SEQ ID NO:15, mycobacterial PE), Rv3873 (SEQ ID NO:16, PPE), Rv3878 (SEQ ID NO:21), Rv3879 (SEQ ID NO:22), Rv3880 (SEQ ID NO:23), Rv3881 (SEQ ID NO:24), Rv3882 (SEQ ID NO:25), Rv3883 (SEQ ID NO:26), Rv3884 (SEQ ID NO:27), and Rv3885 (SEQ ID NO:28).

5. A strain according to claim 3, wherein said strain has integrated a portion of DNA originating from Mycobacterium tuberculosis or any virulent member of the Mycobacterium tuberculosis complex (M. africanum, M. bovis, M. canettii), wherein the integrated DNA further comprises at least the gene Rv3867 (SEQ ID NO:10), combined with at least one gene selected from the group consisting of: Rv3872 (SEQ ID NO:15, mycobacterial PE); and Rv3873 (SEQ ID NO:16, PPE).

6. A strain according to claim 3, wherein said strain has integrated a portion of DNA originating from Mycobacterium tuberculosis or any virulent member of the Mycobacterium tuberculosis complex (M. africanum, M. bovis, M. canettii), wherein the integrated DNA further comprises the gene Rv3872 (SEQ ID NO:15, mycobacterial PE).

7. A strain according to claim 6, wherein said strain has integrated a portion of DNA originating from Mycobacterium tuberculosis or any virulent member of the Mycobacterium tuberculosis complex (M. africanum, M. bovis, M. canettii), wherein the integrated DNA further comprises the gene Rv3873 (SEQ ID NO:16, PPE).

8. A strain according to claim 7, wherein said strain has integrated a portion of DNA originating from Mycobacterium tuberculosis or any virulent member of the Mycobacterium tuberculosis complex (M. africanum, M. bovis, M. canettii), wherein the integrated DNA further comprises at least one gene selected from the group consisting of: Rv3861 (SEQ ID NO:4), Rv3862 (SEQ ID NO:5), Rv3863 (SEQ ID NO:6), Rv3864 (SEQ ID NO:7), Rv3865 (SEQ ID NO:8), Rv3866 (SEQ ID NO:9), Rv3867 (SEQ ID NO:10), Rv3878 (SEQ ID NO:21), Rv3879 (SEQ ID NO:22), Rv3880 (SEQ ID NO:23), Rv3881 (SEQ ID NO:24), Rv3882 (SEQ ID NO:25), Rv3883 (SEQ ID NO:26), Rv3884 (SEQ ID NO:27), and Rv3885 (SEQ ID NO:28).

9. A strain according to claim 3, wherein the coding sequence of the integrated gene is in frame with its natural promoter or with an exogenous promoter, such as a promoter capable of directing high level of expression of said coding sequence.

10. A strain according to claim 9, wherein said strain carries genes coding for ESAT-6 or CFP-10 in a mycobacterial expression vector under the control of a promoter, more particularly an hsp60 promoter.

11. A strain according to claim 9, wherein said strain carries a portion of the esat-6 gene that codes for immunogenic 20-mer peptides of ESAT-6 active as T-cell epitopes.

12. A pharmaceutical composition comprising a strain according to claim 3 and a pharmaceutically acceptable carrier.

13. A pharmaceutical composition according to claim 12, wherein the pharmaceutically-acceptable carrier comprises excipients and auxiliaries which facilitate processing of the living vaccine into preparations which can be used pharmaceutically.

14. A pharmaceutical composition according to claim 12 which is suitable for oral, intravenous, or subcutaneous administration.

15. A vaccine comprising a strain according to claim 3 and a suitable carrier.

16. A product comprising a strain according to claim 3 and at least one protein selected from ESAT-6 and CFP-10 for a separate, simultaneous, or sequential use for treating tuberculosis.

17. A strain according to claim 3, which has integrated a portion of DNA originating from *Mycobacterium tuberculosis* or any virulent member of the *Mycobacterium tuberculosis* complex (*M. africanum, M. bovis, M. canettii*), wherein the integrated DNA further comprises at least one gene selected from the group consisting of: Rv3878 (SEQ ID NO:21), Rv3879 (SEQ ID NO:22), Rv3880 (SEQ ID NO:23), Rv3881 (SEQ ID NO:24), Rv3882 (SEQ ID NO:25), Rv3883 (SEQ ID NO:26), Rv3884 (SEQ ID NO:27), and Rv3885 (SEQ ID NO:28), in combination with at least one gene selected from the group consisting of: Rv3872 (SEQ ID NO:15, mycobacterial PE) and Rv3873 (SEQ ID NO:16, PPE).

18. A strain according to claim 3, wherein the strain has integrated a portion of DNA originating from *Mycobacterium tuberculosis* or any virulent member of the *Mycobacterium tuberculosis* complex (*M. africanum, M. bovis, M. canettii*), wherein the integrated DNA further comprises at least one gene selected from the group consisting of: Rv3861 (SEQ ID NO:4), Rv3862 (SEQ ID NO:5), Rv3863 (SEQ ID NO:6), Rv3864 (SEQ ID NO:7), Rv3865 (SEQ ID NO:8), Rv3866 (SEQ ID NO:9), Rv3867 (SEQ ID NO:10), Rv3880 (SEQ ID NO:23), Rv3881 (SEQ ID NO:24), Rv3882 (SEQ ID NO:25), Rv3883 (SEQ ID NO:26), Rv3884 (SEQ ID NO:27), and Rv3885 (SEQ ID NO:28), in combination with at least one gene selected from the group consisting of: Rv3872 (SEQ ID NO:15, mycobacterial PE) and Rv3873 (SEQ ID NO:16, PPE).

\* \* \* \* \*